US012234450B2

(12) United States Patent
Hutchison et al.

(10) Patent No.: US 12,234,450 B2
(45) Date of Patent: *Feb. 25, 2025

(54) GENERATION OF SYNTHETIC GENOMES

(71) Applicant: Codex DNA, Inc., San Diego, CA (US)

(72) Inventors: Clyde A. Hutchison, La Jolla, CA (US); Ray-Yuan Chuang, Rockville, MD (US); Vladimir N. Noskov, Gaithersburg, MD (US); Bogumil J. Karas, London (CA); Kim S. Wise, San Diego, CA (US); Hamilton O. Smith, San Diego, CA (US); John I. Glass, San Diego, CA (US); Chuck Merryman, Encinitas, CA (US); Daniel G. Gibson, Carlsbad, CA (US); J. Craig Venter, La Jolla, CA (US); Krishna Kannan, San Diego, CA (US); Lin Ding, San Diego, CA (US)

( * ) Notice: Subject to any disclaimer, the term of this patent is extended or adjusted under 35 U.S.C. 154(b) by 1021 days.

This patent is subject to a terminal disclaimer.

(21) Appl. No.: 17/200,633

(22) Filed: Mar. 12, 2021

(65) Prior Publication Data

US 2021/0254046 A1   Aug. 19, 2021

Related U.S. Application Data

(63) Continuation of application No. 15/466,675, filed on Mar. 22, 2017, now Pat. No. 11,085,037.

(60) Provisional application No. 62/312,398, filed on Mar. 23, 2016.

(51) Int. Cl.
| *C12N 15/10* | (2006.01) |
| *C12N 15/74* | (2006.01) |
| *C12N 15/81* | (2006.01) |
| *G16B 30/00* | (2019.01) |
| *G16B 30/20* | (2019.01) |

(52) U.S. Cl.
CPC ..... *C12N 15/1027* (2013.01); *C12N 15/1058* (2013.01); *C12N 15/1079* (2013.01); *C12N 15/1093* (2013.01); *C12N 15/74* (2013.01); *C12N 15/81* (2013.01); *G16B 30/00* (2019.02); *G16B 30/20* (2019.02)

(58) Field of Classification Search
CPC .................................................. C12N 15/1027
USPC ....................................................... 435/455
See application file for complete search history.

(56) References Cited

U.S. PATENT DOCUMENTS

| 9,267,132 B2 | 2/2016 | Benders |
| 9,434,974 B2 | 9/2016 | Glass |
| 2007/0264688 A1 | 11/2007 | Venter et al. |
| 2007/0269862 A1 | 11/2007 | Glass et al. |
| 2008/0286871 A1 | 11/2008 | Holt |
| 2009/0275086 A1 | 11/2009 | Gibson et al. |
| 2011/0053273 A1 | 3/2011 | Benders et al. |

FOREIGN PATENT DOCUMENTS

| WO | WO-9831837 A1 | 7/1998 |
| WO | WO-2006119066 A2 | 11/2006 |
| WO | WO-2007047148 A1 | 4/2007 |
| WO | WO-2008016380 A2 | 2/2008 |
| WO | WO-2008024129 A2 | 2/2008 |
| WO | WO-2010102257 A2 | 9/2010 |

OTHER PUBLICATIONS

Chromosome 15—Wikipedia pp. 1-13; downloaded Aug. 23, 2024.*
A. Svoboda, Microbiology, 1978.
Abdel-Banat., et al., "Yeast," 2010, vol. 27, 1 Page.
Adey, et al., Genome Biology, 2010, vol. 11, p. R119.
Boeke, et al., Molecular & General Genetics (MGG), 1984, vol. 197, pp. 345-346.
Boeke JD et al., Methods Enzymol, (19870000), vol. 154, pp. 164-175.
Brouwer, et al., Nature, 2016, vol. 535, p. 566.
Extended European Search Report for European Application No. 17771095.1, mailed Jul. 24, 2019, 15 Pages.
Fleischmann, et al., Science, 1995, vol. 269, pp. 496-512.
Gibson D.G., et al., "Chemical Synthesis of the Mouse Mitochondrial Genome," Nature Methods, Nature Pub. Group, Nov. 2010, vol. 07, No. 11, pp. 901-903, DOI: 10.1038/nmeth.1515, ISSN 15487091, XP055173787.
Gibson D.G., et al., "Complete Chemical Synthesis, Assembly, And Cloning Of A Mycoplasma Genitalium Genome," Science, American Association for the Advancement of Science, US, Feb. 29, 2008, vol. 319, No. 5867, pp. 1215-1220, DOI: 10.1126/SCIENCE. 1151721, ISSN 0036-8075, XP009101716.
Gibson D.G., et al., "Creation of a Bacterial Cell Controlled by a Chemically Synthesized Genome," Science, Jul. 2, 2010, vol. 329, No. 5987, pp. 52-56, DOI: 10.1126/science.1190719, ISSN 0036-8075, XP055082599.
Gibson, et al., Proceedings of the National Academy of Sciences of the United States of America, 2008, vol. 105, pp. 20404-20409.
Gietz, et al., Nucleic Acids Research, 1992, vol. 20, p. 1425.
Glass J.I., et al., "Essential Genes Of A Minimal Bacterium," Proceedings of the National Academy of Sciences of the United States of America, US, Jan. 10, 2006, vol. 103, No. 2, pp. 425-430, DOI: 10.1073/PNAS.0510013103, ISSN 0027-8424, XP001248497.
Haft, et al., Nucleic Acids Research, 2003, vol. 31, pp. 371-373.
Hill Abloom K, Molecular and Cellular Biology, 1987, vol. 7, No. 7, pp. 2397-2405.
International Preliminary Report on Patentability for International Application No. PCT/US2017/023666, mailed Oct. 4, 2018, 09 Pages.

(Continued)

*Primary Examiner* — Mark L Shibuya

(57) ABSTRACT

Methods for generating synthetic genomes, for example synthetic genomes having desired properties or viable genomes of reduced size, are disclosed. Also disclosed are synthetic genomes produced by the methods disclosed herein and synthetic cells containing the synthetic genomes disclosed herein.

20 Claims, 57 Drawing Sheets

Specification includes a Sequence Listing.

(56) References Cited

OTHER PUBLICATIONS

International Search Report and Written Opinion for International Application No. PCT/US2017/023666, mailed Jul. 6, 2017, 12 Pages.
Jensen, et al., Journal of Clinical Microbiology, 1996, vol. 34, pp. 286-291.
Karas B.J., et al., "Direct Transfer of Whole Genomes From Bacteria to Yeast," Nature Methods, Mar. 31, 2013, vol. 10, No. 5, pp. 410-412, DOI: 10.1038/nmeth.2433, ISSN 1548-7091, XP055089021.
Karas B.J., et al., "Direct Transfer of Whole Genomes from Bacteria to Yeast, Suplementary Materials," Nature Methods, New York, Mar. 31, 2013, vol. 10, No. 5, 19 Pages, DOI: 10.1038/nmeth.2433, ISSN 1548-7091, XP055602458.
Karas B.J., et al., "Rescue of Mutant Fitness Defects using in Vitro Reconstituted Designer Transposons in Mycoplasma Mycoides," Frontiers In Microbiology, Jul. 23, 2014, vol. 5, pp. 1-9, ISSN: 1664-302X, XP002792710.
Karas, et al., Nature Communications, 2015, vol. 6, p. 6925.
Kikuchi M., et al., "Novel Family Shuffling Methods for the in Vitro Evolution of Enzymes," Gene, Elsevier, Amsterdam, NL, Aug. 5, 1999, vol. 236, No. 1, pp. 159-167, DOI: 10.1016/S0378-1119(99)00240-1, ISSN: 0378-1119, XP004175459.
Kouprina, et al., Nature Protocols, 2008, vol. 3, pp. 371-377.
Lartigue, et al., Science, 2009, vol. 325, pp. 1693-1696.
Moriguchi, et al., PLoS One, 2016, vol. 11, p. e0148989.
Mushegian, et al., Proceedings of the National Academy of Sciences of the United States of America, 1996, vol. 93, pp. 10268-10273.
Nonklang, et al., Applied and Environmental Microbiology, 2008, vol. 74, p. 7514.
Noskov, et al., Nucleic Acids Research, 2010, vol. 38, pp. 2570-2576.
Sambrook, et al., Molecular Cloning, A Laboratory Manual, Cold Springs Harbor Press, 1989.
Sharma, et al., Journal of Nucleic Acids, 2010.
Singleton, et al., Dictionary of Microbiology and Molecular Biology, John Wiley & Sons, 1994.
Sleator R.D., "JCVI-syn3.0—A Synthetic Genome Stripped Bare!," Bioengineered, Apr. 2, 2016, vol. 7, No. 2, pp. 53-56, ISSN 2165-5987, XP002792711.
Smith H.O., et al., "Generating A Synthetic Genome By Whole Genome Assembly: PhiX174 Bacteriophage From Synthetic Oligonucleotides," Proceedings of the National Academy of Sciences of the United States of America, Dec. 23, 2003, vol. 100, No. 26, pp. 15440-15445.
Stemmer W.P.C., et al., "Single-Step Assembly Of A Gene And Entire Plasmid From Large Nos. Of Oligodeoxyribonucleotides," GENE, Oct. 15, 1995, vol. 164, No. 1, pp. 49-53, XP004041916.
Strand, et al., PloS One, 2014, vol. 9, p. e90372.
Suzuki, et al., Nature Methods, 2011.
Young L., et al., "Two-step Total Gene Synthesis Method," Nucleic Acids Research, Published Online on Apr. 15, 2004, vol. 32, No. 7, E59, pp. 1-6.
Yung et al., Journal of bacteriology, 2015, vol. 197, p. 3160.
AU Office Action in Australian Application No. 2017238212, dated Aug. 23, 2022, 6 pages.

* cited by examiner

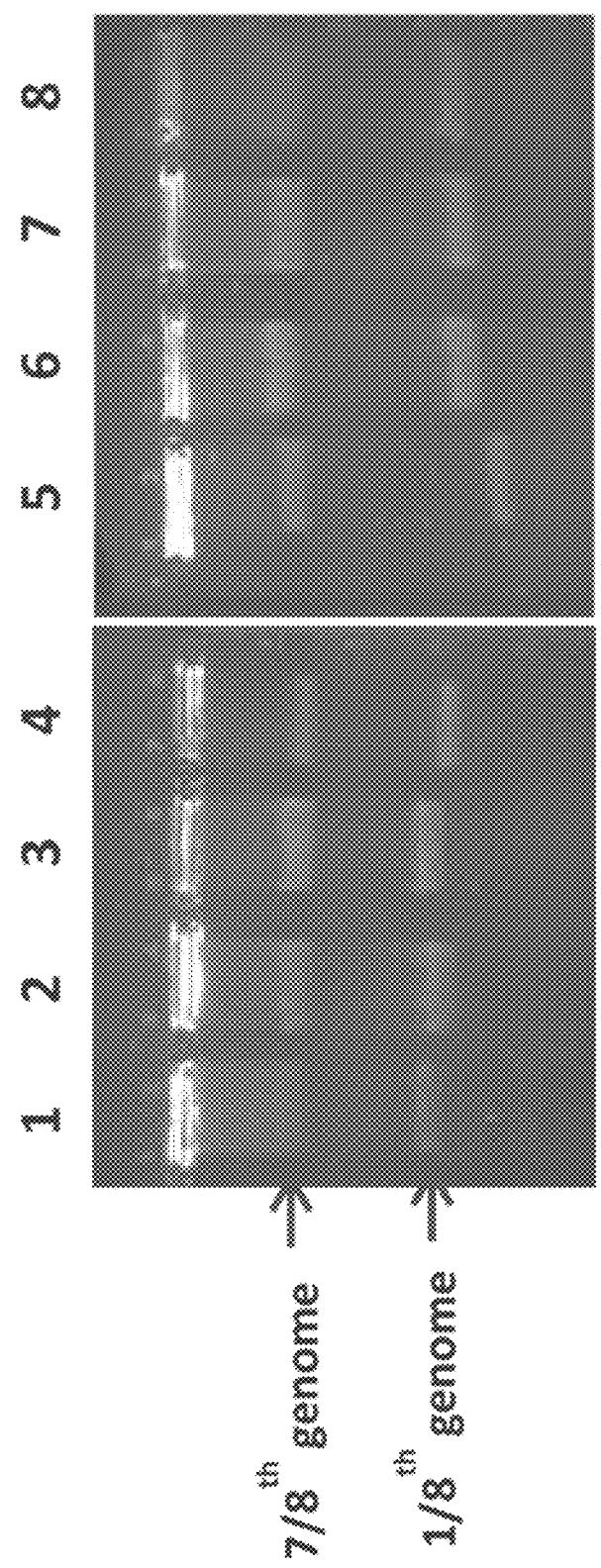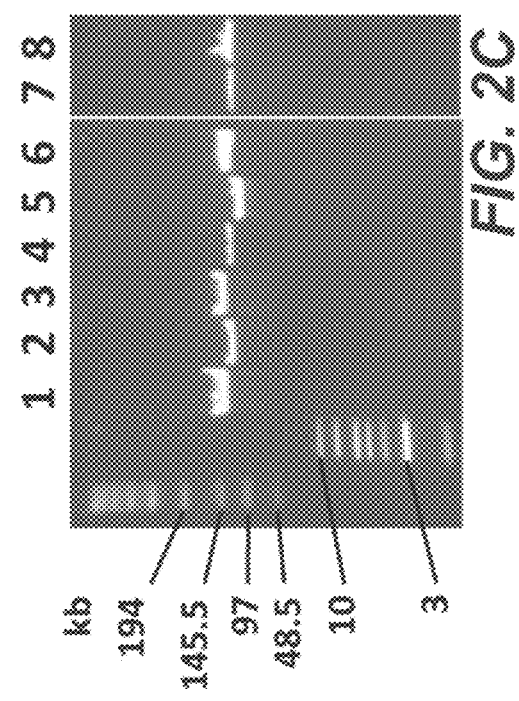
FIG. 2C

Step 1, construct Tn5 transposon containing 19 bp mosaic ends, sequencing primer sites, terminator sequences, and a selectable marker (puromycin-resistance gene). Bind transposase (Epicentre) to 19bp termini to form active transposome.

19bp SqPR ter Ptuf Puro gene ter SqPF 19bp

Step 2, introduce transposome into *Mycoplasma mycoides* JCVI-Syn1.0 R-M (minus) strain by polyethylene glycol (PEG) transformation method. Collect puromycin-resistant colonies and serially propagate to eliminate slow growers.

Prepare Library P0 from DNA isolated from colonies. All viable insertions represented.

~80,000 colonies ~$10^3$ ~$10^4$ ~$10^4$ ~$10^4$

Prepare Library P4 from final passage (~50 doublings). Slow growers are lost.

Step 3, isolate genomic DNA, shear using a nebulizer, ligate to circularize fragments, PCR amplify specific fragments (inverse PCR) and sequence these fragments using MiSeq.

*FIG. 4*

Genes deleted in the segment 5

| ID | Gene | Description | |
|---|---|---|---|
| 682 | MMSYN1_0436 | uracil-DNA glycosylase (UDG) | d |
| 1894 | MMSYN1_0444 | endopeptidase O | d |
| 543 | MMSYN1_0449 | IS1296 transposase protein A | d |
| 730 | MMSYN1_0450 | IS1296 transposase protein B | d |

Cluster 33:
| | | | |
|---|---|---|---|
| 2182 | MMSYN1_0454 | hypothetical protein | d |
| 1516 | MMSYN1_0455 | putative membrane protein | RFG02s-5 |
| 394 | MMSYN1_0034 | conserved domain protein | d |
| 883 | MMSYN1_0460 | bacterial surface protein 26 residue repeat protein | d |
| 730 | MMSYN1_0461 | IS1296 transposase protein B | d |
| 543 | MMSYN1_0462 | IS1296 transposase protein A | d |
| 1177 | MMSYN1_0463 | NADH dependent flavin oxidoreductase | d |
| 1036 | MMSYN1_0464 | lipoate-protein ligase | d |
| 886 | MMSYN1_0465 | conserved hypothetical protein | d |
| 343 | MMSYN1_0466 | glycine cleavage system H protein | d |
| 799 | MMSYN1_0467 | triacylglycerol lipase | RFG02s-5 |
| 793 | MMSYN1_0468 | lipase-esterase | RFG02s-5 |
| 808 | MMSYN1_0469 | lipase-esterase | RFG02s-5 |
| 1132 | MMSYN1_0470 | conserved hypothetical protein | d |
| 130 | MMSYN1_0471 | hypothetical protein | d |
| 1399 | MMSYN1_0472 | putative lipoprotein | d |
| 718 | MMSYN1_0473 | ABC transporter, ATP binding protein | d |
| 754 | MMSYN1_0474 | ABC transporter, ATP binding protein | d |

| 1156 | MMSYN1_0476 | N-acetylglucosamine-6-phosphate deacetylase | d |
| 733 | MMSYN1_0477 | conserved hypothetical protein | d |
| 1999 | MMSYN1_0480 | conserved hypothetical protein | d |

0483-492:

Cluster 36:
| 559 | MMSYN1_0483 | holliday junction DNA helicase RuvA | d |
| 922 | MMSYN1_0484 | holliday junction ATP-dependent DNA helicaseRuvB | d |
| 1357 | MMSYN1_0485 | dihydrolipoamide dehydrogenase | d |
| 808 | MMSYN1_0486 | conserved hypothetical protein | d |
| | MMSYN1_0487+0488 | | |

Cluster 37:
| 1222 | MMSYN1_0489 | DNA polymerase IV | d |
| 2737 | MMSYN1_0490 | papain family cysteine protease, putative | d |
| 682 | MMSYN1_0491 | uridine kinase | d |
| 439 | MMSYN1_0492 | conserved hypothetical protein | d |

| 820 | MMSYN1_0494 | putative N-acetylmannosamine-6-phosphate 2-epimerase | RFG02-5 |

0495-498:
| 874 | MMSYN1_0495 | ROK family protein | d |
| 448 | MMSYN1_0496 | conserved hypothetical protein | d |
| 1702 | MMSYN1_0497 | sodium solute symporter family | d |
| 886 | MMSYN1_0498 | N-acetylneuraminate lyase (N-acetylneuraminic acid) | d |

| 480 | MMSYN1_0503 | conserved hypothetical protein | d |
| 886 | MMSYN1_0504 | conserved hypothetical protein | RFG02-5 |
| 1072 | MMSYN1_0505 | putative lipoprotein | d |

*FIG. 8*

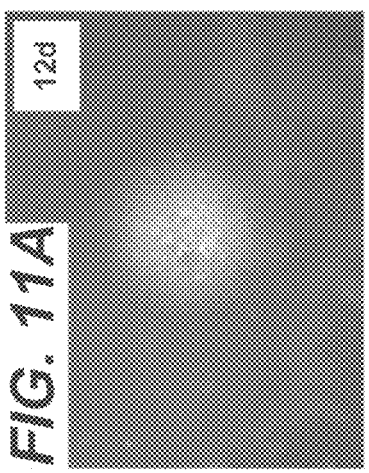
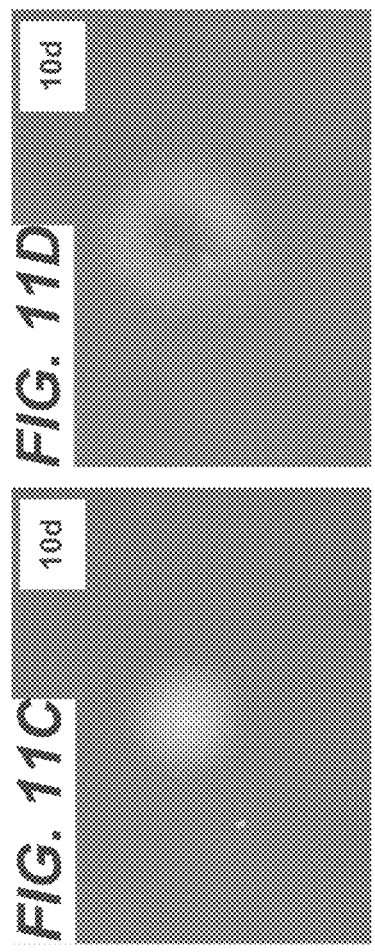
Colonies from transplantation of three different yeast clones of RGD1.0 Segment 6 + 7/8 syn1.0 are shown
FIG. 11A — Yeast clone #5
FIG. 11B — Yeast clone #6
FIG. 11C
FIG. 11D
FIG. 11E — Yeast clone #7
FIG. 11F
FIG. 11G

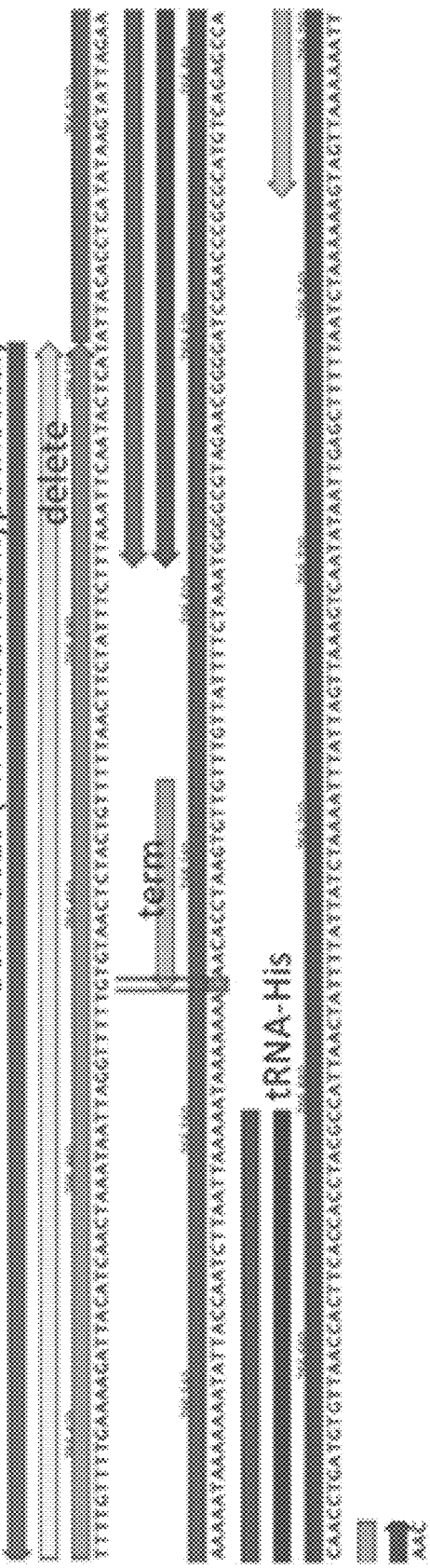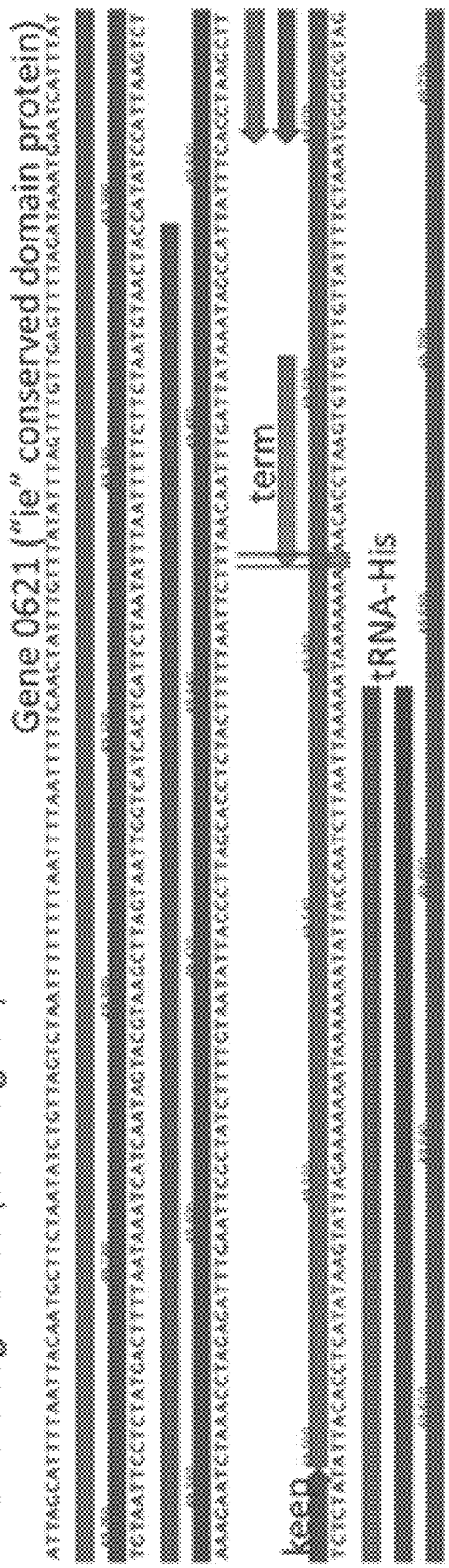
FIG. 12

|  | 672,318 321 | 328 330 333 | colonies |
|---|---|---|---|
| syn1.0 | CAACACCCT | AAGTGTTTG | |
| 6a | ...G..... | ......... | L |
| 6a | ......... | ...C..... | s |
| 7b | ..T...... | ......... | L |
| 5 | ...A..... | ......... | various |
| 5 | ....*.... | ......... | op? |
| 5 | ......... | ...T..... | very sm |
| 5 | ......... | ........A | sm? |

Purified colony from transplant of clone #5, 6, or 7

\* Single base deletion puts an A here.

FIG. 14

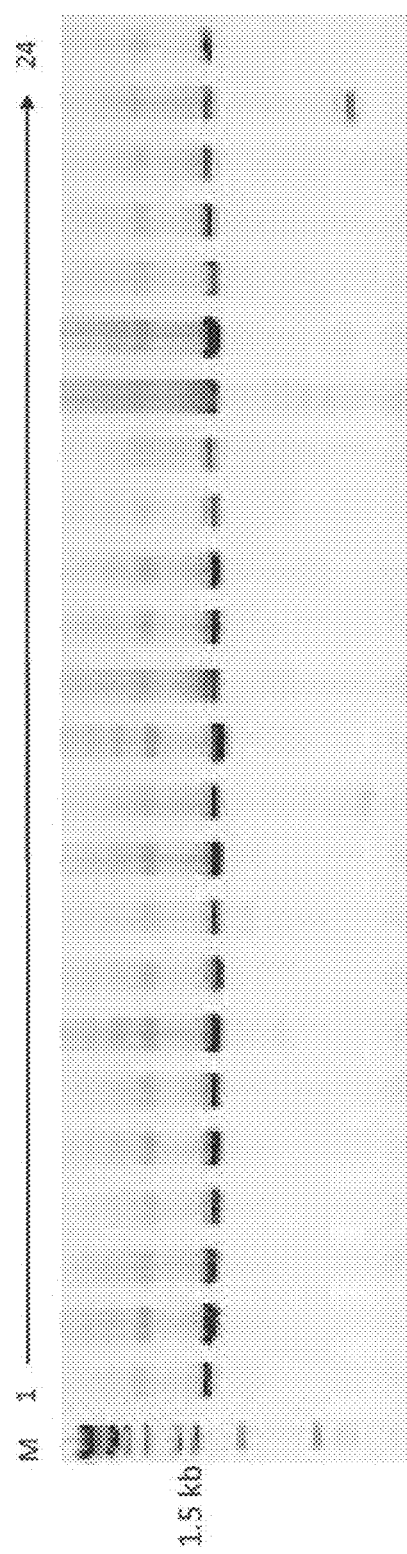

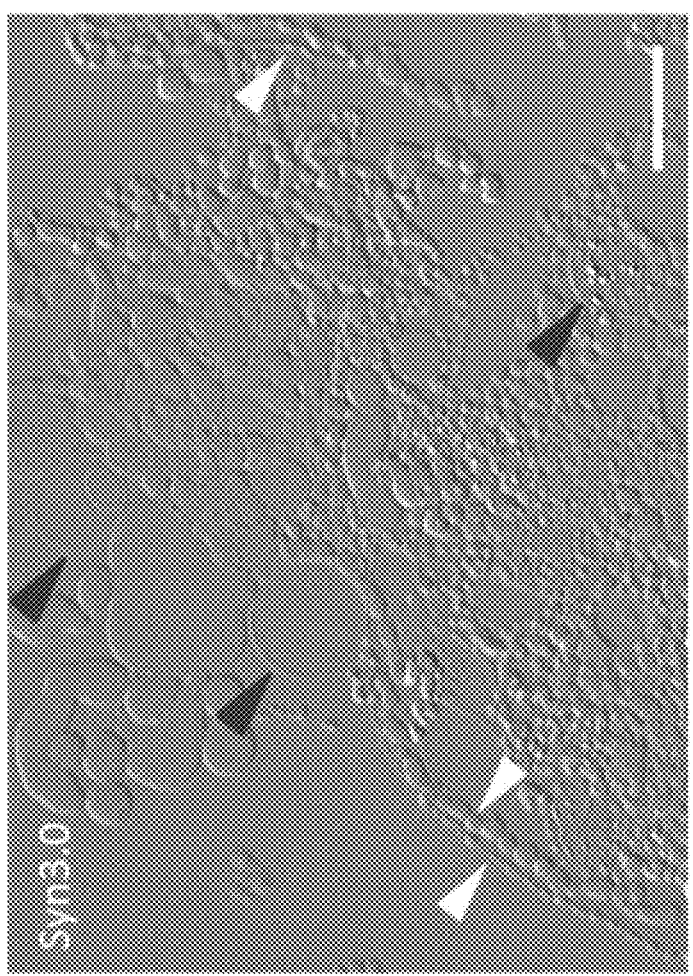
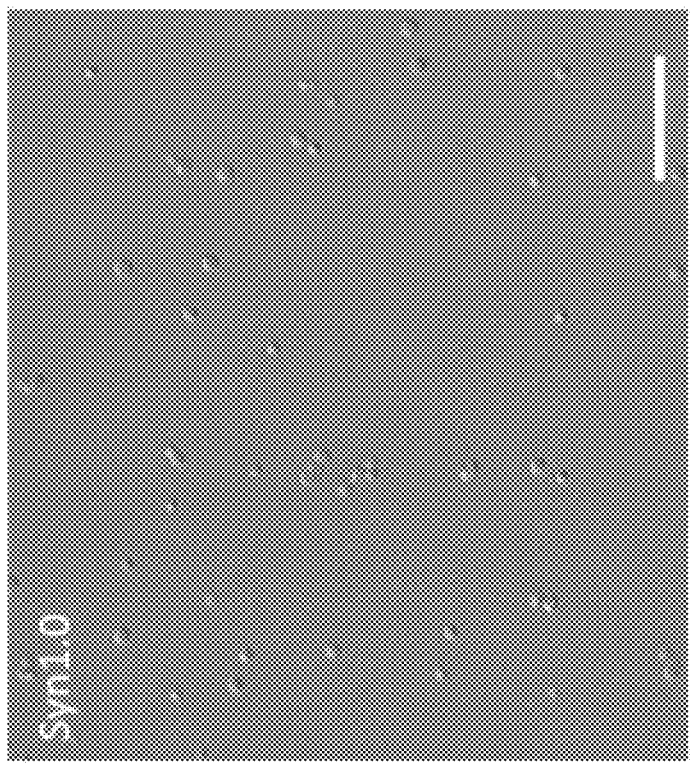
FIG. 28C

| | Plasmid to be transferred | Helper plasmid (pTA-MOB) | #colonies on selective plate |
|---|---|---|---|
| 1 | pCC1BAC-LCyeast_(scHis3)-SYN-KM_CENARS | Yes | 0 |
| 2.1 | pCC1BAC-LCyeast_(scHis3)-SYN-KM_CENARS_oriT | Yes | 41 |
| 2.2 | pCC1BAC-LCyeast_(scHis3)-SYN-KM_CENARS_oriT | Yes | 72 |
| 3 | No | Yes | 0 |
| 4 | pCC1BAC-LCyeast_(scHis3)-SYN-KM_CENARS_oriT | No | 0 |

SEQUENCE LISTING

```
<160> NUMBER OF SEQ ID NOS: 5

<210> SEQ ID NO 1
<211> LENGTH: 354
<212> TYPE: DNA
<213> ORGANISM: Artificial Sequence
<220> FEATURE:
<223> OTHER INFORMATION: /note="Description of Artificial Sequence:
      Synthetic Nucleotide Sequence"

<400> SEQUENCE: 1
ttttgttttg aaaagattac atcaactaaa taattaggtt tttgtgtaac tctactgttt      60
ttaacttcta tttctttaaa ttcaatactc atattacacc tcatataagt attagaaaaa     120
aataaaaaaa tattaccaat cttaattaaa aataaaaaaa caacacctaa gtgttgtttg     180
ttattttcta aatggggcgt agaacgggga tcgaacccgc gcatgtcaga gccacaacct     240
gatgtgttaa ccacttcacc acctacgcca ttaactattt tattatctaa aatttattag     300
ttaaagtcaa tataattgag cttttttaatc taaaaagta gttaaaaaat taac            354

<210> SEQ ID NO 2
<211> LENGTH: 468
<212> TYPE: DNA
<213> ORGANISM: Artificial Sequence
<220> FEATURE:
<223> OTHER INFORMATION: /note="Description of Artificial Sequence:
      Synthetic Nucleotide Sequence"

<400> SEQUENCE: 2
attagcattt taattacaat gcttctaata tctgttagtc taatttttttt taattttaat      60 ttttcaacta tttgtttata tttagtttgt tgagttttag ataaatgaat catttattgt     120
aattcctcta tgactttttaa taaatcatca atagtacgta agcttagtaa ttggtcatca     180
ctgattctaa tatttaattt ttcttctaat gtaactacca tatccattaa gtctaaagaa     240
tctaaaccta gagatttgaa ttcgctatct tttgtaatat tacccttagc acctctactt     300
tttaattctt taacaatttg attataaata gccattattt cacctaagct ttctctatat     360
tacacctcat ataagtatta gaaaaaaata aaaaatatt accaatctta attaaaaata     420
aaaaaacaac acctaagtgt tgtttgttat tttctaaatg gggcgtag                  468

<210> SEQ ID NO 3
<211> LENGTH: 83
<212> TYPE: DNA
<213> ORGANISM: Artificial Sequence
<220> FEATURE:
<223> OTHER INFORMATION: /note="Description of Artificial Sequence:
      Synthetic Nucleotide Sequence"

<400> SEQUENCE: 3
aagtattaga aaaaaataaa aaatattac caatcttaat taaaaataaa aaacaacac        60
```

```
ctaagtgttg tttgttattt tct                                              83

<210> SEQ ID NO 4
<211> LENGTH: 16
<212> TYPE: DNA
<213> ORGANISM: Artificial Sequence
<220> FEATURE:
<223> OTHER INFORMATION: /note="Description of Artificial Sequence:
      Synthetic Nucleotide Sequence"

<400> SEQUENCE: 4
caacacctaa gtgttg                                                      16

<210> SEQ ID NO 5
<211> LENGTH: 35
<212> TYPE: RNA
<213> ORGANISM: Artificial Sequence
<220> FEATURE:
<223> OTHER INFORMATION: /note="Description of Artificial Sequence:
      Synthetic Nucleotide Sequence"

<400> SEQUENCE: 5
cguuaguuac uaacauuaag uugagaacuc uaacg                                 35
```

GENERATION OF SYNTHETIC GENOMES

CROSS-REFERENCE TO RELATED APPLICATIONS

This application is a continuation application of U.S. application Ser. No. 15/466,675 filed Mar. 22, 2017, now pending: which claims the benefit under 35 USC § 119(e) to U.S. Application Ser. No. 62/312,398 filed Mar. 23, 2016, now expired. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under Contract Nos. HR0011-12-C-0063 and HR0011-16-2-0010 awarded by the Defense Advanced Research Projects Agency (DARPA). The government has certain rights in the invention.

INCORPORATION BY REFERENCE OF SEQUENCE LISTING

The material in the accompanying sequence listing is hereby incorporated by reference into this application. The accompanying sequence listing text file, named CODEX2240-2_ST25.txt, was created on May 5, 2021 and is 3 KB in size. The file can be accessed using Microsoft Word on a computer that uses Windows OS.

BACKGROUND OF THE INVENTION

Field

The present application relates generally to molecular biology, and more particularly to synthetic genomes.

Description of the Related Art

Methods and techniques for producing and modifying cellular genomes are useful in the field of cell biology, in particular deciphering the operating system of the cell. Genome reductions of bacterial cells have been achieved by a series of sequential deletion events to facilitate the goal of understanding the molecular and biological function of genes essential for life. After each deletion, viability, growth rate, and other phenotypes of the resulting bacterial genome with a reduced size were determined. However, there is still a need for more systematic and improved method for designing and producing synthetic genomes of interest, and to improve our ability to identify essential genes.

SUMMARY OF THE INVENTION

A method for generating a synthetic genome of interest is disclosed herein. In some embodiments, the method comprises: (a) providing a first genome: (b) designing a second genome based on the first genome, wherein the second genome is hypothesized to have a set of desired properties: (c) dividing each of the first and second genomes into N corresponding fragments, wherein N is an integer equal to or greater than 3: (d) combining at least one fragment of the second genome with fragments of the first genome to generate a third genome having all N corresponding fragments: (e) testing the third genome generated in step (d) for the set of desired properties; and (f) identifying the third genome as a synthetic genome of interest if it has the set of desired properties: otherwise modifying at least one fragment of the second genome and repeating steps (d)-(f) in one or more iterations until a set of desired properties is obtained in the third genome. The first genome can be, for example, a naturally occurring genome. In some embodiments, the first genome is a genome of unicellular organism. In some embodiments, the first genome is a bacterial genome, a yeast genome, a single-cell alga genome, or a combination thereof. In some embodiments, the first genome is a single chromosome genome. In some embodiments, the first genome is a multi-chromosome genome.

In some embodiments, step (b) comprises testing the second genome for the set of desired properties. In some embodiments, designing the second genome comprises modifying the first genome based on the information from literature resources, experimental data, or any combination thereof. In some embodiments, the experimental data comprises data obtained from a mutation study of the first genome, a genome related to the first genome, or any combination thereof. In some embodiments, the experimental data comprises data related to genes of essential function redundancies (EFR). The mutation study can comprise, for example, one or more of mutagenesis study, gene knockout study, and add-back study. The mutagenesis study can comprise, for example, random mutagenesis, targeted mutagenesis, or both. The mutageneis study comprises, in some embodiments, transposon-based mutagenesis, insertional mutagenesis, or both.

In some embodiments, all of the N corresponding fragments are substantially the same length. In some embodiments, at least two of the N corresponding fragments are different in length. In some embodiments, at least one of the N corresponding fragments is a chromosome of the first or second genome. In some embodiments, at least one of the N corresponding fragments is a portion of a chromosome of the first or second genome.

In some embodiments, testing the genome for the set of desired properties comprises introducing the genome into a cell or a cell-like system. The genome can be introduced into the cell or the cell-like system through, for example, conjugation, transformation, transduction, or any combination thereof. In some embodiments, the cell-like systems comprises a membrane-bound volume, a lipid vesicle, a cell from which one or more intracellular components have been removed, a cell from which the resident genome has been removed, or any combination thereof.

In some embodiments, modifying at least one of the second genome fragments in step (f) is at least partly based on the testing of step (e). In some embodiments, modifying at least one fragment of the second genome in step (f) further comprises conducting mutation study of the at least one fragment and modifying the at least one fragment at least partly based on the mutation study. In some embodiments, the mutation study comprises one or more of mutagenesis study, gene knockout study, and add-back study. The mutagenesis study can comprise, for example, random mutagenesis, targeted mutagenesis, or both. The mutageneis study comprises, in some embodiments, transposon-based mutagenesis, insertional mutagenesis, or both. In some embodiments, the set of desired properties comprises one or more of viability, growth rate, adaptability, doubling time, ratio of growth rate to genome size, ratio of doubling time to genome size, expression level of a gene of interest, and expression rate of a gene of interest.

In some embodiments, the first genome is viable. In some embodiments, N is an integer between 4 and 20. In some embodiments, the synthetic genome of interest is a minimal genome. In some embodiments, the second genome is smaller than the first genome in size. In some embodiments, the third genome comprises one or more fragments from a naturally occurring genome and one or more fragments from a synthetic genome. In step (b), the fragments of the first genome can be, in some embodiments, a nucleic acid molecule comprising one or more fragments of the first genome. For example, in step (d), the fragments of the first genome can be present in a single nucleic acid molecule before being combining with the fragment(s) of the second genome. In some embodiments, step (d) comprises deleting a portion or the entire fragment of the first genome that corresponds to one of the at least one fragment of the second genome. In some embodiments, one or more of the at least one fragment of the second genome is present in an extra-chromosomal genetic element in the combining step (d). The extrachromosomal genetic element can be, for example, an episome, a plasmid, a fosmid, a cosmid, a bacterial artificial chromosome, or a yeast artificial chromosome. In some embodiments, the combining step comprises combining each of the two or more fragments of the second genome with fragments of the first genome to generate a plurality of the third genomes having all N corresponding fragments. In some embodiments, each of the plurality of the third genomes is tested for the set of desired properties.

In some embodiments, the combining step comprises chemically synthesizing and assembling the fragments of the first and second genomes to generate the third genome. In some embodiments, assembling the fragments of the first and second genomes comprises assembling chemically synthesized, overlapping oligonucleotides into one or more of nucleic acid cassettes. In some embodiments, a portion or the entire synthetic genome of interest is constructed from nucleic acid components that have been chemically synthesized, or that have been created from copies of the chemically synthesized nucleic acid components.

In some embodiments, the method further comprises modifying one or more genes in the third genomes after identifying the third genome as a synthetic genome of interest. In some embodiments, step (d) further comprises reorganizing gene order in the at least one fragment of the second genome before combining it with fragments of the first genome to generate the third genome. In some embodiments, the method further comprises reorganizing gene order in the third genome after it is identified as a synthetic genome of interest. In some embodiments, reorganizing gene order comprises grouping genes related to the same biological process in the at least one fragment of the second genome. In some embodiments, the same biological process is one or more of glucose transport and catabolismo ribosome biogenesis; protein export, DNA repair: transcription: translation: nucleotide synthesis, metabolism and salvage: glycolysis: metabolic processes: proteolysis: membrane transport: rRNA modification; and tRNA modification.

Also disclosed herein is a method for generating a viable genome of reduced size. In some embodiments, the method comprises: (a) providing a first genome known to be viable: (b) designing a second genome based on the first genome, wherein the second genome comprises a reduced number of genes of the first genome and is hypothesized to be viable: (c) dividing each of the first and second genomes into N corresponding fragments, wherein N is an integer equal to or greater than 3: (d) combining at least one of the N fragments of the second genome with a sufficient number of said fragments of the first genome to generate a third genome having all N corresponding fragments: (e) testing the third genome generated in step (d) for viability: (f) if the third genome is viable, identifying the third genome as a viable genome of reduced size; and (g) if the third genome is not viable, modifying one or more fragments of the second genome based on the testing of (e) and repeating steps (d)-(f) until the third genome is viable.

In some embodiments, the first genome is a naturally occurring genome. In some embodiments, the first genome is a genome of a unicellular organism. In some embodiments, the first genome is a bacterial genome, a yeast genome, a single-cell alga genome, or a combination thereof. In some embodiments, the first genome is a single chromosome genome. In some embodiments, the first genome is a multi-chromosome genome.

In some embodiments, the method further comprises deleting one or more genes from the third genomes after identifying the third genome as a viable genome of reduced size. In some embodiments, step (b) comprises testing the second genome for viability. In some embodiments, the method further comprises deleting one or more genes from at least one fragment of the second genome after identifying the third genome as a viable genome of reduced size and repeating steps (d)-(g) in one or more iterations.

In some embodiments, designing a second genome comprises modifying the first genome based on the information from literature resources, experimental data, or any combination thereof. In some embodiments, the experimental data comprises data obtained from a mutation study of the first genome, a genome related to the first genome, or any combination thereof.

In some embodiments, the experimental data comprises data related to genes of essential function redundancies (EFR). In some embodiments, the mutation study comprises one or more of transposon-based mutagenesis study, gene knockout study, and add-back study. In some embodiments, all of the N corresponding fragments are substantially the same length. In some embodiments, at least two of the N corresponding fragments are different in length. In some embodiments, at least one of the N corresponding fragments is a chromosome of the first or second genome. In some embodiments, at least one of the N corresponding fragments is a portion of a chromosome of the first or second genome.

In some embodiments, in step (d) the fragments of the first genome is a nucleic acid molecule comprising one or more fragments of the first genome. In some embodiments, step (d) comprises deleting a portion or the entire fragment of the first genome that corresponds to one of the at least one fragment of the second genome. In some embodiments, in the combining step (d), one or more of the at least one fragment of the second genome is present in an extrachromosomal genetic element. The extrachromosomal genetic element can be, for example, an episome, a plasmid, a fosmid, a cosmid, a bacterial artificial chromosome, or a yeast artificial chromosome.

In some embodiments, testing the genome for the set of desired properties comprises introducing the genome into a cell or a cell-like system. In some embodiments, the genome is introduced into the cell or the cell-like system by conjugation, transformation, transduction, or a combination thereof. In some embodiments, the cell-like systems comprises a membrane-bound volume, a lipid vesicle, a cell from which one or more intracellular components have been removed, a cell from which the resident genome has been removed, or any combination thereof.

In some embodiments, modifying at least one fragment of the second genome in step (f) is at least partly based on the testing of step (e). In some embodiments, modifying at least one fragment of the second genome fragments in step (f) further comprises conducting mutation study of the at least one fragment and modifying the at least one fragment at least partly based on the mutation study. The mutagenesis study can comprise, for example, random mutagenesis, targeted mutagenesis, or both. The mutageneis study comprises, in some embodiments, transposon-based mutagenesis, insertional mutagenesis, or both. In some embodiments, step (d) comprises chemically synthesizing and assembling the genomic fragments. In some embodiments, combining the fragments of the first and second genomes comprises assembling chemically synthesized, overlapping oligonucleotides into one or more of nucleic acid cassettes.

In some embodiments, the entire viable genome of reduced size is constructed from nucleic acid components that have been chemically synthesized, or that have been created from copies of the chemically synthesized nucleic acid components. In some embodiments, step (d) further comprises reorganizing gene order in the at least one fragment of the second genome before combining it with fragments of the first genome to generate the third genome. In some embodiments, the method further comprises reorganizing gene order in the third genome.

In some embodiments, reorganizing gene order comprises grouping genes related to the same biological process in the at least one fragment of the second genome. In some embodiments, the same biological process is one or more of glucose transport and catabolism; ribosome biogenesis: protein export, DNA repair: transcription: translation; nucleotide synthesis, metabolism and salvage: glycolysis: metabolic processes: proteolysis; membrane transport: rRNA modification; and tRNA modification.

In the methods and compositions disclosed herein, the first genome can have a size of no more than 15 Mb. In some embodiments, the first genome has a size of about 3 Mb to about 13 Mb.

Also disclosed are a synthetic genome produced by any of the methods disclosed herein, a synthetic cell produced by introducing the synthetic genome produced by any one of the methods disclosed herein into a cell-like system. In some embodiments, the cell-like system is a cell from which a resident genome has been removed.

BRIEF DESCRIPTION OF THE DRAWINGS

FIGS. 2A-2C show the method used for creating eight NotI strains. FIG. 2A is a map of Syn1DREDIS genome showing the design of NotI restriction sites for the creation of 8 *mycoides* NotI strains. FIG. 2B is a schematic illustration showing that ⅛th genome segments were released from *mycoides* genomes by restriction enzyme NotI and assembled in yeast. The three panels of FIG. 2C are gel photographs showing 8 NotI-digested genomic DNA (from 1 to 8) subjected to 1% agarose gel electrophoresis to separate ⅞th and ⅛$^{th}$ genome (top).

FIG. 3 is a non-limiting exemplary schematic illustration showing the structure of Tn5 puro transposon used for global mutagenesis, along with the sequence of Tn5 puro transposon.

FIG. 4 is a non-limiting exemplary schematic illustration showing exemplary steps in producing a Tn5 global insert library.

FIG. 5 is a non-limiting exemplary gene map showing that genes can be classified into 3 categories based on data from global Tn5 transposon mutagenesis.

FIG. 6 is a non-limiting exemplary Syn1.0 gene map showing the locations of Tn5 P4 insertions.

FIG. 7 shows the *M. mycoides* JCVI-Syn1.0 genome (1078 kb) displayed using CLC software.

FIG. 8 is a non-limiting exemplary diagram listing the genes deleted in the RGD2.0 design of segment 5.

FIG. 9 is a non-limiting exemplary Syn1.0 gene map showing the three design cycles involved in building Syn3.0.

FIG. 10 is a non-limiting exemplary schematic illustration showing the construction of the ⅛th RGD+⅞ wild type genome by recombinase-mediated cassette exchange (RMCE).

FIGS. 11A-11G are non-limiting exemplary light micrographs showing that RGD1.0, Segment 6 (+⅞ Syn1.0) grew slowly and produced sectored colonies after 10 days. FIG. 11A is a light micrograph from transplantation of yeast clone #5 of RGD1.0 Segment 6+7/8 Syn1.0 at day 12. FIGS. 11B-11D are light micrographs from transplantation of yeast clone #6 of RGD1.0 Segment 6+7/8 Syn1.0 at day 10. FIGS. 11E-11G are light micrographs from transplantation of yeast clone #7 of RGD1.0 Segment 6+7/8 Syn1.0 at day 10.

FIG. 12 is a non-limiting exemplary sequence diagram showing that the mutations in Segment 6 sequence reduced the stability of a stem-loop transcription terminator downstream of the tRNA-His gene. At the top the relevant sequence region is shown for Syn1.0, and at the bottom is the segment 6 design sequence.

FIG. 13 is a non-limiting exemplary sequence diagram showing the mutations in Segment 6+7/8 in colony purified isolates from transplant of clone #5.

FIG. 14 is a non-limiting exemplary sequence diagram showing the mutations of tRNA-His terminator in RGD 1.0 Seg6+7/8 transplants (mutations at GC base pairs in the stem).

FIG. 15 is a non-limiting exemplary schematic illustration showing a non-limiting embodiment of the TREC-IN method.

FIGS. 16A-16B are non-limiting exemplary gel photographs analyzing twenty-four representative 1.4 kb dsDNA fragments assembled during the construction of HMG. FIG. 16A shows the dsDNA fragments following oligonucleotide assembly and amplification, and FIG. 16B shows the same dsDNA fragments following error correction and PCR amplification. Two microliters of each sample were loaded onto a 1% E-gel and run for 20 minutes. M indicates the 1 kb ladder (NEB).

FIG. 17 is a non-limiting exemplary diagram showing clone collapsing for scalable cassette identification. Twenty-four bacterial clones for each cassette were grown separately in liquid culture in 96-well plates and then collapsed into a single set of 24 wells. Each shaded grouping represents a single cassette while the shaded grouping in the last row is the final collapsed group.

FIGS. 18A-18B are non-limiting exemplary gel photographs showing rolling circle amplification (RCA) products derived from the HMG eighth molecule assemblies. FIG. 18A shows supercoil DNA extracted from yeast clones containing the HMG eighth molecule assemblies and used as template in RCA reaction with GE-Templiphi Large Construct kit. FIG. 18B shows supercoil DNA extracted from yeast clones containing the HMG eighth molecule assemblies and used as template in RCA reaction with Qiagen-REPLI-g kit.

FIG. 22A is a gene map showing examples of the 3 gene classifications based on Tn5 mutagenesis data. FIG. 22B is a pie chart showing the number of Syn1.0 genes in each Tn5 mutagenesis classification group. n-genes and in-genes were candidates for deletion in reduced genome designs.

FIGS. 28A-28D compare Syn1.0 and Syn3.0 growth features. The two panels of FIG. 28A are light micrographs comparing colony sizes and morphologies of Syn1.0 and Syn3.0 cells derived from 0.2 µm-filtered liquid cultures diluted and plated on agar medium for 96 h (scale bars=1.0 mm). FIG. 28B is a plot of fluorescent measure (RFU) vs. time showing the growth rates in liquid static culture determined using a RFU of dsDNA accumulation over time to calculate doubling times (td). The panels of FIG. 28C are differential interference contrast micrographs showing native cell morphology in liquid culture imaged in wet mount preparations (scale bars=10 µm). Panels of FIG. 28D are scanning electron micrographs of Syn1.0 (left, scale bars=200 nm) and Syn3.0 (middle, scale bars=200 nm and right, scale bars=1 µm). The panel on the right shows a variety of the structures observed in Syn3.0 cultures.

FIG. 31A is a diagram of the modified rrs gene showing its secondary structure that was successfully incorporated into the Syn3.0 genome carrying *M. capricolum* mutations and h39 (inset) swapped with that of *E. coli*. FIG. 31B shows that three different codon optimization strategies were used for modifying the sequence of the essential genes era, recO and glyS by using M. *mycoides* codon adaption index (CAI) or that of *E. coli* with the codons TGG or TGA encoding tryptophan.

FIG. 32 is a non-limiting exemplary plot showing recovery of cells following electroporation. Cells were allowed to recover in YPDS medium at 30° C. and plated at intervals on CAA-URA medium. FIG. 32 shows that cell viability increased nearly 10-fold in the interval from 8 to 10 hours, and thereafter the cell number increased at about the doubling rate.

FIG. 33 is a non-limiting exemplary plot of a Section of the *K. marxianus* Chromosome 7 ScURA3 insertion map FIG. 34A-34B is a non-limiting exemplary schematic illustration of a proposed NHEJ insertion mechanism to explain the observed types of ScURA3/genome junctions.

FIG. 35 is a non-limiting exemplary map of pCC1BAC-LCyeast_(scHis3)-SYN-KM_CENARS_oriT. oriT sequence was inserted between EcoRI and BamHI.

FIG. 36 shows establishment of *E. coli* to *K. marxianus* conjugation method. *E. coli* (EPI300) was transformed with plasmids in the bottom table.

FIG. 37 shows non-limiting exemplary gel electrophoresis photographs of TAE+EtBr gelsconfirming the presence of pCC1BAC-LCyeast_(scHis3)-SYN-KM_CENARS_oriT in *K. marxianus*. Eight *K. marxianus* conjugation colonies were screened for the presence of pCC1BAC-LCyeast_(scHis3)-SYN-KM_CENARS_oriT. Genomic DNA (left panel): oriT PCR product (right panel).

FIG. 38 is a non-limiting exemplary gel electrophoresis photograph showing that large DNA fragment can be transferred from *E. coli* to *K. marxianus* via conjugation. Lane 1. #4-55-clone 1: Lane 2. #4-55-clone 2: Lane 3. #4-55-*E. coli*: Lane 4. #3: Lane 5. NEB 1 kb ladder. (genomic DNA on TAE gel with SYBR-gold Staining).

FIG. 39 is a non-limiting exemplary schematic illustration of a design-build-test cycle in *K. marxianus.*

FIG. 40 shows a non-limiting exemplary gel electrophoresis photograph illustrating transfer and stable maintenance of Stage-II molecule into #6_12 in *K. marxianus*. Stage-II molecule #6_12 was visualized after transformation and growth in selective media for several generations. Controls—#6_12 extracted from *E. coli* and *S. cerevisiae.*

FIG. 41 shows non-limiting exemplary gel electrophoresis photographs illustrating colony PCR analysis of CRISPR/Cas9 mediated chromosomal deletion. 96 transformants and a wild-type (wt) control were screened using primers. WT PCR was loaded on the last lane of each row (24 samples each). Control colony produced 300 bp and 400 bp PCR amplicons, while none of the 96 transformants did so. Instead, the transformants produced a ~465 bp PCR amplicon, indicative of a ~80 kb deletion of the chromosomal DNA corresponding to the #6_12 episomal DNA.

FIG. 42 is a non-limiting exemplary gel electrophoresis photograph verifying the presence of the #6_12 episomal DNA in six *K. marxianus* strains that lack the corresponding segment from the chromosome. A mixture of 80 kb and 90 kb supercoiled DNA was loaded as a size-estimating control followed by DNA extracted from the transformants 1-6, deemed positive by colony PCR (FIG. 41).

FIG. 43 shows a non-limiting exemplary qPCR design.

FIG. 44 is a non-limiting exemplary plot showing results of using qPCR to determine the copy number of #6_12 DNA fragment in the wild-type strain (WT), strain carrying episomal DNA #6_12 (Episome+chr) and strain carrying episomal DNA #6_12 but with the corresponding chromosomal fragment deleted (Episome only).

FIG. 45 is a non-limiting exemplary pulsed-field gel electrophoresis (PFGE) photograph confirming ~80 kb deletion from the chromosome in the strain carrying the episome #6_12. Lane 1-wild-type strain (WT), lane 2-strain carrying episomal DNA #6_12 (Episome+chr), lane 3-strain carrying episomal DNA #6_12 but with the corresponding chromosomal fragment deleted (Episome only). Chromosome 7 with the 80 kb deletion migrates faster (lane 3) than the corresponding wild-type chromosome (lanes 1 and 2).

FIG. 46 is a non-limiting exemplary gel electrophoresis photograph showing that minimized sub-chromosomal molecule #2_37 was introduced into *K. marxianus* using conjugation. Stable maintenance of this episome was verified by growing the transformed cells in selective media, extracting DNA and resolving the DNA alongside the same episomal molecule extracted from *E. coli*.

DETAILED DESCRIPTION OF THE INVENTION

Figure 1:
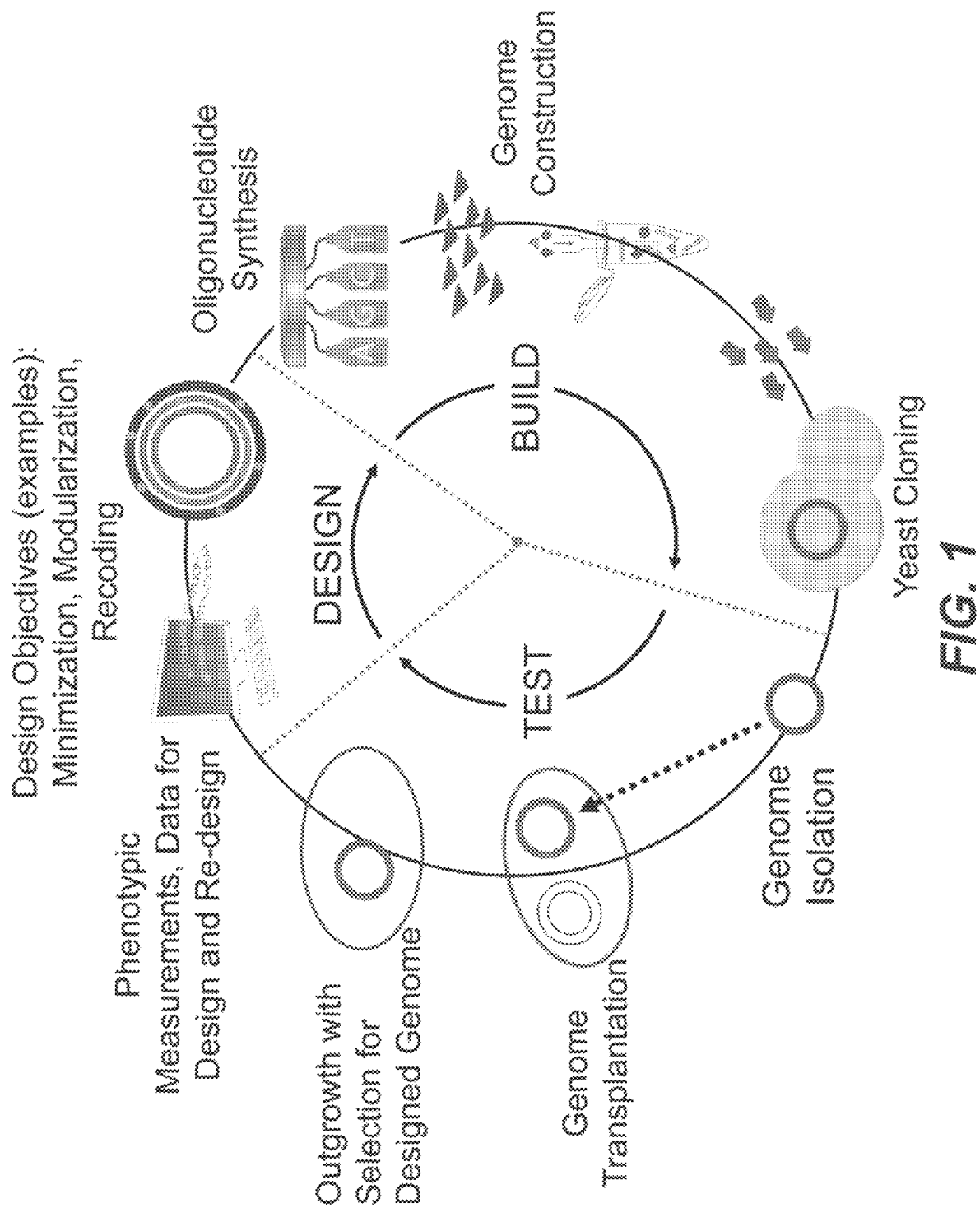
FIG. 1 is a non-limiting exemplary schematic illustration of a non-limiting embodiment of the design-build-test (DBT) cycle described herein for bacterial genomes.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

All patents, published patent applications, other publications, and sequences from GenBank, and other databases referred to herein are incorporated by reference in their entirety with respect to the related technology.

Definitions

Unless defined otherwise, technical and scientific terms used herein have the same meaning as commonly understood by one of ordinary skill in the art to which the present disclosure belongs. See. e.g. Singleton et al., Dictionary of Microbiology and Molecular Biology 2nd ed., J. Wiley & Sons (New York, NY 1994): Sambrook et al., Molecular Cloning, A Laboratory Manual, Cold Springs Harbor Press (Cold Springs Harbor, NY 1989). For purposes of the present disclosure, the following terms are defined below.

As used herein, the terms "nucleic acid," "nucleic acid molecule", and "oligonucleotide" and "polynucleotide" are used interchangeably. Examples of nucleic acids include, but are not limited to, deoxyribonucleic acid (DNA): ribonucleic acid (RNA); modified nucleic acid molecules such as peptide nucleic acid (PNA), locked nucleic acids (LNA): cDNA: genomic DNA, mRNA, synthetic nucleic acid molecule (such as that are chemically synthesized or recombinantly produced), and any combination thereof. Nucleic acid molecules can be double-stranded or single-stranded. Where single-stranded, the nucleic acid molecule can be the sense strand or the antisense strand. The nucleic acid molecules can be circular or linear.

As used herein, the term "genome" refers to whole (complete) genome and portions of whole genomes having nucleic acid sequences sufficient to effect and/or sustain viability of a cell (minimal cellular genome), of an organism that depends on a host cell for viability (e.g., minimal viral genome), or organelle function within a host cell (minimal organelle genome) under at least one set of culturing or environmental conditions. The genome can be a viral genome, a genome of organelles (e.g., mitochondria or chloroplast), and a genome of self-replicating organisms (e.g., cellular organisms, including, but not limited to, prokaroytes and eukaryotes). For example, the genome can be a genome of bacteria (e.g., *Mycoplasma*), yeast (e.g., *S. cerevisiae* and *K. marxianus*), archebacteria, vertebrates, or mammals. A genome can also be an entirely new construct for an organism that does not fall into any known Linnean category. In some embodiments, the genome may be a genome of a microorganism, such as a unicellular microorganism (e.g., a bacterium and yeast). In some embodiments, the genes in a genome may be in the order found in the microorganism, or they may be shuffled. A genome may also include mutant versions of one or more of the genes contained therein.

As used herein, a "cellular genome" or a "synthetic cellular genome" refers to a genome that comprises sequences which encode and may express nucleic acids and proteins required for some or all of the processes of transcription, translation, energy production, transport, production of cell membranes and components of the cell cytoplasm, DNA replication, cell division, and the like. A "cellular genome" differs from a viral genome or the genome of an organelle, at least in that a cellular genome contains the information for replication of a cell, whereas viral and organelle genomes contain the information to replicate themselves (sometimes with the contribution of cellular factors), but they lack the information to replicate the cell in which they reside.

As used herein, a "foreign gene" or a "foreign genome" is a gene or genome derived from a source other than the resident (original) organism, e.g., from a different species of the organism.

As used herein, the term "membrane-bound vesicle" refers to a vesicle in which a lipid-based protective material encapsulates an aqueous solution.

As used herein, the term "minimal genome," with respect to a cell, refers to a genome consisting of or consisting essentially of a minimal set of genetic sequences that are sufficient to allow for cell survival under specified environmental (e.g., nutritional) conditions. A "minimal genome," with respect to an organelle, as used herein, refers to a genome consisting of or consisting essentially of a minimal set of genetic sequences that are sufficient to allow the organelle to function. A minimal genome must contain sufficient information to allow the cell or organelle to carry out essential biological processes, such as, for example, transcription, translation, use of an energy source, transport of salts, nutrients and the like into and out of the organelle or cell, etc. A "minimal replicating genome," with respect to either a cell or an organelle, contains, in addition, genetic sequences sufficient to allow for self-replication of the cell or organelle. Thus, a "minimal replicating synthetic genome" is a single polynucleotide or group of polynucleotides that is at least partially synthetic and that contains the minimal set of genetic sequences for a cell or organelle to survive and replicate under specific environmental conditions.

As used herein, a "synthetic genome" includes a single polynucleotide or group of polynucleotides that contain the information for a functioning organelle or organism to survive and, optionally, replicate itself where particular environmental (e.g., nutritional or physical) conditions are met. All or at least part of the genome (e.g., a cassette) is constructed from components that have been chemically synthesized, or from copies of chemically synthesized nucleic acid components. The copies may be produced by any of a variety of methods, including cloning and amplification by in vivo or in vitro methods. In one embodiment, an entire genome is constructed from nucleic acid that has been chemically synthesized, or from copies of chemically synthesized nucleic acid components. Such a genome is sometimes referred to herein as a "completely synthetic" genome. In other embodiments, one or more portions of the genome may be assembled from naturally occurring nucleic acid, nucleic acid that has been cloned, or the like. Such a genome is sometimes referred to herein as a "partially synthetic" or "semi-synthetic" genome.

As used herein, the term "cell-like system" refers to a system that resembles a naturally occurring cell, but does not occur without human intervention. Non-limiting examples of cell-like systems include mammalian red blood cells (mammalian red blood cells do not naturally contain a genome) into which a genome or partial genome has been installed (or "introduced"): a "ghost" cell into which a foreign genome has been introduced: an aqueous volume enclosed by a phospholipid bilayer (whether derived from a naturally occurring cell membrane, manmade, or a hybrid of naturally occurring and manmade components) into which a genome has been introduced; and an aqueous volume enclosed by a lipid vesicle into which a genome has been introduced. As used herein, a "ghost cell" is a cell that naturally encloses a genome, but from which the naturally occurring genome is absent either as a result of genetic programming causing some cells to be genome-free or because the genome has been removed or inactivated. A naturally occurring genome may be removed from a cell by various methods, for example, by lysis and digestion, as described in US20070269862 (the content of which is incorporated hereby in its entirety). Ghost cells can also be produced by means, including but not limited to physical methods such as ultraviolet and gamma irradiation, genetic methods involving minicells, and treatment with chemical compounds such as antibiotics and peroxides. In a non-limiting exemplary embodiment, the naturally occurring genomes are removed from a cell of *Mycoplasma mycoides* (*M. mycoides*), and a synthetic *M. mycoides* genome of reduced size may be introduced into the *M. pneumoniae* ghost cell. In some embodiments, ghost cells are produced from yeast (e.g., *Kluyveromyces marxianus* (*K. marxianus*)), and a synthetic *K. marxianus* genome of reduced size may be introduced into the *K. marxianus* ghost cell.

The ability to design and produce a synthetic genome, and generate a cell or cell-like system including the synthetic genome along with a membrane and cytoplasm or membrane-bound aqueous volume, is very valuable in the fields like cell biology and biotechnology. In the present disclosure, methods for generating synthetic genomes, for example synthetic genomes having desired properties and viable genomes of reduced size, are disclosed. In some embodiments, the methods include designing a synthetic genome of interest; building the genome of interest through, for example, dividing and combining fragments of various parent genomes; and testing the resulting genome of interest. Such a design-build-test procedure can be iterated for one or more times, for example until a desired synthetic genome of interest is obtained. A non-limiting schematic illustration of the design-build-test (DBT) cycle described herein for bacterial genomes is provided in FIG. 1. The main design objective for the DBT cycle shown in FIG. 1 is genome minimization. As an example, in a DBT cycle, starting from a first genome (e.g., a naturally occurring genome), a reduced genome (i.e., a second genome) is designed by removing non-essential genes (e.g., genes determined as non-essential by global transposon (e.g., Tn5) gene disruption) from the first genome. Each of the first and second genomes is divided into 8 corresponding genomic fragments, and one or more of the genomic fragments of the second genome is combined with the genomic fragments of the first genome to generate a third genome having all 8 corresponding genomic fragments. The third genome is tested for one or more properties (e.g., phenotypes), including but not limited to, viability, growth rate, adaptability, doubling time, ratio of growth rate to genome size, ratio of doubling time to genome size, expression level of a gene of interest, and expression rate of a gene of interest. For example, each of the 8 corresponding genomic fragments from the second genome can be combined with the genomic fragments of the first genome to generate a third genome having all 8 corresponding genomic fragments, and thus all together 8 different third genomes can be produced and each of the third genomes can be tested for the properties. Before the genomic fragment(s) of the second genome combine with the genomic fragment(s) of the first genome, one or more of the genomic fragments (from the second and/or the first genome) can be modified, for example, by deleting or adding one or more genes or non-coding regions. In some embodiments, after the genomic fragment(s) of the second genome combine with the genomic fragment(s) of the first genome, one or more of the genomic fragments (from the second and/or the first genome) can be modified, for example, by deleting or adding one or more genes or non-coding regions. In some embodiments, the modification can be preformed both before and after combining the genomic fragments of the first and the second genomes. At each DBT cycle, gene essentiality can be re-evaluated, for example, by transposon (e.g., Tn5) mutagenesis.

Also disclosed herein are synthetic genomes produced by the methods disclosed herein, synthetic cells containing the synthetic genomes, and the methods for producing the synthetic cells.

In some embodiments, the method for generating a synthetic genome of interest comprises: (a) providing a first genome: (b) designing a second genome based on the first genome, wherein the second genome is hypothesized to have a set of desired properties; (c) dividing each of the first and second genomes into N corresponding fragments, wherein N is a positive integer: (d) combining at least one fragment of the second genome with fragments of the first genome to generate a third genome having all N corresponding fragments; and (e) testing the third genome generated in step (d) for the set of desired properties. In some embodiments, the method can also comprise (f) identifying the third genome as a synthetic genome of interest if it has the set of desired properties: otherwise modifying at least one fragment of the second genome and repeating steps (d)-(f) in one or more iterations until a set of desired properties is obtained in the third genome. The method can be used to produce genome with various desired properties. Non-limiting examples of the desired properties include one or more of viability, growth rate, adaptability, doubling time, ratio of growth rate to genome size, ratio of doubling time to genome size, expression level of a gene of interest, and expression rate of a gene of interest, ratio of viability to genome size, ratio of viability to expression level of a gene of interest, ratio of growth rate of expression level of a gene of interest, and ratio of growth rate to expression level of a gene of interest. In some embodiments, the first genome is a viable genome. As used herein, a viable cellular genome refers to a cellular genome that contains nucleic acid sequences sufficient to cause and/or sustain viability of a cell, e.g., those encoding molecules required for replication, transcription, translation, energy production, transport, production of membranes and cytoplasmic components, and cell division. In some embodiments, the first genome is a naturally occurring genome.

The second genome can be smaller or larger than the first genome in size. In some embodiments, the second genome has the same size as the first genome. In some embodiments, the synthetic genome of interest is a genome of reduced size, for example a minimal genome. The doubling time for the minimal genome can vary, for example from about 1 hour to about 10 days. In some embodiments, the doubling time for the minimal genome can be, or be about, 1 hour, 5 hours, 10 hours, 15 hours, 20 hours, 1 day, 2 days, 3 days, 4 days, 5 days, 6 days, 7 days, 8 days, 9 days, 10 days, or a range between any two of these values. In some embodiments, the doubling time for the minimal genome can be about 4 days.

The methods disclosed herein can be used to generate a viable genome of reduced size. In some embodiments, the method comprises: (a) providing a first genome known to be viable: (b) designing a second genome based on the first genome, wherein the second genome comprises a reduced number of genes of the first genome and is hypothesized to be viable: (c) dividing each of the first and second genomes into N corresponding fragments, wherein N is a positive integer: (d) combining at least one said fragment of the second genome with a sufficient number of said fragments of the first genome to generate a third genome having all N corresponding fragments: (e) testing the third genome generated in step (d) for viability: (f) if the third genome is viable, identifying the third genome as a viable genome of reduced size; and (g) if the third genome is not viable, modifying one or more fragments of the second genome based on the testing of (e) and repeating steps (d)-(f) until the third genome is viable. In some embodiments, the method further comprises deleting one or more genes or non-coding regions from at least one fragment of the second genome after identifying the third genome as a viable genome of reduced size and repeating step (d)-(g) in one or more iterations. In some embodiments, the method further comprises deleting one or more genes or non-coding regions from the third genome after identifying the third genome as a viable genome of reduced size.

In the methods disclosed herein, in combining step (d) the fragments of the first genome can be present in a single nucleic acid molecule. In some embodiments, step (d) comprises combining a fragment of the second genome with the entire or substantial portion of the first genome. Step (d) can, for example, comprise deleting a portion or the entire fragment of the first genome that corresponds to the fragment of the second genome that is combined with the entire or substantial portion of the first genome. In some embodiments, the deletion comprises replacing the portion or the entire fragment of the first genome with the corresponding fragment of the second genome. In some embodiments, it can be advantageous to delete only a portion (for example a half) of the fragment of the first genome to allow identification of the portion of the fragment responsible for the tested properties or the lack of tested properties. The tested properties can comprise, for example, viability. The deletion of genomic fragment(s) can be achieved using any suitable methods known in the art, for example, recombinase-mediated homologous recombination, CRISPR/Cas9 mediated deletion, or a combination thereof. The recombinase can be, for example, Cre-recombinase. As disclosed herein, the fragment(s) of the second genome can be present in an extrachromosomal genetic element before they are combined with the fragment(s) of the first genome to generate the third genome, after they are combined with the fragment(s) of the first genome to generate the third genome, or both. The third genome can comprise one or more extrachromosomal genetic elements. Non-limiting examples of the extrachromosomal genetic element include episomes, plasmids, fosmids, cosmids, bacterial artificial chromosomes, yeast artificial chromosomes, or any combination thereof. In some embodiments, the third genome comprises at least one chromosome comprising both the fragment(s) of the second genome and the fragment(s) of the first genome.

In the methods disclosed herein, the value of N can vary. For example, N can be 2, 3, 4, 5, 6, 7, 8, 9, 10, 11, 12, 13, 14, 15, 16, 17, 18, 19, 20, or a range between any two of these values (including end points). In some embodiments, N is 2, 3, 4, 5, 6, 7, 8, 9, 10, 11, 12, 13, 14, 15, 16, 17, 18, 19, 20, or larger. In some embodiments, N can be an integer equal to or greater than 3. In some embodiments, N is an integer between 4 and 20. In some embodiments, N is 8. In addition, the value of N can vary in the iterations when steps (d)-(f) are performed. The value of N can be different for each of the iterations when steps (d)-(f) are performed, or the value of N can be different for some of the iterations when steps (d)-(f) are performed. For example, the value of N may be 8 in the first iteration and the value of N may be smaller (e.g., 3, 4, 5, 6, or 7) or larger than 8 (e.g., 9, 10, 11, or 12)

in the second iteration when steps (d)-(f) are repeated. As another non-limiting example, N may be 8 in the first iteration, 10 in the second iteration and 12 in the third iteration. In yet another non-limiting example, N may be 9 in the first iteration, 12 in the second iteration, and 9 in the third iteration. As another non-limiting example, for a multi-chromosome genome (e.g., the first genome, the second genome, the synthetic genome of interest), one chromosome of the genome can be divided into a number of fragments and the other chromosomes of the genome can be considered as one fragment or multiple fragments. For example, for a *K. marxianus* genome having 8 chromosomes, Chromosome No. 7 ("chromosome 7") can be divided into 12 fragments, and the remaining seven chromosomes can be considered as one fragment. Therefore, each of a first and second *K. marxianus* genome can be divided into 13 corresponding fragments. One or more of the 1/12th of Chromosome No. 7 of the second K. max genome can, for example, be combined with fragments of the second *K. marxianus* genome to generate a third *K. marxianus* genome having all 13 corresponding fragments.

In some embodiments, one chromosome of a multi-chromosome genome having Z chromosomes (Z is a positive integer>=2) is divided into M fragments (M is a positive integer>=3), and the one chromosome is divided into (M−Z+1) fragments. One or more (e.g., each of) of the (M−Z+1) fragments of the one chromosome (referred to as "the test subchromosomal molecule") can be modified (e.g., by deletion, addition, substitution, or a combination thereof, of one or more genes or non-coding regions) tested entirely or in a portion (e.g., one half) at a time. For example, introduce the test subchromosomal molecule can be encoded in an episome and combine with fragments of the multi-chromosome genome to generate a third genome for testing. In some embodiments, the corresponding chromosomal segment of the multi-chromosome genome can be deleted entirely, for example using CRISPR/Cas9, to test the functionality of the introduced test subchromosomal molecule. In some embodiments, only a portion of the corresponding chromosomal segments (for example, one half) is deleted for testing, which can allow identification of specific region in the test subchromosomal molecule that result in an observed property (e.g., viability). For example, if a minimized subchromosomal molecule is non-functional, this method can be helpful in determining which part of the minimized molecule resulted in a non-viable phenotype. In some embodiments, direct swapping of the chromosomal segment can be used. For example, using a selectable auxotrophic marker, the test subchromosomal molecule can be directly swapped for the corresponding wild-type chromosomal fragment and tested for one or more desired properties (e.g., viability). In some embodiments, the swapping of chromosomal fragments can be achieved using recombinase-mediated homolgous recombination event. For example, loxP sites can be added to the test subchromosomal molecule and at the corresponding locations in the wildtype chromosome to enable Cre-recombinase mediated "swapping" event.

The N corresponding fragments can be of the same or different length. For example, all of the N corresponding fragments can be the same length, or be substantially the same length. As used herein, two genomic fragments are considered to be substantially the same length if the difference in their length is no more than 10% of the entire length of the genomic fragment that is longer. The N corresponding fragments can also be different in length. For example, two or more of the N corresponding fragments may be different in length. In some embodiments, each of the N corresponding fragments is different in length. In some embodiments, at least two, at least three, at least four, at least five, at least six, at least seven, at least eight of the N corresponding fragments are different in length.

Each of the N corresponding fragments can be a portion of the genome (e.g., a portion of the first, the second, or the third genome). A portion of a genome can be, for example, a portion of a chromosome of the genome, a chromosome of the genome, two or more chromosomes of the genome, or a portion of a chromosome of the genome as well as one or more remaining chromosomes of the genome. In some embodiments, a portion of the genome can be one or more chromosomes, one or more chromosome fragments, or any combination thereof. For example, a portion of the genome may be any fraction of a naturally occurring genome, one or more fragments of one or more naturally occurring chromosomes, one or more fragments of one or more naturally occurring chromosomes and one or more manmade nucleic acid sequences, one or more manmade nucleic acid sequences or fragments of manmade nucleic acid sequences, or any combination thereof. For example, for a single-chromosome genome, one of the N corresponding fragments can be, or be about, 1/N of the genome: or longer than or shorter than 1/N of the genome. As another example, for an eight-chromosome genome, one of the N corresponding fragments can be two of the eight chromosomes of the genome or 1/12th of one of the eight chromosomes (e.g., Chromosome No. 7), or the fragment can be one and a half of the eight chromosomes of the genome.

One or more of the N corresponding fragments of a genome may overlap with one or more of the remaining genomic fragments of the genome. For example, if the first genome is divided into four fragments, the first fragment may overlap with the second and the fourth fragment at 5' and 3' terminus, respectfully: the second fragment may overlap with the third and the first fragment at 5' and 3' terminus, respectfully: the third fragment may overlap with the second and the four fragment at 5' and 3' terminus, respectfully; and the fourth fragment may overlap with the third and the first fragment at 5' and 3' terminus, respectfully. It may also be that one or more of the fragments only overlap with one fragment (e.g., the second fragment), but not overlap with other fragments. The overlapping between two genomic fragments can vary in length. For example, the length of the overlapping can be 1 bp to 100 kb, or longer. In some embodiments, the overlapping between two genomic fragments is, or is about, 1 bp, 10 bp, 50 bp, 100 bp, 200 bp, 300 bp, 400 bp, 500 bp, 600 bp, 700 bp, 800 bp, 900 bp, 1 kb, 5 kb, 10 kb, 20 kb, 30 kb, 40 kb, 50 kb, 60 kb, 70 kb, 80 kb, 90 kb, 100 kb, or a range between any two of these values.

One or more of the N corresponding genomic fragments of the first genome and/or the second genome can be modified before being combined to generate the third genome. In some embodiments, only fragment(s) of the first genome is modified before being combined to generate the third genome, and none of the fragments of the second genome is not modified. For example, one, two, three, four, or more of the fragments of the first genome are modified before being combined with the fragments of the second genome to generate the third genome. In some embodiments, only fragment(s) of the second genome is modified before being combined to generate the third genome, and none of the fragments of the first genome is not modified. For example, one, two, three, four, or more of the fragments of the second genome are modified before being combined with the fragments of the first genome to generate the third genome. In some embodiments, at least one fragment of the first genome and at least one fragment of the second genome are modified before being combined with other fragments of the first and second genome to generate the third genome. The genomic fragments can be modified based on information from various sources as described herein, for example, including but not limited to, knowledge known in the art, scientific publications, experimental data, and any combination thereof.

The type of the genome (e.g., the first genome, the second genome, the third genome, and the genome of interest) can vary. For example, the genome can be a viral genome, an organelle genome, a genome from a unicellular (i.e., single-cell) organism, or a genome from a multicellular organism. In some embodiments, the genome is a prokaryotic genome. In some embodiments, the genome is a eukaryotic genome. Examples of the genome includes, but are not limited to, *Aeropyrum pernix: Agrobacterium tumefaciens: Anabaena: Anopheles gambiae: Apis mellifera: Aquifex aeolicus: Arabidopsis thaliana: Archaeoglobus fulgidus; Ashbya gossypii: Bacillus anthracis: Bacillus cereus: Bacillus halodurans: Bacillus licheniformis: Bacillus subtilis: Bacteroides fragilis: Bacteroides thetaiotaomicron; Bartonella henselae: Bartonella quintana: Bdellovibrio bacteriovirus: Bifidobacterium longum: Blochmannia floridanus: Bordetella bronchiseptica: Bordetella parapertussis; Bordetella pertussis: Borrelia burgdorferi: Bradyrhizobium japonicum: Brucella melitensis; Brucella suis: Buchnera aphidicola: Burkholderia mallei: Burkholderia pseudomallei; Caenorhabditis briggsae: Caenorhabditis elegans: Campylobacter jejuni: Candida glabrata; Canis familiaris: Caulobacter crescentus: Chlamydia muridarum: Chlamydia trachomatis; Chlamydophila caviae: Chlamydophila pneumoniae: Chlorobium tepidum: Chromobacterium violaceum: Ciona intestinalis: Clostridium acetobutylicum: Clostridium perfringens; Clostridium tetania Corynebacterium diphtheriae: Corynebacterium efficiens: Coxiella burnetii: Cryptosporidium hominis: Cryptosporidium parvum: Cyanidioschyzon merolae; Debaryomyces hansenii: Deinococcus radiodurans: Desulfotalea psychrophila: Desulfovibrio vulgaris: Drosophila melanogaster: Encephalitozoon cuniculi: Enterococcus faecalis; Erwinia carotovora: E. coli: Fusobacterium nucleatum: Gallus gallus: Geobacter sulfurreducens: Gloeobacter violaceus: Guillardia theta: Haemophilus ducreyi: Haemophilus influenzae: Halobacterium: Helicobacter hepaticus: Helicobacter pylori: Homo sapiens; Kluyveromyces sp: Kluyveromyces marxianus: Kluyveromyces waltii: Lactobacillus johnsonii; Lactobacillus plantarum: Legionella pneumophila: Leifsonia xyli: Lactococcus lactis; Leptospira interrogans: Listeria innocua: Listeria monocytogenes: Magnaporthe grisea; Mannheimia succiniciproducens: Mesoplasma florum: Mesorhizobium loti; Methanobacterium thermoautotrophicum: Methanococcoides burtonii: Methanococcus jannaschii: Methanococcus maripaludis: Methanogenium frigidum: Methanopyrus kandleri; Methanosarcina acetivorans: Methanosarcina mazei: Methylococcus capsulatus: Mus musculus: Mycobacterium Bovis: Mycobacterium leprae: Mycobacterium paratuberculosis; Mycobacterium tuberculosis: Mycoplasma gallisepticum: Mycoplasma genitalium; Mycoplasma mycoides: Mycoplasma penetrans: Mycoplasma pneumoniae: Mycoplasma pulmonis: Mycoplasma mobile: Nanoarchaeum equitans: Neisseria meningitidis: Neurospora crassa: Nitrosomonas europaea: Nocardia farcinica: Oceanobacillus iheyensis: Onions yellows phytoplasma: Oryza sativa: Pan troglodytes: Pasteurella multocida: Phanerochaete chrysosporium: Photorhabdus luminescens: Picrophilus torridus: Plasmodium falciparum; Plasmodium yoelii yoelii: Populus trichocarpa: Porphyromonas gingivalis Prochlorococcus marinus: Propionibacterium acnes: Protochlamydia amoebophila: Pseudomonas aeruginosa; Pseudomonas putida: Pseudomonas syringae; Pyrobaculum aerophilum; Pyrococcus abyssi; Pyrococcus furiosus: Pyrococcus horikoshii: Pyrolobus fumarii: Ralstonia solanacearum; Rattus norvegicus: Rhodopirellula baltica: Rhodopseudomonas palustris: Rickettsia conorii; Rickettsia typhi: Rickettsia prowazekii: Rickettsia sibirica: Saccharomyces cerevisiae; Saccharomyces bayanus: Saccharomyces boulardii: Saccharopolyspora erythraea; Salmonella enterica: Salmonella typhimurium: Schizosaccharomyces pombe: S. cerevisiae; Shewanella oneidensis: Shigella flexneria: Sinorhizobium meliloti: Staphylococcus aureus; Staphylococcus epidermidis: Streptococcus agalactiae: Streptococcus mutans: Streptococcus pneumoniae: Streptococcus pyogenes: Streptococcus thermophilus: Streptomyces avermitilis; Streptomyces coelicolor: Sulfolobus solfataricus: Sulfolobus tokodaii: Synechococcus; Synechocystis: Takifugu rubripes: Tetraodon nigroviridis: Thalassiosira pseudonana; Thermoanaerobacter tengcongensis: Thermoplasma acidophilum: Thermoplasma volcanium; Thermosynechococcus elongatus: Thermotagoa maritima: Thermus thermophilus: Treponema denticola: Treponema pallidum: Tropheryma whipplei: Ureaplasma urealyticum: Vibrio cholerae: Vibrio natriegens: Vibrio parahaemolyticus: Vibrio vulnificus: Vibrio species: adaptatus, aerogenes, aestivus, aestuarianus, agarivorans, albensis, alfacsensis, alginolyticus, anguillarum, areninigrae, artabrorum, atlanticus, atypicus, azureus, brasiliensis, bubulus, calviensis, campbellii, casei, chagasii, cholera, cincinnatiensis, coralliilyticus, crassostreae, cyclitrophicus, diabolicus, diazotrophicus, ezurae, fischeri, fluvialis, fortis, furnissii, gallicus, gazogenes, gigantis, halioticoli, harveyi, hepatarius, hippocampi, hispanicus, hollisae, ichthyoenteri, indicus, kanaloae, lentus, litoralis, logei, mediterranei, metschnikovii, mimicus, mytili, natriegens, navarrensis, neonates, neptunius, nereis, nigripulchritudo, ordalii, orientalis, pacinii, parahaemolyticus, pectenicida, penaeicida, pomeroyi, ponticus, proteolyticus, rotiferianus, ruber, rumoiensis, salmonicida, scophthalmi, splendidus, superstes, tapetis, tasmaniensis, tubiashii, vulnificus, wodanis, and xuii; Wigglesworthia glossinidia: Wolbachia pipientis: Wolinella succinogenes; Xanthomonas axonopodis; Xanthomonas campestris: Xylella fastidiosa: Yarrowia lipolytica: Yersinia pseudotuberculosis*; and *Yersinia pestis*.

Other examples of genomes include, but are not limited to any microorganism of the class Labyrinthulomycetes. While the classification of the Thraustochytrids and Labyrinthulids has evolved over the years, for the purposes of the present application, "labyrinthulomycetes" is a comprehensive term that includes microorganisms of the orders Thraustochytrid and Labyrinthulid, and includes (without limitation) the genera *Althornia, Aplanochytrium, Aurantiochytrium, Botyrochytrium, Corallochytrium, Diplophryids, Diplophrys, Elina, Japonochytrium, Labyrinthula, Labyrinthuloides, Oblongichytrium, Pyrrhosorus, Schizochytrium, Thraustochytrium*, and *Ulkenia*. Examples of suitable microbial species within the genera include, but are not limited to: any *Schizochytrium* species, including, but not limited to, *Schizochytrium aggregatum, Schizochytrium limacinum, Schizochytrium minutum, Schizochytrium mangrovei, Schizochytrium marinum. Schizochytrium octosporum*, and any *Aurantiochytrium* species, any *Thraustochytrium* species (including former *Ulkenia* species such as *U. visurgensis. U. amoeboida. U. sarkariana. U. profunda. U. radiata*,

*U. minuta* and *Ulkenia* sp. BP-5601), and including *Thraustochytrium striatum, Thraustochytrium aureum, Thraustochytrium roseum*; and any *Japonochytrium* species.

In some embodiments, the genome is a bacterial genome, an archaea genome, a yeast genome, an algae (e.g., a single-cell algae) genome, a fungi (e.g., a single-cell fungi) genome, or a protozoa genome. Examples of bacterial genome include, but are not limited to, genome of gram positive bacteria, genome of gram negative bacteria. In some embodiments, the genome is a genome of *Mycoplasma* genitalia (*M. genitalium*), genome of *M. mycoides*, genome of *M. capricolumn* (e.g., subspecies capricolum), genome of *E. coli*, genome of *B. subtilis*, or a combination thereof. The genome can also vary in the number of chromosome. For example, the genome may only have a single chromosome or multiple chromosomes (e.g., 2, 3, 4, 5, 6, 7, 8, 9, 10, or more chromosomes). In some embodiments, the genome is a single chromosome genome. In some embodiments, the genome is a multi-chromosome genome. In some embodiments, the genome is a genome of *S. cerevisiae*, a genome of *K. marxianus*, or a combination thereof. In some embodiments, the genome has three to ten chromosomes. In some embodiments, the genome has eight chromosomes.

As used herein, the term "algae" includes cyanobacteria (Cyanophyceae), green algae (Chlorophyceae), yellow-green algae (Xanthophyceae), golden algae (Chrysophyceae), brown algae (Phaeophyceae), red algae (Rhodophyceae), diatoms (Bacillariophyceae), and "pica-plankton" (Prasinophyceae and Eustigmatophyceae). Also included in the term "algae" are members of the taxonomic classes Dinophyceae, Cryptophyceae, Euglenophyceae, Glaucophyceae, and Prymnesiophyceae. Microalgae are unicellular or colonial algae that can be seen as single organisms only with the aid of a microscope. Microalgae include both eukaryotic and prokaryotic algae (e.g., cyanobacteria). Photosynthetic bacteria include cyanobacteria, green sulfur bacteria, purple sulfur bacteria, purple nonsulfur bacteria, and green nonsulfur bacteria. Examples of genomes suitable for use in the methods disclosed herein include, but are not limited to, *Achnanthes, Amphiprora. Amphora. Ankistrodesmus. Asteromonas. Boekelovia. Borodinella. Botryococcus. Bracteococcus. Chaetoceros. Carteria. Chlamydomonas. Chlorococcum. Chlorogonium. Chlorella. Chroomonas. Chrysosphaera. Cricosphaera. Crypthecodinium. Cryptomonas. Cyclotella. Dunaliella. Ellipsoidon. Emiliania. Eremosphaera. Ernodesmius. Euglena. Franceia. Fragilaria. Gloeothamnion. Haematococcus. Halocafeteria. Hymenomonas. Isochrysis. Lepocinclis. Micractinium. Monoraphidium. Nannochloris. Nannochloropsis. Navicula. Neochloris. Nephrochloris. Nephroselmis. Nitzschia. Ochromonas. Oedogonium. Oocystis. Ostreococcus. Pavlova. Parachlorella. Pascheria. Phaeodactylum. Phagus. Platymonas. Pkurochrysis. Pleurococcus. Prototheca. Pseudochlorella. Pyramimonas. Pyrobotrys. Scenedesmus. Schizochytrium. Skeletonema. Spyrogyra. Stichococcus. Tetraselmis. Thraustochytrium. Thalassiosira. Viridiella,* and *Volvox* species. Photosynthetic bacteria include, for example, green sulfur bacteria, purple sulfur bacteria, green nonsulfur bacteria, purple nonsulfur bacteria, and cyanobacteria. Cyanobacterial species include, without limitation, *Agmenellum. Anabaena. Anabaenopsis. Anacystis. Aphanizomenon. Arthrospira. Asterocapsa. Borzia. Calothrix. Chamaesiphon. Chlorogloeopsis. Chroococcidiopsis. Chroococcus. Crinalium. Cyanobacterium. Cyanobium. Cyanocystis. Cyanospira. Cyanothece. Cylindrospermopsis. Cylindrospermum. Dactylococcopsis. Dermocarpella. Fischerella. Fremyella. Geitleria. Geitlerinema. Gloeobacter. Gloeocapsa. Gloeothece. Halospirulina. Iyengariella. Leptolyngbya. Limnothrix. Lyngbya. Microcoleus. Microcystis. Myxosarcina. Nodularia. Nostoc. Nostochopsis. Oscillatoria. Phormidium. Planktothrix. Pieurocapsa. Prochlorococcus. Prochloron. Prochlorothrix. Pseudanabaena. Rivularia. Schizothrix. Scytonema. Spirulina. Stanieria. Starria. Stigonema. Symploca. Synechococcus. Synechocystis, Tolypothrix, Trichodesmium, Tychonema,* and *Xenococcus* species.

The size of the genome (e.g., the first genome, the second genome, the third genome, and the synthetic genome of interest) can vary. For example, the genome can be, be about, be at least, or be at least about, 10 kilobase (kb) to about 200 megabase (Mb) in length. In some embodiments, the genome is, or is about, 10 kb, 50 kb, 100 kb, 150 kb, 200 kb, 250 kb, 300 kb, 350 kb, 400 kb, 450 kb, 500 kb, 550 kb, 600 kb, 650 kb, 700 kb, 750 kb, 800 kb, 850 kb, 900 kb, 950 kb, 1 Mb, 1.1 Mb, 1.2 Mb, 1.3 Mb, 1.4 Mb, 1.5 Mb, 1.6 Mb, 1.7 Mb, 1.8 Mb, 1.9 Mb, 2 Mb, 2.1 Mb, 2.2 Mb, 2.3 Mb, 2.4 Mb, 2.5 Mb, 2.6 Mb, 2.7 Mb, 2.8 Mb, 2.9 Mb, 3 Mb, 3.1 Mb, 3.2 Mb, 3.3 Mb, 3.4 Mb, 3.5 Mb, 3.6 Mb, 3.7 Mb, 3.8 Mb, 3.9 Mb, 4 Mb, 4.5 Mb, 5 Mb, 6 Mb, 7 Mb, 8 Mb, 9 Mb, 10 Mb, 15 Mb, 20 Mb, 30 Mb, 40 Mb, 50 Mb, 100 Mb, 200 Mb in length, or a range of any two of these values (including the end points). In some embodiments, the genome is at least, or is at least about, 10 kb, 50 kb, 100 kb, 150 kb, 200 kb, 250 kb, 300 kb, 350 kb, 400 kb, 450 kb, 500 kb, 550 kb, 600 kb, 650 kb, 700 kb, 750 kb, 800 kb, 850 kb, 900 kb, 950 kb, 1 Mb, 1.1 Mb, 1.2 Mb, 1.3 Mb, 1.4 Mb, 1.5 Mb, 1.6 Mb, 1.7 Mb, 1.8 Mb, 1.9 Mb, 2 Mb, 2.1 Mb, 2.2 Mb, 2.3 Mb, 2.4 Mb, 2.5 Mb, 2.6 Mb, 2.7 Mb, 2.8 Mb, 2.9 Mb, 3 Mb, 3.1 Mb, 3.2 Mb, 3.3 Mb, 3.4 Mb, 3.5 Mb, 3.6 Mb, 3.7 Mb, 3.8 Mb, 3.9 Mb, 4 Mb, 4.5 Mb, 5 Mb, 6 Mb, 7 Mb, 8 Mb, 9 Mb, 10 Mb, 15 Mb, 20 Mb, 30 Mb, 40 Mb, 50 Mb, 100 Mb, or 200 Mb in length. In some embodiments, the genome size is no more than 5 Mb, no more than 8 Mb, no more than 10 Mb, no more than 12 Mb, no more than 15 Mb, no more than 18 Mb, or no more than 20 Mb. In some embodiments, the genome size is about 3 Mb to about 13 Mb.

The methods described herein can comprise testing a genome for one or more properties, for example a set of desired properties. For example, in some embodiments, step (b) comprises testing the second genome for the set of desired properties. In some embodiments, the method comprises a step (e) testing the third genome for the set of desired properties. The genome can be tested for properties such as viability in one or more environments (e.g., in vivo or in vitro chemical or biological systems), growth rate, doubling time, certain metabolism capability, adaptability, or a combination thereof. As described herein, testing a genome (e.g., the second genome or the third genome) for one or more properties can comprise, for example, introducing the genome into a cell or a cell-like system and testing for the properties. The genome can be introduced to the cell or the cell-like system by, for example, conjugation, transformation, transduction, or any combination thereof. In some embodiments, the cell-like system can be, or can comprise, a membrane-bound volume, a lipid vesicle, a cell from which one or more intracellular components have been removed, a cell from which the resident genome has been removed, or any combination thereof. In the method disclosed herein, modifying at least one of the second genome fragments in step (f) is, in some embodiments, at least partly based on the testing of step (e). In some embodiments, modifying at least one fragment of the second genome in step (f) further comprises conducting mutation study of the at least one fragment and modifying the at least one fragment at least partly based on the mutation study.

As disclosed herein, it can be advantageous to use conjugation to transfer synthetic chromosome(s) into *K. marxianus* cell. In some embodiments, shortly after or during the transfer, the resident (e.g., native) chromosome of the *K. marxianus* cells can be targeted at multiple locations using CRISPR/Cas9, which can result in a strain that only carries the synthetic genome. The resident (e.g., native) chromosome can, in some embodiments, be lost during propagation, unable to replicate, after multiple double-stranded breaks are introduced by CRISPR/Cas9. Non-limiting examples of methods suitable for use to remove resident (e.g., native) chromosome after introduction of the synthetic genome include URA3-FOA based negative selection of the native chromosome described in Boeke J D, et al. (1987) Methods Enzymol 154:164-75 and onducible-inactivation of the centromere of the native chromosome described in Hill A, Bloom K (1987). Mol Cell Biol. 7 (7): 2397-405.

The methods described herein can include designing a second genome based on the first genome and the second genome is hypothesized to have a set of desired properties. Information from various sources can be used in modifying nucleic acid sequences, for example genomic fragments. In some embodiments, information from various sources can be used to modify the first genome for designing the second genome, and/or to modify the fragment(s) of the second genome, e.g., before repeating steps (d)-(f) in one or more iterations. For example, information from knowledge known in the art, literature resources, experimental data, or any combination thereof can be used. The literature resources can be, for example, scientific publications (e.g., journal articles, conference posters, online publications). The experimental data can, for example, comprises data obtained from mutation studies of the first genome, a genome related to the first genome, or any combination thereof. The mutation studies can be studies of deletion and/or modification of single or multiple genes or non-coding regions, mutagenesis studies (e.g., targeted or random mutagenesis), studies of deletions and/or modification of non-coding genomic regions, gene knockout studies, and add-back studies. Non-limiting examples of mutagenesis studies include transposon mutagenesis, insertional mutagenesis, site-directed mutagenesis, and single- or multiple-site plasmid mutagenesis. In some embodiments, the experimental data comprises data related to genes of essential function redundancies (EFR), which are also referred to as essential function pairs (EFP). In organisms (e.g., a bacterium), certain essential (or quasi-essential) functions is provided by more than one gene. These genes may or may not be paralogs. Suppose gene A and gene B, each supply an essential function E1. The gene pair (gene A and B) represents an EFP. Either gene (gene A or B) can be deleted without loss of the essential function E1, so each gene by itself in a single knockout study is classified as non-essential. However, if both gene (i.e., genes A and B) are deleted, the cell is not viable because the essential function E1 is no longer provided. In some embodiments, one of the EFP is deleted from the first genome in designing the second genome. In some embodiments, only one of the EFP is kept in the second genome.

In some embodiments, the third genome comprises one or more fragments from a naturally occurring genome and one or more fragments from a synthetic genome.

Synthesizing and Assembling Nucleic Acid Molecules

In some embodiments of the method disclosed herein, the combining step comprises combining each of the fragments of the second genome with fragments of the first genome to generate a plurality of third genomes having all N corresponding fragments. In some embodiments, each of the plurality of third genomes is tested for the set of desired properties. In some embodiments, two or more of the plurality of third genomes is tested for the set of desired properties. In some embodiments, one or more of the plurality of third genomes is not tested for the set of desired properties.

Nucleic acid molecules (e.g., genomic fragments) can be produced by a variety of methods, including but not limited to, genetically engineered, amplified, and/or expressed/generated recombinantly. Techniques for the manipulation of nucleic acid sequences, such as, e.g., subcloning, labeling probes (e.g., random-primer labeling using Klenow polymerase, nick translation, amplification), sequencing, hybridization and the like are well described in the scientific and patent literature. In addition, the nucleic acid molecules can be synthesized in vitro, such as by well-known chemical synthesis techniques, and/or obtained from commercial sources, and optionally assembled, such as for large nucleic acids and genomes, for example, as described in US20090275086.

Any methods or techniques suitable for combining genomic fragments may be used herein to combine the fragment(s) of the second genome with fragment(s) of the first genome to generate a third genome having all N corresponding fragments. The fragments of the first and the second genomes can be produced using any methods for suitable nucleic acid synthesis, including but not limited to, chemical synthesis, recombinant production, and any combination thereof. Each of the fragments of one genome does not need to be synthesized or produced using the same method. For example, one fragment of the first genome may be synthesized chemically and the remaining fragments of the first genome may be recombinantly produced. In some embodiments, all fragments of the first gnome are synthesized chemically. In some embodiments, all fragments of the first gnome are synthesized chemically. In some embodiments, at least one fragment of the first gnome is produced recombinantly. In some embodiments, at least one fragment of the second gnome is produced recombinantly. In some embodiments, at least one fragment of the first gnome is synthesized chemically. In some embodiments, at least one fragment of the second gnome is synthesized chemically. In some embodiments, all fragments of the first gnome are produced recombinantly. In some embodiments, all fragments of the second gnome are produced recombinantly. In some embodiments, two or more fragments of the first genome are produced together, for example, and present in the same nucleic acid molecule.

In some embodiments, the combining step comprises chemically synthesizing and assembling the fragments of the first and second genomes to generate the third genome. In some embodiments, assembling the fragments of the first and second genomes comprises assembling chemically synthesized, overlapping oligonucleotides into one or more of nucleic acid cassettes. In some embodiments, the entire synthetic genome of interest is constructed from nucleic acid components that have been chemically synthesized, or that have been created from copies of the chemically synthesized nucleic acid components. Genomic fragments can be constructed using methods know in the art. For example, the genomic fragments can be synthetically constructed using the methods described in US20070264688. In some embodiments, a set of overlapping nucleic acid cassettes are constructed, each generally having about 1.4 kb, 5 kb or 7 kb, which comprise subsets of the genes; and the cassettes are then assembled to form the genomic fragments. The function and/or activity of the genome can be further studied by introducing the assembled genome into a suitable biological system and monitoring one or more functions and/or activities encoded by the genome.

Various methods can be used to generate and assemble nucleic acid cassettes. For example, a cassette of interest can be firstly subdivided into smaller portions from which it may be assembled. In some embodiments, the smaller portions are oligonucleotides of about 30 nucleotides (nt) (e.g., 27 nt, 28 nt, 29 nt, 30 nt, 31 nt, or 32 nt) and about 1 kilobase (kb) in length. In some embodiments, the oligonucleotides about 50 nt (e.g., between about 45 nt and about 55 nt) in length. In some embodiments, the oligonucleotides are designed so that they overlap adjacent oligonucleotides, to facilitate their assembly into cassettes. For example, for *M. genitalium*, the entire genome sequence may be divided into a list of overlapping 48-mers with 24 nucleotide overlaps between adjacent top and bottom oligonucleotides. The oligonucleotides may be synthesized using conventional methods and apparatus, or they may be obtained from well-known commercial suppliers.

Many methods that can be used to assemble oligonucleotides to form longer molecules, such as cassettes of interest, have been described, e.g., in Stemmer et al. (1995) (Gene 164, 49-53) and Young et al. (2004) (Nucleic Acids Research 32, e59). One non-limiting suitable method, called polymerase cycle assembly (PCA), was used by Smith et al. (2003) (Proc Natl Acad Sci USA 100, 15440-5) for the synthesis of the 5386 nt genome of bioteriophage phiX174. In some embodiments, the cassettes are cloned and/or amplified to generate enough material to manipulate readily. In some embodiments, the cassettes are cloned and amplified by conventional cell-based methods. In some embodiments, e.g., when it is difficult to clone a cassette by conventional cell-based methods, the cassettes are cloned in vitro. One non-limiting example of such in vitro method is described in WO 2006/119066 which uses rolling circle amplification, under conditions in which background synthesis is significantly reduced.

Cassettes which may be generated according to various exemplary methods may be of any suitable size. For example, cassettes may range from about 1 kb to about 20 kb in length. In some embodiments, the cassettes is about 4 to about 7 kb, e.g., about 4.5 to about 6.5 kb, preferably about 5 kb in size. The term "about" with regard to a particular polynucleotide length, as used herein, refers to a polynucleotide that ranges from about 10% smaller than to about 10% greater than the size of the polynucleotide. In order to facilitate the assembly of cassettes, it is preferable that each cassette overlaps the cassettes on either side, e.g., by at least about 50, 80, 100, 150, 200, 250 or 1300 nt. Larger constructs (up to the size of, e.g., a minimal genome) comprising groups of such cassettes are also included, and may be used in a modular fashion according to various exemplary embodiments and methods.

A variety of methods may be used to assemble the cassettes. For example, cassettes may be assembled in vitro, using methods of recombination involving "chew-back" and repair steps, which employ either 3' or 5' exonuclease activities, in a single step or in multiple steps. Alternatively, the cassettes may be assembled with an in vitro recombination system that includes enzymes from the *Dienocuccus radiodurans* homologous recombination system. Methods of in vivo assembly may also be used.

The synthetic genome, for example the third genome, can be further manipulated, either before or after it is identified as the synthetic genome of interest. Non-limiting examples of manipulation include modifying (e.g., deleting, altering individual nucleotides, etc.) one or more of genes in the synthetic genome or deleting entire genes within one or more of the cassettes: replacing genes or cassettes by other genes or cassettes, such as functionally related genes or groups of genes: rearranging the order of the genes or cassettes (e.g., by combinatorial assembly): or a combination thereof. The effects of such manipulations can be examined by re-introducing the synthetic genes into a suitable biological system. Non-limiting factors that can be considered include, e.g., growth rate, nutritional requirements and other metabolic factors.

Any of the genomes disclosed herein, for example the first genome, the second genome, the third genome, and the synthetic genome of interest, can be modified to reorganize gene order. In some embodiments, the order of one or more genes in the genome is changed. In some embodiments of the method disclosed herein, step (d) further comprises reorganizing gene order in the at least one fragment of the second genome before combining it with fragments of the first genome to generate the third genome. In some embodiments, the method disclosed herein further comprises reorganizing gene order in the third genome after it is identified as a synthetic genome of interest. In some embodiments, reorganizing gene order comprises grouping genes related to the same biological process in the at least one fragment of the genome. Non-limiting examples of the same biological process include glucose transport and catabolismo ribosome biogenesis: protein export, DNA repair: transcription: translation; nucleotide synthesis, metabolism and salvage: glycolysis: metabolic processes: proteolysis; membrane transport: rRNA modification: tRNA modification; and any combination thereof.

When the method is used to generate a viable genome of reduced size, in some embodiments, the size of the third genome may be further reduced after the third genome is identified as a viable genome of reduced size. The size of the third genome may be further reduced by, for example, deleting one or more genes from the third genome, deleting one or more non-coding region(s) (e.g., promoter region, enhancer region, and intron region) from the third genome, or a combination thereof. In some embodiments, step (b) comprises testing the second genome for viability. In some embodiments, modifying at least one fragment of the second genome fragments in step (f) further comprises conducting mutation study of the at least one fragment and modifying the at least one fragment at least partly based on the mutation study Modularization of Genomes Also provided herein are methods for modulating genomes. In some instances, it can advantageous to reorganize genes in a genome. For example, genes involved in the related biological processes may not be present in a naturally-occurring genome in adjacent location, and downstream genetic engineering can be more efficient by placing these genes in the same genomic location. In some embodiments, the genes involved in the related biological processes are identified and the orders of these genes are changed to make these genes grouped together in a given location of the genome.

The modularization genomes can be done in a stepwise fashion. For example, a genome of interest can be divided into small fragments (e.g., 32, 64, 72, or more fragments), and orders of the genes in each of the genomic fragments can be changed to form gene clusters. Then, the resulting genome with the first round of gene organization can be divided into larger fragments (e.g., 2, 4 or 8 fragments) for further gene shuffling. The steps can be repeated until a genome with desired gene orders is generated.

Various steps can be performed in the process of modularizing and minimizing a genome, including but are not limited to the following:

(1) Determine essential genes.

(2) Remove non-essential genes and intergenic regions.

(3) Classify essential genes according to function. In some embodiments, genes with related functions (subsystems) will ultimately be represented as contiguous modules of DNA sequence, which can decrease labor and material costs during strain engineering. Multiple change—and hence redirection or optimization of a bug and its subsystems—can be installed by altering the DNA module instead of numerous genes scattered about a genome.

(4) Determine breakpoints between co-located genes that do not impinge on the same function or subsystem. In general, each desired gene must be transcribed for its function to be expressed, and most genes are proteins. These require translation in addition to transcription. Each structural gene (or cotranscribed set of genes) therefore be preferred to be accompanied by intergenic DNA sequences that ensure the gene itself is transcribed and translated as required. In some embodiments, when genes with unrelated functions are physically separated and modules are remade (i.e., co-locating related gene functions), the intergenic regions for co-transcribed genes can be duplicated and/or assigned to one of the genes in the transcription unit. In some embodiments, assignment is preferred over duplication since duplicated sequences can result in genome instability.

(5) The first gene transcribed by a promoter (used by many downstream genes) is assigned to that promoter. In some embodiments, this step includes determining the upstream boundary of the promoter (i.e. intergenic region) that is responsible for transcription and translation of the first gene.

(6) The promoter boundaries are identified and set. Various factors that can be used in the step include, but are not limited to, (6a) the location of terminators can be used. Terminators stop transcription and routinely include an RNA hairpin followed by a T-rich run of 5-20 nucleotides. As they stop transcription, a terminator is unlikely to be located between a gene and its promoter. (6b) Transposon mutagenesis provides a second means for identifying the upstream boundary of a genes promoter. Insertion within a promoter or between a promoter and its gene would likely disrupt the promoters function. In many cases, transposon insertions within or on the gene-proximal side of a promoter are absent or rare. Starting at the upstream boundary the number of insertions can increase dramatically. 6c) Size of the intergenic region, RNAseq data, promoter prediction etc, can all be used to define a probable upstream boundary. And 6d) all of metrics a-c can be assigned scores and scores for different metrics weighted by hand or according to some optimization scheme. These can be used to produce graphical outputs of likely breakpoints on a genome annotated with ORFs, terminators, etc. A person with skill in the art can then make a final decision about breakpoints based on all of this data and its presentation without undue experimentation.

(7) The genome can be fragmented at the breakpoints (e.g., in silico). Fragments that represent a particular subsystem are binned. Thus, for instance, all fragments for glycolysis (i.e. all of the genes encoding the glycolysis) are grouped. All other targeted subsystems are similarly binned.

(8) Some of the genes (or transcription units) that represent a subsystem will have promoters and some of them will not.

(9) Genes without promoters are assigned new promoters from the pool of intergenic regions that were removed during minimization. Alternatively, promoters from other organisms could be used. Several metrics can be employed to match the genes original expression strength and the expression strength of the new promoter. RNAseq data for instance. The point is, such data can be collected, scored, and weighted to identify a likely match. So far, an apparent similarity in the strength of the Shine-Dalgarno sequence (of the new promoter) and the Shine-Dalgarno of the promoterless gene has been sufficient.

(10) After all genes have old or new transcription and translation signals, they are assembled and tested. In some embodiments, a subsection of a genome is modularized and built. Once its function is ensured, the submodules within it can be combined with equivalent submodules from other genome locations to produce a fully modularized organism. Combining submodules into a full module can require no new sequence changes, and only involve changing the relative location of a submodule(s) within a genome.

Many public resources are available for identifying functions of genes and/or enzymes, and for classifying genes and/or enzymes of particular function(s). Non-limiting examples of the public resources include: IUBMB enzyme nomenclature (http://www.chem.qmul.ac.uk/iubmb/), Kyoto Encyclopedia of Genes and Genomes (KEGG) (Kanehisa and Goto 2000, http://www.genome.jp/kegg/), the GenomeNet (Kanehisa et al. 2002, http://www.genome.jp/), MetaCyc (Caspi et al. 2006, http://metacyc.org/), the Comprehensive Microbial Resource (CMR) (Peterson et al. 2001) at The Institute for Genomic Research (TIGR) the Protein (http://www.tigr.org/), Data Bank (PDB, http://www.rcsb.org/pdb/home/home.do), UniProt (http://www.uniprot.org/), the STRING database (http://string-db.org/), and the PROFESS (protein function evolution structure sequence) database (http://cse.unl.edu/~profess/). Moreover, the BRENDA enzymatic database (Schomburg et al. 2004, http://www.brenda-enzymes.org/) and ExPASy ENZYME database (Bairoch 2000, http://enzyme.expasy.org/) can be used to, for example, identify substrates and/or products and stoichiometry of reactions catalyzed by individual enzymes and characterize unresolved pathways. The BRENDA database can also be parsed to obtain a list of all enzymes catalyzing irreversible reactions under physiological conditions.

Testing Properties of Genomes

The genomes described herein (e.g., the third genome produced by combining fragments of the first and second genomes) can be introduced to various environments (e.g., biological systems) that allow it to function for testing for its properties (e.g., one or more of the desired properties). For example, the genome may be present in (e.g., introduced into) a suitable biological system allowing proteins, RNAs, DNAs to be produced from the genome.

Prior to being introduced to various environments for testing properties, the genome may be propagated in and/or isolated from cells or tissues. The genome can be isolated from cells or tissues, or can be introduced (for example, conjugated, transformed, transduced, or a combination thereof) into and propagated within other cells, using well-known cloning, cell, and plasmid techniques and systems. The genome sequence in the cells can be natural or synthetic, including partially synthetic. In some cases, the genome sequences may be amplified, such as by PCR, after isolation from cells or tissues. The genome sequence can also be chemically synthesized in vitro using chemical synthesis and assembly methods and, thus, are not isolated from any particular tissue or cell prior to use in the described methods. Methods for chemical synthesis of DNA and RNA and assembly of nucleic acids are known, and include oligonucleotide synthesis, assembly, and polymerase chain reaction (PCR) and other amplification methods (such as, for example, rolling circle amplification, whole genome amplification), such as those described herein and in US20090275086. Synthesis of DNA, for example, can be from DNA (e.g., by PCR) or from RNA, e.g., by reverse transcription. Among the nucleic acids are synthetic genomes. Synthetic genomes can be produced, for example, as described herein and in US20090275086.

A variety of suitable biological systems may be used for testing properties of the genome. For example, the genome can contact a solution comprising a conventional coupled transcription/translation system. In such a system, the genome may be able to replicate itself, or it may be necessary to replenish the nucleic acid, e.g., periodically. In some embodiments, the genome is introduced into a vesicle such that the genome is encapsulated by a protective lipid-based material. For example, the genome can be introduced into a vesicle by contacting the genome, optionally in the presence of desirable cytoplasmic elements such complex organelles (e.g., ribosomes) and/or small molecules, with a lipid composition or with a combination of lipids and other components of functional cell membranes, under conditions in which the lipid components encapsulate the synthetic genome and other optional components to form a synthetic cell. In some embodiments, the genome is contacted with a coupled transcription/translation system and is then packaged into a lipid-based vesicle. In some embodiments, the internal components are encapsulated spontaneously by the lipid materials.

The genome can also be introduced into a recipient cell, such as a bacterial or yeast cell, from which some or all of the resident (original) genome has been removed. For example, the entire resident genome may be removed to form a cell devoid of its functional natural genome and the resident genome may be replaced by the foreign genome. Alternatively, the genome may be introduced into a recipient cell which contains some or all of its resident genome. Following replication of the cell, the resident (original) and the introduced (foreign) genome can segregate, and a progeny cell can form that contains cytoplasmic and other epigenetic elements from the cell, but that contains, as the sole genomic material, the introduced genome. Such a cell is a synthetic cell according to various embodiments and methods, and may, in some embodiments, differ from the recipient cell in certain characteristics, e.g., nucleotide sequence, nucleotide source, or non-nucleotide biochemical components.

Various methods, for example in vitro methods, can be used to introduce a genome (synthetic, natural, or a combination thereof) into a cell. Examples of these methods include, but are not limited to, conjugation, transfection, transduction, transformation, electroporation, lipofection, the use of gene guns, and any combination thereof. In some embodiments, the genome, such as a synthetic genome, is immobilized in agar; and the agar plug is laid on a liposome, which is then inserted into a host cell. In some embodiments, the genome is treated to fold and compress before it is introduced into a cell. Methods for inserting or introducing large nucleic acid molecules, such as bacterial genomes, into a cell are sometimes referred to herein as chromosome transfer, transport, or transplantation.

In some embodiments, the synthetic cell comprises elements from a host cell into which it has been introduced, e.g., the whole or part of the host genome, cytoplasm, ribosomes, and membrane. In some embodiments, the components of a synthetic cell are derived entirely from products encoded by the genes of the synthetic genome and by products generated by those genes. Of course, nutritive, metabolic and other substances as well as physical conditions such as light and heat may be provided externally to facilitate the growth, replication and expression of a synthetic cell.

Various exemplary methods may be readily adapted to computer-mediated and/or automated (e.g., robotic) formats. Many synthetic genomes (including a variety of combinatorial variants of a synthetic genome of interest) may be prepared and/or analyzed simultaneously, using high throughput methods. Automated systems for performing various methods as described herein are included. An automated system permits design of a desired genome from genetic components by selection using a bioinformatics computer system, assembly and construction of numerous genomes and synthetic cells, and automatic analysis of their characteristics, feeding back to suggested design modifications.

Also disclosed are synthetic genomes produced by any one of the methods disclosed herein, and synthetic cells produced by introducing the synthetic genome produced by any one of the methods disclosed herein into a cell or a cell-like system. In some embodiments, the cell-like system is a cell from which a resident genome has been removed.

EXAMPLES

Some aspects of the embodiments discussed above are disclosed in further detail in the following examples, which are not in any way intended to limit the scope of the present disclosure.

Experimental Materials and Methods

The following experimental materials and methods were used for Examples 1-6 described below.

Figure 2A:
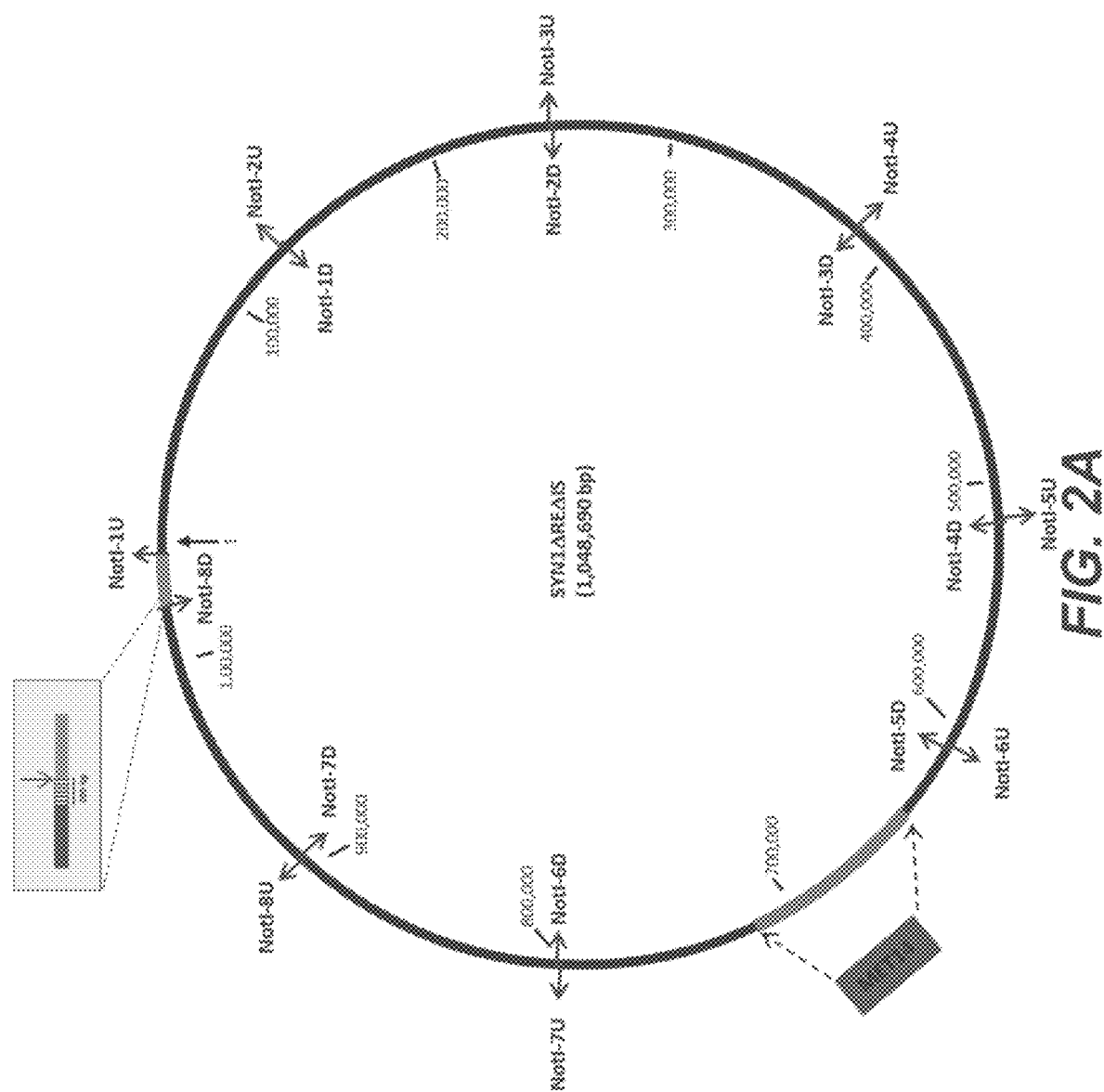

Method for Creating Eight Genomic Segments Flanked by NotI Sites to Facilitate Design and Genome Assembly Purifying large (~100 kb) centromeric plasmid DNA from yeast for genome assembly is a lengthy procedure. See. e.g., Mushegian, et al., Proc. Natl. Acad. Sci. USA 93:10268-73 (1996): Hutchison et al., Science 286:2165-9 (1999), the content of which is hereby incorporated by reference. Instead of purifying DNA from yeast, a segmented approach allowed the isolation of DNA from the parental bacterial genome. The Syn1.0ΔREΔIS strain (Table 9) was used as the parental strain to create eight NotI strains (NotI-1 to -8 strains). Eight genomes were modified by the TREC method to engineer two NotI recognition sites (GCGGCCGC) in yeast. The locations of NotI sites were either in an intergenic region or Tn5-defined non-essential gene coding region. NotI sites encompassed approximately $\frac{1}{8}^{th}$ of the genome (FIG. 2A). Each of the eight $\frac{1}{8}^{th}$ genome segments (NotI-1 to NotI-8) overlapped adjacent segments by 200 base pair (bp) allowing assembly of the segments into a complete genome in yeast via homologous recombination. A non-essential region (24,916-bp) was not included in the design of the $1^{st}$ $\frac{1}{8}^{th}$ genome (between NotI-8 and NotI-1), thus a 200-bp overlapping to the adjacent segment 1 was introduced to the end of segment 8 next to the Not site (FIG. 2A). To further enhance the efficiency of complete genome assembly, the yeast selection markers MET14, was inserted to the genome of the NotI-6 strain by replacing a non-essential cluster (from MMSYN1_0550 to 0591) (FIG. 2A2A). These engineered genomes were transplanted into M. capricolum recipient cell to produce 8 NotI *mycoides* strains (NotI-1 to -8 strains). To assemble the *mycoides* genome, genome DNA was prepared in agarose plugs and digested with restriction enzyme NotI, which generated two fragments, the ⅛th and the ⅞th genome. The ⅛th genome was separated from ⅞th genome by field-inversion gel electrophoresis (FIGE), shown in FIG. 2C. The ⅛th genome was then recovered by electro-elution from the agarose gel (FIG. 2C). To assemble the *mycoides* genome, 8 purified ⅛th genome segments were co-transformed into yeast spheroplasts and selected on appropriate media. A complete genome assembly was evaluated by multiplex PCR (MPCR) and sized by electrophoresis. In general, the rate of successful complete genome assembly was greater than 50%. Both double markers (HIS3 and MET14) selection and lack of yeast DNA contamination in DNA preparation potentially contributed to the high efficiency of genome assembly.

FIGS. 2A-2C show the method used for creating eight NotI strains. FIG. 2A shows the design of NotI restriction sites around the Syn1DREDIS genome for the creation of 8 mycoides NotI strains. The Syn1DREDIS genome was used as the parental genome to create 8 NotI strains. The genome in each strain was engineered by TREC method in yeast with only two unique NotI restriction sites flanking an approximately ⅛th segment of the genome. For example, two NotI site in the genome of NotI strain 1 were generated at locations of NotI-1U and NotI-ID, indicated by arrows. And in the genome of the NotI strain 2, locations of NotI site were generated at locations of NotI-2U and NotI-2D. Each of the ⅛th segment overlaps adjacent segments by 200 bp for genome assembly. A non-essential region (24,916-bp, from gene MMSYN1_0889 to 0904), flanked by two NotI site (NotI-8D and NotI-1U), was not included in the design (indicated in light grey between NotI-1U and NotI-8D at the top of the figure). Thus, a 200 bp overlapping region, represented by vertical line, was inserted upstream of the NotI site, located at the NotI-8D. One non-essential region (from MMSYN1_0550 to 0591) was replaced with the yeast selection markersMET14 in the genome of the NotI strain 6. This non-essential region is indicated in gray between NotI-5D/NotI-6U and NotI-6D/NotI-7U at the bottom left of the figure. Eight NotI-engineered genomes were transplanted from yeast to *M. capricolum* recipient cells to produce 8 NotI *mycoides* strains. FIG. 2B shows that ⅛th genome segments were released from *mycoides* genomes by restriction enzyme NotI and assembled in yeast. FIG. 2C shows that 8 NotI-digested genomic DNA (from 1 to 8) were subjected to 1% agarose gel electrophoresis to separate ⅞th and ⅛th genome (top). The ⅛th genome segments were recovered by electro-elution from the agarose gel and analyzed in 1% agarose gel electrophoresis (bottom).

Global Tn5 Transposon Mutagenesis

Tn5 puro transposon structure and sequence. FIG. 3 shows the structure and sequence of Tn5 puro transposon used for global mutagenesis. DNA was ligated into the SmaI site of the multiple cloning site (MCS) in the EZ-Tn5 pMOD2 construction vector (Epicentre) to form the complete transposon sequence. EZ-Tn5 pMOD2 containing the transposon was digested with PshA1 (New England Biolabs) and gel purified to obtain the Tn5 puro DNA. Puro is the puromycin resistance marker gene. Ptuf is the tuf promoter. Ter triangle is a bidirectional terminator that is downstream of the gyrA gene of Syn1.0. SqPR and SqPF triangles are primer sites for inverse PCR. 19 bp triangles are the Tn5 inverse termini to which Tn5 transposase binds to form the activated transposome used for generating Tn5 mutagenesis libraries.

Tn5 mutagenesis procedure. To make active transposomes, Tn5 transposase was reacted with Tn5 puro DNA according to Epicentre instructions. Briefly, 2 μl of Tn5 transposon DNA (0.1 μg/μl), 2 μl of glycerol, and 4 μl of Tn5 transposase were mixed together by vortexing, incubated for 30 min at room temperature, and then stored at −20° C.

*M. Mycoides* cells were grown in SP4 media to pH 6.3-6.8. A 40 ml culture was centrifuged at 10° C. for 15 min at 4700 rpm in a 50 ml tube. The pellet was resuspended in 3 ml of Tris 10 mM, sucrose 0.5 M, pH 6.5 (Buffer S/T). The resuspended cells were centrifuged for 15 min at 4700 rpm at 10° C. The pellet, still in the 50 ml tube, was suspended in 250 μl of 0.1 M $CaCl_2$) and incubated for 30 min on ice. Transposomes (2 μl) and yeast tRNA (Life Technologies) 10 mg/ml (1 μl) were added and mixed gently with the cells. Two mls of 70% Polyethylene glycol (PEG) 6000 (Sigma) dissolved in S/T buffer was added. The suspension was incubated at room temperature with gentle mixing, and then 20 ml S/T buffer was added and mixed well. Cells were centrifuged at 8° C. for 15 min at 10,000×g. The supernatant was discarded and the tube drained well to remove the PEG. The cells were resuspended in 1 ml of warm SP4 media, incubated for 2 hours at 37° C., and then plated on SP4 agar containing 10 μg/ml of Puromycin (Puro) (Sigma). Colonies were generally visible after 3 to 4 days at 37° C.

Colonies (>40,000 total) from several plates were suspended in 22 ml of SP4 media containing puro 10 μg/ml (P0). Fifty μl of P0 cells were diluted into 50 ml SP4 puro media and incubated at 37° C. for 24 hours (P1 passage). P1 cells (3 μl) were diluted into 50 ml of fresh SP4 puro medium and grown for 24 h (P2). Two more serial passages were done to yield P3 and P4 cell cultures.

P4 cells were centrifuged at 4700 rpm for 15 min. The cell pellet was resuspended in 300 μl of 0.1 M NaCl, 20 mM NaEDTA solution (pH 8.0) in a 1.5 ml of Eppendorf tube. SDS 10% (30 μl) and proteinase K 5 μg (USB Corporation) were added and mixed well. The tube was incubated overnight at 37° C. The mixture was extracted with 330 μl of aqueous phenol (Sigma) and then centrifuged at 15,000 RPM for 5 min. The supernatant was transferred to a new 1.5 ml tube and extracted with an equal volume of phenol/chloroform/isoamyl alcohol (25:24:1) (Sigma). After centrifugation the supernatant was transferred to a new 1.5 ml tube. A $\frac{1}{10}$ volume of 3 M sodium acetate (Sigma) was added and the DNA was ethanol precipitated. After centrifugation at 8,000×g for 5 min the pellet was dissolved in 200 μl of TE buffer (pH 8.0) (Teknova). One μl of RiboShredder™ RNase Blend (Epicentre) was added and the mixture incubated it at 37° C. for 1 hour. The DNA was then extracted with phenol/chloroform, ethanol precipitated, and the pellet dissolved in 200 μl of TE. P0 DNA was similarly prepared from a sample of P0 cells.

DNA enriched for transposon/genomic DNA junctions was obtained by inverse PCR as follows. P0 or P4 DNA (40 μl) in 0.5 ml of TE was sheared in a Nebulizer (Invitrogen™) at 15 lb/in$^2$ for 30 sec to obtain 1.5 to 2 kb fragments of DNA. The DNA was ethanol-precipitated, dissolved in 100 µl TE, diluted with 100 µl of 2×BAL31 nuclease buffer and digested with 1 µl of BAL31 nuclease (New England Biolabs, IU/µl) for 5 min at room temperature to produce blunt-ended DNA. After phenol extraction and ethanol precipitation, DNA was circularized using quick DNA ligase (New England Biolabs). Ligase was inactivated at 65° C. for 20 min. The library was amplified by PCR using 2.5 µl of SqFP and SqRP primers (10 µM each), 20 µl of ligation reaction, and 25 µl of Phusion R: High-Fidelity PCR Master Mix (New England Biolabs). The cycling conditions were one cycle at 98° C. for 30 sec, 29 cycles at 98° C. for 15 sec, 58° C. for 20 sec, 72° C. for 3 min with a final extension for 5 min at 72° C. The PCR product, ranging from ~ 0.5 to 1 kb, was purified using phenol/chloroform extraction and ethanol precipitation and dissolved in TE at 40 ng/µl.

Tn5 mutagenesis to detect non-essential genes. FIG. 4 shows the steps in producing a Tn5 global insert library. Step 1, Tn5 transposon containing 19 bp mosaic ends, sequencing primer sites, terminator sequences, and a selectable marker (puromycin-resistance gene) was constructed. Transposase (Epicentre) was bound to 19 bp termini to form active transposome. Step 2, transposome was introduced into *Mycoplasma mycoides* JCVI-Syn1.0 R-M (minus) strain by polyethylene glycol (PEG) transformation method. Puromycin-resistant colonies were collected and were serially propagated to eliminate slow growers. Library P0 was prepared from DNA isolated from colonies. All viable insertions were represented in the library. Library P4 was prepared from final passage (~50 doublings). Slow growers were lost. Step 3, genomic DNA was isolated, sheared using a nebulizer, and ligated to circularize fragments. Specific fragments were PCR amplified (inverse PCR), and these fragments were sequenced using MiSeq.

Miseq sequencing. Paired-end libraries for next generation sequencing were constructed from template DNA according to the manufacturer's protocol (Nextera XT DNA, Illumina, San Diego, CA, USA). Briefly this method involved using a transposase loaded with adapter oligonucleotides to simultaneously fragment the input DNA and ligate adapter sequences in a single reaction. The adapter sequences were then used to amplify the DNA in a reduced-cycle PCR reaction. During the PCR reaction, unique index sequences were added to both ends of the DNA to allow for dual-indexed sequencing of the pooled libraries. PCR cleanup was performed using a 5:1 ratio of Ampure XP (Beckman Coulter) to PCR reaction. Libraries were normalized following Illumina's instructions for XT bead-based normalization. In preparation for cluster generation and sequencing, equal volumes of each normalized library was combined, diluted 25-fold in hybridization buffer, and heat denatured. The final library pool was sequenced according to standard protocols (MiSeq, Illumina, San Diego, CA, USA).

Tn5 sequencing data analysis and gene classification. The sequence reads were searched for the 19-bp terminus of the Tn5 transposon followed by a 30-bp exact match to genome DNA sequence. In earlier mapping procedures BLAST was used to locate the insertion sites, but this led to a low background of erroneous site locations. This was discovered while investigating Tn5 insertions occurring in known essential genes. For example, it was found consistent insertions at 3 or 4 points in 5'-terminal third of the dnaA gene. These spurious insertions disappeared when the requirement was shifted to an exact 30-bp match immediately following the 19-bp Tn5 terminus. The junction point between the Tn5 sequence and the genome sequence was taken as the insertion point. A large number of insertions were found. And there were a number of hot spots for insertion, but only the set of unique insertion coordinates were used.

Figure 5:
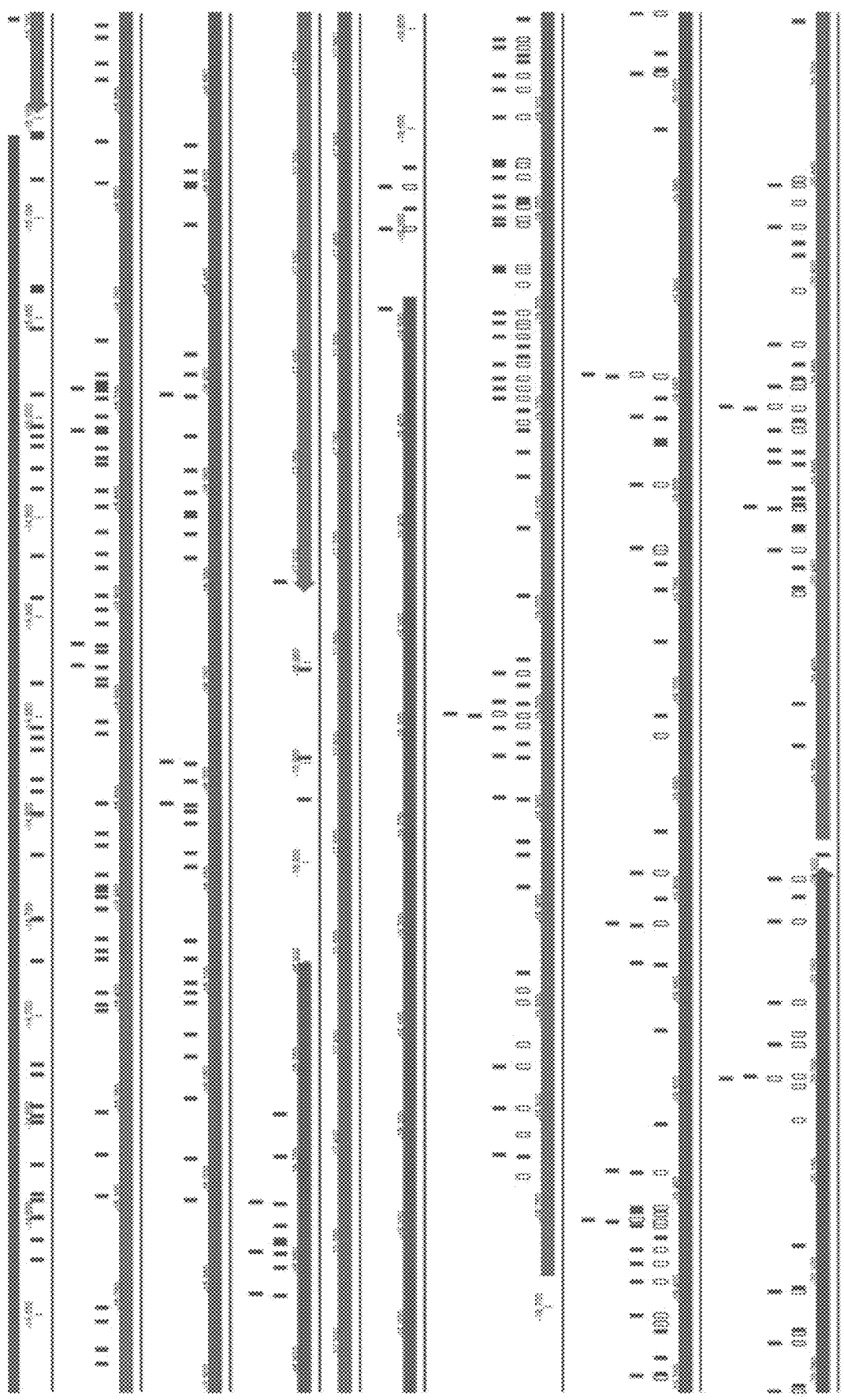

FIG. 5 shows that genes can be classified into 3 categories based on data from global Tn5 transposon mutagenesis. Genes that were hit frequently by both P0 and P4 insertions were classified as non-essential n-genes. Genes hit primarily by P0 insertions but not P4 insertions were classified as quasi-essential, growth impaired i-genes. Genes that were not hit at all, or were sparsely hit in the terminal 20% of 3'-end or the first few bases of 5'-end were classified as essential e-genes. The use of transposon mutagenesis to identify non-essential, quasi-essential, growth impaired genes, and essential genes has been described in Hutchison et al., Science 286:2165-9 (1999), which is hereby incorporated by reference. The first complete gene in the figure is a quasi-essential i-gene. The second gene is an essential e-gene. The third complete gene at bottom of figure is classified as an n-gene. Library P0, black bars: library P4, open bars.

Figure 6:
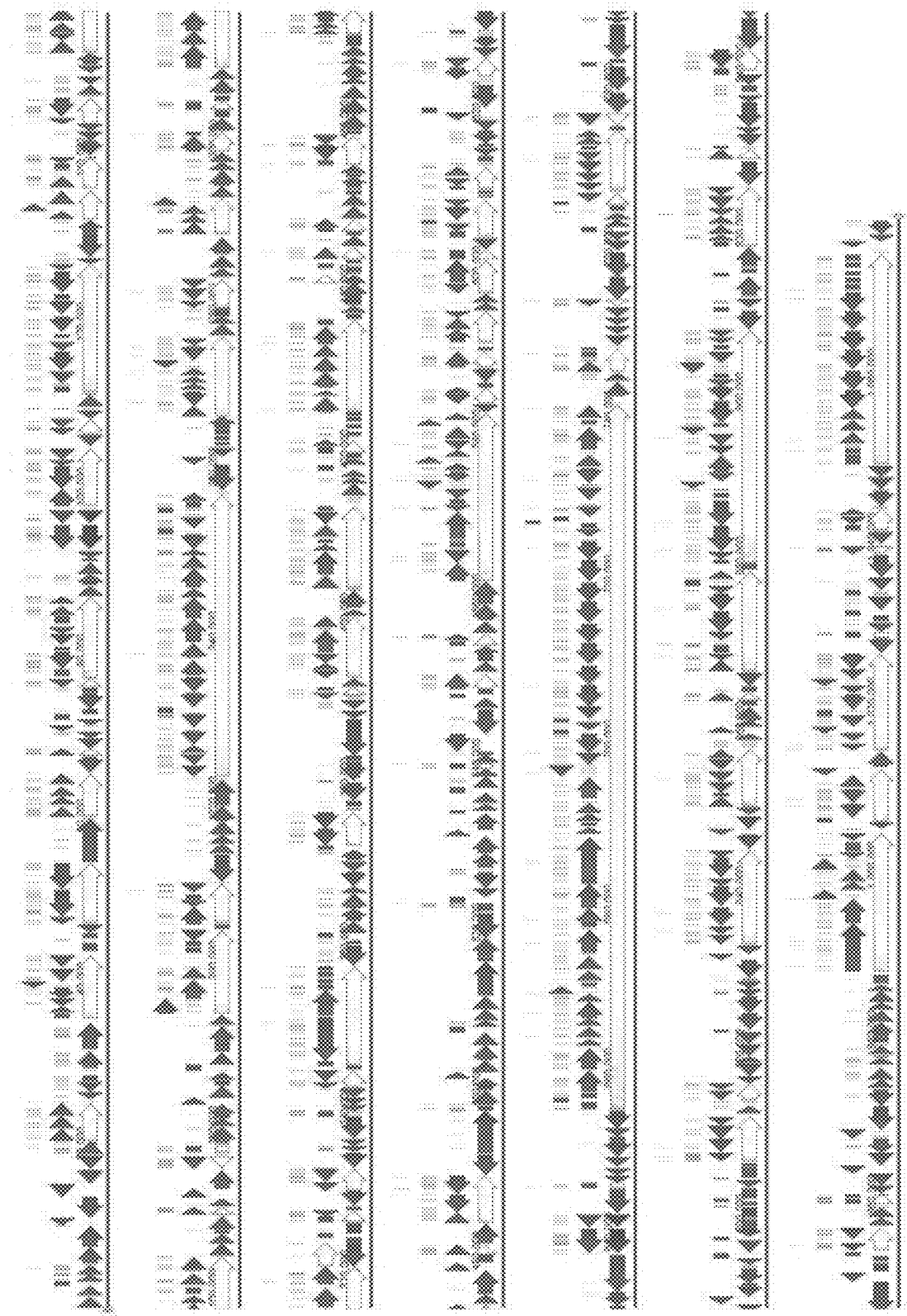

FIG. 6 shows the Syn1.0 gene map with Tn5 P4 insertions. Genes are indicated as black arrows. Fine black marks indicate P4 Tn5 insertions. P4 insertions most clearly identified the n-genes since e-genes and i-genes had no hits or were sparsely hit, respectively. Non-essential genes tended to occur in clusters (white arrows) far more than expected by chance. The white arrows indicate the deletions in the RGD1.0 design. Regions of the map between the white arrows were mainly occupied by e-genes and i-genes.

Reduced Genome Designs RGD1.0, RGD2.0, RGD3.0

Each segment was designed separately by deleting the coding sequences of non-essential n-genes following the design rules:

(1) Contiguous clusters of n-genes were deleted, along with intergenic regions internal to the cluster.
(2) Intergenic regions flanking the cluster were retained.
(3) Parts of n-genes that overlapped an e- or i-gene were retained.
(4) Parts of n-genes that contained a ribosome binding site or promoter for an e- or i-gene were retained.
(5) When two adjacent genes were divergently transcribed, it was assumed that the intergenic region separating them contained promoters for transcription in both directions.
(6) If a deletion resulted in converging transcripts, a bidirectional terminator was inserted if not already present.

RGD1.0 and RGD2.0 design. Table 1 gives statistics on the sizes of fragments of the designed segments for RGD1.0 and RGD2.0. Sizes and fractional sizes of the 8 segments are listed in Table 1 for the RGD1.0 design and the RGD2.0 design. The final genome lengths were corrected for the 200 bp overlaps between the segments. Segments 1, 3, 4, and 5 were redesigned in RGD2.0, whereas segments 2, 6, 7, and 8 remain the same for both designs. Genes deleted in the RGD1.0 design are indicated by light grey arrows in FIG. 7. The 26 genes added back to RGD1.0 to yield the RGD2.0 design are listed in Table 2 and shown in FIG. 7.

TABLE 1

Comparison of RGD2.0 Design to RGD1.0 Design

| A<br>Segment | B<br>syn1.0 bp | C<br>RGD1<br>bp | D<br>Ratio<br>C/B | E<br>RGD2<br>bp | F<br>Ratio<br>E/B |
|---|---|---|---|---|---|
| 1 | 140,739 | 75,732 | 0.54 | 90,161 | 0.64 |
| 2 | 120,912 | 49,888 | 0.41 | 49,888 | 0.41 |
| 3 | 133,208 | 73,958 | 0.56 | 88,059 | 0.66 |

TABLE 1-continued

Comparison of RGD2.0 Design to RGD1.0 Design

| A Segment | B syn1.0 bp | C RGD1 bp | D Ratio C/B | E RGD2 bp | F Ratio E/B |
|---|---|---|---|---|---|
| 4 | 131,623 | 82,531 | 0.63 | 84,750 | 0.64 |
| 5 | 101,708 | 56,501 | 0.56 | 61,324 | 0.60 |
| 6 | 189,357 | 80,747 | 0.43 | 80,747 | 0.43 |
| 7 | 124,976 | 54,482 | 0.44 | 54,482 | 0.44 |
| 8 | 137,887 | 66,717 | 0.48 | 66,717 | 0.48 |
| | | | | | |
| Total | 1,080,410 | 540,566 | N/A | 576,527 | N/A |
| Overlaps | −1,601 | −1,601 | N/A | −1,601 | N/A |
| Genome Length | 1,078,809 | 538,965 | 0.5 | 574,926 | 0.53 |

Figure 7:
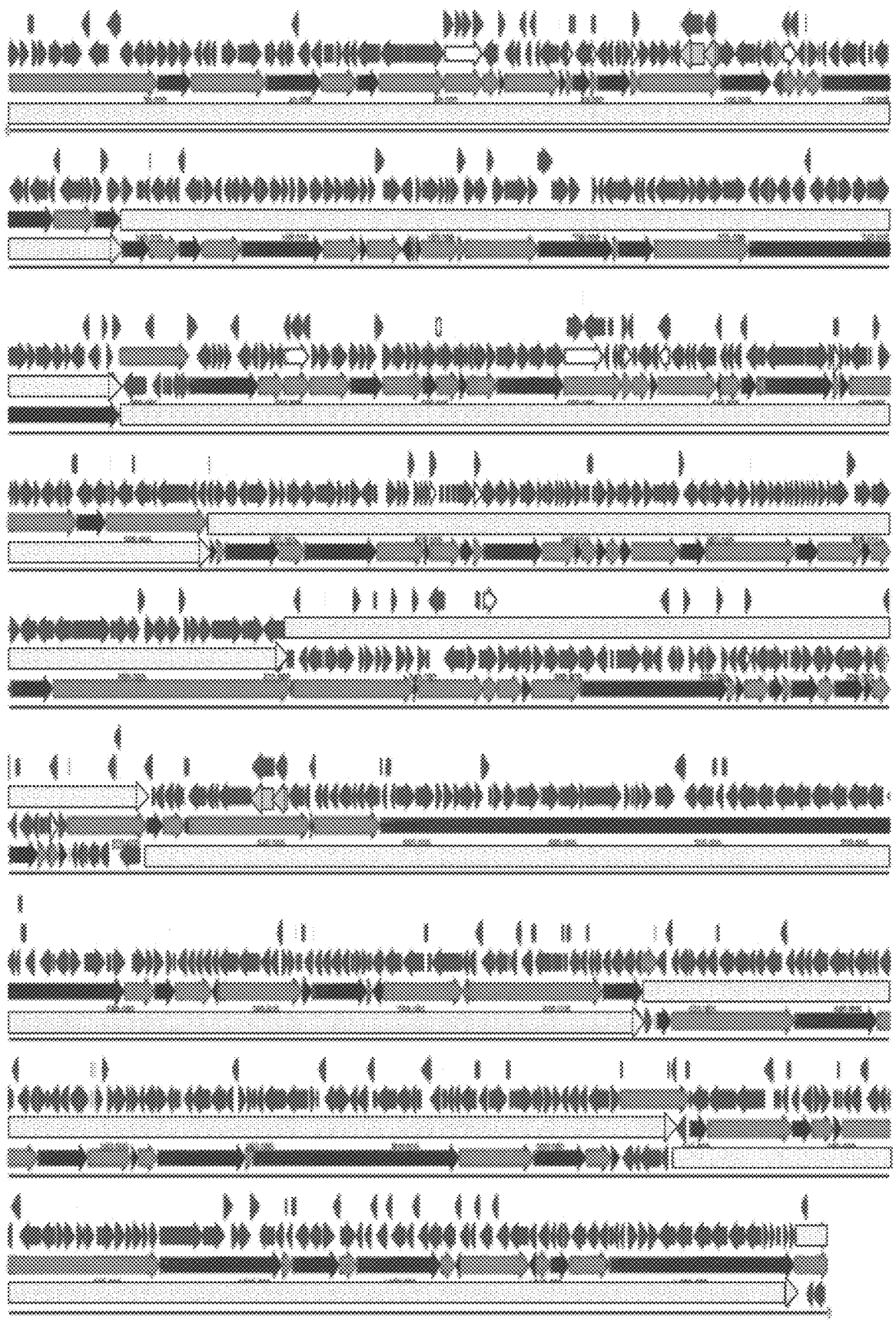

FIG. 7 shows the M. mycoides JCVI-Syn1.0 genome (1078 kb) displayed using CLC software. Dark gray arrows are protein coding genes and white arrows with vertical lines are RNA genes. White dotted arrows are the 8 segments. Light grey arrows are the regions kept in the RGD2.0 design and black arrows are deleted regions. White arrows indicate regions added back to the RGD1.0 design to produce the RGD2.0 design.

Table 2 shows the 26 genes that were identified for add back to RGD1.0 segments 1, 3, 4, and 5 to yield the new RGD2.0 design. Two methods were used to identify genes for add back: (1) Tn5 mutagenesis of RGD2678. The Tn5 mutagenesis data for RGD2678 is shown for lib P0 (0

Fixing segment 5 in Syn2.0. An assembly of all 8 RGD2.0 segments with genes 0455, 0467-0469 added back to RGD2.0 segment 5 did not yield a viable transplant. WT Syn1.0 segment 5 was substituted for the RGD2.0 version. When this assembly (RGD2.0 segs 1234WT5678) was transplanted, colonies were obtained in 3 days and the doubling time in liquid SP4 culture in one measurement was 144 min. Systematic deletion of gene clusters from the WT segment 5 was then undertaken as shown in FIG. 8. More details are given in, for example, Tables 4A-4B.

FIG. 8 shows the list of genes deleted in the RGD2.0 design of segment 5. To arrive at the final structure of the segment 5 used in JCVI-Syn2.0, scarless (TREC) deletions of cluster 33, 36, and 37 were carried out on WT segment 5. The 2 genes 0487 and 0488 that were between cluster 36 and 37 were replaced with gene 0154, which had been deleted from segment 2, but had converted to strong i-genes in the RGD2678 intermediate assembly. These changes to segment 5 resulted in the viable cell, Syn2.0.

Tn5 mutagenesis of Syn2.0 and identification of 37 non-essential genes for removal in RGD3.0 design. Tn5 mutagenesis of Syn2.0 was carried out, and 90 genes were reclassified as potentially non-essential in the new Syn2.0 background. These were sub-divided into 3 groups. The first group contained 26 genes frequently classified as i or e in previous rounds of mutagenesis. The second group contained 27 genes that were classified as i- or borderline i-genes in some of the previous Tn5 studies. The third group contained 37 genes that had previously been classified as non-essential in several iterations of Tn5 mutagenesis involving various genome contexts. To create the new RGD3.0 design these 37 were selected for deletion from Syn2.0 (Table 12).

Figure 9:
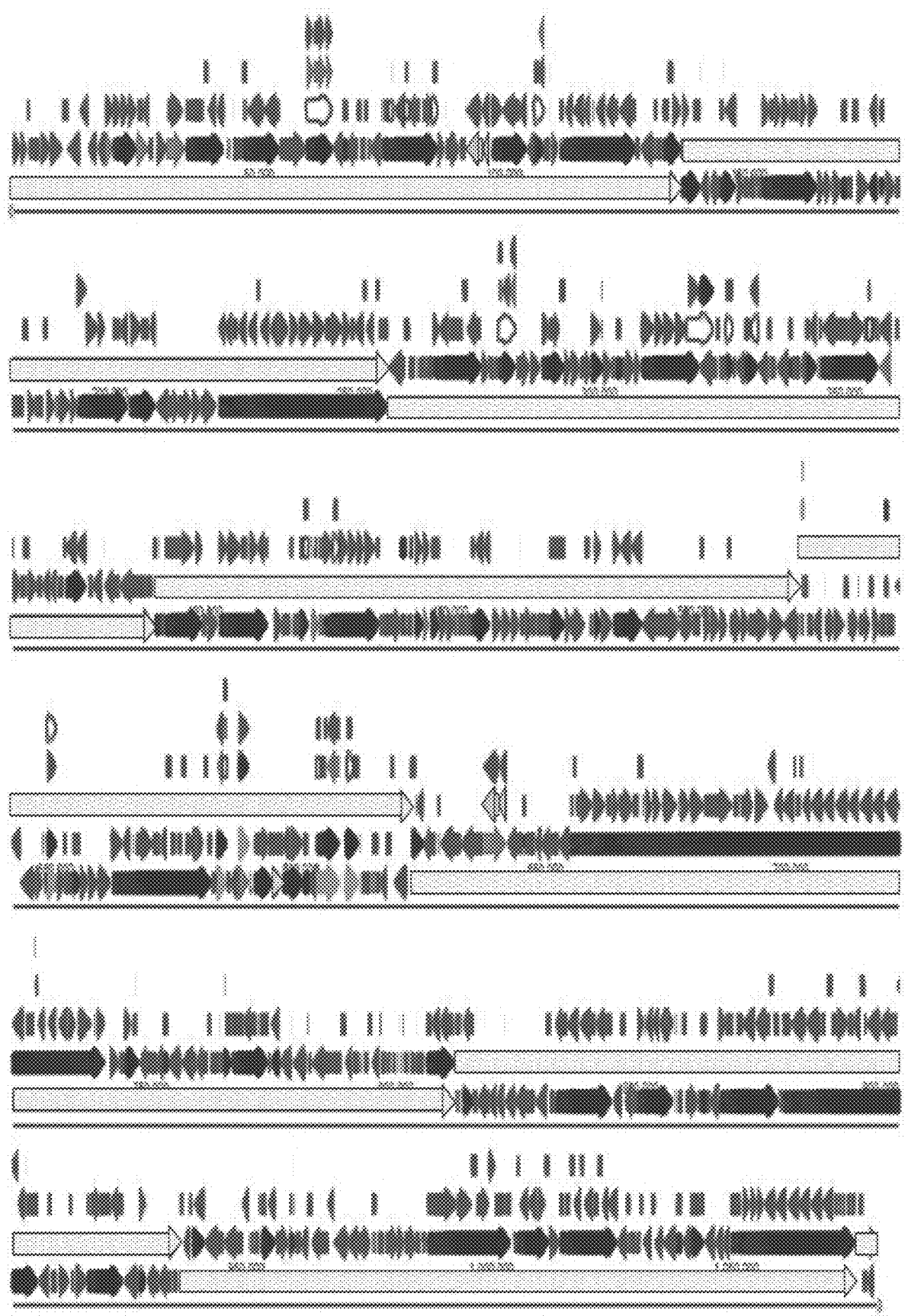

FIG. 9 shows the three design cycles involved in building Syn3.0. The map shows details of the deleted and added back genes in the various cycles. The starting cell was Syn1.0 (1,078,809 bp). Dark grey arrows indicate the Syn1.0 genes. White dotted arrows indicate the 8 segments with 200 bp overlaps. Design cycle 1: Black arrows indicate deletions in the RGD1.0 design. RGD1.0 was not viable, but a combination Syn1.0 segments 1,3,4,5 and RGD1.0 segments 2,6,7,8 was viable (referred to as RGD2678). Design cycle 2A: The white arrows indicate 26 genes that were added back to RGD1.0 segments 1,3,4,5 in an attempt to enable those segments to give a viable cell in combination with RGD2678. This version was only viable when Syn1.0 segment 5 was substituted for the RGD1.0 add back version. Design cycle 2B: Deletions of genes 454-474 and 483-492 from the Syn1.0 segment 5 yielded a viable RGD2.0 (576,028 bp). This was equivalent to adding back additional genes (light grey arrows) to RGD1.0 segment 5 and deleting genes 487-488 (white arrow with horizontal lines). Not shown is the insertion of gene154 in place of 487-488. Design cycle 3: The white arrows with vertical lines indicate an additional 37 Syn1.0 mycoplasma genes plus 2 vector genes (bla and lacZ) and the rRNA operon in segment 6 that were deleted from Syn2.0 to produce a viable Syn3.0 cell (531,560 bp).

Tn5 mutagenesis of Syn3.0. Tn5 mutagenesis was performed on Syn3.0 to determine which genes had Tn5 insertions after serial passaging (P4). Genes originally classified as quasi-essential made up almost the whole population of P4 cells, since the genes in Syn3.0 were then primarily essential e-genes, or quasi-essential i-genes by the original Syn1.0 classification, and only the latter were able to grow. The most highly represented in-, i-, and ie-genes are shown in Tables 3A-3C. Twelve genes originally classified in Syn1.0 as non-essential also had significant inserts in passage P4 (Table 3D).

Tables 3A-3D show Tn5 mutagenesis of Syn3.0 with genes listed having significant numbers of inserts after four serial passages (P4). Columns 1 and 2 show P0 forward and reverse orientation inserts, columns 3 and 4 are for passage P1, and columns 5 and 6 are for passage P4. Column 7 shows the sum of forward and reverse oriented insertions for P4. Column 8 is the gene name, column 9 is the original Syn1.0 gene classification based on Tn5 mutagenesis, and column 10 is the gene functional annotation. The genes were classified into 4 groups A, B, C, and D, shown in Tables 3A, 3B, 3C, and 3D respectively, based on their original Syn1.0 classifications as in, i, ie, and n, respectively. They were further classified according to the numbers of P4 inserts from small to large.

Tables 3A-3D. Tn5 mutagenesis of Syn3.0 with genes listed showing significant numbers of inserts after four serial passages (P4). The genes shown in Tables 3A, 3B, 3C, and 3D were classified as in-, i-, ie-, and n-genes respectively based on the original Syn1.0 classifications.

TABLE 3A

Tn5 mutagenesis of Syn3.0 with genes listed classified as in-genes based on the original Syn1.0 classifications.

| g19P0_F | g19P0_R | g19P1_F | g19P1_R | g19P4_F | g19P4_R | P4_F + P4_R | MMSYN1 | HSW 130821 | Hand annotation |
|---|---|---|---|---|---|---|---|---|---|
| 8 | 8 | 5 | 8 | 1 | 1 | 2 | _0400 | in | ThiJ/PfpI family protein |
| 3 | 1 | 10 | 3 | 2 | 1 | 3 | _0004 | in | rsmA, ksgA, 16S rRNA m6 2A1518, m6 2A1519 |
| 4 | 1 | 3 | 1 | 2 | 1 | 3 | _0376 | in | conserved hypothetical protein |
| 2 | 2 | 7 | 10 | 1 | 2 | 3 | _0401 | in | peptidase C39 family protein |
| 4 | 3 | 5 | 3 | 1 | 2 | 3 | _0504 | in | rsmI, 16S rRNA Cm1402 |
| 1 | 1 | 6 | 6 | 2 | 2 | 4 | _0409 | in | NIF3 family protein |
| 1 | 2 | 2 | 5 | 2 | 2 | 4 | _0851 | in | real? |
| 5 | 3 | 12 | 8 | 3 | 2 | 5 | _0416 | in | conserved hypothetical protein |
| 1 | 1 | 5 | 2 | 2 | 3 | 5 | _0113 | in | glycosyltransferase |
| 0 | 3 | 0 | 11 | 1 | 4 | 5 | _0421 | in | conserved hypothetical protein |
| 6 | 5 | 11 | 7 | 4 | 2 | 6 | _0381 | in | MTA/SAH nucleosidase |
| 4 | 5 | 1 | 8 | 1 | 5 | 6 | _0046 | in | recR |
| 6 | 2 | 8 | 6 | 5 | 2 | 7 | _0382 | in | deoxynucleoside kinase |
| 2 | 4 | 14 | 10 | 5 | 3 | 8 | _0326 | in | conserved hypothetical protein |
| 3 | 4 | 11 | 9 | 3 | 5 | 8 | _0495 | in | ROK family protein |
| 5 | 3 | 3 | 1 | 6 | 3 | 9 | _0214 | in | PAP2 superfamily domain membrane protein |
| 6 | 1 | 6 | 6 | 5 | 4 | 9 | _0114 | in | glycosyltransferase |

TABLE 3A-continued

Tn5 mutagenesis of Syn3.0 with genes listed classified as in-genes based on the original Syn1.0 classifications.

| g19P0_F | g19P0_R | g19P1_F | g19P1_R | g19P4_F | g19P4_R | P4_F + P4_R | MMSYN1 | HSW 130821 | Hand annotation |
|---|---|---|---|---|---|---|---|---|---|
| 3 | 0 | 6 | 6 | 5 | 4 | 9 | _0852 | in | real? |
| 7 | 7 | 11 | 11 | 4 | 5 | 9 | _0838 | in | rlmB, 23S rRNA Gm2251 |
| 36 | 25 | 18 | 15 | 4 | 6 | 10 | _0095 | in | secA |
| 14 | 19 | 27 | 26 | 7 | 4 | 11 | _0127 | in | HD domain protein |
| 19 | 16 | 22 | 21 | 6 | 5 | 11 | _0264 | in | serine/threonine protein kinase |
| 6 | 8 | 13 | 19 | 5 | 6 | 11 | _0517 | in | rluD |
| 13 | 18 | 12 | 23 | 3 | 11 | 14 | _0042 | in | transcriptional regulator, RpiR family protein |
| 6 | 8 | 17 | 14 | 5 | 10 | 15 | _0907 | in | conserved hypothetical protein |
| 3 | 9 | 5 | 15 | 2 | 13 | 15 | _0080 | in | conserved hypothetical protein |
| 9 | 7 | 18 | 14 | 12 | 6 | 18 | _0043 | in | might be rsmC or rlmF |
| 15 | 5 | 16 | 9 | 11 | 8 | 19 | _0005 | in | real? |
| 9 | 10 | 20 | 22 | 11 | 8 | 19 | _0494 | in | putativeN—acetylmannosamine—6—phosphate2—epim |
| 22 | 28 | 40 | 45 | 9 | 13 | 22 | _0305 | in | Xaa—Pro peptidase, M24 family |
| 67 | 72 | 61 | 73 | 10 | 15 | 25 | _0824 | in | uvrA |
| 12 | 16 | 19 | 31 | 11 | 17 | 28 | _0732 | in | deoxyribose—phosphate aldolase |
| 55 | 53 | 69 | 55 | 18 | 16 | 34 | _0825 | in | uvrB |

TABLE 3B

Tn5 mutagenesis of Syn3.0 with genes listed classified as i-genes based on the original Syn1.0 classifications.

| | | | | | | | | | |
|---|---|---|---|---|---|---|---|---|---|
| 52 | 46 | 45 | 23 | 0 | 2 | 2 | _0316 | i | transketolase |
| 7 | 4 | 0 | 0 | 0 | 2 | 2 | _0394 | i | ATP-dependent protease La |
| 4 | 3 | 0 | 5 | 0 | 2 | 2 | _0525 | i | protein MraZ |
| 30 | 31 | 11 | 17 | 0 | 2 | 2 | _0799 | i | glycine hydroxymethyltransferase |
| 10 | 11 | 14 | 14 | 0 | 2 | 2 | _0823 | i | folC folate synthetase-polyglutamyl folate syntheta |
| 24 | 21 | 16 | 13 | 0 | 2 | 2 | _0872 | i | ychF |
| 17 | 9 | 10 | 10 | 1 | 2 | 3 | _0240 | i | thiI, s4U modification in tRNA with icsS |
| 1 | 3 | 6 | 4 | 0 | 3 | 3 | _0777 | i | conserved hypothetical protein |
| 12 | 24 | 23 | 14 | 2 | 2 | 4 | _0887 | i | cdr |
| 6 | 15 | 4 | 13 | 1 | 3 | 4 | _0132 | i | AAA family ATPase |
| 3 | 5 | 12 | 16 | 1 | 3 | 4 | _0239 | i | conserved hypothetical protein |
| 1 | 0 | 8 | 4 | 4 | 2 | 6 | _0814 | i | UDP-galactopyranose mutase |
| 27 | 20 | 25 | 17 | 3 | 3 | 6 | _0414 | i | RelA/SpoT family protein |
| 3 | 7 | 5 | 10 | 3 | 3 | 6 | _0620 | i | ferric uptake regulator |
| 6 | 6 | 23 | 29 | 3 | 5 | 8 | _0479 | i | conserved hypothetical protein |
| 2 | 6 | 3 | 10 | 3 | 5 | 8 | _0817 | i | conserved hypothetical protein (WhiA) |
| 8 | 4 | 14 | 9 | 7 | 3 | 10 | _0142 | i | protein-(glutamine-N5)methyl transferase, release |
| 7 | 3 | 21 | 11 | 7 | 4 | 11 | _0347 | i | cytidylate kinase |
| 10 | 20 | 6 | 24 | 1 | 10 | 11 | _0108 | i | putative lipoprotein |
| 3 | 4 | 15 | 14 | 7 | 5 | 12 | _0404 | i | recO |
| 2 | 5 | 6 | 12 | 5 | 7 | 12 | _0853 | i | conserved hypothetical protein |
| 15 | 14 | 20 | 17 | 8 | 5 | 13 | _0697 | i | glycosyltransferase |
| 48 | 40 | 43 | 46 | 6 | 10 | 16 | _0708 | i | alkyl phosphonate ABC transporter, substrate-bindin |
| 22 | 29 | 44 | 41 | 6 | 10 | 16 | _0878 | i | amino acid permease |
| 8 | 13 | 23 | 22 | 15 | 5 | 20 | _0329 | i | rluB n23 or rsuA n23 |
| 21 | 15 | 27 | 31 | 14 | 11 | 25 | _0434 | i | tRNA:M(5)U-54 methyltransferase |
| 16 | 18 | 25 | 30 | 2 | 23 | 25 | _0106 | i | xseA |
| 13 | 14 | 20 | 29 | 11 | 17 | 28 | _0435 | i | phosphomannose isomerase type I |
| 9 | 15 | 26 | 27 | 10 | 18 | 28 | _0216 | i | hypoxanthine phosphoribosyltransferase |
| 13 | 13 | 26 | 26 | 17 | 13 | 30 | _0097 | i | dna polymerase I, 5'-3' exonuclease |
| 29 | 17 | 40 | 35 | 25 | 17 | 42 | _0876 | i | amino acid permease |
| 3 | 2 | 13 | 16 | 23 | 30 | 53 | _0115 | i | utp-glucose-1-phosphateuridylyl transferase(udp-g |
| 80 | 77 | 83 | 96 | 33 | 28 | 61 | _0228 | i | pdhD |
| 20 | 27 | 40 | 42 | 31 | 31 | 62 | _0433 | i | copper homeostasis protein |
| 46 | 43 | 69 | 70 | 30 | 39 | 69 | _0133 | i | conserved hypothetical protein |
| 14 | 10 | 47 | 42 | 42 | 29 | 71 | _0411 | i | putative membrane protein |
| 89 | 76 | 94 | 91 | 46 | 35 | 81 | _0227 | i | pdhC |
| 9 | 2 | 21 | 14 | 53 | 41 | 94 | _0733 | i | phosphoglucomutase or phosphomannomutase |

TABLE 3C

Tn5 mutagenesis of Syn3.0 with genes classified as ie-genes based on the original Syn1.0 classifications.

| | | | | | | | | | |
|---|---|---|---|---|---|---|---|---|---|
| 0 | 1 | 3 | 2 | 1 | 1 | 2 | _0789 | ie | ATP synthase, delta subunit |
| 1 | 1 | 1 | 1 | 0 | 2 | 2 | _0067 | ie | 5S ribosomal RNA |
| 8 | 20 | 6 | 7 | 0 | 2 | 2 | _0068 | ie | 23S ribosomal RNA |
| 0 | 1 | 1 | 3 | 0 | 2 | 2 | _0910 | ie | ribosomal protein L34 |
| 0 | 5 | 2 | 14 | 1 | 2 | 3 | _0301 | ie | rimP |
| 0 | 3 | 1 | 6 | 1 | 2 | 3 | _0873 | ie | conserved hypothetical protein |
| 2 | 2 | 0 | 2 | 0 | 3 | 3 | _0693 | ie | conserved, caax amino protease family |
| 0 | 3 | 10 | 4 | 3 | 1 | 4 | _0346 | ie | conserved hypothetical protein |
| 3 | 2 | 6 | 2 | 3 | 1 | 4 | _0632 | ie | conserved hypothetical protein |
| 9 | 5 | 15 | 9 | 8 | 2 | 10 | _0481 | ie | lipoprotein, putative (VlcE) |
| 2 | 2 | 12 | 8 | 6 | 5 | 11 | _0726 | ie | glucosamine-6-hosphate deaminase |
| 8 | 10 | 9 | 27 | 13 | 35 | 48 | _0109 | ie | apurinic endonuclease Apn1 |

TABLE 3D

Tn5 mutagenesis of Syn3.0 with genes listed classified as n-genes based on the original Syn1.0 classifications.

| | | | | | | | | | |
|---|---|---|---|---|---|---|---|---|---|
| 2 | 7 | 2 | 7 | 1 | 2 | _0874 | n | 16S rRNA methyltransferase GidB |
| 6 | 5 | 13 | 16 | 4 | 0 | _0640 | n | tRNA pseudouridine |
| 2 | 5 | 8 | 9 | 1 | 4 | _0290 | n | tRNA pseudouridine synthase B |
| 1 | 0 | 2 | 1 | 1 | 4 | _0462 | n | IS1296 transposase protein A |
| 5 | 5 | 13 | 11 | 5 | 1 | _0601 | n | putative membrane protein |
| 16 | 22 | 22 | 24 | 5 | 3 | _0060 | n | putative membrane protein |
| 3 | 3 | 15 | 11 | 3 | 6 | _0094 | n | putative membrane protein |
| 4 | 6 | 17 | 16 | 3 | 7 | _0692 | n | 23S rRNA pseudouridine synthase |
| 17 | 9 | 19 | 21 | 8 | 6 | _0505 | n | putative lipoprotein |
| 15 | 13 | 18 | 21 | 12 | 9 | _0306 | n | hypothetical protein |
| 12 | 17 | 31 | 37 | 9 | 15 | _0444 | n | endopeptidase O |
| 29 | 10 | 39 | 10 | 21 | 6 | _0063 | n | tRNA—dihydrouridine synthase B |

Combinatorial Assembly of Intermediate RGDs

All individual ⅛th RGD1.0 segment, together with a ⅞th JCVI-Syn1.0 genome, generated viable transplants, but the assembled complete RGD1.0 genome did not. To analyze potential synthetic growth defects or lethality among ⅛$^{th}$ RGDs, various intermediate RGD was constructed. Intermediate RGD, consisting of different combinations of ⅛$^{th}$ RGD segments, was assembled in a combinatorial manner in yeast and then tested by transplantation. A number of transplants were obtained after two independent assemblies (Tables 4A-4B). A combination of RGD fragments of an intermediate RGD can be determined by the amplicons' patterns of two MPCRs, demonstrated in Table 4B. Among these intermediate RGDs, the RGD2678 which contained 4 RGD segments (RGD1.0-2, -6, -7, and -8) and 4 WT segments (1, 3, 4, and 5) exhibited an acceptable growth rate. The genome of the RGD2678 was sequenced and subjected to the Tn5 mutagenesis to find any non-essential n-gene(s) might become critical for cell growth in the background of this combination genome. From the second assembly screening, another intermediate RGD, RGD24*678, also exhibited an acceptable growth phenotype. Original MPCR data suggested that the genome contained 5 RGD fragments (RGD1.0-2, -4, -6, -7, and -8), but genome sequence data showed that segment 4 is a "hybrid" segment which approximately first ⅓$^{rd}$ WT segment 4 was substituted by RGD1.0-4 sequence. This might result from a recombination between the RGD1.0-4 and the WT 4 segment during genome assembly in yeast. Instead of using the Tn5 mutagenesis approach, this clone was subjected to deletion targeting 39 gene clusters and single genes which had been removed in the design of RGD1.0-1, -3, -4, and -5 (Table 5).

Tables 4A-4B show generation of intermediate RGD transplants. Table 4A shows a list of RGD and WT segments. Different versions of RGD segments were used in each assembly. Table 4B shows various intermediate RGD transplants isolated from 4 independent assemblies. Assembly 1: (RGD1.0-1, -2, -4, -6, -7, and -8)+ (WT 1 to 8). Assembly 2: (RGD1.0-1 to -8)+ (WT1, 3, 4, 5). Assembly 3: (RGD2.0-3, -4, and -5)+RGD1.0-2, -6, -7, and -8)+WT1: (RGD2.0-1, -4, and -5)+ (RGD1.0-2, -6, -7, and -8)+WT3: (RGD2.0-1, -3, and -5)+ (RGD1.0-2, -6, -7, and -8)+WT4; and (RGD2.0-1, -3, and -4)+ (RGD1.0-2, -6, -7, and -8)+WT5. Assembly 4: (RGD2.0-4, and -5)+RGD1.0-2, -3s, -6, -7, and -8)+WT1; (RGD2.0-1, -4, and -5)+ (RGD1.0-2, -6, -7, and -8)+WT3: (RGD2.0-1 and -5)+ (RGD1.0-2, -3s, -6, -7, and -8)+WT4; and (RGD2.0-1 and -4)+ (RGD1.0-2, -3s, -6, -7, and -8)+WT5. Assembly 1 and 2 were performed by a combinatorial manner. Assembly 3 and 4 were carried out by a combination of 7 RGD segments along with 1 WT segment. The WT6M was used in Assembly 1: the RGD1.0-6sf-LP was used in Assembly 1 and 2; and the RGD1.0-6P-LP was used for Assembly 3 and 4.

Tables 4A-4B. Generation of intermediate RGD transplants. Table 4A shows a list of RGD and WT segments. Table 4B shows various intermediate RGD transplants isolated from 4 independent assemblies.

TABLE 4A

A List of RGD and WT Segments

| 1/8 genome | Note |
|---|---|
| RGD segment | |
| RGD1.0-1 | |
| RGD1.0-2 | |

TABLE 4A-continued

A List of RGD and WT Segments

| 1/8 genome | Note |
|---|---|
| RGD1.0-3 | |
| RGD1.0-3s | added back three genes (0217, 0218, and 0219) |
| RGD1.0-4 | |
| RGD1.0-5 | |
| RGD1.0-6 | |
| RGD1.0-6sf | self-fixed isolate |
| RGD1.0-6sf-LP | self-fixed isolate with the insertion of a landing pad |
| RGD1.0-6P | fixed promoter |
| RGD1.0-6P-LP | fixed promoter with the insertion of a landing pad |
| RGD1.0-7 | |
| RGD1.0-8 | |
| RGD2.0-1 | reversion |
| RGD2.0-3 | reversion |
| RGD2.0-4 | reversion |
| RGD2.0-5 | reversion |
| | WT segment |
| WT 1 | |
| WT 2 | |
| WT 3 | |
| WT 4 | |
| WT 5 | |
| WT 6 | |
| WT 6M | The MET14 marker insertion |
| WT 7 | |
| WT 8 | |

TABLE 4B

Various intermediate RGD transplants isolated from 4 independent assemblies.

| Assembly | clone# | semi-RGD | colony appears (days)* |
|---|---|---|---|
| 1 | 13 | RGD27 | 3 |
| | 91 | RGD2478 | 4 |
| | 105 | RGD47 | 3 |
| | 110 | RGD46 | 3 |
| | 124 | RGD24678 | 4 |
| | 139 | RGD478 | 3 |
| | 140 | RGD2678 | 3 |
| | 168 | RGD478 | 3 |
| 2 | 11 | RGD12678 | 6 |
| | 19 | RGD24*678 | 4 |
| | 90 | RGD25678 | 4 |
| 3 | 18 | RGD2345678 | 5 |
| | 32 | RGD1235678 | 6 |
| | 49 | RGD1234678 | 4 |
| 4 | 48 | RGD1234678 | 4 |

*The colony seen by the naked eyes in days after transplantation.

Table 5 shows a list of 39 genes and cluster deletions. Thirty-nine single genes and gene clusters that had been deleted in the RGD1.0 design were subjected to individual deletion in the RGD2678 clone 140. Deletion of two clusters (0077-0078 and 0217-0219) did not produce transplants (Transplantation column, rows 7 and 11). Deletion of 4 targets (0080, 0331-0332, and 0393, and 0503-0505) produced transplants with a slower growth phenotype (indicated as "S" in column 5).

TABLE 5

List of 39 Genes and Cluster Deletions

| | Gene or Cluster | Segment | Transplantation | Colony Size |
|---|---|---|---|---|
| 1 | 0014-0016 | Seg1 | yes | |
| 2 | 0019-0024 | Seg1 | yes | |
| 3 | 0035-0038 | Seg1 | yes | S |
| 4 | 0041 | Seg1 | yes | |
| 5 | 0050-0060 | Seg1 | yes | S |
| 6 | 0072-0075 | Seg1 | yes | |
| 7 | 0077-0078 | Seg1 | no | |
| 8 | 0080 | Seg1 | yes | S |
| 9 | 0083-0093 | Seg1 | yes | |
| 10 | 0204-0212 | Seg3 | yes | |
| 11 | 0217-0219 | Seg3 | no | |
| 12 | 0223-0226 | Seg3 | yes | |
| 13 | 0231-0232 | Seg3 | yes | |
| 14 | 0236-0237 | Seg3 | yes | |
| 15 | 0241-0246 | Seg3 | yes | |
| 16 | 0251-0252 | Seg3 | yes | |
| 17 | 0255-0256 | Seg3 | yes | |
| 18 | 0261 | Seg3 | yes | |
| 19 | 0268-0269 | Seg3 | yes | |
| 20 | 0272-0277 | Seg3 | yes | |
| 21 | 0292-0293 | Seg3 | yes | |
| 22 | 0331-0332 | Seg4 | yes | S |
| 23 | 0349 | Seg4 | yes | |
| 24 | 0354 | Seg4 | yes | |
| 25 | 0357-0358 | Seg4 | yes | |
| 26 | 0367-0369 | Seg4 | yes | |
| 27 | 0383-0386 | Seg4 | yes | |
| 28 | 0393 | Seg4 | yes | S |
| 29 | 0395-0397 | Seg4 | yes | |
| 30 | 0417 | Seg5 | yes | |
| 31 | 0436 | Seg5 | yes | |
| 32 | 0444 | Seg5 | yes | |
| 33 | 0454-0474 | Seg5 | yes | |
| 34 | 0476-0477 | Seg5 | yes | |
| 35 | 0480 | Seg5 | yes | |
| 36 | 0483-0486 | Seg5 | yes | |
| 37 | 0489-0492 | Seg5 | yes | |
| 38 | 0494-0498 | Seg5 | yes | |
| 39 | 0503-0505 | Seg5 | yes | S |

TABLE 6

Deletions of 39 gene and gene clusters.
39 gene or gene clusters deleted 0014-0016
0019-0024
0035-0038
41
0050-0060
0072-0075
0077-0078
80
0083-0093
0204-0212
0217-0219
0223-0226
0231-0232
0236-0237
0241-0246
0251-0252
0255-0256
261
0268-00269
0272-0277
0292-0293
0331-0332
349
354
0357-0358
0367-0369
0383-0386

TABLE 6-continued

Deletions of 39 gene and gene clusters.
39 gene or gene clusters deleted 393
0395-0397
417
436
444
0454-0474
0476-0477
480
0483-0486
0489-0492
0494-0498
0503-0505

Deletions of 39 gene clusters and single genes in the RGD24*678 genome. The plasmid pCORE6 was used as DNA template to amplify the CORE6 cassette for the deletions. Two rounds of PCR were performed at the gene or gene clusters listed in the Table 6. Yeast transformations were selected on SD URA and correct deletions were screened by PCR to detect insertion junctions. Viability of each deletion was examined by transplantation. Table 6 shows the primers used to amplify the CORE6 cassette for the deletions of 39 gene and gene clusters and to detect insertion junctions.

Data from both Tn5 mutagenesis and 39 individual deletions. Data from both Tn5 mutagenesis and 39 individual deletions found that 26 n-genes among these 4 WT segments became i- or e-genes. Thus, the RGD was re-designed by adding back 26 genes to RGD1.0-1, -3, -4, and -5 to produce RGD2.0-1, -3, -4, and -5 segments (Table 10). The new design of RGD2.0 thus consisted of 4 segments of RGD1.0-2, -6, -7, and -8, and 4 segments of RGD2.0-1, -3, -4, and -5. The RGD2.0 was assembled and multiple clones of complete genome assemblies were isolated and tested by genome transplantation. No viable transplant was obtained. To analyze potential synthetic growth defect and lethality among RGD segments, 4 genomes consisted of 7 RGD and 1 WT segments (1, 3, 4, or 5) were assembled and transplanted. Three genomes were able to produce transplants, except the genome assembled from 7 RGD and WT segment 3 (Assembly 3 in Table 4B). Among three transplant clones, clone 49 with 7 RGD and the WT 5 combination had a smallest size of the genome and yet exhibited a better growth rate. In parallel, a similar assembly of 7 RGD and 1 WT segment was performed, except the RGD2.0-3 segment was replaced with the RGD1.0-3s, a modified RGD1.0-3 supplemented with three genes (See the Experimental Materials and Methods section). Transplantation result showed that only one genome, clone 48, containing 7 RGD and WT 5 produced transplant. The size of the clone 48 genome was about 10 kb smaller than that of the clone 49 since the RGD2.0-3 contained 7 more genes than RGD1.0-3s does (Table 4B).

Construction of RGD1.0-3s by Adding a Gene Cluster to RGD1.0-3

The gene cluster (MMSYN1_0217 to 0219) was seamlessly inserted back into its original locus by the TREC-IN method as described in Noskov et al., Biol. Proced. Online. 17, 6 (2015), which is hereby incorporated by reference. It was done by 2 rounds of transformation. The CORE6 cassette was first PCR-amplified. About 0.5 to 1 μg of the purified PCR product was transformed to yeast harboring the semi-RGD genome containing the ⅛th RGD1-3 segment and selected on SD (−) URA plate. After junction PCR screening, a positive clone was subjected to the second round of transformation to insert the cluster (3.6 kb) by a knock-in module, consisting of 3' KanMX4 gene, a 50-bp repeat sequence, and the cluster. The 3' KanMX4 gene was PCR-amplified for 18 cycles using the pFA6a-kanMX4 as template. The second round of PCR was performed for 22 cycles using the first round PCR product as DNA template. The cluster was PCR-amplified using the JCVI-Syn1.0 genome as. The second step was performed by co-transformation of these two PCR products with a 50-bp overlapping sequence (shown in bold). The cluster recombined with 3' Kan was inserted into the target locus by selection of restoration of kanamycin resistance. After transformation, cells were incubated at YEPD liquid medium overnight 30° C., followed by growing on YEPD plates, supplemented with Geneticin G418. Precise integration was screened by PCR. The procedure of recycling the cassette to produce a scarless insertion was identical to that of the TREC cassette described in the TREC method. The viability of the modified genome was tested by transplantation.

Yeast Strains, Growth Condition, and Genetic Engineering

The yeast Saccharomyces cerevisiae (S. cerevisiae) strains used were VL6-48 (MAT α, his3Δ200, trp1Δ1, ura3-52, lys2, ade2-101, met14) containing the JCVI-Syn1.0 or Syn1/ΔREΔIS genome, and VL6-4IX. 8 (MATa, his3Δ200, trp1Δ1, ura3-52, lys2, ade2-101, met14). The JCVI Syn1.0 genome has been described in Gibson et al., Science 329:52-56. (2010), which is hereby incorporated by reference. The Syn1/ΔREΔIS genome has been described in Karas et al., Nature methods 10:410-412 (2013), which is hereby incorporated by reference. Yeast cells were grown in standard rich medium containing glucose (YEPD) or galactose (YEPG): or in synthetic defined (SD) minimal dropout medium. Yeast growth media have been described in Noskov et al., Nucleic Acids Res. 38:2570-2576 (2010), which is hereby incorporated by reference. For the URA3/5-FOA counter-selection, cells were grown on SD (−) HIS, supplemented with 5-fluoroorotic acid (5-FOA) (1 mg/ml). URA3/5-FOA counter-selection has been described in Boeke et al., Molecular & general genetics: MGG 197:345-346 (1984), which is hereby incorporated by reference. For kanamycin selection, cells were grown on YEPD, supplemented with 200 μg/ml of Geneticin G418 (Cat #: 11811-023, Life technologies). Yeast transformation was carried out by either lithium-acetate or spheroplast methods. Yeast transformation using the Lithium-acetate method has been described in Gietz et al., Nucleic Acids Res. 20:1425 (1992), which is hereby incorporated by reference. Yeast transformation using the spheroplast method has been described in Kouprina et al., Nature protocols 3:371-377 (2008), which is hereby incorporated by reference.

A number of genetic tools were used to perform gene(s) deletion and insertion in a mycoides genome cloned in yeast. These included (a) the TREC method for scarless gene cluster deletion in the D-serial genome production and in generation of restriction NotI site in 8 NotI strains, (b) the TREC-IN method for scarless gene knock-in and knock-out, (c) insertion of the MET14 marker or a landing pad cassette, and (d) gene or gene cluster deletion by the TRP1 marker and the CORE6 cassette. All cassettes or markers for yeast transformation were generated by PCR using chimeric primers to introduce additional 40 to 50 bp to ends of PCR products for homologous recombination to upstream and downstream of target site. All primers were purchased from IDT (Integrated DNA Technologies). The Advantage HD Polymerase (Clontech), unless otherwise indicated, was used for polymerase chain reaction (PCR). In general, PCR was performed for 30 cycles. In some cases, if two rounds of PCR were involved, the first round was performed for 18 cycles and the second round was performed for 22 cycles using the first round of PCR product as DNA template. The PCR product was, if needed, purified by the MinElute PCR Purification Kit (Qiagen) according the manufacturer's instruction. Approximately 0.5 to 1 μg of PCR product was used for yeast transformation. Correct integration was screened by junction PCR, unless otherwise indicated, to detect the presence of 2 junctions between an insertion marker (or a cassette), and upstream and downstream of target region. In general, at least two positive clones of all engineering *mycoides* genome were chosen for genome transplantation.

Method for Construction of Single-Segment-RGD Genomes (⅛$^{th}$ RGD+⅞$^{th}$ JCVI Syn1.0)

To aid in testing the functionality of each RGD synthetic segment, semi-RGD genomes consisting of ⅛$^{th}$ RGD piece and ⅞$^{th}$ Syn1.0 genome were constructed and transplanted. A swapping approach, based on recombinase-mediated cassette exchange (RMCE), was developed to improve the efficiency of genome construction. This RMCE approach has been described in Noskov et al., Biol. Proced. Online. 17, 6 (2015), which is hereby incorporated by reference. Eight landing pad yeast strains containing truncated genomes were constructed by replacing individual ⅛$^{th}$ genome segments with a landing pad cassette containing a truncated URA3 gene and MET14 marker flanked by two mutant loxP sites (FIG. 10). These 8 deleted segments were the same regions of the 8 NotI segments described in the Eight-NotI-strains strategy. To build a semi-RGD genome, a landing pad strain was mated with a corresponding opposite mating type yeast strain containing a donor vector with a RGD segment flanked by another two mutant loxP sites. Diploid strains were selected, followed by galactose induction to trigger the exchange of RGD segment with the landing pad via the cre recombinase (FIG. 10). The structure of semi-RGD genome was first verified by PCR analysis for the boundaries between RGD segment and ⅞$^{th}$ Syn 1.0 genome. The PCR products were further digested with restriction enzyme NotI to confirm ⅛$^{th}$ RGD segment was flanked with NotI site as design. In general, the successful rate of swapping varied from 10 to 50%. At least two independent yeast clones were chosen for transplantation. All 8 semi-RGD genomes were able to produce colonies on the SP4 medium containing tetracycline and X-gal at 37° C. Generally, colonies could be seen in 3 to 4 days after genome transplantation, except the transplanted cell from the RGD1.0-6+⅞th WT genome which required about 10 days to produce a similar colony size as the others. Several faster growing cells were later isolated from the RGD1-6 transplant. All ⅛th RGD segments can be released by NotI restriction enzyme and purified for genome assembly.

FIG. 10 shows the construction of the ⅛$^{th}$ th RGD+⅞ wild type genome by recombinase-mediated cassette exchange (RMCE). Step 1, an approximate ⅛th genome (colored in gray for WT Syn1.0) of the M. *mycoides* JCVI-Syn1.0 cloned in yeast was replaced with a landing pad cassette flanked by two 34-bp hetero-specific lox sites. Step 2, a donor plasmid containing a corresponding ⅛th RGD, flanked by another two hetero-specific lox sites was introduced into the landing pad strain by yeast mating. Step 3, the ⅛th RGD was exchanged with the landing pad locus via the Cre-mediated recombination. An intron-containing URA3 gene was split into the landing pad and the donor plasmid so that the cassette exchange can be selected by restoration of uracil prototrophy. Step 4, the ⅛th RGD+⅞th WT genome was transplanted to *M. capricolum* recipient cells to produce a *mycoides* strain. Step 5, a ⅛$^{th}$ RGD fragment was purified by NotI digestion and then used for genome assembly.

Construction of Single-Reduced Segment Genomes by RMCE

To build a single RGD segment genome, ⅛th RGD and ⅞th JCVI Syn1.0 were brought together in a diploid strain. A landing pad strain containing the MET14 marker was first crossed with a corresponding opposite mating type yeast strain that contained an ⅛th RGD segment carried by a donor vector with the TRP1 marker. It was done by mixing two opposite strains on yeast extract peptone dextrose (YEPD) plate and incubating the plate overnight at 30° C. Diploid strains were selected on SD (−) TRP (−) MET plate. The expression of Cre recombinase was induced by growing diploid cells on YEP-galactose plate for two days. The event of cassette exchange was screened by the restoration of uracil prototrophy. The cells from the YEPG were replica plated on SD minus uracil [(−) URA] for 2 to 3 days until colonies appeared. The structure of the semi-RGD genome was first verified by PCR analysis for the boundaries between the RGD segment and the JCVI Syn1.0 genome. The PCR products were further digested with restriction enzyme NotI to confirm ⅛th RGD segment was flanked with NotI site as design. Multiple positive clones were chosen for transplantation. Generally, colonies could be seen in 3 to 4 days after genome transplantation, except transplanted cells from the RGD1.0-6 semi-genome which required about 10 days to give a colony similar in size to the others. All ⅛th RGD segments in semi-genomes could be released by NotI restriction enzyme and purified for genome assembly.

The one exception, segment 6, initially was detected as a very small colony which after 10 days produced faster growing sectors as shown in FIGS. 11A-11G. The sequence of several independent clonal isolates revealed mutations that reduced the stability of a stem-loop transcription terminator downstream of the tRNA-His gene. This allowed read through and expression of the essential gene 0621. FIG. 12 shows the sequence of this region in Syn1.0 and as designed in RGD1.0 segment 6. FIGS. 13 and 14 show the various mutations that restored expression of gene 0621 and yielded a viable segment 6.

Engineering Restriction NotI Sites into the Genome

Generation of a NotI site was performed by the TREC method. To engineer a NotI site, 5 to 9 nucleotides were embedded into the primers used for PCR-amplifying the CORE cassette. If a NotI site was generated within a coding region, a reading frame was maintained by inserting either 9 bp or 6 bp to generate a NotI site together with adjacent nucleotides. The production of the CORE cassette was generated by two rounds of PCR. Since a non-essential region (24.9 kb) between the ⅛th segments 1 and 8 was not included in the 8-NotI-segments design (FIG. 2A2A), 208 bp which contained 8 bp of NotI site and a 200 bp overlapping to the adjacent segment 1 was inserted into the location of the NotI-8D. Using the JCVI1.0-Syn1.0 genome DNA as template, a 305-bp fragment was PCR-amplified by a pair of chimeric primers. The 50-bp of 5' PCR product was for homologous recombination to the target site and the 50-bp of 3' PCR product was overlapped with 5' end of a CORE cassette amplified by another chimeric primers. Approximately 0.5 μg of two purified PCR products were co-transformed to yeast. Correct insertion was screened by junction PCR. The procedure of recycling of the CORE cassette was same as that in the D serial strains.

Primers were designed to amplify the cassette for engineering NotI sites, to detect junctions of the CORE3 cassette insertion, and the cassette recycling (pop out). 208 bp was inserted into the location of NotI (FIG. 2A). The CORE cassette for engineering NotI site at the NotI-8D location was PCR-amplified by only 1 round (30 cycles) and the 305 bp containing the 208 bp was also amplified by 1 round (30 cycles). 5 to 9 nucleotides were embedded into primers for the NotI site engineering.

Insertion of MET14 into WT Segment 6

The yeast MET14 marker was PCR-amplified using Yeast W303 genome DNA as template and the Ex Taq DNA Polymerase (TaKaRa), according to the manufacturer's instructions. The PCR product was transformed to the NotI strain 6 and selected on SD (−) without methionine (MET) plate. The correct MET14 marker replacement was screened by colony PCR.

Constructions of 8 Landing Pad Strains

PCR amplification was used to produce a unique landing pad cassette (2,250 bp) that allowed individual replacement of each 1/8th segment into the JCVI Syn1.0 genome by homologous recombination in yeast. Seven landing pad cassettes were PCR-amplified using a plasmid pRC72 as the DNA template to replace segments from 2 to 8. One landing pad cassette was PCR-amplified using a plasmid pRC73 as a DNA template to replace segment 1, which contained a yeast centromeric plasmid (YCp). After transformation, cells were selected on SD (−) MET, transformants with correct replacement of the cassette were screened by junction PCR. The landing pad insertion genome was further confirmed by contour-clamped homogeneous electric field CHEF gel electrophoresis.

Modification of RGD Segment 6 by an Insertion of a Landing Pad

Two versions of RGD segment 6 (RGD1.0-6sf and RGD1.0-6P) were further modified by inserting a special landing pad cassette to produce the RGD1.0-6sf-LP and RGD1.0-6P-LP, respectively. The first one was the *mycoides* strain that spontaneously self-fixed the expression of gene MMSYN1_0621 and the second was a redesigned segment 6 that contained a corrected promotor for gene 0621. A modified landing pad was generated by 2 rounds of PCR. The first round PCR was performed using a *mycoides* genome with the insertion of the modified landing pad as DNA template. The second PCR was carried out using the first round PCR product as template. The PCR product was transformed into yeast containing a single-RGD segment genome with either the RGD1.0-6sf or RGD1.0-6P. The cassette was inserted between genes 0601 and 0606 in RGD segment 6. A correct insertion was detected by screening the junctions. Two modified RGD genomes were transplanted to produce cells containing either RGD1.0-6sf-LP or RGD1.0-6P-LP.

Purification of $⅛^{th}$ Genome Segments

All ⅛th genome segments were isolated from *mycoides* genomes. The medium and growth condition of growing *mycoides* cells were described previously in Lartigue et al., Science 317:632-638 (2007), which is hereby incorporated by reference. Briefly, cells were grown in 10 ml SP4 medium containing tetracycline-resistance (tetM) overnight at 37° C. Cells were harvested by centrifugation at 4,575 g for 15 min at 10° C. Cell pellets were washed with 5 ml of washing buffer (10 mM Tris and 0.5 M sucrose, pH 6.5) and harvested again as before. Cells were re-suspended in 100 µl of washing buffer and incubated at 50° C. for 5 min. Cell suspensions were mixed with 120 µl of 2% agarose (Cat #: 16500-500, Invitrogen) in 1×TAE buffer (40 mM Tris-acetate and 1 mM EDTA), pre-warmed at 50° C. Approximately 100 µl of this mixture was added to agarose plug molds (Cat #170-3713 Bio-Rad). After setting 30 min at room temperature, plugs were lysed and proteins were digested with proteinase-K solution [500 µl of the proteinase-K buffer (Bio-Rad) and 20 µl of Proteainase K (>600 mAU/ml) (Cat #19133, Qiagen)] at 50° C. overnight. Agarose plugs were washed once with 1 ml of 0.1× Wash Buffer (Bio-Rad CHEF Genomic DNA Plug Kit) for 30 to 60 min, followed by washing the same buffer containing 0.5 mM PMSF (phenylmethylsulfonyl fluoride) for 30 min. Plugs were equilibrated with 1 ml of 1× Buffer 3 (NEB) for 30 min twice. The plug was treated with 50 units of NotI for 5 hours at 37° C. in 250 µl 1× buffer 3 containing bovine serum albumin BSA (NEB) in 100 µg/ml concentration. After digestion, the plug was loaded on a 1% agarose gel and subjected to Field-Inversion Gel Electrophoresis (FIGE, BioRad, catalog #161-3016) in 1×TAE buffer. The parameters of the electrophoresis were forward 90 V, initial switch 0.1 sec, final switch 10 sec, with linear ramp, and reverse 60 V, initial switch 0.1 sec, final switch 10 sec, with linear ramp for 16 hours at room temperature. Gel was then stained with 1×TAE buffer containing ethidium bromide (0.5 µg/ml) for 30 minutes. To elute ⅛th genome segments, a RECO-CHIP membrane filter (Takara, code #9039) was inserted next to the band. The gel was re-orientated by 90° so that the DNA could be run into the membrane. The gel was subjected to electrophoresis for 2 hours at 3.5 Volt/cm. The RECO-CHIP filter was placed into the RECO-CHIP DNA collection tube and spun for 2 min at 500×g. In general, about 20 to 30 µl DNA solution was collected and kept at 4° C. 1 to 2 µl of purified DNA was analyzed on a 1% agarose gel by FIGE using the same conditions.

Genome Assembly by the Yeast Method

All ⅛th segments of RGD and WT segments used for genome assembly are listed in the Table 4A. Genome assembly was carried out in the yeast VL6-48 strain. The spheroplast transformation procedure has been described previously in Gibson et al., Science 329:52-56. (2010), which is hereby incorporated by reference, with some modifications. Yeast culture a were harvested at an $OD_{600}≈2$. After centrifugation, cell pellets were re-suspended in 20 ml of 1M sorbitol solution and kept at 4° C. for 4 to 20 hours. Approximately 20 to 50 ng of each of the $⅛^{th}$ genome segments were mixed in a final volume of 50 µl and then added to about $1×10^8$ yeast spheroplasts. After transformation, yeast spheroplasts were regenerated and selected on a sorbitol-containing SD (synthetic defined) medium with appropriate amino acids missing, either (1) SD-HIS, (2) SD-HIS-TRP, or (3) SD-HIS-TRP-MET.

Yeast DNA Preparation for PCR

Yeast cells were patched to an appropriate selection medium and grown overnight at 30° C. Cells (visible amount equal to approximately 1 µl of cell mass) were then picked by pipette tip and twirled in 0.5 ml of a PCR tube containing 10 µl of the zymolyase solution (10 µl of sterile water+0.5 µl of 10 mg/ml of zymolyase 20T (ICN Biochemicals)). The tube was incubated at 37° C. for 1 hour, followed by 15 min incubation at 98° C. 1 µl of zymolyase-treated cells was analyzed by PCR in 10 µl reaction volume using the QIAGEN Fast Cycling PCR Kit (cat #203741, Qiagen), according to the manufacturer's instructions. About $⅓^{rd}$ of the PCR product was analyzed on a 2% E-gel (Invitrogen) using the E-Gel Power Base Version 4 (Cat #G6200-04, Invitrogen) for 30 min.

Multiplex PCR Screening to Confirm Genome Assemblies To screen for complete genome assembly, multiplex PCR was performed by QIAGEN Multiplex PCR Kit (cat #206143, Qiagen) using a unique set of primer mixes, each of which contained 8 primer pairs, with the expected amplicon sizes listed in Table 7. DNA prepared from yeast for PCR was described above. In a 15 µl PCR reaction, it contained 1 µl of zymolase-treated yeast cell suspension, 1.5 µl of 10× primer mix, 6 µl of PCR-grade water, and 7.5 µl of the 2× master mix. The PCR conditions were 94° C. for 15 min, then 35 cycles of 94° C. for 30 s, 52° C. for 90 s, and 68° C. for 2 min, followed by 5 min at 68° C. for one cycle. 5 µl of PCR product was analyzed on a 2% E-gel for 30 min.

Combinatorial genome assembly was performed. Each MPCR primer set contained 8 primer pairs to produce amplicons representing each ⅛th segment (WT or RGD). The Set 9 (WT) produced 8 amplicons only from WT segments and the Set 9 (RGD) only produced 8 amplicons from RGD1.0 segments. The Set 10 primer mix can produce 8 amplicons from both WT and RGD. Similarly, the Set 15 and 16 can detect specifically for WT and RGD2.0 segments, respectively in assembly 3 and 4 (See Table 4B).

TABLE 7

Expected Amplicon Size.

| MPCR set | Amplicons (bp) |
| --- | --- |
| Set 9 (WT) | 121 |
| | 204 |
| | 256 |
| | 301 |
| | 408 |
| | 515 |
| | 612 |
| | 724 |
| Set 9 (RGD) | 129 |
| | 186 |
| | 257 |
| | 306 |
| | 400 |
| | 486 |
| | 618 |
| | 724 |
| Set 10 | 108 |
| | 176 |
| | 266 |
| | 323 |
| | 412 |
| | 513 |
| | 619 |
| | 741 |
| Set 15 | 129 |
| | 186 |
| | 268 |
| | 314 |
| | 400 |
| | 486 |
| | 618 |
| | 724 |
| Set 16 | 129 |
| | 220 |
| | 258 |
| | 301 |
| | 408 |
| | 515 |
| | 612 |
| | 718 |

Bacterial Strains and Growth Conditions

*M. mycoides* strain JCVI-Syn1.0 and strains with altered genomes were grown in SP-4 liquid medium supplemented with 17% fetal bovine serum (FBS) or SP-4 solid medium supplemented with 17% either FBS, 1% agar and 150 mg/L X-gal as described previously in Lartigue et al., Science 317:632-638 (2007), which is hereby incorporated by reference. Syn1.0 genome has been described in Gibson et al., Science 329:52-6 (2010), which is hereby incorporated by reference. In some cases, FBS was replaced with same percentage of horse serum (Catalog #: 26050-088, Life technologies) to enhance cell growth.

Genomic DNA Preparation and Transplantation

Total DNA, including *mycoides* genomic DNA from yeast was prepared in agarose plugs using a CHEF Mammalian Genomic DNA Plug Kit (Bio-Rad), according to the manufacturer's instructions with some modifications. Two agarose plugs were prepared from 30 ml of yeast culture ($OD_{600}$=1.5 to 2.5). Plugs were incubated in 400 μl of lytic buffer supplemented with 2 mg of zymolyase 20T (US Biological) at 37° C. for 2 hrs. The procedure of genome transplantation has been described previously in Lartigue et al., Science 325:1693-1696 (2009), which is hereby incorporated by reference, except that the *M. capricolum* RE (−) recipient cells were grown at 30° C.

The TREC-IN Method

FIG. 15 shows a diagram of the TREC-IN method. The CORE6 cassette, consisted of the CORE cassette and a 5' truncated KanMX4 gene, was produced by PCR amplification. Step 1, the PCR product was transformed and selected on SD (−) URA. Correct insertion was verified by junction PCR (L and R). Step 2, two PCR products, 3' KanMX4 truncated gene and a gene to be knocked in (represented by YFG), were generated and co-transformed into the yeast strain. Two PCR fragments were recombined via an identical sequence ("U" block) after transformation. A 250 bp overlapping sequence (indicated as black bars above 5'Kan and 3'Kan) between 5' and 3' KanMX4 gene would recombine to join 2 PCR DNA fragments to integrate to the target site. Transformation was selected on G418 (Geneticin) for the restoration of KanMX4 gene and a correct integration was verified by junction (R1) PCR. Step 3, the identical procedure for removal of the cassette described in FIG. 23 generated a scarless gene insertion confirmed by junction (L1) PCR.

Synthesis and Assembly of Reduced Genomes

Oligonucleotide Design Software. The oligonucleotide design software searched for a combination of parameters including dsDNA fragment overlap length, number of assembly stages, maximum fragment size, maximum number of fragments to be assembled per assembly stage, and appended vector and restriction site sequences that will yield overlapping oligonucleotides that do not exceed 80 bases in length. An oligonucleotide overlap size equal to half the oligonucleotide length was used. And dsDNA fragment overlap size of 40-80 bp with the exception of the eighth molecules which contained defined 200-bp overlaps was used. At each stage of assembly, a unique set of vector sequences (30 bp) and restriction sites (8 bp) were appended to the 5' and 3' ends of each resulting fragment while ensuring the restriction sites were unique to each sequence. These appended sequences facilitated vector assembly for cloning or PCR amplification and insert release (i.e. removal of vector sequences) to expose overlaps for subsequent assembly stages.

Oligonucleotide Pooling. Oligonucleotides were purchased from Integrated

DNA Technologies (IDT), resuspended in TE pH 8.0 to a final concentration of 100 μM, and then pooled and diluted to a per-oligonucleotide concentration of 25 nM. Upon receiving oligonucleotides from IDT in 96 or 384-well plates, plate barcodes were scanned and plates were loaded onto an automated platform (Nxp system from Beckman Coulter). A oligonucleotide design manifest file was used to drive the pooling of partitioned oligonucleotides into pools of approximately 50 oligonucleotides per pool, which constituted a single dsDNA fragment. Two styles of automated pooling were leveraged: (1) pooling via a span-8 style pipetting system in which oligonucleotides were re-arrayed in a slower fashion, but with less intervention; and (2) pooling via a 96-well pipetting head in which oligonucleotides were instantly pooled once placed into a partitioned reservoir (high-speed with more intervention).

Single-Reaction Assembly of dsDNA Fragments from Overlapping Oligonucleotides. Oligonucleotide pools were copied into 96-well PCR plates using Beckman Coulter's Nxp system and enzyme master-mixes were dispensed using a bulk reagent dispenser (Preddator from Redd & Whyte). One-step oligonucleotide assembly and amplification reactions were setup using an enzyme-master mix consisting of 1×Q5 (NEB) or 1× Phusion (Thermo Fisher) PCR master mix, 0.04% PEG-8000, 500 nM forward and reverse Stage01 PCR primers, and 2.5 nM of the oligonucleotide pool generated above. In general, PCR cycling parameters were 98° C. for 2 min, then 30 cycles of 98° C. for 30s and 65° C. for 6 min (increasing 15 sec/cycle), followed by a single 72° C. incubation for 5 min. All thermal-cycling was carried out on Bio-Rad C1000/S1000 cyclers. Products were analyzed on 1% E-gels (Invitrogen) alongside a 1 kb DNA ladder (NEB) (FIG. 16A). In some cases, due to extreme AT content, a 55° C. or 60° C. annealing/extension temperature was used. In general, 48 oligonucleotides of 60-bases in length were combined to generate ~1.4 kb dsDNA fragments.

Error Correction and Re-Amplification Reactions. PCR reactions from above were cycled at 98° C. for 2 min, 2° C./s to 85° C., 85° C. for 2 min, 0.1° C./s to 25° C., 25° C. for 2 min, and then stored at 4° C. 2.7 µl template DNA was combined with an 8.3 µl error correction mix containing 5.3 µl water, 2 µl Surveyor mismatch-recognition endonuclease (IDT), and 1 µl Exonuclease III (NEB) diluted 1:4000 in water to 25 units/ml. Reactions were then incubated at 42° C. for 1 hour. Error corrected templates were then PCR amplified in reactions containing 1×Q5 (NEB) or 1× Phusion (Thermo Fisher) PCR master mix, 500 nM forward and reverse Stage01 PCR primers, and 1:50 error corrected DNA template. In general, PCR cycling parameters were 98° C. for 2 min, then 30 cycles of 98° C. for 30s and 65° C. for 6 min (increasing 15 sec/cycle), followed by a single 72° C. incubation for 5 min. Products were analyzed on 1% E-gels (Invitrogen) alongside a 1 kb DNA ladder (NEB). (FIG. 16B). In some cases, due to extreme AT content, a 55° C. or 60° C. annealing/extension temperature was used to recover synthetic DNA fragments. In general, a 5-10x reduction in error rates was observed compared to untreated samples.

Assembly, Cloning, and MiSeq Sequence Verification of 7-kb Cassettes. Equal amounts (~500 ng) of stage 1 error-corrected PCR fragments were combined 4- or 5-at-a time. One-fifth volume of NotI restriction enzyme (NEB) was added and the reactions were carried out at 37° C. for one hour. The reactions were then processed and concentrated with a PCR cleanup kit (Qiagen). Reactions were then separated on a 1% agarose gel and fragment pools were gel extracted and purified (Qiagen). The overlapping fragments were then simultaneously assembled into a PCR-amplified pCC1BAC cloning vector (REF) using the Gibson Assembly R: HiFi 1-step kit (SGI-DNA) and transformed into Epi300 electrocompetent E. coli cells (Illumina) as previously described. Twenty-four colonies from each first stage cassettes were picked from petri plates using an automated colony picking system (QPix system from Molecular Devices). Picking this number of colonies ensured that it was possible to identify error-free cassettes during this initial pass thus reducing the need to recirculate back through the process.

Figure 17:
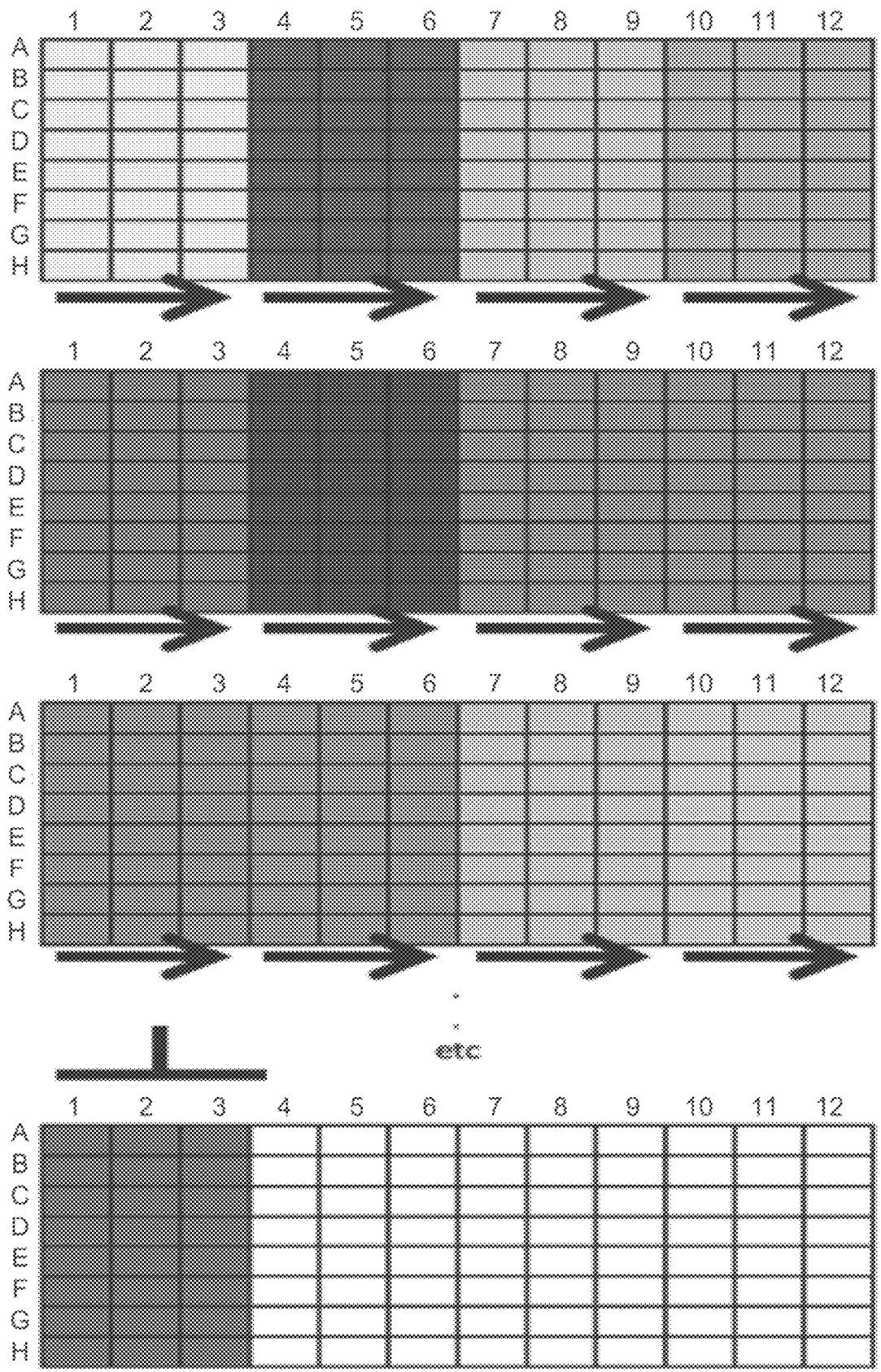

Bacterial colonies were formatted within a deep-well growth block in such a way that dozens of first stage cassettes could be "collapsed" into a single group of 24 wells via Beckman Coulter's NXp (96-well head) after 20 hours of growth in a shaking incubator (FIG. 17). Formatting in this fashion allowed us to screen many clones without having to increase next-generation sequencing libraries construction throughput by 10x. This single grouping of 24 wells was plasmid prepped using Agencourt CosMCPrep (Beckman Coulter) on an automated platform (Nxp system from Beckman Coulter), and the resulting plasmid DNA was used to create 24 indexed libraries using Illumina's Nextera XT system per the manufacturer's protocol. Samples were then sequenced on Illumina's MiSeq platform using reagent kit V2 and a 2×150 bp run type. Illumina's Nextera process was also automated by using Eppendorf's epMotion 5073 and Alpaqua's LE Magnet Plate for low volume bead elution.

After MiSeq sequencing was complete, Clone Verification Analysis (CVA) pipeline was then initiated to identify and select error-free cassettes. A manifest file describing a library-reference association matrix was filled out prior to launch of analysis. The sequenced libraries were quality-trimmed using Trimmomatic 0.32. Concurrently, a comprehensive reference sequence was created by inserting the expected cassette sequence at insertion sites of the vector used. The reference indexes were built using bowtie2-build. Mapping of each library was then performed using bowtie2 with default alignment parameters against all appropriate references described in the manifest file.

The variants in the library were detected by analyzing each BAM file using samtools mpileup. The result was then filtered using bcftools' varfilter and saved as a VCF file. Finally, the VCF files were summarized into a single table that would allow quick identification of the error-free cassettes. Furthermore, this output file was used to drive the automated selection of the cultured clones by using Beckman Coulter's NXp platform (span-8).

Assembly of Overlapping DNA Fragments in Yeast. Error-free cassettes were prepared from 10-ml induced E. coli cultures and inserts were released by digestion with the AsiSI restriction enzyme (NEB). Equal amounts (~500 ng) were combined as many as 15-at-a time and then processed and concentrated with a PCR cleanup kit (Qiagen). Between 50-250 ng of each fragment were combined with 50 ng EVW vector and transformed into yeast as previously described in Gibson et al., Science 319:1215-1220 (2008), Gibson et al., Science 371:632-638 (2007), Gibson, Curr. Protoc. Mol. Biol. Chapter 3: Unit3.22 (2011), and Gibson et al., Proc. Natl. Acad. Sci. U.S.A. 105:20404-20409 (2008). Yeast clones were first screened by multiplex PCR at the assembly junctions and then by separation of supercoiled DNA on agarose gels alongside a supercoil ladder.

Plasmid DNA Isolation from Yeast. Yeast centromeric plasmid (YCp) DNA was prepared as follows. The preparation of yeast centromeric plasmic has been described in Gibson et al., Science 371:632-638 (2007) and Gibson, Curr. Protoc. Mol. Biol. Chapter 3: Unit3.22 (2011), which are hereby incorporated by reference. A 5-10 ml S. cerevisiae culture was grown overnight at 30° C. in complete minimal (CM) medium minus tryptophan (Teknova). Cells were centrifuged and resuspended in 250 µl of buffer P1 (Qiagen), containing 5 µl of Zymolyase-100T solution (10 mg/ml zymolyase-100T [US Biological cat. no. Z1004], 50% (w/v) glycerol, 2.5% (w/v) glucose, 50 mM Tris·Cl, pH 7.5). Following an incubation at 37° C. for 1 hour, 250 µl of lysis buffer P2 (Qiagen) were added. Tubes were inverted several times and incubated at room temperature for 5 min. Then, 250 µl cold neutralization buffer P3 (Qiagen) were added, and the tubes were inverted several times, and the samples were microcentrifuged for 10 min at 16,500×g. The supernatant was transferred into a fresh tube and precipitated with 700 µl isopropanol followed by a 70% ethanol wash. The DNA pellet was resuspended in 30-50 µl TE buffer, pH 8.0. To estimate the size of the purified YCp DNA, 10 µl of the plasmid preparation were separated on a 1% agarose gel in lxTAE buffer (No ethidium bromide) by constant voltage (3 hr at 4.5V cm-1). After the electrophoresis the gel was stained with SYBR Gold and scanned with a Typhoon 9410 imager (GE Healthcare Life Sciences).

Rolling Circle Amplification (RCA) Reactions. MDA reactions were generally performed using the TempliPhi™ Large Construct DNA Amplification kit (GE Healthcare). Briefly, 4 µl of yeast plasmid preparation were added to 9 µl of sample buffer. The mixture was incubated at 95° C. for 3 min and then placed on ice. Ten microliters of reaction buffer and 0.5 µl of the enzyme were added to the denatured sample mixture. The amplification reactions were incubated at 30° C. for 16-18 hours. The enzyme was inactivated at 65° C. for 10 min. Five microliters of amplified DNA were digested with the restriction enzyme NotI in 50 µl volume at 37° C. for one hour. Twenty microliters of the digest were separated on a 1% agarose gel with EtBr in lxTAE buffer by FIGE/U9 electrophoresis. In some cases the REPLI-g mini kit (Qiagen) was used for the amplification following the manufacturer's instructions for purified genomic DNA. Five microliters of yeast plasmid preparation were used as template in an amplification reaction of 50 µl. Reactions were incubated overnight at 30° C. Five to ten microliters of amplified DNA were digested with the restriction enzyme NotI in 50 µl volume at 37° C. for one hour. Twenty microliters of the digest were separated on a 1% agarose gel with EtBr in lxTAE buffer by FIGE/U9 electrophoresis (FIGS. 18A-18B).

Figure 18A:
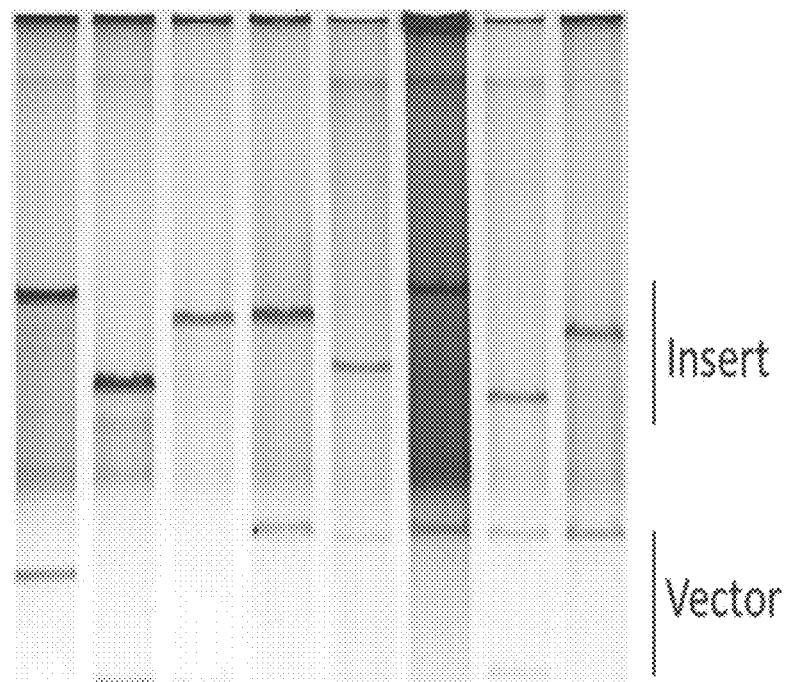
Figure 18B:
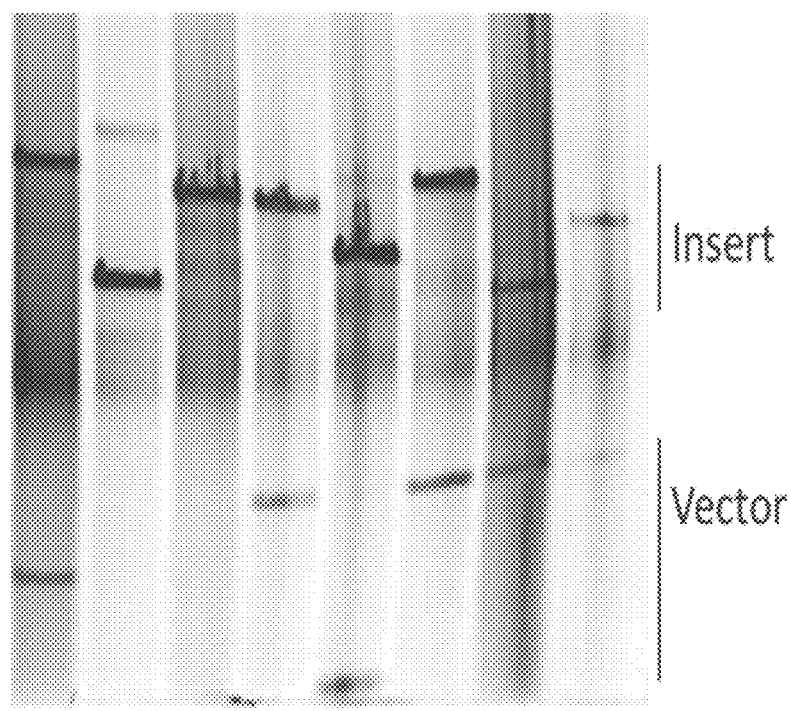

FIGS. 18A-18B show rolling circle amplification (RCA) products derived from the HMG eighth molecule assemblies. FIG. 18A shows supercoil DNA extracted from yeast clones containing the HMG eighth molecule assemblies and used as template in RCA reaction with GE-Templiphi Large Construct kit. FIG. 18B shows supercoil DNA extracted from yeast clones containing the HMG eighth molecule assemblies and used as template in RCA reaction with Qiagen-REPLI-g kit. The RCA products were digested with NotI and separated on an agarose gel subjected to field-inverted gel electrophoresis (FIGE) using the U-9 program as previously described in Gibson et al., Science 319:1215-1220 (2008), which is hereby incorporated by reference. The expected insert size for each eighth molecule is indicated above each lane.

Figure 19:
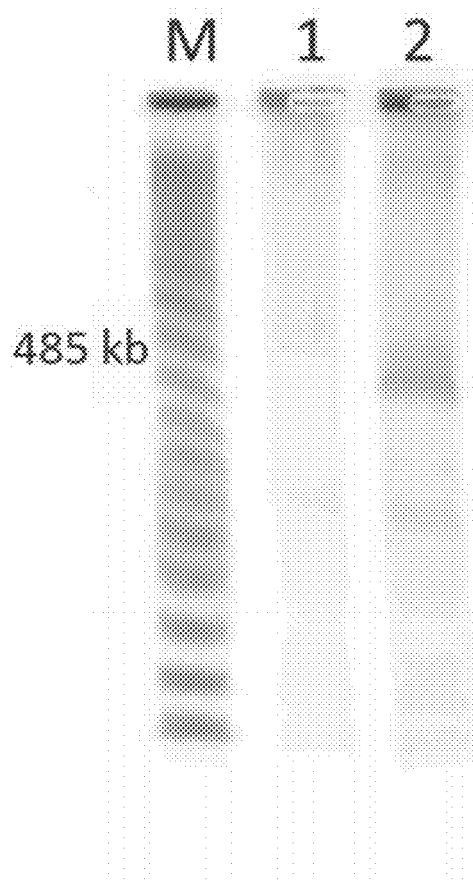
FIG. 19 is a non-limiting exemplary gel photograph showing field-inverted gel electrophoresis analysis of HMG.

FIG. 19 shows field-inverted gel electrophoresis analysis of HMG. Yeast clones harboring HMG (lane 2) was purified from yeast in agarose plugs, digested with AscI to linearize the 483-kb genome, and then analyzed by FIGE using the U-2 program, which has been described in Gibson et al., Science 319:1215-1220 (2008). The same analysis was performed with yeast not harboring HMG as a negative control (lane 1). M indicates the lambda ladder (NEB).

Figure 20:
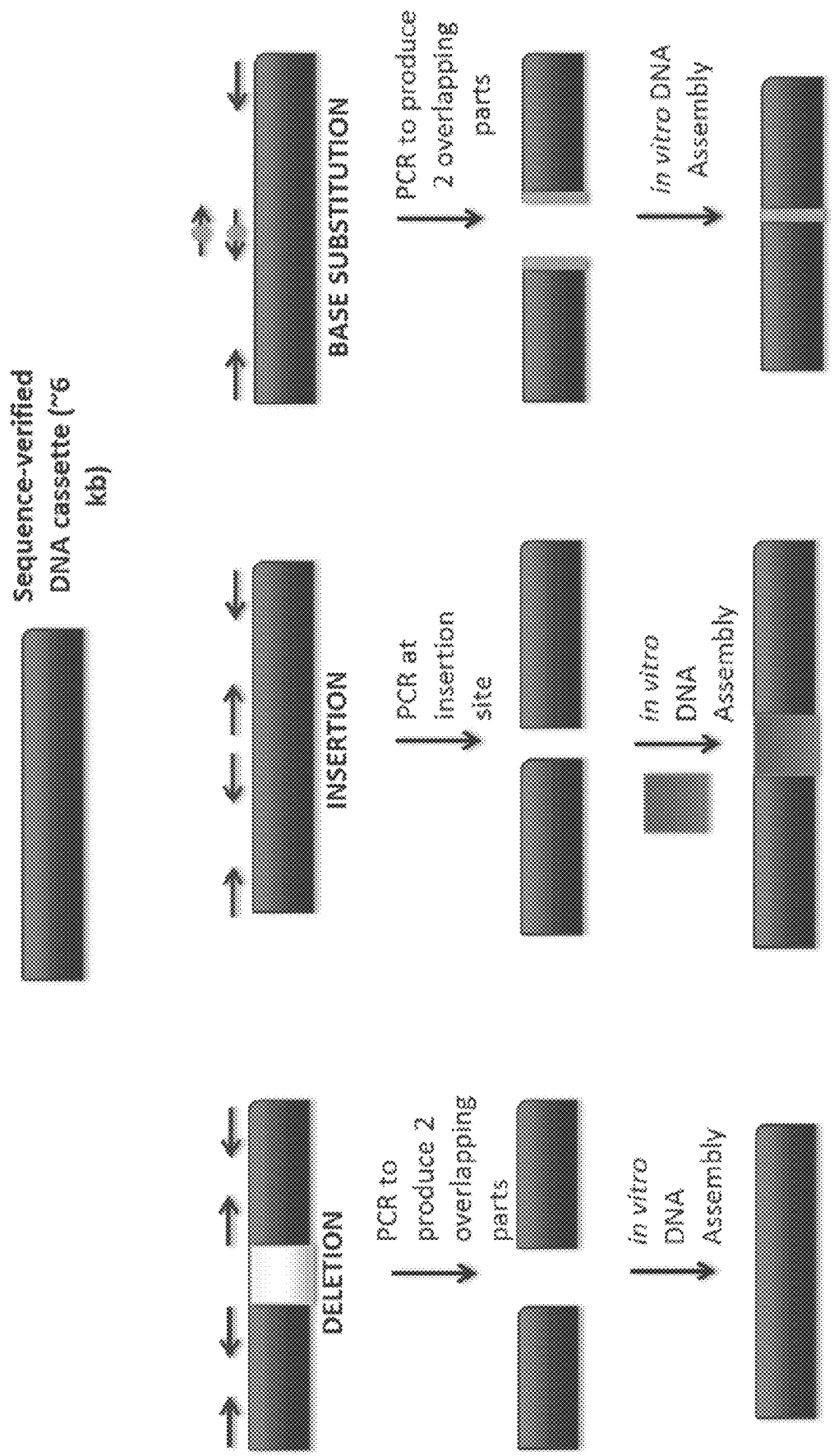
FIG. 20 is a non-limiting exemplary schematic illustration showing the editing of previously generated sequence-verified cassettes.

Cassette Manipulations. In some cases, sequence-verified cassettes from HMG, RGD1, and RGD2 were further manipulated to match the present design. FIG. 20 illustrates how this was performed. Cassettes were PCR amplified upstream and downstream of a site of insertion or deletion. Genes to be added back were amplified using JCVI-Syn1.0 genomic DNA as template. To make a base substitution, the change was made within the PCR primer. Vector and insert DNA fragments were designed such that they contained 40 bp overlaps to facilitate in vitro DNA assembly. Newly assembled cassettes were sequence verified following cloning, as described above, prior to assembly in yeast to generate the new version of the respective $\frac{1}{8}^{th}$ molecule.

FIG. 20 is a schematic illustration showing the editing of previously generated sequence-verified cassettes. Cassettes (black rectangles) generated during the construction of HMG, RGD1, and RGD2 were manipulated to remove genes (white square), add genes (dark grey square), and make single nucleotide substitutions (light grey circle). This was readily performed by generating overlapping fragments via PCR (black arrows) and then assembling the resulting fragments in vitro.

PacBio Complete Genome De Novo Assemblies. An alkaline-lysis approach followed by phenol extraction and ethanol precipitation was used to isolate high molecular weight DNA from Syn3.0 transplants. DNA was quantitated (Qubit, Thermo Fisher Scientific) and quality controlled using an E-Gel (Thermo Fisher Scientific) and then purified using AMPure PB (Pacific Biosciences). The samples (approximately 8-10 µg) were then sheared to an average of 8-20 kb using a g-TUBE (Covaris) at 4500 RPM in an Eppendorf 5424 centrifuge. The samples were then cleaned (Power Clean Pro DNA Clean-Up kit, Mo Bio), quantitated (Qubit, Thermo Fisher Scientific) and quality controlled (Bioanalyzer, Agilent). Adhering to the Pacific Biosciences template preparation protocol (SMRTbell Template Prep Kit 1.0), the samples were first treated with Exo VII to remove single-stranded ends from the DNA fragments, and then taken through DNA damage and end repair before being re-purified using AMPure PB beads. SMRTbell adapter ligation was then performed overnight and failed ligation products were removed with Exo III and Exo VII. AMPure purified DNA was again quantitated (Qubit, Thermo Fisher Scientific) and quality controlled (Bioanalyzer, Agilent) before being size selected (2 or 8 kb to 50 kb) using the BluePippin (0.75%, DF Marker S1 high pass 6-10 kb v3, Sage Science). The size selection was then AMPure PB purified and verified on the Bioanalyzer (Agilent). Sequencing primer was then annealed to the size-selected SMRTbell templates followed by polymerase binding (DNA/Polymerase Binding Kit P6 v2). The prepared libraries were then bound to magnetic beads and loaded onto the Pac Bio RS II at a concentration of 0.200 nM (DNA Sequencing Kit 4.0, Pacific Biosciences). Between 210 and 760 MB of data was generated using one SMRT Cell (V3) per library. Reads of insert ranged from 3700 bp and 9500 bp with polymerase lengths ranging from 11,000 bp to 15,000 bp.

Each sample was assembled de novo using SMRT Analysis 2.3.0 RS_HGAP_Assembly.3 protocol. In short, subreads were extracted using the standard SMRT Analysis 2.3.0 P_Filter protocol using readScore=0.75 and minSubReadLength=500 yielding between 709 and 1151 Mbp of filtered subreads per sample with mean subread lengths between 3475 and 8427 bp. Subreads were then error corrected using the P_PreAssemblerDagcon module using computeLengthCutoff=True and genomeSize=600000 yielding between 6.3 and 9.9 Mbp error corrected reads per sample with N50 lengths between 8780 and 24344 bp. Error corrected reads were assembled to unitigs using the P_AssembleUnitig module and polished using the P_Assembly Polishing module both using default parameters. The assembly resulted in a single circular contig matching the expected Syn3.0 reference size. Overlapping regions on 5' and 3' end of the circular contigs were later manually trimmed using CLC Genomics Workbench, finalizing the complete genome. In order to identify the differences between the expected and assembled genomes, each assembled reference genome was mapped to its corresponding expected reference using BWA-mem Version: 0.7.12-r1039 with default settings. Variants were then called with CLC Genomics Workbench 8.0.2 using the Basic Variant Detection tool with "Minimum coverage=1" and "Minimum count=1", resulting in 9 to 27 variant calls per sample. These variants were confirmed using Illumina MiSeq 2×250 bp reads (processed as described above).

Figure 21:
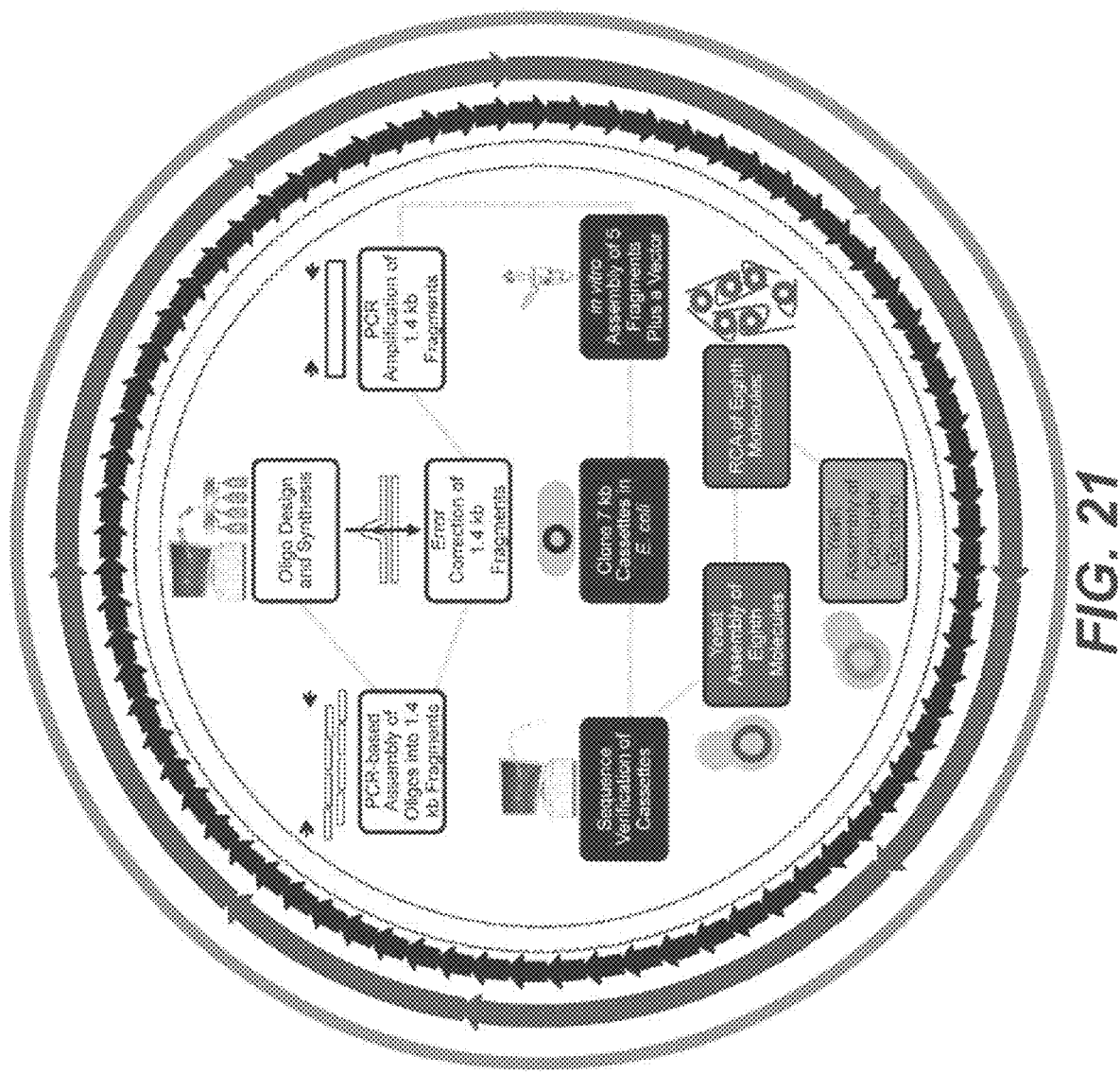
FIG. 21 is a non-limiting exemplary schematic illustration showing the strategy for whole genome synthesis.

FIG. 21 illustrates the general approach used for whole genome synthesis and assembly using HMG as an example. Overlapping oligonucleotides were designed, chemically synthesized, and assembled into 1.4-kb fragments (white). Following error correction and PCR amplification, five fragments were assembled into 7-kb cassettes (black). Cassettes were sequence verified and then assembled in yeast to generate eighth molecules (dark grey). The eight molecules were amplified by RCA and then assembled in yeast to generate the complete genome (light grey).

An automated genome synthesis protocol was established to generate overlapping oligonucleotide sequences starting from a DNA sequence design. Briefly, the software parameters included the number of assembly stages, overlap length, maximum oligonucleotide size, and appended sequences to facilitate PCR amplification or cloning and hierarchical DNA assembly. Approximately 48 oligonucleotides were pooled, assembled, and amplified to generate 1.4-kb DNA fragments in a single reaction (FIGS. 16A-16B, 17). The 1.4-kb DNA fragments were then error corrected, re-amplified, assembled five-at-a-time into a vector, and then transformed into *E. coli*. Error-free 7-kb cassettes were identified on an Illumina MiSeq DNA sequencer and as many as 15 cassettes were assembled in yeast to generate ⅛th molecules. Supercoiled plasmid DNA was prepared from positively-screened yeast clones and rolling circle amplification was performed to generate microgram quantities of DNA for whole-genome assembly, which was performed again in yeast (FIGS. 18A-18B, 19, 20).

Example 1

Knowledge-Based "Hypothetical Minimal Genome" (HMG) Design

This example described a knowledge-based design of "Hypothetical Minimal Genome" (HMG), which was 483 kb in size and contained 432 protein genes and 39 RNA genes.

*M. mycoides* JCVI-Syn1.0 (1,078,809 bp, referred herein as "Syn1.0") described in Gibson et al., Science 329:52-6 (2010), the content of which is hereby incorporated by reference in its entirety) was used as a starting point to design and create a minimized cell. The genome of JCVI-Syn1.0 is virtually identical as the wild-type M. *mycoides* genome, with a few watermark and vector sequences added. The first step of rational minimal cell design was to design a genome of reduced size from Syn1.0 based on available knowledge, including biochemical literature and some transposon mutagenesis data which consisted of approximately 16,000 Tn4001 and Tn5 insertions into the Syn1.0 genome. With this information a total of 440 apparently non-essential genes were found and deleted from the Syn1.0 genome. The resulting "Hypothetical Minimal Genome" design (HMG) was 483 kb in size and contained 432 protein genes and 39 RNA genes (Table 8 shows a detailed gene list).

Table 8. List of genes kept in various genome designs.

TABLE 10

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

End. The last nucleotide that is also part of the gene. As with genbank nomenclature, this may be the complement of the first nucleotide of the start codon or the last nucleotide of the stop codon. Numbering according to accession CP002027.
Direction. Forward and reverse. Direction according to accession CP002027
Fragment. From 1 to 8 the numbers indicate which HMG and RGD fragment the gene is part of.
Locus tag (accession CP002027) MMSYN1_x
KeepDelete. HMG design. k = keep, d = delete, j = other, r = RNA
KeepDelete. Syn2.0. k = keep, d = delete, j = other, r = RNA
KeepDelete. Syn3.0. k = keep, d = delete, j = other, r = RNA
KeepDelete. RGD1 design. k = keep, d = delete, j = other, r = RNA
KeepDelete. RGD2 design. k = keep, d = delete, j = other, r = RNA
Essential? Date = 130821
Essential? Date = 150126
Current annotation
Functional classification
Functional category

| | | | | | | | | | | | | | |
|---|---|---|---|---|---|---|---|---|---|---|---|---|---|
| 4064 | 5155 | f | 1 | 0005 | k | k | k | k | k | in | n | hypothetical protein | 1 = Unknown | Unclear |
| 151368 | 151808 | r | 2 | 0116 | k | k | k | k | k | ie | i | hypothetical protein | 1 = Unknown | Unclear |
| 177917 | 179815 | f | 2 | 0138 | d | k | k | k | k | in | i | hypothetical protein | 1 = Unknown | Unclear |
| 183353 | 184825 | f | 2 | 0143 | k | k | k | k | k | e | e | membrane protein, putative | 1 = Unknown | Unclear |
| 186592 | 187299 | f | 2 | 0146 | k | k | k | k | k | e | e | hypothetical protein | 1 = Unknown | Unclear |
| 212293 | 212787 | r | 2 | 0164 | k | k | k | k | k | ie | i | hypothetical protein | 1 = Unknown | Unclear |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 303170 | 303460 | f | 3 | 0235 | | k | k | k | k | in | in | hypothetical protein | 1 = Unknown | Unclear |
| 305488 | 307275 | f | 3 | 0239 | d | k | k | k | k | i | i | hypothetical protein | 1 = Unknown | Unclear |
| 323909 | 324469 | r | 3 | 0248 | | k | k | k | k | ie | ie | hypothetical protein | 1 = Unknown | Unclear |
| 324471 | 325049 | r | 3 | 0249 | | k | k | k | k | e | n? | hypothetical protein | 1 = Unknown | Unclear |
| 325052 | 325741 | r | 3 | 0250 | d | k | k | k | k | n | i | hypothetical protein | 1 = Unknown | Unclear |
| 360428 | 361108 | f | 3 | 0281 | d | k | k | k | k | i | e | hypothetical protein | 1 = Unknown | Unclear |
| 365884 | 366690 | f | 3 | 0286 | | k | k | k | k | e | n | hypothetical protein | 1 = Unknown | Unclear |
| 376464 | 377108 | f | 3 | 0296 | | k | k | k | k | e | e? | hypothetical protein | 1 = Unknown | Unclear |
| 379011 | 379310 | r | 3 | 0298 | | k | k | k | k | e | i | hypothetical protein | 1 = Unknown | Unclear |
| 379297 | 379578 | r | 3 | 0299 | | k | k | k | k | e | i | PF04296 family protein | 1 = Unknown | Unclear |
| 381929 | 382579 | r | 3 | 0302 | | k | k | k | k | e | ie | hypothetical protein | 1 = Unknown | Cofactor transport and salvage |
| 400483 | 400635 | f | 4 | 0315 | | k | k | k | k | e | i | hypothetical protein | 1 = Unknown | Unclear |
| 402680 | 402925 | f | 4 | 0317 | | k | k | k | k | e | e | PF03672 family protein | 1 = Unknown | Unclear |
| 415769 | 416530 | f | 4 | 0326 | | k | k | k | k | in | n | hypothetical protein | 1 = Unknown | Unclear |
| 437411 | 438106 | f | 4 | 0346 | d | k | k | k | k | ie | i | hypothetical protein | 1 = Unknown | Unclear |
| 442525 | 442902 | f | 4 | 0353 | d | k | k | k | k | in | i | hypothetical protein | 1 = Unknown | Unclear |
| 462590 | 464197 | f | 4 | 0373 | d | k | k | k | k | e | e | hypothetical protein | 1 = Unknown | Unclear |
| 464383 | 465123 | f | 4 | 0375 | | k | k | k | k | e | n | hypothetical protein | 1 = Unknown | Unclear |
| 465125 | 465439 | f | 4 | 0376 | d | k | k | k | k | in | in | hypothetical protein | 1 = Unknown | Unclear |
| 467567 | 467845 | f | 4 | 0379 | | k | k | k | k | e | e | hypothetical protein | 1 = Unknown | Unclear |
| 474783 | 475400 | f | 4 | 0388 | | k | k | k | k | e | e | hypothetical protein | 1 = Unknown | Unclear |
| 475476 | 477620 | f | 4 | 0389 | d | k | k | k | k | i | i | PF11074 domain protein | 1 = Unknown | Unclear |
| 479222 | 479524 | f | 4 | 0392 | | k | k | k | k | e | n | hypothetical protein | 1 = Unknown | Unclear |
| 489280 | 491742 | r | 4 | 0398 | d | k | k | k | k | i | ie | lipoprotein, putative | 1 = Unknown | Lipoprotein |
| 509471 | 510985 | f | 4 | 0411 | d | k | k | k | k | i | i | membrane protein, PF02588 family | 1 = Unknown | Unclear |
| 521435 | 521824 | r | 5 | 0416 | | k | k | k | k | in | n | hypothetical protein | 1 = Unknown | Unclear |
| 525808 | 526119 | r | 5 | 0421 | | k | k | k | k | in | i | alkaline shock protein Asp23 family protein | 1 = Unknown | Unclear |
| 526716 | 527159 | f | 5 | 0424 | | k | k | k | k | ie | n | hypothetical protein | 1 = Unknown | Unclear |
| 535751 | 536434 | f | 5 | 0433 | d | k | k | k | k | i | i | CutC family protein | 1 = Unknown | Unclear |
| 540829 | 542985 | r | 5 | 0439 | d | k | k | k | k | i | e | lipoprotein, putative | 1 = Unknown | Lipoprotein |
| 542985 | 545921 | r | 5 | 0440 | | k | k | k | k | i | i | lipoprotein, putative | 1 = Unknown | Lipoprotein |
| 585152 | 585736 | r | 5 | 0478 | | k | k | k | k | e | e | hypothetical protein | 1 = Unknown | Unclear |
| 589611 | 590048 | r | 5 | 0481 | | k | k | k | k | ie | n | lipoprotein, putative | 1 = Unknown | Lipoprotein |
| 608468 | 608731 | r | 5 | 0500 | | k | k | k | k | e | e | PF04327 family protein | 1 = Unknown | Unclear |
| 612638 | 613261 | r | 5 | 0511 | | k | k | k | k | i | e | hypothetical protein | 1 = Unknown | Unclear |
| 616368 | 617669 | r | 5 | 0516 | d | k | k | k | k | i | i | membrane protein, putative | 1 = Unknown | Unclear |
| 632115 | 632723 | r | 6 | 0530 | | k | k | k | k | ie | ie | hypothetical protein | 1 = Unknown | Unclear |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 632732 | 637180 | r | 6 | 0531 | d | k | k | k | k | i | e | efflux | 1 = Unknown | Efflux |
| 740801 | 740941 | r | 6 | 0599 | k | k | k | k | k | ie | n | hypothetical protein | 1 = Unknown | Unclear |
| 774071 | 774547 | r | 6 | 0632 | d | k | k | k | k | ie | i | hypothetical protein | 1 = Unknown | Unclear |
| 778965 | 781754 | r | 6 | 0636 | d | k | k | k | k | e | e | lipoprotein, putative | 1 = Unknown | Lipoprotein |
| 830816 | 831571 | r | 7 | 0696 | k | k | k | k | k | ie | ie | RDD family protein | 1 = Unknown | Unclear |
| 861788 | 862387 | f | 7 | 0730 | k | k | k | k | k | n? | in | hypothetical protein | 1 = Unknown | Unclear |
| 914429 | 914914 | f | 7 | 0777 | k | k | k | k | k | i | in | hypothetical protein | 1 = Unknown | Unclear |
| 915034 | 915285 | f | 7 | 0778 | k | k | k | k | k | e | e | hypothetical protein | 1 = Unknown | Unclear |
| 936077 | 936313 | r | 7 | 0797 | d | k | k | k | k | e | e | hypothetical protein | 1 = Unknown | Unclear |
| 973981 | 975447 | f | 8 | 0827 | d | k | k | k | k | i | i | hypothetical protein | 1 = Unknown | Unclear |
| 976624 | 976884 | f | 8 | 0830 | k | k | k | k | k | ie | ie | hypothetical protein | 1 = Unknown | Unclear |
| 981034 | 982341 | f | 8 | 0835 | k | k | k | k | k | ie | e | lipoprotein, putative | 1 = Unknown | Lipoprotein |
| 1004037 | 1004219 | r | 8 | 0851 | d | k | k | k | k | in | n | lipoprotein, putative | 1 = Unknown | Lipoprotein |
| 1004385 | 1004615 | r | 8 | 0852 | k | k | k | k | k | in | n | hypothetical protein | 1 = Unknown | Unclear |
| 1004605 | 1005324 | r | 8 | 0853 | k | k | k | k | k | i | n | hypothetical protein | 1 = Unknown | Unclear |
| 1029540 | 1029740 | r | 8 | 0873 | k | k | k | k | k | ie | n? | PF06107 family protein | 1 = Unknown | Unclear |
| 50958 | 54116 | r | 1 | 0033 | k | k | k | d | k | n | ie | hypothetical protein | 1 = Unknown | Unclear |
| 85704 | 86528 | f | 1 | 0060 | d | k | k | d | k | n | i | membrane protein, putative | 1 = Unknown | Unclear |
| 109294 | 109515 | r | 1 | 0080 | d | k | k | d | k | in | n | PF09954 family protein | 1 = Unknown | Unclear |
| 420267 | 421094 | f | 4 | 0332 | d | k | k | d | k | n | i | hypothetical protein | 1 = Unknown | Unclear |
| 426379 | 427098 | f | 4 | 0338 | d | k | k | d | k | n | i | lipoprotein, putative | 1 = Unknown | Lipoprotein |
| 609233 | 609634 | r | 5 | 0503 | k | k | k | d | d | in | in | hypothetical protein | 1 = Unknown | Unclear |
| 44998 | 45597 | f | 1 | 0029 | k | k | k | k | k | e | ie | FMN-dependent NADH-azoreductase 1 | 2 = Generic | Unclear |
| 45634 | 46668 | r | 1 | 0030 | k | k | k | k | k | ie | e | ABC transporter, ATP-binding protein | 2 = Generic | Transport |
| 54281 | 59650 | f | 1 | 0034 | d | k | k | k | k | i | i | efflux ABC transporter, permease protein | 2 = Generic | Efflux |
| 65087 | 67033 | r | 1 | 0039 | k | k | k | k | k | e | e | ftsH peptidase? | 2 = Generic | Protein export |
| 69302 | 70129 | r | 1 | 0042 | k | k | k | k | k | in | i | transcriptional regulator, RpiR family | 2 = Generic | Regulation |
| 70181 | 70903 | r | 1 | 0043 | k | k | k | k | k | in | n | ribosomal protein L11 methyltransferase-like protein | 2 = Generic | rRNA modification |
| 88297 | 89271 | f | 1 | 0063 | k | k | k | k | k | n | n | putative tRNA-dihydrouridine synthase B | 2 = Generic | tRNA modification |
| 91185 | 92027 | r | 1 | 0066 | d | k | k | k | k | i | i | Cof-like hydrolase | 2 = Generic | Unclear |
| 126974 | 127690 | r | 1 | 0094 | d | k | k | k | k | n | in | membrane protein, putative | 2 = Generic | Unclear |
| 131380 | 132291 | f | 1 | 0097 | d | k | k | k | k | i | i | 5'-3' exonuclease, N-terminal resolvase-like domain protein | 2 = Generic | DNA metabolism |
| 142042 | 143154 | r | 2 | 0108 | k | k | k | k | k | i | i | lipoprotein, putative | 2 = Generic | Lipoprotein |
| 143180 | 144049 | r | 2 | 0109 | k | k | k | k | k | ie | e | apurinic endonuclease (APN1)? | 2 = Generic | DNA repair |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 165521 | 166735 | f | 2 | 0127 | d | k | k | k | k | in | i | HD domain protein | 2 = Generic | Unclear |
| 171185 | 172246 | f | 2 | 0132 | d | k | k | k | k | i | i | ATPase, AAA family | 2 = Generic | Unclear |
| 172239 | 174512 | f | 2 | 0133 | d | k | k | k | k | i | n | peptidase, S8/S53 family | 2 = Generic | Proteolysis |
| 179825 | 180775 | f | 2 | 0139 | d | k | k | k | k | i | e | DHHA1 domain protein | 2 = Generic | Unclear |
| 185449 | 186363 | f | 2 | 0145 | k | k | k | k | k | ie | ie | Acetyltransferase, GNAT family | 2 = Generic | Unclear |
| 213005 | 214249 | f | 2 | 0165 | k | k | k | k | k | i | i | AmiC? | 2 = Generic | Transport |
| 214265 | 215275 | f | 2 | 0166 | k | k | k | k | k | i | i | AmiD? | 2 = Generic | Transport |
| 215289 | 216989 | f | 2 | 0167 | k | k | k | k | k | i | i | AmiE? | 2 = Generic | Transport |
| 216991 | 218859 | f | 2 | 0168 | k | k | k | k | k | i | i | AmiF? | 2 = Generic | Transport |
| 218876 | 221977 | f | 2 | 0169 | d | k | k | k | k | i | i | AmiA? | 2 = Generic | Lipoprotein |
| 257213 | 260323 | r | 3 | 0195 | k | k | k | k | k | n | i | potCD or potHI? | 2 = Generic | Lipoprotein |
| 260308 | 261300 | r | 3 | 0196 | k | k | k | k | k | i | i | potB or potG? | 2 = Generic | Transport |
| 261300 | 262355 | r | 3 | 0197 | k | k | k | k | k | i | i | potA or potF? | 2 = Generic | Transport |
| 278321 | 278752 | f | 3 | 0215 | k | k | k | k | k | e | ie | RNAse H domain protein, YqgF family | 2 = Generic | Unclear |
| 341011 | 342126 | r | 3 | 0264 | d | k | k | k | k | in | in | kinase domain protein | 2 = Generic | Unclear |
| 362526 | 363143 | f | 3 | 0283 | k | k | k | k | k | ie | ie | caulimovirus viroplasmin/ ribonuclease HI multi-domain protein | 2 = Generic | DNA replication |
| 388276 | 389352 | r | 3 | 0305 | d | k | k | k | k | in | n | metallopeptidase family M24 | 2 = Generic | Proteolysis |
| 399627 | 400361 | f | 4 | 0314 | k | k | k | k | k | i | ie | ecfS | 2 = Generic | Cofactor transport and salvage |
| 414261 | 415751 | f | 4 | 0325 | k | k | k | k | k | i | ie | membrane protein, putative | 2 = Generic | Unclear |
| 416540 | 417376 | f | 4 | 0327 | k | k | k | k | k | ie | ie | scpA? | 2 = Generic | Chromosome segregation |
| 436455 | 437345 | f | 4 | 0345 | k | k | k | k | k | e | ie | ecfS | 2 = Generic | Cofactor transport and salvage |
| 441114 | 441386 | f | 4 | 0350 | k | k | k | k | k | e | ie | putative DNA-binding protein HU 1 | 2 = Generic | Unclear |
| 441441 | 441989 | f | 4 | 0352 | k | k | k | k | k | in | e? | dnaD? | 2 = Generic | Unclear |
| 458816 | 460687 | f | 4 | 0371 | k | k | k | k | k | i | e | ABC transporter, ATP-binding protein | 2 = Generic | Efflux |
| 460703 | 462556 | f | 4 | 0372 | d | k | k | k | k | i | e | ABC transporter, ATP-binding protein | 2 = Generic | Efflux |
| 469634 | 470272 | f | 4 | 0382 | k | k | k | k | k | in | n | deoxynucleoside kinase | 2 = Generic | Nucleotide salvage |
| 491892 | 497153 | f | 4 | 0399 | d | k | k | k | k | i | ie | efflux ABC transporter, permease protein | 2 = Generic | Efflux |
| 497201 | 497752 | f | 4 | 0400 | d | k | k | k | k | in | i | DJ-1 family protein | 2 = Generic | Ribosome biogenesis |
| 497850 | 499634 | f | 4 | 0401 | k | k | k | k | k | in | in | peptidase, C39 family | 2 = Generic | Proteolysis |
| 506621 | 507298 | f | 4 | 0408 | k | k | k | k | k | i | n | tRNA: m1A22 methyltransferase? | 2 = Generic | tRNA modification |
| 507285 | 508061 | f | 4 | 0409 | d | k | k | k | k | in | in | folE? | 2 = Generic | Cofactor transport and salvage |
| 508070 | 509431 | f | 4 | 0410 | d | k | k | k | k | i | i | DEAD/DEAH box helicase | 2 = Generic | Ribosome biogenesis |
| 524140 | 525783 | r | 5 | 0420 | k | k | k | k | k | e | e | DAK2 domain fusion protein YloV | 2 = Generic | Unclear |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 533291 | 533626 | f | 5 | 0430 | k | k | k | k | k | e | n | Sigma3 and sigma4 domains of RNA polymerase sigma factors? | 2 = Generic | Regulation |
| 533614 | 534387 | f | 5 | 0431 | k | k | k | k | k | e | ie | putative metallophosphoesterase | 2 = Generic | Unclear |
| 539417 | 540397 | f | 5 | 0437 | k | k | k | k | k | e | e | putative 3'-5' exoribonuclease YhaM | 2 = Generic | RNA metabolism |
| 540428 | 540826 | r | 5 | 0438 | k | k | k | k | k | e? | n | Histidine triad (HIT) hydrolase-like protein | 2 = Generic | Unclear |
| 552275 | 552778 | f | 5 | 0447 | k | k | k | k | k | e | e | dUTP diphosphatase? | 2 = Generic | Nucleotide salvage |
| 555218 | 556633 | f | 5 | 0451 | k | k | k | k | k | e | e | putative glyceraldehyde-3-phosphate dehydrogenase (NADP+) | 2 = Generic | Glucose transport & catabolism |
| 585741 | 587387 | r | 5 | 0479 | d | k | k | k | k | i | i | peptidase | 2 = Generic | Proteolysis |
| 601858 | 603207 | r | 5 | 0493 | d | k | k | k | k | i | ie | putative dipeptidase | 2 = Generic | Proteolysis |
| 743662 | 744606 | f | 6 | 0601 | d | k | k | k | k | n | i | membrane protein, putative | 2 = Generic | Unclear |
| 761690 | 762298 | r | 6 | 0615 | k | k | k | k | k | i | i | tRNA binding domain protein | 2 = Generic | Unclear |
| 764373 | 764837 | r | 6 | 0620 | k | k | k | k | k | i | i | transcription factor, Fur family | 2 = Generic | Regulation |
| 782896 | 787041 | r | 6 | 0639 | k | k | k | k | k | e | e | efflux ABC transporter, permease protein | 2 = Generic | Efflux |
| 787136 | 787891 | r | 6 | 0640 | k | k | k | k | k | n | in | putative tRNA pseudouridine(38-40) synthase | 2 = Generic | tRNA modification |
| 824338 | 826359 | r | 7 | 0691 | k | k | k | k | k | e | e | membrane protein, putative | 2 = Generic | Efflux |
| 826362 | 827270 | r | 7 | 0692 | k | k | k | k | k | n | n | pseudouridine synthase, RluA family | 2 = Generic | rRNA modification |
| 827273 | 828241 | r | 7 | 0693 | k | k | k | k | k | ie | ie | CAAX protease | 2 = Generic | Proteolysis |
| 831571 | 832527 | r | 7 | 0697 | d | k | k | k | k | i | n | glycosyltransferase, group 2 family protein | 2 = Generic | Unclear |
| 848530 | 849393 | r | 7 | 0710 | d | k | k | k | k | i | i | Cof-like hydrolase | 2 = Generic | Unclear |
| 859254 | 860090 | f | 7 | 0728 | k | k | k | k | k | in | i | HAD hydrolase, family IIB | 2 = Generic | Unclear |
| 949315 | 950490 | r | 8 | 0805 | d | k | k | k | k | i | i | transcription factor | 2 = Generic | Regulation |
| 960185 | 961114 | r | 8 | 0817 | d | k | k | k | k | i | i | transcription factor, WhiA like | 2 = Generic | Regulation |
| 966098 | 966772 | r | 8 | 0822 | k | k | k | k | k | i | i | ecfS | 2 = Generic | Cofactor transport and salvage |
| 982483 | 983409 | f | 8 | 0836 | k | k | k | k | k | e | e | ecfS | 2 = Generic | Cofactor transport and salvage |
| 984745 | 985479 | f | 8 | 0838 | k | k | k | k | k | in | i | RNA methyltransferase, TrmH family, group 3 | 2 = Generic | rRNA modification |
| 1025896 | 1027662 | r | 8 | 0870 | k | k | k | k | k | i | e | C4-dicarboxylate anaerobic carrier | 2 = Generic | Transport |
| 1028410 | 1029504 | r | 8 | 0872 | k | k | k | k | k | i | i | GTP-binding protein YchF | 2 = Generic | Ribosome biogenesis |
| 1031135 | 1032715 | r | 8 | 0876 | k | k | k | k | k | i | i | amino acid permease | 2 = Generic | Transport |
| 1032862 | 1033542 | r | 8 | 0877 | d | k | k | k | k | i | e | membrane protein, putative | 2 = Generic | Unclear |
| 1033514 | 1035007 | r | 8 | 0878 | k | k | k | k | k | i | i | amino acid permease | 2 = Generic | Transport |
| 1035110 | 1037767 | r | 8 | 0879 | d | k | k | k | k | i | n | putative magnesium-2 importing ATPase | 2 = Generic | Transport |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| Start | End | Dir | # | ID | | | | | | | | Gene | Category | Function |
|---|---|---|---|---|---|---|---|---|---|---|---|---|---|---|
| 1039138 | 1040565 | r | 8 | 0881 | d | k | k | k | k | i | e | membrane protein, putative | 2 = Generic | Unclear |
| 1075251 | 1075967 | r | 1 | 0906 | d | k | k | k | k | in | i | choline/ethanolamine kinase? | 2 = Generic | Lipid salvage and biogenesis |
| 1075967 | 1076761 | r | 1 | 0907 | d | k | k | k | k | in | n | Cof-like hydrolase | 2 = Generic | Unclear |
| 80000 | 80449 | r | 1 | 0054 | d | k | k | d | k | in | n | redoxin | 2 = Generic | Redox homeostasis |
| 106239 | 107078 | r | 1 | 0077 | k | k | k | d | k | n | n | Cof-like hydrolase | 2 = Generic | Unclear |
| 548379 | 550274 | f | 5 | 0444 | d | k | k | d | k | n | n | peptidase family M13 | 2 = Generic | Proteolysis |
| 604102 | 604977 | r | 5 | 0495 | k | k | k | d | d | in | n | ROK family protein | 2 = Generic | Regulation |
| 609657 | 610544 | r | 5 | 0504 | d | k | k | d | k | in | i | 16S rRNA (cytidine(1402)-2'-O)-methyltransferase? | 2 = Generic | rRNA modification |
| 610920 | 611993 | f | 5 | 0505 | d | k | k | d | d | n | i | lipoprotein, putative | 2 = Generic | Lipoprotein |
| 9991 | 10968 | r | 1 | 0008 | d | k | k | k | k | i | e | rnsD | 3 = Putative | Transport |
| 10968 | 13535 | r | 1 | 0009 | d | k | k | k | k | i | ie | rnsC | 3 = Putative | Transport |
| 13525 | 15141 | r | 1 | 0010 | d | k | k | k | k | i | e | rnsA | 3 = Putative | Transport |
| 15153 | 16799 | r | 1 | 0011 | d | k | k | k | k | i | ie | rnsB | 3 = Putative | Lipoprotein |
| 147625 | 148869 | f | 2 | 0113 | d | k | k | k | k | in | ie | glycosyltransferase, group 2 family protein | 3 = Putative | Lipid salvage and biogenesis |
| 148943 | 149863 | r | 2 | 0114 | d | k | k | k | k | in | i | glycosyltransferase, group 2 family protein | 3 = Putative | Lipid salvage and biogenesis |
| 277498 | 278319 | f | 3 | 0214 | d | k | k | k | k | in | i | phosphatidylglycerophosphatase | 3 = Putative | Lipid salvage and biogenesis |
| 335106 | 335903 | r | 3 | 0259 | k | k | k | k | k | e | e | nadK | 3 = Putative | Cofactor transport and salvage |
| 371137 | 371691 | f | 3 | 0291 | k | k | k | k | k | e | ie | ribF | 3 = Putative | Cofactor transport and salvage |
| 381322 | 381816 | r | 3 | 0301 | k | k | k | k | k | ie | i | rimP | 3 = Putative | Ribosome biogenesis |
| 387049 | 388077 | r | 3 | 0304 | k | k | k | k | k | e | e | cdsA transferase | 3 = Putative | Lipid salvage and biogenesis |
| 546124 | 547362 | f | 5 | 0441 | k | k | k | k | k | e | e | iscS | 3 = Putative | tRNA modification |
| 547365 | 547802 | f | 5 | 0442 | k | k | k | k | k | e | e | iscU | 3 = Putative | tRNA modification |
| 552795 | 553562 | f | 5 | 0448 | d | k | k | k | k | i | ie | trmH-like | 3 = Putative | rRNA modification |
| 613310 | 614248 | r | 5 | 0512 | k | k | k | k | k | e | e | plsC | 3 = Putative | Lipid salvage and biogenesis |
| 617662 | 618594 | r | 5 | 0517 | k | k | k | k | k | in | in | rluD | 3 = Putative | rRNA modification |
| 618575 | 619183 | r | 5 | 0518 | k | k | k | k | k | ie | ie | lspA | 3 = Putative | Protein export |
| 625316 | 626476 | r | 6 | 0523 | d | k | k | k | k | i | i | ftsA | 3 = Putative | Cell division |
| 751320 | 752504 | r | 6 | 0609 | k | k | k | k | k | e | e | dnaB | 3 = Putative | DNA replication |
| 762373 | 763212 | f | 6 | 0616 | d | k | k | k | k | i | e | fakB | 3 = Putative | Lipid salvage and biogenesis |
| 763223 | 764074 | f | 6 | 0617 | d | k | k | k | k | i | i | fakB | 3 = Putative | Lipid salvage and biogenesis |
| 816697 | 818298 | r | 7 | 0685 | k | k | k | k | k | i | e | ktrAB | 3 = Putative | Transport |
| 818377 | 819105 | f | 7 | 0686 | d | k | k | k | k | i | e | trkA | 3 = Putative | Transport |
| 844369 | 846117 | r | 7 | 0706 | k | k | k | k | k | i | i | ABC transporter, permease protein | 3 = Putative | Cofactor transport and salvage |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 846081 | 846830 | r | 7 | 0707 | k | k | k | k | e | i | ABC transporter, ATP-binding protein | 3 = Putative | Transport |
| 846844 | 848307 | r | 7 | 0708 | k | k | k | k | i | i | high affinity transport system protein p37 | 3 = Putative | Lipoprotein |
| 863454 | 864122 | r | 7 | 0732 | d | k | k | k | in | n | deoC: deoxyribose-phosphate aldolase | 3 = Putative | Metabolic process |
| 937338 | 938579 | r | 8 | 0799 | d | k | k | k | i | i | glyA, transferase | 3 = Putative | Cofactor transport and salvage |
| 961127 | 962557 | r | 8 | 0818 | k | k | k | k | ie | ie | lgt | 3 = Putative | Lipid salvage and biogenesis |
| 963482 | 965062 | r | 8 | 0820 | k | k | k | k | e | e | lgt | 3 = Putative | Lipid salvage and biogenesis |
| 1045710 | 1047287 | r | 8 | 0886 | d | k | k | k | i | i | gltP | 3 = Putative | Transport |
| 1047307 | 1048650 | r | 8 | 0887 | k | k | k | k | i | i | pyridine nucleotide-disulfide oxidoreductase | 3 = Putative | Redox homeostasis |
| 197743 | 199098 | f | 2 | 0154 | d | k | k | d | in | i | cytosol aminopeptidase family, catalytic domain protein | 3 = Putative | Proteolysis |
| 603363 | 604043 | r | 5 | 0494 | k | k | k | d | in | n | putative N-acetylmannosamine-6-P epimerase | 3 = Putative | Transport |
| 43531 | 43971 | r | 1 | 0026 | k | k | k | k | e | e | priB | 4 = Probable | DNA replication |
| 70903 | 71643 | r | 1 | 0044 | k | k | k | k | e | e | DNA polymerase III delta subunit | 4 = Probable | DNA replication |
| 140016 | 140231 | r | 2 | 0105 | k | k | k | k | e | i | xseB | 4 = Probable | DNA metabolism |
| 150311 | 151183 | r | 2 | 0115 | k | k | k | k | i | i | galU | 4 = Probable | Lipid salvage and biogenesis |
| 166761 | 167189 | f | 2 | 0128 | d | k | k | k | i | i | RNA polymerase delta subunit | 4 = Probable | Transcription |
| 180777 | 181406 | f | 2 | 0140 | k | k | k | k | i | ie | tdk | 4 = Probable | Nucleotide salvage |
| 184834 | 185334 | f | 2 | 0144 | k | k | k | k | e | i | tsaC | 4 = Probable | RNA modification |
| 292935 | 294260 | f | 3 | 0227 | d | k | k | k | i | i | pdhC | 4 = Probable | Metabolic process |
| 300902 | 302623 | f | 3 | 0233 | k | k | k | k | ie | ie | phosphoenolpyruvate-protein phosphotransferase | 4 = Probable | Glucose transport & catabolism |
| 302705 | 303169 | f | 3 | 0234 | k | k | k | k | ie | e | glucose-specific phosphotransferase enzyme IIA component | 4 = Probable | Glucose transport & catabolism |
| 307283 | 308470 | f | 3 | 4002 | k | k | k | k | i | i | thiI | 4 = Probable | tRNA modification |
| 327283 | 327756 | r | 3 | 0253 | k | k | k | k | ie | e | greA | 4 = Probable | Transcription |
| 332498 | 334249 | r | 3 | 0257 | k | k | k | k | ie | ie | rnjB | 4 = Probable | RNA metabolism |
| 418057 | 418815 | f | 4 | 0329 | k | k | k | k | i | n | Ribosomal large subunit pseudouridine synthase B | 4 = Probable | rRNA modification |
| 418825 | 419442 | f | 4 | 0330 | k | k | k | k | i | n | dgk | 4 = Probable | Nucleotide salvage |
| 435756 | 436316 | r | 4 | 0344 | k | k | k | k | e | e | Ppase | 4 = Probable | Metabolic process |
| 505101 | 506621 | f | 4 | 0407 | k | k | k | k | e | e | rpoD | 4 = Probable | Transcription |
| 511101 | 515255 | f | 4 | 0412 | k | k | k | k | e | e | secDF | 4 = Probable | Protein export |
| 515862 | 518126 | f | 4 | 0414 | d | k | k | k | i | n | relA | 4 = Probable | Regulation |
| 527248 | 528378 | f | 5 | 0425 | k | k | k | k | i | e | pstS | 4 = Probable | Lipoprotein |
| 550494 | 551777 | f | 5 | 0445 | k | k | k | k | e | e | gpi | 4 = Probable | Glucose transport & catabolism |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 614414 | 614746 | r | 5 | 0513 | k | k | k | k | k | e | e | acpS | 4 = Probable | Lipid salvage and biogenesis |
| 615883 | 616365 | r | 5 | 0515 | k | k | k | k | k | i | n | dctD | 4 = Probable | Nucleotide salvage |
| 651017 | 651619 | r | 6 | 0543 | k | k | k | k | k | e | e | grpE | 4 = Probable | Protein folding |
| 652648 | 654789 | r | 6 | 0545 | d | k | k | k | k | ie | ie | clpB | 4 = Probable | Proteolysis |
| 741755 | 743587 | f | 6 | 0600 | k | k | k | k | k | e | e | rnjA | 4 = Probable | RNA metabolism |
| 747929 | 749143 | r | 6 | 0606 | k | k | k | k | k | e | e | pgk | 4 = Probable | Glucose transport & catabolism |
| 750372 | 751310 | r | 6 | 0608 | k | k | k | k | k | e | e | dnaI | 4 = Probable | DNA replication |
| 756240 | 759203 | r | 6 | 0612 | k | k | k | k | k | e | ie | dnaE | 4 = Probable | DNA replication |
| 760651 | 761712 | r | 6 | 0614 | k | k | k | k | k | e | e | pncB | 4 = Probable | Cofactor transport and salvage |
| 764838 | 765059 | r | 6 | 0621 | k | k | k | k | k | ie | e | acpA | 4 = Probable | Lipid salvage and biogenesis |
| 781913 | 782311 | r | 6 | 0637 | k | k | k | k | k | e | e | rpsE | 4 = Probable | Translation |
| 787894 | 788904 | r | 6 | 0641 | k | k | k | k | k | e | e | ecfT | 4 = Probable | Cofactor transport and salvage |
| 788918 | 789829 | r | 6 | 0642 | k | k | k | k | k | e | e | ecfA | 4 = Probable | Cofactor transport and salvage |
| 789817 | 791043 | r | 6 | 0643 | k | k | k | k | k | e | e | ecfA | 4 = Probable | Cofactor transport and salvage |
| 794477 | 795118 | r | 6 | 0651 | k | k | k | k | k | e | e | adk | 4 = Probable | Nucleotide salvage |
| 798865 | 799254 | r | 6 | 0657 | k | k | k | k | k | e | e | rpsH | 4 = Probable | Translation |
| 799274 | 799459 | r | 6 | 0658 | k | k | k | k | k | e | e | rpsN | 4 = Probable | Translation |
| 799478 | 800020 | r | 6 | 0659 | k | k | k | k | k | e | e | rplE | 4 = Probable | Translation |
| 804121 | 804405 | r | 6 | 0669 | k | k | k | k | k | e | e | rplW | 4 = Probable | Translation |
| 815822 | 816688 | r | 7 | 0684 | d | k | k | k | k | i | e | folD | 4 = Probable | Cofactor transport and salvage |
| 820573 | 822030 | r | 7 | 0688 | k | k | k | k | k | e | e | egatA | 4 = Probable | Translation |
| 828297 | 828566 | r | 7 | 0694 | k | k | k | k | k | e | ie | ptsH | 4 = Probable | Glucose transport & catabolism |
| 828631 | 830799 | r | 7 | 0695 | d | k | k | k | k | i | i | pcrA | 4 = Probable | DNA replication |
| 864134 | 865810 | r | 7 | 0733 | d | k | k | k | k | i | i | pgcA | 4 = Probable | Lipid salvage and biogenesis |
| 878368 | 879021 | f | 7 | 0747 | d | k | k | k | k | i | i | punA | 4 = Probable | Nucleotide salvage |
| 910221 | 911240 | r | 7 | 0773 | d | k | k | k | k | i | ie | nrdF | 4 = Probable | Nucleotide salvage |
| 915336 | 917573 | f | 7 | 0779 | d | k | k | k | k | ie | ie | ptsG | 4 = Probable | Glucose transport & catabolism |
| 929590 | 929889 | r | 7 | 0789 | k | k | k | k | k | ie | ie | atpC | 4 = Probable | Transport |
| 929889 | 931316 | r | 7 | 0790 | k | k | k | k | k | i | i | atpD | 4 = Probable | Transport |
| 935214 | 936077 | r | 7 | 0796 | k | k | k | k | k | ie | e | atpB | 4 = Probable | Transport |
| 951098 | 951595 | r | 8 | 0807 | k | k | k | k | k | e | e | rplJ | 4 = Probable | Translation |
| 966789 | 967904 | r | 8 | 0823 | k | k | k | k | k | i | n | folC | 4 = Probable | Cofactor transport and salvage |
| 973028 | 973978 | f | 8 | 0826 | d | k | k | k | k | e | e | yqeN | 4 = Probable | DNA replication |
| 977064 | 978098 | f | 8 | 0831 | k | k | k | k | k | e | i | prs | 4 = Probable | Nucleotide salvage |
| 986041 | 986682 | f | 8 | 0840 | k | k | k | k | k | i | e | nusG | 4 = Probable | Transcription |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 1012008 | 1013969 | f | 8 | 0859 | k | k | k | k | k | e | i | topA | 4 = Probable | DNA topology |
| 1076838 | 1078028 | r | 1 | 0908 | k | k | k | k | k | e | e | misC | 4 = Probable | Protein export |
| 75393 | 75491 | r | 1 | 0049 | r | r | r | r | r | e | e | srpB | 5 = Equivalog | RNA |
| 92148 | 92256 | r | 1 | 0067 | r | r | r | r | r | ie | i | 5S rRNA | 5 = Equivalog | RNA |
| 92331 | 95225 | r | 1 | 0068 | r | r | r | r | r | ie | i | 23S rrna | 5 = Equivalog | RNA |
| 95457 | 96980 | r | 1 | 0069 | r | r | r | r | r | ie | i | 16S rRNA | 5 = Equivalog | RNA |
| 97263 | 97346 | r | 1 | 0070 | r | r | r | r | r | e | e | tRNA-Leu | 5 = Equivalog | RNA |
| 97349 | 97424 | r | 1 | 0071 | r | r | r | r | r | e | e | tRNA-Lys | 5 = Equivalog | RNA |
| 203879 | 204289 | f | 2 | 0158 | r | r | r | r | r | e | e | ssrA | 5 = Equivalog | RNA |
| 360219 | 360308 | f | 3 | 0280 | r | r | r | r | r | e | e | tRNA-Ser | 5 = Equivalog | RNA |
| 376293 | 376366 | f | 3 | 0295 | r | r | r | r | r | e | e | tRNA-Gly | 5 = Equivalog | RNA |
| 445958 | 446302 | f | 4 | 0356 | r | r | r | r | r | e | e | RNAse P | 5 = Equivalog | RNA |
| 464253 | 464329 | f | 4 | 0374 | r | r | r | r | r | e | e | tRNA-Arg | 5 = Equivalog | RNA |
| 526549 | 526633 | f | 5 | 0423 | r | r | r | r | r | e | i | tRNA-Leu | 5 = Equivalog | RNA |
| 612086 | 612174 | r | 5 | 0506 | r | r | r | r | r | e | e | tRNA-Leu | 5 = Equivalog | RNA |
| 612185 | 612260 | r | 5 | 0507 | r | r | r | r | r | e | e | tRNA-Lys | 5 = Equivalog | RNA |
| 612265 | 612339 | r | 5 | 0508 | r | r | r | r | r | e | e | tRNA-Gln | 5 = Equivalog | RNA |
| 612346 | 612429 | r | 5 | 0509 | r | r | r | r | r | e | e | tRNA-Tyr | 5 = Equivalog | RNA |
| 612436 | 612511 | r | 5 | 0510 | r | r | r | r | r | e | e | tRNA-Thr | 5 = Equivalog | RNA |
| 764110 | 764184 | r | 6 | 0618 | r | r | r | r | r | ie | ie | tRNA-Trp | 5 = Equivalog | RNA |
| 764222 | 764297 | r | 6 | 0619 | r | r | r | r | r | e | e | tRNA-Trp | 5 = Equivalog | RNA |
| 766603 | 766678 | r | 6 | 0624 | r | r | r | r | r | e | ie | tRNA-His | 5 = Equivalog | RNA |
| 778816 | 778892 | r | 6 | 0635 | r | r | r | r | r | e | e | tRNA-Ile | 5 = Equivalog | RNA |
| 813370 | 813445 | r | 7 | 0678 | r | r | r | r | r | e | e | tRNA-Thr | 5 = Equivalog | RNA |
| 813458 | 813533 | r | 7 | 0679 | r | r | r | r | r | e | e | tRNA-Val | 5 = Equivalog | RNA |
| 813541 | 813616 | r | 7 | 0680 | r | r | r | r | r | e | e | tRNA-Glu | 5 = Equivalog | RNA |
| 813624 | 813699 | r | 7 | 0681 | r | r | r | r | r | e | e | tRNA-Asn | 5 = Equivalog | RNA |
| 856724 | 856800 | f | 7 | 0717 | r | r | r | r | r | e | e | tRNA-Arg | 5 = Equivalog | RNA |
| 856848 | 856924 | f | 7 | 0718 | r | r | r | r | r | e | e | tRNA-Pro | 5 = Equivalog | RNA |
| 856935 | 857010 | f | 7 | 0719 | r | r | r | r | r | e | e | tRNA-Ala | 5 = Equivalog | RNA |
| 857015 | 857091 | f | 7 | 0720 | r | r | r | r | r | e | e | tRNA-Met | 5 = Equivalog | RNA |
| 857103 | 857179 | f | 7 | 0721 | r | r | r | r | r | e | e | tRNA-Met | 5 = Equivalog | RNA |
| 857222 | 857314 | f | 7 | 0722 | r | r | r | r | r | e | e | tRNA-Ser | 5 = Equivalog | RNA |
| 857337 | 857412 | f | 7 | 0723 | r | r | r | r | r | e | e | tRNA-Met | 5 = Equivalog | RNA |
| 857415 | 857491 | f | 7 | 0724 | r | r | r | r | r | e | e | tRNA-Asp | 5 = Equivalog | RNA |
| 857500 | 857575 | f | 7 | 0725 | r | r | r | r | r | e | i | tRNA-Phe | 5 = Equivalog | RNA |
| 975613 | 975687 | f | 8 | 0828 | r | r | r | r | r | e | e | tRNA-Cys | 5 = Equivalog | RNA |
| 1 | 1353 | f | 1 | 0001 | k | k | k | k | k | e | e | dnaA | 5 = Equivalog | DNA replication |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | |
|---|---|---|---|---|---|---|---|---|---|---|---|---|
| 1511 | 2638 | f | 1 | 0002 | k | k | k | k | e | e | DNA polymerase III, beta subunit | 5 = Equivalog | DNA replication |
| 2675 | 3217 | f | 1 | 0003 | k | k | k | k | i | i | rnmV | 5 = Equivalog | Ribosome biogenesis |
| 3207 | 4007 | f | 1 | 0004 | k | k | k | k | in | n | ksgA | 5 = Equivalog | rRNA modification |
| 5515 | 7419 | f | 1 | 0006 | k | k | k | k | e | e | gyrB | 5 = Equivalog | DNA topology |
| 7435 | 9939 | f | 1 | 0007 | k | k | k | k | e | e | gyrA | 5 = Equivalog | DNA topology |
| 16986 | 18515 | r | 1 | 0012 | k | k | k | k | e | ie | metRS | 5 = Equivalog | Translation |
| 43284 | 43511 | r | 1 | 0025 | k | k | k | k | e | e | rpsR | 5 = Equivalog | Translation |
| 43983 | 44396 | r | 1 | 0027 | k | k | k | k | e | e | rpsF | 5 = Equivalog | Translation |
| 68094 | 69299 | r | 1 | 0040 | k | k | k | k | e | e | tilS | 5 = Equivalog | tRNA modification |
| 71621 | 72262 | r | 1 | 0045 | k | k | k | k | e | e | tmk | 5 = Equivalog | Nucleotide salvage |
| 72265 | 72855 | r | 1 | 0046 | k | k | k | k | in | n | recR: recombination protein RecR | 5 = Equivalog | DNA repair |
| 72857 | 74863 | r | 1 | 0047 | k | k | k | k | e | e | DNA polymerase III, subunit gamma and tau | 5 = Equivalog | DNA replication |
| 86611 | 87879 | f | 1 | 0061 | k | k | k | k | e | e | serRS | 5 = Equivalog | Translation |
| 89274 | 90776 | f | 1 | 0064 | k | k | k | k | e | ie | lysRS | 5 = Equivalog | Translation |
| 90866 | 91174 | r | 1 | 0065 | k | k | k | k | e | e | trxA | 5 = Equivalog | Redox homeostasis |
| 104866 | 106230 | r | 1 | 0076 | k | k | k | k | e | ie | asnRS | 5 = Equivalog | Translation |
| 108243 | 109199 | r | 1 | 0079 | k | k | k | k | ie | ie | tsaD tRNA threonylcarbamoyla denosine. Found in tRNAs decoding ANN (ile, Met, Thr, Lys, Asn, Ser and Arg). | 5 = Equivalog | tRNA modification |
| 109715 | 111073 | f | 1 | 0081 | k | k | k | k | i | i | mnmE_trmE_thdF: tRNA modification GTPase TrmE | 5 = Equivalog | tRNA modification |
| 111124 | 111369 | r | 1 | 0082 | k | k | k | k | in | i | S20: ribosomal protein S20 | 5 = Equivalog | Translation |
| 127805 | 130639 | r | 1 | 0095 | k | k | k | k | in | ie | secA: preprotein translocase, SecA subunit | 5 = Equivalog | Protein export |
| 140221 | 141630 | r | 2 | 0106 | k | k | k | k | i | n | xseA, exodeoxyribonuclease VII, large subunit | 5 = Equivalog | DNA metabolism |
| 141632 | 142030 | r | 2 | 0107 | k | k | k | k | i | e | nusB: transcription antitermination factor NusB | 5 = Equivalog | Transcription |
| 151878 | 152639 | f | 2 | 0117 | k | k | k | k | ie | ie | plsY | 5 = Equivalog | Lipid salvage and biogenesis |
| 164067 | 165518 | f | 2 | 0126 | k | k | k | k | e | ie | gluRS | 5 = Equivalog | Translation |
| 167281 | 168879 | f | 2 | 0129 | k | k | k | k | e | ie | PyrG: CTP synthase | 5 = Equivalog | Nucleotide salvage |
| 170143 | 171036 | f | 2 | 0131 | k | k | k | k | e | e | fruc_bis_ald_: fructose-1,6-bisphosphate aldolase, class II | 5 = Equivalog | Glucose transport & catabolism |
| 177566 | 177844 | f | 2 | 0137 | k | k | k | k | ie | i | L31: ribosomal protein L31 | 5 = Equivalog | Translation |
| 181409 | 182503 | f | 2 | 0141 | k | k | k | k | e | ie | prfA: peptide chain release factor 1 | 5 = Equivalog | Translation |
| 182496 | 183344 | f | 2 | 0142 | k | k | k | k | i | i | PrmC | 5 = Equivalog | Translation |
| 187299 | 188828 | f | 2 | 0147 | k | k | k | k | e | e | bac_cardiolipin: cardiolipin synthase | 5 = Equivalog | Lipid salvage and biogenesis |
| 188952 | 189371 | f | 2 | 0148 | k | k | k | k | e | e | rpsL_bact: ribosomal protein S12 | 5 = Equivalog | Translation |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 189458 | 189925 | f | 2 | 0149 | k | k | k | k | e | e | rpsG_bact: ribosomal protein S7 | 5 = Equivalog | Translation |
| 189950 | 192019 | f | 2 | 0150 | k | k | k | k | e | e | EF-G: translation elongation factor G | 5 = Equivalog | Translation |
| 192151 | 193338 | f | 2 | 0151 | k | k | k | k | e | e | EF-Tu: translation elongation factor Tu | 5 = Equivalog | Translation |
| 209529 | 212219 | r | 2 | 0163 | k | k | k | k | e | e | alaRS | 5 = Equivalog | Translation |
| 262729 | 263088 | r | 3 | 0198 | k | k | k | k | e | e | rplT_bact: ribosomal protein L20 | 5 = Equivalog | Translation |
| 263107 | 263298 | r | 3 | 0199 | k | k | k | k | e | e | L35 | 5 = Equivalog | Translation |
| 263324 | 263869 | r | 3 | 0200 | k | k | k | k | e | e | infC: translation initiation factor IF-3 | 5 = Equivalog | Translation |
| 264058 | 264660 | r | 3 | 0201 | k | k | k | k | e | e | pept_deformyl: peptide deformylase | 5 = Equivalog | Translation |
| 264734 | 265291 | f | 3 | 0202 | k | k | k | k | i | i | 16S rRNA (guanine(966)-N(2))-methyltransferase RsmD | 5 = Equivalog | rRNA modification |
| 265294 | 266187 | f | 3 | 0203 | k | k | k | k | e | e | guanyl_kin: guanylate kinase | 5 = Equivalog | Nucleotide salvage |
| 276076 | 277431 | f | 3 | 0213 | k | k | k | k | e | e | eno: phosphopyruvate hydratase | 5 = Equivalog | Glucose transport & catabolism |
| 278758 | 279330 | f | 3 | 0216 | d | k | k | k | i | i | HGPRTase: hypoxanthine phosphoribosyltransferase | 5 = Equivalog | Nucleotide salvage |
| 283236 | 284216 | f | 3 | 0220 | k | k | k | k | e | e | PFKA_ATP: 6-phosphofructokinase | 5 = Equivalog | Glucose transport & catabolism |
| 284287 | 285723 | f | 3 | 0221 | k | k | k | k | e | ie | pyruv_kin: pyruvate kinase | 5 = Equivalog | Glucose transport & catabolism |
| 285988 | 287907 | f | 2 | 0222 | k | k | k | k | e | e | thrRS | 5 = Equivalog | Translation |
| 294279 | 296168 | f | 3 | 0228 | d | k | k | k | i | i | lipoamide_DH: dihydrolipoyl dehydrogenase | 5 = Equivalog | Metabolic process |
| 296190 | 297158 | f | 3 | 0229 | k | k | k | k | in | e | pta: phosphate acetyltransferase | 5 = Equivalog | Metabolic process |
| 297171 | 298352 | f | 3 | 0230 | k | k | k | k | in | i | ackA: acetate kinase | 5 = Equivalog | Metabolic process |
| 304607 | 305233 | r | 3 | 0238 | k | k | k | k | e | e | rpsD_bact: ribosomal protein S4 | 5 = Equivalog | Translation |
| 323325 | 323915 | r | 3 | 0247 | k | k | k | k | e | e | GTPase_YsxC: ribosome biogenesis GTP-binding protein YsxC, bsub homolog is essential | 5 = Equivalog | Ribosome biogenesis |
| 327879 | 329633 | r | 3 | 0254 | d | k | k | k | n | n | uvrC: excinuclease ABC subunit C | 5 = Equivalog | DNA repair |
| 336014 | 338632 | r | 3 | 0260 | k | k | k | k | e | e | valRS | 5 = Equivalog | Translation |
| 339335 | 340097 | r | 3 | 0262 | d | k | k | k | i | i | ribulose-phosphate 3-epimerase | 5 = Equivalog | Metabolic process |
| 340099 | 341001 | r | 3 | 0263 | d | k | k | k | i | i | ribosome small subunit-dependent GTPase A, bsub rsgA is not essential | 5 = Equivalog | Ribosome biogenesis |
| 344441 | 344857 | f | 3 | 0270 | k | k | k | k | e | e | T6A_YjeE: tRNA threonylcarbamoyl adenosine modification protein YjeE | 5 = Equivalog | tRNA modification |
| 361089 | 362513 | f | 3 | 0282 | k | k | k | k | e | e | proRS | 5 = Equivalog | Translation |
| 364056 | 365858 | f | 3 | 0285 | k | k | k | k | n | i | lepA: elongation factor 4 | 5 = Equivalog | Translation |
| 366707 | 368431 | r | 3 | 0287 | k | k | k | k | e | ie | aspRS | 5 = Equivalog | Translation |
| 368440 | 369684 | r | 3 | 0288 | k | k | k | k | e | ie | hisRS | 5 = Equivalog | Translation |
| 369869 | 370222 | f | 3 | 0289 | k | k | k | k | ie | ie | rbfA: ribosome-binding factor A | 5 = Equivalog | Ribosome biogenesis |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 370272 | 371150 | f | 3 | 0290 | k | k | k | k | k | n | n | TruB: tRNA pseudouridine(55) synthase | 5 = Equivalog | tRNA modification |
| 375967 | 376233 | f | 3 | 0294 | k | k | k | k | k | e | i | S15_bact: ribosomal protein S15 | 5 = Equivalog | Translation |
| 377127 | 378989 | r | 3 | 0297 | k | k | k | k | k | e | i | IF-2: translation initiation factor IF-2 | 5 = Equivalog | Translation |
| 379559 | 381313 | r | 3 | 0300 | k | k | k | k | k | ie | ie | nusA | 5 = Equivalog | Transcription |
| 382592 | 387040 | r | 3 | 0303 | k | k | k | k | k | e | e | polC_Gram_pos: DNA polymerase III, alpha subunit, Gram-positive type | 5 = Equivalog | DNA replication |
| 391003 | 392013 | f | 4 | 0308 | k | k | k | k | k | e | ie | trpRS | 5 = Equivalog | Translation |
| 400694 | 402664 | f | 4 | 0316 | d | k | k | k | k | i | i | tkt | 5 = Equivalog | Metabolic process |
| 417360 | 417989 | f | 4 | 0328 | k | k | k | k | k | e | ie | segregation and condensation protein B | 5 = Equivalog | Chromosome segregation |
| 438115 | 438777 | f | 4 | 0347 | k | k | k | k | k | i | i | cmk: cytidylate kinase | 5 = Equivalog | Nucleotide salvage |
| 438784 | 440091 | f | 4 | 0348 | k | k | k | k | k | e | e | GTPase_EngA: ribosome-associated GTPase EngA | 5 = Equivalog | Ribosome biogenesis |
| 448025 | 449554 | f | 4 | 0359 | k | k | k | k | k | e | ie | RNase_Y: ribonuclease Y | 5 = Equivalog | RNA metabolism |
| 449588 | 450931 | f | 4 | 0360 | k | k | k | k | k | e | ie | ffh: signal recognition particle protein | 5 = Equivalog | Protein export |
| 450935 | 451402 | f | 4 | 0361 | k | k | k | k | k | e | n | rlmH | 5 = Equivalog | rRNA modification |
| 451493 | 451771 | f | 4 | 0362 | k | k | k | k | k | e | e | ribosomal protein S16 | 5 = Equivalog | Translation |
| 451803 | 452297 | f | 4 | 0363 | k | k | k | k | k | e | e | 16S_RimM: 16S rRNA processing protein RimM | 5 = Equivalog | Ribosome biogenesis |
| 452299 | 453021 | f | 4 | 0364 | k | k | k | k | k | i | e | trmD: tRNA (guanine(37)-N(1))-methyltransferase | 5 = Equivalog | tRNA modification |
| 453023 | 453406 | f | 4 | 0365 | k | k | k | k | k | e | ie | rplS_bact: ribosomal protein L19 | 5 = Equivalog | Translation |
| 453505 | 454455 | f | 4 | 0366 | k | k | k | k | k | e | e | GTPase_YlqF: ribosome biogenesis GTP-binding protein YlqF | 5 = Equivalog | Ribosome biogenesis |
| 465510 | 466811 | f | 4 | 0377 | k | k | k | k | k | e | e | Obg_CgtA: Obg family GTPase CgtA | 5 = Equivalog | Ribosome biogenesis |
| 466813 | 467550 | f | 4 | 0378 | k | k | k | k | k | e | e | NAD+ synthetase | 5 = Equivalog | Cofactor transport and salvage |
| 467863 | 468960 | f | 4 | 0380 | k | k | k | k | k | e | ie | nicotinate (nicotinamide) nucleotide adenylyltransferase | 5 = Equivalog | Cofactor transport and salvage |
| 468965 | 469624 | f | 4 | 0381 | k | k | k | k | k | in | n | MTA/SAH-Nsdase: MTA/SAH nucleosidase | 5 = Equivalog | Cofactor transport and salvage |
| 473609 | 474736 | f | 4 | 0387 | k | k | k | k | k | e | e | trmU: tRNA (5-methylaminomethyl-2-thiouridylate)-methyltransferase | 5 = Equivalog | tRNA modification |
| 477610 | 478563 | f | 4 | 0390 | k | k | k | k | k | i | ie | fmt: methionyl-tRNA formyltransferase | 5 = Equivalog | Translation |
| 478650 | 479204 | f | 4 | 0391 | k | k | k | k | k | i | ie | efp: translation elongation factor P | 5 = Equivalog | Translation |
| 480950 | 483310 | f | 4 | 0394 | d | k | k | k | k | i | i | lon: endopeptidase La | 5 = Equivalog | Proteolysis |
| 499639 | 500133 | f | 4 | 0402 | k | k | k | k | k | e | ie | rRNA maturation RNase YbeY | 5 = Equivalog | Ribosome biogenesis |
| 500137 | 501042 | f | 4 | 0403 | k | k | k | k | k | i | ie | era: GTP-binding protein Era | 5 = Equivalog | Ribosome biogenesis |
| 501042 | 501791 | f | 4 | 0404 | k | k | k | k | k | i | n | reco: DNA repair protein RecO | 5 = Equivalog | DNA repair |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 501855 | 503225 | f | 4 | 0405 | k | k | k | k | k | e | e | glyRS | 5 = Equivalog | Translation |
| 503260 | 505098 | f | 4 | 0406 | k | k | k | k | k | e | e | dnaG | 5 = Equivalog | DNA replication |
| 515267 | 515779 | f | 4 | 0413 | k | k | k | k | k | e | e | apt: adenine phosphoribosyltransferase | 5 = Equivalog | Nucleotide salvage |
| 518163 | 521129 | r | 4 | 0415 | k | k | k | k | k | ie | i | chromosome segregation protein SMC | 5 = Equivalog | Chromosome segregation |
| 522415 | 523113 | r | 5 | 0418 | k | k | k | k | k | i | e | RNaseIII: ribonuclease III | 5 = Equivalog | RNA metabolism |
| 523103 | 524107 | r | 5 | 0419 | k | k | k | k | k | e | e | plsX: fatty acid/phospholipid synthesis protein PlsX | 5 = Equivalog | Lipid salvage and biogenesis |
| 526288 | 526485 | f | 5 | 0422 | k | k | k | k | k | e? | n | L28: ribosomal protein L28 | 5 = Equivalog | Translation |
| 528430 | 530520 | f | 5 | 0426 | k | k | k | k | k | i | e | phosphate ABC transporter, permease protein PstA, phosphate_pstC: phosphate ABC transporter, permease protein PstC | 5 = Equivalog | Transport |
| 530513 | 531322 | f | 5 | 0427 | k | k | k | k | k | i | e | phosphate ABC transporter, ATP-binding protein | 5 = Equivalog | Transport |
| 531331 | 532005 | f | 5 | 0428 | k | k | k | k | k | i | e | phoU_full: phosphate transport system regulatory protein PhoU | 5 = Equivalog | Transport |
| 532072 | 533301 | f | 5 | 0429 | k | k | kk | | k | e | e | ftsY: signal recognition particle-docking protein FtsY | 5 = Equivalog | Protein export |
| 534597 | 535760 | f | 5 | 0432 | d | k | k | k | k | e | i | metK: methionine adenosyltransferase | 5 = Equivalog | Cofactor transport and salvage |
| 536427 | 537743 | f | 5 | 0434 | k | k | k | k | k | i | n | gid_trmFO: tRNA:m(5)U-54 methyltransferase | 5 = Equivalog | tRNA modification |
| 537769 | 538698 | f | 5 | 0435 | k | k | k | k | k | i | n | manA: mannose-6-phosphate isomerase, class I | 5 = Equivalog | Carbon source transport & catabolism |
| 547795 | 548358 | f | 5 | 0443 | k | k | k | k | k | e? | n | 5-formyltetrahydrofolate cyclo-ligase | 5 = Equivalog | Cofactor transport and salvage |
| 556820 | 558751 | f | 5 | 0452 | k | k | k | k | k | e | e | DNA topoisomerase IV, B subunit | 5 = Equivalog | DNA topology |
| 558753 | 561449 | f | 5 | 0453 | k | k | k | k | k | e | e | DNA topoisomerase IV, A subunit | 5 = Equivalog | DNA topology |
| 582072 | 583028 | r | 5 | 0475 | d | k | k | k | k | i | ie | L-LDH-NAD: L-lactate dehydrogenase | 5 = Equivalog | Metabolic process |
| 590364 | 590528 | f | 5 | 0482 | k | k | k | k | k | e | e | S21p: ribosomal protein S21 | 5 = Equivalog | Translation |
| 608185 | 608466 | r | 5 | 0499 | k | k | k | k | k | e | e | L27: ribosomal protein L27 | 5 = Equivalog | Translation |
| 608785 | 609087 | r | 5 | 0501 | k | k | k | k | k | e | e | L21: ribosomal protein L21 | 5 = Equivalog | Translation |
| 619174 | 621921 | r | 5 | 0519 | k | k | k | k | k | e | e | ileRS | 5 = Equivalog | Translation |
| 626485 | 627411 | r | 6 | 0524 | k | k | k | k | k | i | i | rsmH, 16S rRNA m4C1402 | 5 = Equivalog | rRNA modification |
| 627420 | 627821 | r | 6 | 0525 | d | k | k | k | k | i | i | mraZ | 5 = Equivalog | Regulation |
| 627928 | 628107 | r | 6 | 0526 | k | k | k | k | k | i | i | rpmF_bact: ribosomal protein L32 | 5 = Equivalog | Translation |
| 628640 | 631024 | r | 6 | 0528 | k | k | k | k | k | e | e | pheRS | 5 = Equivalog | Translation |
| 631033 | 632085 | r | 6 | 0529 | k | k | k | k | k | e | e | cheRS | 5 = Equivalog | Translation |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 642339 | 644003 | r | 6 | 0535 | k | k | k | k | k | e | e | argRS | 5 = Equivalog | Translation |
| 644005 | 644553 | r | 6 | 0536 | k | k | k | k | k | e | e | frr: ribosome recycling factor | 5 = Equivalog | Translation |
| 644564 | 645277 | r | 6 | 0537 | k | k | k | k | k | e | e | pyrH_bact: UMP kinase | 5 = Equivalog | Nucleotide salvage |
| 646016 | 646903 | r | 6 | 0539 | k | k | k | k | k | e | e | tsf: translation elongation factor Ts | 5 = Equivalog | Translation |
| 646915 | 647793 | r | 6 | 0540 | k | k | k | k | k | e | e | rpsB_bact: ribosomal protein S2 | 5 = Equivalog | Translation |
| 648001 | 649119 | r | 6 | 0541 | d | k | k | k | k | e | e | DnaJ_bact: chaperone protein DnaJ | 5 = Equivalog | Protein folding |
| 649183 | 650958 | r | 6 | 0542 | k | k | k | k | k | e | e | prok_dnaK: chaperone protein DnaK | 5 = Equivalog | Protein folding |
| 651621 | 652643 | r | 6 | 0544 | k | k | k | k | k | e | e | hrcA: heat-inducible transcription repressor HrcA | 5 = Equivalog | Regulation |
| 749255 | 750271 | r | 6 | 0607 | k | k | k | k | k | e | e | GAPDH-I: glyceraldehyde-3-phosphate dehydrogenase, type I | 5 = Equivalog | Glucose transport & catabolism |
| 753496 | 756231 | r | 6 | 0611 | k | k | k | k | k | e | e | polA: DNA polymerase I | 5 = Equivalog | DNA replication |
| 759398 | 760642 | r | 6 | 0613 | k | k | k | k | k | e | e | tyrRS | 5 = Equivalog | Translation |
| 776264 | 778678 | r | 6 | 0634 | k | k | k | k | k | e | e | leuRS | 5 = Equivalog | Translation |
| 782311 | 782766 | r | 6 | 0638 | k | k | k | k | k | e | e | ribosomal protein L13 | 5 = Equivalog | Translation |
| 791151 | 791510 | r | 6 | 0644 | k | k | k | k | k | e | e | L17: ribosomal protein L17 | 5 = Equivalog | Translation |
| 791530 | 792483 | r | 6 | 0645 | k | k | k | k | k | e | e | rpoA: DNA-directed RNA polymerase, alpha subunit | 5 = Equivalog | Transcription |
| 792487 | 792876 | r | 6 | 0646 | k | k | k | k | k | e | e | bact_S11: 30S ribosomal protein S11 | 5 = Equivalog | Translation |
| 792902 | 793267 | r | 6 | 0647 | k | k | k | k | k | e | e | bact_S13: 30S ribosomal protein S13 | 5 = Equivalog | Translation |
| 793304 | 793417 | r | 6 | 0648 | k | k | k | k | k | e | e | rpmJ_bact: ribosomal protein L36 | 5 = Equivalog | Translation |
| 793486 | 793710 | r | 6 | 0649 | k | k | k | k | k | e | e | infA: translation initiation factor IF-1 | 5 = Equivalog | Translation |
| 793722 | 794477 | r | 6 | 0650 | k | k | k | k | k | e | e | met_pdase_I: methionine aminopeptidase, type I | 5 = Equivalog | Translation |
| 795246 | 796694 | r | 6 | 0652 | k | k | k | k | k | e | e | preprotein translocase, SecY subunit | 5 = Equivalog | Protein export |
| 796694 | 797131 | r | 6 | 0653 | k | k | k | k | k | i | e | rplO_bact: ribosomal protein L15 | 5 = Equivalog | Translation |
| 797150 | 797914 | r | 6 | 0654 | k | k | k | k | k | e | e | rpsE_bact: ribosomal protein S5 | 5 = Equivalog | Translation |
| 797933 | 798283 | r | 6 | 0655 | k | k | k | k | k | e | e | L18_bact: ribosomal protein L18 | 5 = Equivalog | Translation |
| 798309 | 798851 | r | 6 | 0656 | k | k | k | k | k | e | e | L6_bact: ribosomal protein L6 | 5 = Equivalog | Translation |
| 800039 | 800365 | r | 6 | 0660 | k | k | k | k | k | e | e | rplX_bact: ribosomal protein L24 | 5 = Equivalog | Translation |
| 800379 | 800747 | r | 6 | 0661 | k | k | k | k | k | e | e | rplN_bact: ribosomal protein L14 | 5 = Equivalog | Translation |
| 800763 | 801020 | r | 6 | 0662 | k | k | k | k | k | e | e | S17_bact: 30S ribosomal protein S17 | 5 = Equivalog | Translation |
| 801020 | 801436 | r | 6 | 0663 | k | k | k | k | k | e | e | L29: ribosomal protein L29 | 5 = Equivalog | Translation |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 801436 | 801849 | r | 6 | 0664 | k | k | k | k | k | e | e | rplP_bact: ribosomal protein L16 | 5 = Equivalog | Translation |
| 801852 | 802553 | r | 6 | 0665 | k | k | k | k | k | e | e | rpsC_bact: ribosomal protein S3 | 5 = Equivalog | Translation |
| 802571 | 802906 | r | 6 | 0666 | k | k | k | k | k | e | e | rplV_bact: ribosomal protein L22 | 5 = Equivalog | Translation |
| 802930 | 803196 | r | 6 | 0667 | k | k | k | k | k | e | e | rpsS_bact: ribosomal protein S19 | 5 = Equivalog | Translation |
| 803218 | 804066 | r | 6 | 0668 | k | k | k | k | k | e | e | rplB_bact: ribosomal protein L2 | 5 = Equivalog | Translation |
| 804405 | 805031 | r | 6 | 0670 | k | k | k | k | k | e | e | rplD_bact: 50S ribosomal protein L4 | 5 = Equivalog | Translation |
| 805044 | 805715 | r | 6 | 0671 | k | k | k | k | k | e | e | L3_bact: 50S ribosomal protein L3 | 5 = Equivalog | Translation |
| 805791 | 806099 | r | 6 | 0672 | k | k | k | k | k | e | e | rpsJ_bact: ribosomal protein S10 | 5 = Equivalog | Translation |
| 819132 | 820571 | r | 7 | 0687 | k | k | k | k | k | e | e | gatB: aspartyl/glutamyl-tRNA(Asn/Gln) amidotransferase, B subunit | 5 = Equivalog | Translation |
| 822030 | 822326 | r | 7 | 0689 | k | k | k | k | k | e | e | gatC: aspartyl/glutamyl-tRNA(Asn/Gln) amidotransferase, C subunit | 5 = Equivalog | Translation |
| 822328 | 824334 | r | 7 | 0690 | k | k | k | k | k | e | e | dnlj: DNA ligase, NAD-dependent | 5 = Equivalog | DNA replication |
| 857683 | 858417 | f | 7 | 0726 | k | k | k | k | k | ie | in | nagB: glucosamine-6-phosphate deaminase | 5 = Equivalog | Carbon source transport & catabolism |
| 858515 | 859261 | f | 7 | 0727 | k | k | k | k | k | e | e | tpiA, tim: triose-phosphate isomerase | 5 = Equivalog | Glucose transport & catabolism |
| 860093 | 861688 | f | 7 | 0729 | k | k | k | k | k | e | e | pgm_bpd_ind: phosphoglycerate mutase (2,3-diphosphoglycerate-independent) | 5 = Equivalog | Glucose transport & catabolism |
| 907590 | 909752 | r | 7 | 0771 | d | k | k | k | k | i | i | NrdE NrdA: ribonucleoside-diphosphate reductase, alpha subunit | 5 = Equivalog | Nucleotide salvage |
| 909739 | 910212 | r | 7 | 0772 | k | k | k | k | k | i | e | NrdI | 5 = Equivalog | Nucleotide salvage |
| 911539 | 911823 | f | 7 | 0774 | k | k | k | k | k | e | e | secG: preprotein translocase, SecG subunit | 5 = Equivalog | Protein export |
| 911859 | 913973 | f | 7 | 0775 | d | k | k | k | k | i | i | RNase_R: ribonuclease R | 5 = Equivalog | RNA metabolism |
| 913983 | 914429 | f | 7 | 0776 | k | k | k | k | k | e | e | smpB: SsrA-binding protein | 5 = Equivalog | Translation |
| 925156 | 927984 | r | 7 | 0787 | k | k | k | k | k | ie | e | ATPase-IIIB_Mg: magnesium-translocating P-type ATPase | 5 = Equivalog | Transport |
| 931325 | 932167 | r | 7 | 0791 | k | k | k | k | k | e | e | ATPsyn_F1gamma: ATP synthase F1, gamma subunit | 5 = Equivalog | Transport |
| 932169 | 933746 | r | 7 | 0792 | k | k | k | k | k | i | ie | atpA: ATP synthase F1, alpha subunit | 5 = Equivalog | Transport |
| 933758 | 934303 | r | 7 | 0793 | k | k | k | k | k | ie | e | ATP_synt_delta: ATP synthase F1, delta subunit subunit | 5 = Equivalog | Transport |
| 934305 | 934850 | r | 7 | 0794 | k | k | k | k | k | ie | ie | ATP_synt_b: ATP synthase F0, B | 5 = Equivalog | Transport |
| 934879 | 935184 | r | 7 | 0795 | k | k | k | k | k | ie | e | ATP_synt_c: ATP synthase F0, C subunit | 5 = Equivalog | Transport |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 936615 | 937238 | r | 8 | 0798 | d | k | k | k | k | in | i | upp: uracil phosphoribosyltransf5erase | 5 = Equivalog | Nucleotide salvage |
| 938563 | 939006 | r | 8 | 0800 | d | k | k | k | k | i | i | rpiB: ribose 5-phosphate isomerase B | 5 = Equivalog | Metabolic process |
| 941671 | 945438 | r | 8 | 0803 | k | k | k | k | k | e | e | rpoC_TIGR: DNA-directed RNA polymerase, beta' subunit | 5 = Equivalog | Transcription |
| 945450 | 949325 | r | 8 | 0804 | k | k | k | k | k | e | e | rpoB: DNA-directed RNA polymerase, beta subunit | 5 = Equivalog | Transcription |
| 950661 | 951029 | r | 8 | 0806 | k | k | k | k | k | e | e | L12: ribosomal protein L7/L12 | 5 = Equivalog | Translation |
| 951822 | 952502 | r | 8 | 0809 | k | k | k | k | k | i | i | rplA_bact: ribosomal protein L1 | 5 = Equivalog | Translation |
| 952502 | 952930 | r | 8 | 0810 | k | k | k | k | k | i | e | L11_bact: ribosomal protein L11 | 5 = Equivalog | Translation |
| 956226 | 957224 | f | 8 | 0813 | d | k | k | k | k | i | i | galE: UDP-glucose 4-epimerase GalE | 5 = Equivalog | Lipid salvage and biogenesis |
| 957238 | 958425 | f | 8 | 0814 | d | k | k | k | k | i | i | glf: UDP-GALP_mutase: UDP-galactopyranose mutase | 5 = Equivalog | Lipid salvage and biogenesis |
| 962566 | 963498 | r | 8 | 0819 | k | k | k | k | k | e | e | TRX reduct: thioredoxin-disulfide reductase | 5 = Equivalog | Redox homeostasis |
| 965073 | 966014 | r | 8 | 0821 | d | k | k | k | k | in | i | hpr-ser: HPr(Ser) kinase/phosphatase | 5 = Equivalog | Glucose transport & catabolism |
| 967897 | 970737 | r | 8 | 0824 | d | k | k | k | k | in | n | uvra: excinuclease ABC subunit A | 5 = Equivalog | DNA repair |
| 970746 | 972743 | r | 8 | 0825 | d | k | k | k | k | in | n | uvrb: excinuclease ABC subunit B | 5 = Equivalog | DNA repair |
| 978524 | 979084 | f | 8 | 0832 | k | k | k | k | k | e | ie | pth: aminoacyl-tRNA hydrolase | 5 = Equivalog | Translation |
| 979205 | 979648 | f | 8 | 0833 | k | k | k | k | k | ie | n | L9: ribosomal protein L9 | 5 = Equivalog | Translation |
| 979651 | 980967 | f | 8 | 0834 | k | k | k | k | k | e | e | dnaC | 5 = Equivalog | DNA replication |
| 983418 | 984743 | f | 8 | 0837 | k | k | k | k | k | e | e | cysRS | 5 = Equivalog | Translation |
| 985701 | 986024 | f | 8 | 0839 | k | k | k | k | k | e | e | secE_bact: preprotein translocase, SecE subunit | 5 = Equivalog | Protein export |
| 1029742 | 1030437 | r | 8 | 0874 | k | k | k | k | k | n | i | rsmG_gidB: | 5 = Equivalog | rRNA modification |
| 1030437 | 1031033 | r | 8 | 0875 | k | k | k | k | k | e | e | pgsA: CDP-diacylglycerol--glycerol-3-phosphate 3-phosphatidyltransferase | 5 = Equivalog | Lipid salvage and biogenesis |
| 1043673 | 1045562 | r | 8 | 0885 | k | k | k | k | k | i | i | gidA: tRNA uridine 5-carboxymethyl-aminomethyl modification enzyme GidA | 5 = Equivalog | modification tRNA |
| 1078046 | 1078375 | r | 1 | 0909 | k | k | k | k | k | e | e | rnpA: ribonuclease P protein component | 5 = Equivalog | RNA metabolism |
| 1078382 | 1078516 | r | 1 | 0910 | k | k | k | k | k | ie | e | rpmH_bact: ribosomal protein L34 | 5 = Equivalog | Translation |
| 280204 | 281721 | r | 3 | 0218 | d | k | k | d | k | n | e | glycerol_kin: glycerol kinase | 5 = Equivalog | Lipid salvage and biogenesis |
| 344859 | 345422 | f | 3 | 0271 | k | k | k | d | k | e | ie | T6A_YeaZ: tRNA threonylcarbamoyl adenosine modification protein YeaZ | 5 = Equivalog | tRNA modification |
| 176449 | 176562 | r | 2 | 0135 | j | j | j | j | j | x | x | x | 6 = not a real gene | x |
| 746854 | 746941 | x | x | 0603 | j | j | j | j | j | x | x | x, not Small nucleolar RNA snR69 | 6 = not a real gene | x |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 958511 | 958648 | f | 8 | 0815 | j | j | j | j | x | x | x | | 6 = not a real gene | x |
| 76906 | 77202 | r | 1 | 0051 | j | j | j | d | k | x | x | x | 6 = not a real gene | x |
| 27639 | 28301 | r | 1 | 0918 | j | j | j | j | j | x | x | imidazoleglycerol-phosphate dehydratase | 7 = plasmid | plasmid |
| 29270 | 31258 | f | 1 | 0913 | j | j | j | j | j | x | x | tetracycline resistance protein TetM | 7 = plasmid | plasmid |
| 637296 | 637404 | r | 6 | 0532 | i | r | d | r | r | e | e | 5S rRNA | 8 = deleted | RNA |
| 637479 | 640373 | r | 6 | 0533 | i | r | d | r | r | e | e | 23S rRNA | 8 = deleted | RNA |
| 640604 | 642127 | r | 6 | 0534 | i | r | d | r | r | e | e | 16S rRNA | 8 = deleted | RNA |
| 18716 | 20302 | f | 1 | 0013 | k | k | d | k | k | n | n | mycoides cluster lipoprotein, LppA/P72 family | 8 = deleted | Lipoprotein |
| 44601 | 44810 | r | 1 | 0028 | k | k | d | k | k | n | n | cspB, RNA/DNA chaperone | 8 = deleted | Unclear |
| 74945 | 75412 | r | 1 | 0048 | k | k | d | k | k | n | n | cytidine and deoxycytidylate deaminase zinc-binding region | 8 = deleted | Nucleotide salvage |
| 87981 | 88295 | f | 1 | 0062 | k | k | d | k | k | n | n | PF08921 domain protein | 8 = deleted | Unclear |
| 130730 | 131305 | f | 1 | 0096 | d | k | d | k | k | n | n | YigZ family protein | 8 = deleted | Proteolysis |
| 334375 | 335094 | r | 3 | 0258 | d | k | d | k | k | n | n | KR domain protein | 8 = deleted | Proteolysis |
| 357015 | 359429 | r | 3 | 0278 | d | k | d | k | k | n | n | phosphoenolpyruvate-dependent sugar PTS family porter, EIIA 2 component | 8 = deleted | Carbon source transport & catabolism |
| 359688 | 359975 | f | 3 | 0279 | d | k | d | k | k | n | n | hypothetical protein | 8 = deleted | Unclear |
| 363145 | 364032 | f | 3 | 0284 | k | k | d | k | k | n | n | hypothetical protein | 8 = deleted | Unclear |
| 421586 | 422005 | f | 4 | 0333 | k | k | d | k | k | n | n | hypothetical protein | 8 = deleted | Lipoprotein |
| 422445 | 422924 | f | 4 | 0334 | k | k | d | k | k | n | n | lipoprotein, putative | 8 = deleted | Lipoprotein |
| 423315 | 423773 | f | 4 | 0335 | k | k | d | k | k | n | n | lipoprotein, putative | 8 = deleted | Lipoprotein |
| 423939 | 424388 | f | 4 | 0336 | k | k | d | k | k | n | n | phosphoenolpyruvate-dependent sugar PTS family porter, EIIA 2 component | 8 = deleted | Transport |
| 441952 | 442461 | r | 4 | 0351 | d | k | d | k | k | n | n | recombination protein U | 8 = deleted | DNA repair |
| 444649 | 445872 | f | 4 | 0355 | d | k | d | k | k | n | n | PF03382 family protein | 8 = deleted | Lipoprotein |
| 458292 | 458597 | f | 4 | 0370 | k | k | d | k | k | n | n | single-strand binding family protein | 8 = deleted | DNA replication |
| 551789 | 552253 | f | 5 | 0446 | k | k | d | k | k | n | n | hypothetical protein | 8 = deleted | Unclear |
| 614766 | 615842 | r | 5 | 0514 | d | k | d | k | k | n | n | hypothetical protein | 8 = deleted | Unclear |
| 812217 | 813128 | f | 7 | 0677 | d | k | d | k | k | n | n | membrane protein, putative | 8 = deleted | Unclear |
| 975825 | 976622 | f | 8 | 0829 | d | k | d | k | k | n | n | putative deoxyribonuclease YcfH | 8 = deleted | Unclear |
| 1074592 | 1074750 | r | 1 | 0905 | k | k | d | k | k | n | n | ATPase, AAA domain protein | 8 = deleted | Unclear |
| 594474 | 595394 | f | 5 | 0487 | k | d | d | k | k | i | — | unknown | 8 = deleted | Unclear |
| 595403 | 596506 | f | 5 | 0488 | d | d | d | k | k | i | — | GTPase_YqeH: ribosome biogenesis GTPase YqeH, bsub ygeH is essential | 8 = deleted | Ribosome biogenesis |
| 25111 | 25215 | f | 1 | 0916 | j | j | d | j | j | x | x | RNAI | 8 = deleted | plasmid |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 25426 | 26286 | r | 1 | 0914 | j | j | d | j | j | x | x | beta-lactamase | 8 = deleted | plasmid |
| 26357 | 27529 | r | 1 | 0917 | j | j | d | j | j | x | x | transposase, mutator family | 8 = deleted | plasmid |
| 31535 | 34618 | f | 1 | 0915 | j | j | d | j | j | x | x | beta-galactosidase | 8 = deleted | plasmid |
| 46716 | 47582 | r | 1 | 0031 | d | k | d | d | k | n | n | Hsp33, targetted EF-Tu degradation | 8 = deleted | Proteolysis |
| 59775 | 60968 | f | 1 | 0035 | d | k | d | d | k | n | n | PF03382 family protein | 8 = deleted | Lipoprotein |
| 61277 | 62263 | f | 1 | 0036 | k | k | d | d | k | n | n | putative D-lactate dehydrogenase | 8 = deleted | Metabolic process |
| 62282 | 63406 | f | 1 | 0037 | d | k | d | d | k | n | n | transporter, auxin efflux carrier domain protein | 8 = deleted | Efflux |
| 63762 | 65045 | f | 1 | 0038 | d | k | d | d | k | n | n | AAA domain protein | 8 = deleted | Unclear |
| 107089 | 108219 | r | 1 | 0078 | k | k | d | d | k | n | n | alpha/beta hydrolase family protein | 8 = deleted | Unclear |
| 279390 | 280163 | r | 3 | 0217 | d | k | d | d | k | n | n | transporter, major intrinsic protein (MIP) family protein | 8 = deleted | Lipid salvage and biogenesis |
| 281738 | 282901 | r | 3 | 0219 | d | k | d | d | k | n | n | FAD dependent oxidoreductase | 8 = deleted | Lipid salvage and biogenesis |
| 521827 | 522282 | r | 5 | 0417 | k | k | d | d | d | n | n | PF13274 family protein | 8 = deleted | Mobile element & DNA restriction |
| 538691 | 539344 | f | 5 | 0436 | k | k | d | d | d | n | n | ung: uracil-DNA glycosylase | 8 = deleted | DNA repair |
| 583080 | 584237 | r | 5 | 0476 | d | k | d | d | d | n | n | nagA: N-acetylglucosamine-6-phosphate deacetylase | 8 = deleted | Carbon source transport & catabolism |
| 584406 | 585140 | f | 5 | 0477 | d | k | d | d | k | n | n | hypothetical protein | 8 = deleted | Unclear |
| 587539 | 589539 | f | 5 | 0480 | d | k | d | d | d | n | n | hypothetical protein | 8 = deleted | Unclear |
| 604970 | 605419 | r | 5 | 0496 | k | k | d | d | d | n | n | YhcH/YjgK/YiaL family protein | 8 = deleted | Unclear |
| 605428 | 607131 | r | 5 | 0497 | k | k | d | d | d | n | n | transporter, SSS family | 8 = deleted | Transport |
| 607133 | 608020 | r | 5 | 0498 | d | k | d | d | d | n | n | N-acetylneuraminate lyase | 8 = deleted | Carbon source transport & catabolism |
| 20317 | 21831 | f | 1 | 0014 | k | d | d | d | d | n | — | mycoides cluster lipoprotein, LppA/P72 family | 8 = deleted | Lipoprotein |
| 21864 | 23393 | f | 1 | 0015 | k | d | d | d | d | n | — | mycoides cluster lipoprotein, LppA/P72 family | 8 = deleted | Lipoprotein |
| 23411 | 25009 | f | 1 | 0016 | k | d | d | d | d | n | — | mycoides cluster lipoprotein, LppA/P72 family | 8 = deleted | Lipoprotein |
| 35234 | 35776 | f | 1 | 0921 | d | d | d | d | d | n | — | transposase | 8 = deleted | Mobile element & DNA restriction |
| 35914 | 36645 | f | 1 | 0922 | d | d | d | d | d | n | — | integrase core domain protein | 8 = deleted | Mobile element & DNA restriction |
| 36687 | 37673 | r | 1 | 0019 | d | d | d | d | d | n | — | mannitol dehydrogenase C-terminal domain protein | 8 = deleted | Carbon source transport & catabolism |
| 37674 | 38471 | r | 1 | 0020 | d | d | d | d | d | n | — | transcriptional regulator, RpiR family | 8 = deleted | Regulation |
| 38505 | 38921 | r | 1 | 0021 | d | d | d | d | d | n | — | phosphoenolpyruvate-dependent sugar PTS family porter, EIIA 2 component | 8 = deleted | Carbon source transport & catabolism |
| 38921 | 39679 | r | 1 | 0022 | d | d | d | d | d | n | — | sorbitol-6-phosphate 2-dehydrogenase | 8 = deleted | Carbon source transport & catabolism |
| 39679 | 41238 | r | 1 | 0023 | d | d | d | d | d | n | — | PTS system EIIC component | 8 = deleted | Carbon source transport & catabolism |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 41509 | 42891 | r | 1 | 0024 | d | d | d | d | d | n | — | divergent AAA domain protein | 8 = deleted | Unclear |
| 47674 | 50835 | r | 1 | 0032 | d | d | d | d | d | n | — | GnsA/GnsB family protein | 8 = deleted | Regulation |
| 67265 | 68110 | f | 1 | 0041 | k | d | d | d | d | n | — | hypothetical protein | 8 = deleted | Unclear |
| 75529 | 76491 | r | 1 | 0050 | k | d | d | d | d | n | — | guanosine monophosphate reductase | 8 = deleted | Nucleotide salvage |
| 77327 | 77647 | r | 1 | 0052 | d | d | d | d | d | n | — | hypothetical protein | 8 = deleted | Unclear |
| 77755 | 79851 | r | 1 | 0053 | d | d | d | d | d | n | — | putative peptidase | 8 = deleted | Lipoprotein |
| 80688 | 81977 | r | 1 | 0055 | d | d | d | d | d | n | — | hypothetical protein | 8 = deleted | Mobile element & DNA restriction |
| 81979 | 82818 | r | 1 | 0056 | d | d | d | d | d | n | — | DNA adenine methylase | 8 = deleted | Mobile element & DNA restriction |
| 83287 | 83577 | f | 1 | 0057 | d | d | d | d | d | n | — | hypothetical protein | 8 = deleted | Unclear |
| 83596 | 84177 | f | 1 | 0058 | d | d | d | d | d | n | — | hypothetical protein | 8 = deleted | Unclear |
| 84292 | 85410 | f | 1 | 0059 | d | d | d | d | d | n | — | alaDH: alanine dehydrogenase | 8 = deleted | Unclear |
| 97603 | 99669 | f | 1 | 0072 | d | d | d | d | d | n | — | beta-lactamase family protein | 8 = deleted | Unclear |
| 99702 | 102434 | r | 1 | 0073 | d | d | d | d | d | n | — | PhnE: phosphonate ABC transporter, permease protein PhnE | 8 = deleted | Transport |
| 102438 | 103190 | r | 1 | 0074 | k | d | d | d | d | n | — | ABC_phnC: phosphonate ABC transporter, ATP-binding protein | 8 = deleted | Transport |
| 103204 | 104574 | r | 1 | 0075 | k | d | d | d | d | n | — | lipoprotein, putative | 8 = deleted | Lipoprotein |
| 111503 | 112138 | r | 1 | 0083 | k | d | d | d | d | in | — | hypothetical protein | 8 = deleted | Unclear |
| 112555 | 113967 | r | 1 | 0084 | d | d | d | d | d | n | — | lipoprotein, putative | 8 = deleted | Lipoprotein |
| 114118 | 116367 | r | 1 | 0085 | d | d | d | d | d | n | — | lipoprotein, putative | 8 = deleted | Lipoprotein |
| 116412 | 117539 | r | 1 | 0086 | d | d | d | d | d | n | — | hypothetical protein | 8 = deleted | Lipoprotein |
| 118095 | 118508 | r | 1 | 0087 | d | d | d | d | d | n | — | lipoprotein, putative | 8 = deleted | Lipoprotein |
| 118767 | 120617 | r | 1 | 0088 | d | d | d | d | d | n | — | hypothetical protein | 8 = deleted | Unclear |
| 120876 | 122567 | r | 1 | 0089 | d | d | d | d | d | n | — | lipoprotein, putative | 8 = deleted | Lipoprotein |
| 122730 | 123332 | r | 1 | 0923 | k | d | d | d | d | n | — | lipoprotein, putative | 8 = deleted | Lipoprotein |
| 123560 | 126049 | r | 1 | 0092 | d | d | d | d | d | n | — | lipoprotein, putative | 8 = deleted | Lipoprotein |
| 126220 | 126990 | r | 1 | 0093 | d | d | d | d | d | n | — | lipoprotein, putative | 8 = deleted | Lipoprotein |
| 132495 | 133511 | f | 1 | 0098 | d | d | d | d | d | n | — | CCATC-recognizing TypeIIrestrictionmodification | 8 = deleted | Mobile element & DNA restriction |
| 133501 | 134418 | f | 1 | 0099 | d | d | d | d | d | n | — | CCATC-recognizing TypeIIrestrictionmodification | 8 = deleted | Mobile element & DNA restriction |
| 134396 | 135979 | f | 1 | 0100 | d | d | d | d | d | n | — | CCATC-recognizing TypeIIrestrictionmodification | 8 = deleted | Mobile element & DNA restriction |
| 136419 | 137714 | f | 2 | 0101 | d | d | d | d | d | n | — | AAA domain protein | 8 = deleted | Unclear |
| 138374 | 138649 | f | 2 | 0102 | k | d | d | d | d | in | — | hypothetical protein | 8 = deleted | Unclear |
| 138651 | 139208 | f | 2 | 0103 | k | d | d | d | d | n | — | ytaG | 8 = deleted | Cofactor transport and salvage |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 139210 | 140016 | r | 2 | 0104 | k | d | d | d | d | n | — | ribosomal RNA large subunit methyltransferase J | 8 = deleted | rRNA modification |
| 144042 | 144794 | r | 2 | 0110 | k | d | d | d | d | n | — | riboflavin kinase/FAD synthetase | 8 = deleted | Cofactor transport and salvage |
| 144869 | 144944 | r | 2 | 0111 | r | d | d | d | d | n | — | tRNA-Lys | 8 = deleted | RNA |
| 145008 | 147287 | r | 2 | 0112 | d | d | d | d | d | n | — | peptidase, S41 family | 8 = deleted | Proteolysis |
| 152703 | 154241 | f | 2 | 0118 | d | d | d | d | d | n | — | ccmA: heme ABC exporter, ATP-binding protein CcmA | 8 = deleted | Transport |
| 154271 | 155068 | r | 2 | 0119 | d | d | d | d | d | n | — | hydrolase, TatD family | 8 = deleted | Unclear |
| 155264 | 156490 | f | 2 | 0120 | d | d | d | d | d | n | — | threonine ammonia-lyase | 8 = deleted | Unclear |
| 156705 | 158285 | f | 2 | 0121 | d | d | d | d | d | n | — | membrane protein, putative | 8 = deleted | Unclear |
| 158297 | 159157 | f | 2 | 0122 | d | d | d | d | d | n | — | alpha/beta hydrolase family protein | 8 = deleted | Unclear |
| 159440 | 160150 | f | 2 | 0123 | d | d | d | d | d | n | — | lipoprotein, putative | 8 = deleted | Lipoprotein |
| 160552 | 161883 | f | 2 | 0124 | d | d | d | d | d | n | — | membrane protein, putative | 8 = deleted | Carbon source transport & catabolism |
| 162231 | 163934 | f | 2 | 0125 | d | d | d | d | d | n | — | PTS system EIIC component | 8 = deleted | Carbon source transport & catabolism |
| 169010 | 169984 | f | 2 | 0130 | d | d | d | d | d | n | — | PF03382 family protein | 8 = deleted | Lipoprotein |
| 174619 | 176106 | r | 2 | 0134 | d | d | d | d | d | n | — | transporter, major facilitator family protein | 8 = deleted | Transport |
| 176702 | 177406 | f | 2 | 0136 | d | d | d | d | d | n | — | glycerophosphodiester phosphodiesterase family protein | 8 = deleted | Lipid salvage and biogenesis |
| 193471 | 195336 | f | 2 | 0152 | d | d | d | d | d | in | — | putative PTS system IIBC component | 8 = deleted | Transport |
| 195320 | 197590 | f | 2 | 0153 | d | d | d | d | d | n | — | glycoside hydrolase, family 31 | 8 = deleted | Carbon source transport & catabolism |
| 200904 | 201506 | f | 2 | 0155 | d | d | d | d | d | n | — | hypothetical protein | 8 = deleted | Unclear |
| 201664 | 202329 | r | 2 | 0156 | k | d | d | d | d | n | — | tRNA (guanine-N(7)-)-methyltransferase | 8 = deleted | tRNA modification |
| 202331 | 203734 | r | 2 | 0157 | d | d | d | d | d | n | — | mgtE: magnesium transporter | 8 = deleted | Transport |
| 204414 | 206543 | f | 2 | 0159 | d | d | d | d | d | n | — | transglutaminase-like protein | 8 = deleted | Lipoprotein |
| 206563 | 207315 | r | 2 | 0160 | d | d | d | d | d | n | — | nucleotidyl transferase, PF08843 family | 8 = deleted | Unclear |
| 207402 | 207998 | r | 2 | 0161 | d | d | d | d | d | n | — | PF13338 domain protein | 8 = deleted | Unclear |
| 208209 | 209415 | r | 2 | 0162 | d | d | d | d | d | n | — | PF03382 family protein | 8 = deleted | Lipoprotein |
| 222395 | 223690 | r | 2 | 0170 | d | d | d | d | d | n | — | AAA domain protein | 8 = deleted | Unclear |
| 223785 | 225089 | r | 2 | 0171 | d | d | d | d | d | n | — | AAA domain protein | 8 = deleted | Unclear |
| 225321 | 226202 | f | 2 | 0172 | d | d | d | d | d | n | — | Cof-like hydrolase | 8 = deleted | Unclear |
| 226236 | 227933 | r | 2 | 0173 | k | d | d | d | d | n | — | mycoides cluster lipoprotein, LppA/P72 family | 8 = deleted | Lipoprotein |
| 228150 | 228296 | f | 2 | 0174 | d | d | d | d | d | n | — | haloacid dehalogenase-like hydrolase domain protein | 8 = deleted | Unclear |
| 228333 | 230015 | r | 2 | 0175 | d | d | d | d | d | n | — | mycoides cluster lipoprotein, LppA/P72 family | 8 = deleted | Lipoprotein |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 230125 | 230754 | r | 2 | 0176 | k | d | d | d | d | n | — | beta-phosphoglucomutase | 8 = deleted | Carbon source transport & catabolism |
| 230754 | 232553 | r | 2 | 0177 | d | d | d | d | d | n | — | neopullulanase | 8 = deleted | Unclear |
| 232672 | 234468 | r | 2 | 0178 | d | d | d | d | d | n | — | neopullulanase | 8 = deleted | Unclear |
| 234726 | 236525 | f | 2 | 0179 | d | d | d | d | d | n | — | lipoprotein, putative | 8 = deleted | Lipoprotein |
| 236820 | 238610 | f | 2 | 0180 | d | d | d | d | d | n | — | lipoprotein, putative | 8 = deleted | Lipoprotein |
| 238692 | 239183 | f | 2 | 0181 | d | d | d | d | d | n | — | hypothetical protein | 8 = deleted | Unclear |
| 239198 | 241615 | f | 2 | 0182 | d | d | d | d | d | n | — | ABC transporter, permease protein | 8 = deleted | Carbon source transport & catabolism |
| 241630 | 244170 | f | 2 | 0183 | d | d | d | d | d | n | — | ABC transporter, permease protein | 8 = deleted | Carbon source transport & catabolism |
| 244172 | 245257 | f | 2 | 0184 | d | d | d | d | d | n | — | putative spermidine/putrescine ABC transporter, ATP-binding protein PotA | 8 = deleted | Carbon source transport & catabolism |
| 245365 | 247662 | f | 2 | 0185 | d | d | d | d | d | in | — | glycoside hydrolase, family 65, central catalytic domain protein | 8 = deleted | Carbon source transport & catabolism |
| 247664 | 249268 | f | 2 | 0186 | d | d | d | d | d | n | — | putative glucan 1,6-alpha-glucosidase | 8 = deleted | Carbon source transport & catabolism |
| 249291 | 250010 | f | 2 | 0187 | k | d | d | d | d | n | — | UbiC transcription regulator-associated domain protein | 8 = deleted | Regulation |
| 250039 | 251832 | r | 2 | 0188 | d | d | d | d | d | n | — | pepF: oligoendopeptidase F | 8 = deleted | Proteolysis |
| 251832 | 252515 | r | 2 | 0189 | d | d | d | d | d | n | — | hypothetical protein | 8 = deleted | Unclear |
| 252531 | 253886 | r | 2 | 0190 | d | d | d | d | d | n | — | cytosol aminopeptidase family, catalytic domain protein | 8 = deleted | Proteolysis |
| 253998 | 254180 | r | 2 | 0191 | d | d | d | d | d | e | — | hypothetical protein | 8 = deleted | Unclear |
| 254459 | 255079 | f | 2 | 0192 | d | d | d | d | d | n | — | chromate transport protein | 8 = deleted | Transport |
| 255079 | 255756 | f | 2 | 0193 | d | d | d | d | d | n | — | chromate transport protein | 8 = deleted | Transport |
| 255890 | 256849 | f | 2 | 0194 | d | d | d | d | d | n | — | Abi-like protein | 8 = deleted | Unclear |
| 266177 | 267436 | f | 3 | 0204 | k | d | d | d | d | n | — | rsmB: 16S rRNA (cytosine(967)-C(5))-methyltransferase | 8 = deleted | rRNA modification |
| 267440 | 269269 | r | 3 | 0205 | d | d | d | d | d | n | — | TypA_BipA: GTP-binding protein TypA/BipA | 8 = deleted | Translation |
| 269514 | 270271 | f | 3 | 0206 | d | d | d | d | d | n | — | lipoprotein, putative | 8 = deleted | Lipoprotein |
| 270334 | 271125 | f | 3 | 0207 | d | d | d | d | d | n | — | hypothetical protein | 8 = deleted | Lipoprotein |
| 271254 | 272045 | f | 3 | 0208 | d | d | d | d | d | n | — | PF03382 family protein | 8 = deleted | Lipoprotein |
| 272099 | 273016 | r | 3 | 0209 | k | d | d | d | d | n | — | N-acetylmuramic acid 6-phosphate etherase | 8 = deleted | Carbon source transport & catabolism |
| 273009 | 274706 | r | 3 | 0210 | k | d | d | d | d | n | — | PTS system EIIC component | 8 = deleted | Carbon source transport & catabolism |
| 274828 | 275661 | r | 3 | 0211 | k | d | d | d | d | n | — | SIS domain protein | 8 = deleted | Regulation |
| 275665 | 275868 | r | 3 | 0212 | k | d | d | d | d | n | — | hypothetical protein | 8 = deleted | Unclear |
| 288390 | 289754 | f | 3 | 0223 | d | d | d | d | d | n | — | putative NADH oxidase | 8 = deleted | Redox homeostasis |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 289757 | 290761 | f | 3 | 0224 | d | d | d | d | d | n | — | lipoyltransferase and lipoate-protein ligase | 8 = deleted | Metabolic process |
| 290805 | 291917 | f | 3 | 0225 | d | d | d | d | d | n | — | PDH_E1_alph_x: pyruvate dehydrogenase (acetyl-transferring) Ecomponent, alpha subunit | 8 = deleted | Metabolic process |
| 291917 | 292906 | f | 3 | 0226 | d | d | d | d | d | n | — | K00162 pyruvate dehydrogenase E1 component | 8 = deleted | Metabolic process |
| 298421 | 300376 | f | 3 | 0231 | d | d | d | d | d | n | — | putative lipoprotein | 8 = deleted | Lipoprotein |
| 300386 | 300808 | f | 3 | 0232 | d | d | d | d | k | n | e | coaD_prev_kdtB: pantetheine-phosphate adenylyltransferase | 8 = deleted | Cofactor transport and salvage |
| 303533 | 304159 | f | 3 | 0236 | d | d | d | d | d | n | — | dha_L_ycgS: dihydroxyacetone kinase, L subunit | 8 = deleted | Metabolic process |
| 304167 | 304562 | f | 3 | 0237 | d | d | d | d | d | n | — | domain | 8 = deleted | Metabolic process |
| 308601 | 311333 | f | 3 | 0241 | d | d | d | d | 2 | n | — | hypothetical protein | 8 = deleted | Unclear |
| 311451 | 313136 | f | 3 | 0242 | d | d | d | d | d | n | — | hypothetical protein | 8 = deleted | Unclear |
| 313147 | 315438 | f | 3 | 0243 | d | d | d | d | d | n | — | PF03382 family protein | 8 = deleted | Lipoprotein |
| 315501 | 317768 | f | 3 | 0244 | d | d | d | d | d | n | — | PF03382 family protein | 8 = deleted | Lipoprotein |
| 318242 | 320383 | f | 3 | 0245 | d | d | d | d | k | n | — | PTS system EIIC component domain protein | 8 = deleted | Transport |
| 320410 | 323316 | r | 3 | 0246 | d | d | d | d | k | in | — | putative calcium-translocating P-type ATPase, PMCA-type | 8 = deleted | Transport |
| 325823 | 326515 | f | 3 | 0251 | d | d | d | d | k | n | — | hypothetical protein | 8 = deleted | Unclear |
| 326516 | 327238 | r | 3 | 0252 | d | d | d | d | k | n | — | NAD(P)H-binding protein, PF13460 family | 8 = deleted | Redox homeostasis |
| 329643 | 330704 | r | 3 | 0255 | d | d | d | d | d | n | — | hypothetical protein | 8 = deleted | Unclear |
| 330770 | 332392 | r | 3 | 0256 | k | d | d | d | k | n | — | amino acid permease | 8 = deleted | Transport |
| 338719 | 339345 | r | 3 | 0261 | d | d | d | d | d | n | — | thiamine diphosphokinase | 8 = deleted | Cofactor transport and salvage |
| 342126 | 342883 | r | 3 | 0268 | d | d | d | d | d | n | — | phosphoprotein phosphatase | 8 = deleted | Unclear |
| 342912 | 344321 | r | 3 | 0269 | d | d | d | d | d | n | — | hypothetical protein | 8 = deleted | Unclear |
| 345458 | 350779 | r | 3 | 0272 | d | d | d | d | d | n | — | efflux ABC transporter, permease protein | 8 = deleted | Efflux |
| 350992 | 354132 | f | 3 | 0273 | d | d | d | d | d | n | — | hypothetical protein | 8 = deleted | Unclear |
| 354147 | 354761 | f | 3 | 0274 | d | d | d | d | d | n | — | lipoprotein, putative | 8 = deleted | Lipoprotein |
| 354901 | 355422 | f | 3 | 0275 | d | d | d | d | k | n | — | lipoprotein, putative | 8 = deleted | Lipoprotein |
| 355682 | 356302 | f | 3 | 0276 | d | d | d | d | d | n | — | lipoprotein, putative | 8 = deleted | Lipoprotein |
| 356463 | 356975 | f | 3 | 0277 | k | d | d | d | d | n | — | lipoprotein, putative | 8 = deleted | Lipoprotein |
| 371714 | 373759 | r | 3 | 0292 | d | d | d | d | d | n | — | peptidase, S41 family | 8 = deleted | Proteolysis |
| 373784 | 375754 | r | 3 | 0293 | k | d | d | d | d | n | — | putative lipoprotein | 8 = deleted | Lipoprotein |
| 389506 | 390282 | r | 4 | 0306 | d | d | d | d | d | n | — | hypothetical protein | 8 = deleted | Unclear |
| 390558 | 390911 | f | 4 | 0307 | k | d | d | d | d | n | — | integrase core domain protein | 8 = deleted | Mobile element & DNA restriction |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 392042 | 392911 | r | 4 | 0309 | k | d | d | d | d | n | — | hypothetical protein | 8 = deleted | Unclear |
| 393024 | 393824 | f | 4 | 0310 | d | d | d | d | d | n | — | hypothetical protein | 8 = deleted | Unclear |
| 393879 | 394955 | r | 4 | 0311 | d | d | d | d | d | n | — | RmuC domain protein | 8 = deleted | Unclear |
| 395171 | 397891 | f | 4 | 0312 | d | d | d | d | d | n | — | papain family cysteine protease | 8 = deleted | Unclear |
| 398248 | 399522 | f | 4 | 0313 | k | d | d | d | d | n | — | putative RNA:m(5)U-54 methyltransferase | 8 = deleted | tRNA modification |
| 402993 | 404537 | f | 4 | 0318 | d | d | d | d | d | n | — | SNF2 family N-terminal domain protein | 8 = deleted | Unclear |
| 404627 | 407524 | f | 4 | 0319 | d | d | d | d | d | n | — | transglutaminase-like protein | 8 = deleted | Lipoprotein |
| 407532 | 408329 | f | 4 | 0320 | d | d | d | d | d | n | — | Ndr family protein | 8 = deleted | Acylglycerol breakdown |
| 408482 | 408910 | f | 4 | 0321 | d | d | d | d | d | n | — | lipoprotein, putative | 8 = deleted | Lipoprotein |
| 409235 | 410692 | f | 4 | 0322 | d | d | d | d | d | n | — | divergent AAA domain protein | 8 = deleted | Unclear |
| 410710 | 412203 | r | 4 | 0323 | d | d | d | d | d | n | — | lipoprotein, putative | 8 = deleted | Lipoprotein |
| 412372 | 412896 | r | 4 | 0324 | d | d | d | d | d | n | — | PF03382 family protein | 8 = deleted | Lipoprotein |
| 419454 | 420167 | f | 4 | 0331 | d | d | d | d | d | n | — | putative transcriptional regulator, YeeN | 8 = deleted | Regulation |
| 424400 | 426208 | f | 4 | 0337 | d | d | d | d | d | n | — | PTS system sugar-specific permease component | 8 = deleted | Transport |
| 427501 | 429321 | f | 4 | 0339 | k | d | d | d | d | n | — | Na+ ABC transporter, ATP-binding component | 8 = deleted | Transport |
| 429337 | 431127 | f | 4 | 0340 | k | d | d | d | d | n | — | membrane protein, putative | 8 = deleted | Transport |
| 431156 | 432556 | f | 4 | 0341 | k | d | d | d | d | n | — | lipoprotein, putative | 8 = deleted | Lipoprotein |
| 432682 | 434868 | f | 4 | 0342 | d | d | d | d | d | n | — | hypothetical protein | 8 = deleted | Lipoprotein |
| 435005 | 435700 | f | 4 | 0343 | k | d | d | d | d | n | — | hypothetical protein | 8 = deleted | Unclear |
| 440093 | 441082 | f | 4 | 0349 | k | d | d | d | d | n | — | NAD-dependent glycerol-3-phosphate dehydrogenase N-terminal | 8 = deleted | Metabolic process |
| 443061 | 444476 | f | 4 | 0354 | d | d | d | d | d | n | — | PF03382 family protein | 8 = deleted | Lipoprotein |
| 446339 | 446809 | f | 4 | 0357 | d | d | d | d | d | n | — | competence/damage-inducible protein CinA | 8 = deleted | Unclear |
| 446852 | 447889 | f | 4 | 0358 | d | d | d | d | d | n | — | recA: protein RecA | 8 = deleted | DNA repair |
| 454449 | 455072 | f | 4 | 0367 | d | d | d | d | d | n | — | ribonuclease HII | 8 = deleted | DNA replication |
| 455094 | 456890 | r | 4 | 0368 | d | d | d | d | d | n | — | rhodanese-like protein | 8 = deleted | Unclear |
| 456893 | 458131 | r | 4 | 0369 | d | d | d | d | d | n | — | sulfur transport | 8 = deleted | Transport |
| 470394 | 471113 | f | 4 | 0383 | k | d | d | d | d | n | — | lipoprotein, putative | 8 = deleted | Lipoprotein |
| 471190 | 471927 | f | 4 | 0384 | d | d | d | d | d | n | — | lipoprotein, putative | 8 = deleted | Lipoprotein |
| 471937 | 472617 | f | 4 | 0385 | k | d | d | d | d | n | — | lipoprotein, putative | 8 = deleted | Lipoprotein |
| 472656 | 473501 | f | 4 | 0386 | d | d | d | d | d | in | — | lipoprotein, putative | 8 = deleted | Lipoprotein |
| 479541 | 480827 | f | 4 | 0393 | d | d | d | d | d | n | — | tig: trigger factor | 8 = deleted | Translation |
| 483409 | 484644 | f | 4 | 0395 | d | d | d | d | d | n | — | MgsA AAA+ ATPase family protein | 8 = deleted | Unclear |
| 484673 | 486898 | r | 4 | 0396 | d | d | d | d | d | n | — | transglutaminase-like protein | 8 = deleted | Lipoprotein |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 486949 | 489240 | r | 4 | 0397 | d | d | d | d | d | n | — | transglutaminase-like protein | 8 = deleted | Lipoprotein |
| 553645 | 554187 | f | 5 | 0449 | d | d | d | d | d | n | — | transposase | 8 = deleted | Mobile element & DNA restriction |
| 554325 | 555056 | f | 5 | 0450 | d | d | d | d | d | n | — | integrase core domain protein | 8 = deleted | Mobile element & DNA restriction |
| 561557 | 563740 | f | 5 | 0454 | k | d | d | d | d | n | — | putative helicase, RecD/TraA family | 8 = deleted | DNA repair |
| 563782 | 565299 | r | 5 | 0455 | d | d | d | d | d | n | — | hypothetical protein | 8 = deleted | Unclear |
| 565789 | 566184 | f | 5 | 0924 | d | d | d | d | d | n | — | hypothetical protein | 8 = deleted | Unclear |
| 566641 | 570003 | f | 5 | 0460 | d | d | d | d | d | e | — | PF03382 family protein | 8 = deleted | Unclear |
| 570054 | 570785 | r | 5 | 0461 | d | d | d | d | d | n | — | integrase core domain protein | 8 = deleted | Mobile element & DNA restriction |
| 570923 | 571465 | r | 5 | 0462 | d | d | d | d | d | n | — | transposase | 8 = deleted | Mobile element & DNA restriction |
| 571530 | 572708 | r | 5 | 0463 | d | d | d | d | d | n | — | oxidoreductase, FAD/FMN dependent | 8 = deleted | Redox homeostasis |
| 572708 | 573745 | r | 5 | 0464 | d | d | d | d | d | n | — | lipoyltransferase and lipoate-protein ligase | 8 = deleted | Metabolic process |
| 573723 | 574580 | r | 5 | 0465 | d | d | d | d | d | n | — | hypothetical protein | 8 = deleted | Unclear |
| 574582 | 574926 | r | 5 | 0466 | k | d | d | d | d | n | — | glycine cleavage H-protein | 8 = deleted | Unclear |
| 575113 | 575907 | f | 5 | 0467 | d | d | d | d | d | n | — | alpha/beta hydrolase family protein | 8 = deleted | Acylglycerol breakdown |
| 575909 | 576703 | f | 5 | 0468 | d | d | d | d | d | n | — | alpha/beta hydrolase family protein | 8 = deleted | Acylglycerol breakdown |
| 576697 | 577506 | f | 5 | 0469 | d | d | d | d | d | n | — | PF05057 family protein | 8 = deleted | Acylglycerol breakdown |
| 577525 | 578658 | r | 5 | 0470 | d | d | d | d | d | n | — | PF03382 family protein | 8 = deleted | Lipoprotein |
| 578789 | 578920 | r | 5 | 0471 | d | d | d | d | d | n | — | hypothetical protein | 8 = deleted | Unclear |
| 578922 | 580322 | f | 5 | 0472 | d | d | d | d | d | n | — | lipoprotein, putative | 8 = deleted | Lipoprotein |
| 580469 | 581188 | f | 5 | 0473 | d | d | d | d | d | n | — | ABC transporter, ATP-binding protein | 8 = deleted | Transport |
| 581188 | 581943 | f | 5 | 0474 | k | d | d | d | d | n | — | ABC transporter, ATP-binding protein | 8 = deleted | Transport |
| 590637 | 591197 | f | 5 | 0483 | k | d | d | d | d | n | — | putative Holliday junction DNA helicase RuvA | 8 = deleted | DNA repair |
| 591214 | 592137 | f | 5 | 0484 | k | d | d | d | d | n | — | ruvB: Holliday junction DNA helicase RuvB | 8 = deleted | DNA repair |
| 592215 | 593573 | f | 5 | 0485 | d | d | d | d | d | n | — | pyridine nucleotide-disulfide oxidoreductase | 8 = deleted | Unclear |
| 593589 | 594398 | r | 5 | 0486 | d | d | d | d | d | n | — | hypothetical protein | 8 = deleted | Unclear |
| 596515 | 597738 | r | 5 | 0489 | d | d | d | d | d | n | — | ImpB/MucB/SamB family protein | 8 = deleted | DNA repair |
| 597882 | 600620 | f | 5 | 0490 | d | d | d | d | d | n | — | papain family cysteine protease | 8 = deleted | Proteolysis |
| 600698 | 601321 | r | 5 | 0491 | k | d | d | d | d | n | — | udk: uridine kinase | 8 = deleted | Nucleotide salvage |
| 601345 | 601785 | r | 5 | 0492 | d | d | d | d | d | n | — | hypothetical protein | 8 = deleted | Unclear |
| 622614 | 623603 | r | 6 | 0520 | d | d | d | d | d | in | — | alpha/beta hydrolase family protein | 8 = deleted | Unclear |
| 623616 | 624032 | r | 6 | 0521 | k | d | d | d | d | n | — | PF04472 family protein | 8 = deleted | Unclear |
| 624044 | 625201 | r | 6 | 0522 | k | d | d | d | d | n | — | ftsZ: cell division protein FtsZ | 8 = deleted | Cell division |
| 628122 | 628640 | r | 6 | 0527 | d | d | d | d | d | n | — | hypothetical protein | 8 = deleted | Unclear |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 645411 | 646016 | r | 6 | 0538 | d | d | d | d | d | n | — | hypothetical protein | 8 = deleted | Unclear |
| 654952 | 655188 | r | 6 | 0546 | k | d | d | d | d | n | — | sucrose-6F-phosphate phosphohydrolase domain protein | 8 = deleted | Carbon source transport & catabolism |
| 655176 | 655817 | r | 6 | 0547 | k | d | d | d | d | n | — | HAD hydrolase, family IIB | 8 = deleted | Unclear |
| 655817 | 656362 | r | 6 | 0548 | d | d | d | d | d | n | — | putative tRNA (cytidine(34)-2'-O)-methyltransferase | 8 = deleted | rRNA modification |
| 656375 | 656977 | r | 6 | 0549 | k | d | d | d | d | n | — | non-canonical purine NTP pyrophosphatase, RdgB/HAMfamily | 8 = deleted | Nucleotide salvage |
| 657179 | 659694 | f | 6 | 0550 | d | d | d | d | d | n | — | hypothetical protein | 8 = deleted | Mobile element & DNA restriction |
| 659874 | 662378 | f | 6 | 0551 | d | d | d | d | d | n | — | hypothetical protein | 8 = deleted | Mobile element & DNA restriction |
| 662695 | 663483 | f | 6 | 0552 | d | d | d | d | d | n | — | hypothetical protein | 8 = deleted | Mobile element & DNA restriction |
| 663752 | 664993 | f | 6 | 0553 | d | d | d | d | d | n | — | hypothetical protein | 8 = deleted | Mobile element & DNA restriction |
| 665166 | 665999 | f | 6 | 0554 | d | d | d | d | d | n | — | hypothetical protein | 8 = deleted | Mobile element & DNA restriction |
| 666028 | 668043 | f | 6 | 0555 | d | d | d | d | d | n | — | type IV secretory system Conjugative DNA transfer | 8 = deleted | Mobile element & DNA restriction |
| 668059 | 669015 | f | 6 | 0556 | d | d | d | d | d | n | — | PF03382 family protein | 8 = deleted | Mobile element & DNA restriction |
| 668999 | 669916 | f | 6 | 0557 | d | d | d | d | d | n | — | PF03382 family protein | 8 = deleted | Mobile element & DNA restriction |
| 669931 | 670347 | f | 6 | 0558 | k | d | d | d | d | n | — | single-strand binding family protein | 8 = deleted | Mobile element & DNA restriction |
| 670612 | 671802 | f | 6 | 0559 | d | d | d | d | d | n | — | PF06114 domain protein | 8 = deleted | Mobile element & DNA restriction |
| 672040 | 673572 | f | 6 | 0560 | d | d | d | d | d | n | — | lipoprotein, putative | 8 = deleted | Mobile element & DNA restriction |
| 673574 | 673765 | f | 6 | 0561 | d | d | d | d | d | n | — | hypothetical protein | 8 = deleted | Mobile element & DNA restriction |
| 673862 | 674092 | f | 6 | 0562 | d | d | d | d | d | n | — | hypothetical protein | 8 = deleted | Mobile element & DNA restriction |
| 674120 | 676843 | f | 6 | 0563 | d | d | d | d | d | n | — | hypothetical protein | 8 = deleted | Mobile element & DNA restriction |
| 676950 | 677135 | f | 6 | 0564 | d | d | d | d | d | n | — | hypothetical protein | 8 = deleted | Mobile element & DNA restriction |
| 677225 | 677602 | f | 6 | 0565 | d | d | d | d | d | n | — | hypothetical protein | 8 = deleted | Mobile element & DNA restriction |
| 677609 | 679531 | f | 6 | 0566 | d | d | d | d | d | n | — | membrane protein, putative | 8 = deleted | Mobile element & DNA restriction |
| 679556 | 682399 | f | 6 | 0567 | d | d | d | d | d | n | — | AAA-like domain protein | 8 = deleted | Mobile element & DNA restriction |
| 682412 | 683077 | f | 6 | 0568 | d | d | d | d | d | n | — | hypothetical protein | 8 = deleted | Mobile element & DNA restriction |
| 683124 | 688091 | f | 6 | 0569 | d | d | d | d | d | n | — | hypothetical protein | 8 = deleted | Mobile element & DNA restriction |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 688547 | 689293 | f | 6 | 0570 | d | d | d | d | d | n | — | hypothetical protein | 8 = deleted | Mobile element & DNA restriction |
| 689489 | 689854 | f | 6 | 0571 | d | d | d | d | d | n | — | hypothetical protein | 8 = deleted | Mobile element & DNA restriction |
| 690078 | 690992 | f | 6 | 0572 | d | d | d | d | d | n | — | CobQ/CobB/MinD/ ParA nucleotide binding domain protein | 8 = deleted | Mobile element & DNA restriction |
| 691042 | 692274 | f | 6 | 0573 | d | d | d | d | d | n | — | hypothetical protein | 8 = deleted | Mobile element & DNA restriction |
| 692861 | 695401 | f | 6 | 0574 | d | d | d | d | d | n | — | hypothetical protein | 8 = deleted | Mobile element & DNA restriction |
| 695457 | 696836 | r | 6 | 0575 | d | d | d | d | d | n | — | ATP synthase alpha/beta chain, C-terminal domain | 8 = deleted | Mobile element & DNA restriction |
| 696836 | 698383 | r | 6 | 0576 | d | d | d | d | d | n | — | putative ATP synthase F1, alpha subunit | 8 = deleted | Mobile element & DNA restriction |
| 698388 | 700691 | r | 6 | 0577 | d | d | d | d | d | n | — | hypothetical protein | 8 = deleted | Mobile element & DNA restriction |
| 700693 | 701136 | r | 6 | 0578 | k | d | d | d | d | n | — | hypothetical protein | 8 = deleted | Mobile element & DNA restriction |
| 701136 | 702047 | r | 6 | 0579 | d | d | d | d | d | n | — | hypothetical protein | 8 = deleted | Mobile element & DNA restriction |
| 702049 | 702543 | r | 6 | 0580 | d | d | d | d | d | n | — | PF10896 family protein | 8 = deleted | Mobile element & DNA restriction |
| 702518 | 703981 | r | 6 | 0581 | d | d | d | d | d | n | — | hypothetical protein | 8 = deleted | Mobile element & DNA restriction |
| 704013 | 706598 | r | 6 | 0582 | d | d | d | d | d | n | — | putative peptidase | 8 = deleted | Mobile element & DNA restriction |
| 706621 | 708873 | r | 6 | 0583 | d | d | d | d | d | n | — | mycoplasma virulence signal region (Myco_arth_vir_N) | 8 = deleted | Mobile element & DNA restriction |
| 709145 | 711715 | r | 6 | 0584 | d | d | d | d | d | n | — | putative peptidase | 8 = deleted | Mobile element & DNA restriction |
| 711735 | 713984 | r | 6 | 0585 | d | d | d | d | d | n | — | mycoplasma virulence signal region (Myco_arth_vir_N) | 8 = deleted | Mobile element & DNA restriction |
| 714177 | 716732 | r | 6 | 0586 | d | d | d | d | d | n | — | putative peptidase | 8 = deleted | Proteolysis |
| 716747 | 718999 | r | 6 | 0587 | d | d | d | d | d | n | — | mycoplasma virulence signal region (Myco_arth_vir_N) | 8 = deleted | Mobile element & DNA restriction |
| 719219 | 721780 | r | 6 | 0588 | d | d | d | d | d | n | — | putative peptidase | 8 = deleted | Proteolysis |
| 721800 | 724058 | r | 6 | 0589 | d | d | d | d | d | n | — | mycoplasma virulence signal region (Myco_arth_vir_N) | 8 = deleted | Mobile element & DNA restriction |
| 724657 | 725553 | r | 6 | 0925 | d | d | d | d | d | n | — | hypothetical protein | 8 = deleted | Mobile element & DNA restriction |
| 725660 | 726226 | r | 6 | 0926 | k | d | d | d | d | n | — | hypothetical protein | 8 = deleted | Mobile element & DNA restriction |
| 726177 | 726560 | f | 6 | 0927 | k | d | d | d | d | n | — | hypothetical protein | 8 = deleted | Mobile element & DNA restriction |
| 726553 | 727071 | r | 6 | 0590 | d | d | d | d | d | n | — | type III restriction enzyme, res subunit | 8 = deleted | Mobile element & DNA restriction |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | | |
|---|---|---|---|---|---|---|---|---|---|---|---|---|---|---|
| 727058 | 728260 | r | 6 | 0591 | d | d | d | d | d | n | — | DNA methylase family protein | 8 = deleted | Mobile element & DNA restriction |
| 729115 | 730587 | r | 6 | 0592 | d | d | d | d | d | n | — | PF09903 family protein | 8 = deleted | Unclear |
| 730811 | 731089 | r | 6 | 0593 | k | d | d | d | d | n | — | hypothetical protein | 8 = deleted | Unclear |
| 731220 | 732998 | r | 6 | 0594 | d | d | d | d | d | n | — | MATE domain protein | 8 = deleted | Efflux |
| 733270 | 734646 | f | 6 | 0595 | d | d | d | d | d | n | — | type III restriction enzyme, res subunit | 8 = deleted | Mobile element & DNA restriction |
| 735282 | 737948 | f | 6 | 0596 | d | d | d | d | d | n | — | AAA domain protein | 8 = deleted | Unclear |
| 738368 | 738793 | f | 6 | 0597 | d | d | d | d | d | n | — | Fic/DOC family protein | 8 = deleted | Cell division |
| 739136 | 740662 | f | 6 | 0598 | d | d | d | d | d | n | — | PF03382 family protein | 8 = deleted | Lipoprotein |
| 744738 | 746000 | f | 6 | 0602 | k | d | d | d | d | n | — | hypothetical protein | 8 = deleted | Unclear |
| 746503 | 747171 | f | 6 | 0604 | d | d | d | d | d | n | — | LemA family protein | 8 = deleted | Unclear |
| 747354 | 747662 | f | 6 | 0605 | k | d | d | d | d | n | — | hypothetical protein | 8 = deleted | Unclear |
| 752661 | 753485 | r | 6 | 0610 | d | d | d | d | d | n | — | fpg: DNA-formamidopyrimidine glycosylase | 8 = deleted | DNA repair |
| 765083 | 765445 | r | 6 | 0622 | k | d | d | d | d | n | — | lipoprotein, putative | 8 = deleted | Lipoprotein |
| 765432 | 766502 | r | 6 | 0623 | d | d | d | d | d | n | — | hypothetical protein | 8 = deleted | Unclear |
| 766799 | 767731 | r | 6 | 0625 | d | d | d | d | d | n | — | putative carbamate kinase | 8 = deleted | Carbon source transport & catabolism |
| 767848 | 768942 | r | 6 | 0626 | d | d | d | d | d | n | — | aguA, agmatine deiminase, agmatine to putrescine via N-carbamoylputrescine | 8 = deleted | Carbon source transport & catabolism |
| 768949 | 770367 | r | 6 | 0627 | d | d | d | d | d | n | — | amino acid permease | 8 = deleted | Transport |
| 770394 | 771491 | r | 6 | 0628 | d | d | d | d | d | n | — | ornithine carbamoyltransferase | 8 = deleted | Carbon source transport & catabolism |
| 771786 | 772163 | r | 6 | 0629 | d | d | d | d | d | n | — | hypothetical protein | 8 = deleted | Unclear |
| 772384 | 773271 | f | 6 | 0630 | d | d | d | d | d | n | — | ABC transporter, ATP-binding protein | 8 = deleted | Transport |
| 773273 | 774037 | f | 6 | 0631 | d | d | d | d | d | n | — | ABC-2 family transporter protein | 8 = deleted | Transport |
| 774638 | 776197 | r | 6 | 0633 | d | d | d | d | d | n | — | membrane protein, putative | 8 = deleted | Unclear |
| 806351 | 807349 | r | 6 | 0673 | d | d | d | d | d | n | — | dhaK1: dihydroxyacetone kinase, DhaK subunit | 8 = deleted | Metabolic process |
| 807457 | 809085 | r | 6 | 0674 | d | d | d | d | d | n | — | putative alpha, alpha-phosphotrehalase | 8 = deleted | Carbon source transport & catabolism |
| 809093 | 810640 | r | 6 | 0675 | d | d | d | d | d | n | — | PTS system EIIC component | 8 = deleted | Carbon source transport & catabolism |
| 810706 | 811692 | r | 6 | 0676 | d | d | d | d | d | n | — | transcriptional regulator, LacI family | 8 = deleted | Regulation |
| 813801 | 814964 | r | 7 | 0682 | d | d | d | d | d | n | — | PF03382 family protein | 8 = deleted | Lipoprotein |
| 815077 | 815832 | r | 7 | 0683 | d | d | d | d | d | n | — | tetraspanin family protein | 8 = deleted | Unclear |
| 832678 | 833904 | r | 7 | 0698 | d | d | d | d | d | n | — | PF03382 family protein | 8 = deleted | Lipoprotein |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 833993 | 834922 | r | 7 | 0699 | d | d | d | d | d | n | — | peptide-methionine (S)-S-oxide reductase MsrA/ methionine-R-sulfoxide reductase MsrB multi-domain protein | 8 = deleted | Redox homeostasis |
| 835036 | 837222 | r | 7 | 0700 | d | d | d | d | d | n | — | lipoprotein, putative | 8 = deleted | Lipoprotein |
| 837470 | 839818 | r | 7 | 0701 | d | d | d | d | d | n | — | lipoprotein, putative | 8 = deleted | Lipoprotein |
| 839827 | 840729 | r | 7 | 0702 | d | d | d | d | d | n | — | membrane protein, putative | 8 = deleted | Unclear |
| 840856 | 842691 | r | 7 | 0703 | d | d | d | d | d | n | — | PF03235 family protein | 8 = deleted | Unclear |
| 842694 | 843260 | r | 7 | 0704 | d | d | d | d | d | n | — | hypothetical protein | 8 = deleted | Unclear |
| 843263 | 844099 | r | 7 | 0705 | k | d | d | d | d | n | — | hypothetical protein | 8 = deleted | Mobile element & DNA restriction |
| 849525 | 850715 | f | 7 | 0711 | d | d | d | d | d | n | — | aminotransferase, class I/II | 8 = deleted | Unclear |
| 850725 | 851126 | f | 7 | 0712 | d | d | d | d | d | n | — | putative endoribonuclease L-PSP domain protein | 8 = deleted | Unclear |
| 851162 | 852493 | r | 7 | 0713 | d | d | d | d | d | n | — | PF03382 family protein | 8 = deleted | Unclear |
| 852523 | 853779 | r | 7 | 0714 | d | d | d | d | d | n | — | PF03382 family protein | 8 = deleted | Unclear |
| 853966 | 855234 | r | 7 | 0715 | d | d | d | d | d | n | — | PF03382 family protein | 8 = deleted | Unclear |
| 855376 | 856518 | f | 7 | 0716 | d | d | d | d | d | n | — | alpha/beta hydrolase family protein | 8 = deleted | Unclear |
| 862389 | 863402 | f | 7 | 0731 | d | d | d | d | d | n | — | nucleotidyl transferase, PF08843 family | 8 = deleted | Unclear |
| 865972 | 867285 | f | 7 | 0734 | d | d | d | d | d | n | — | putative pyrimidine-nucleoside phosphorylase | 8 = deleted | Nucleotide salvage |
| 867340 | 868071 | r | 7 | 0735 | d | d | d | d | d | n | — | integrase core domain protein | 8 = deleted | Mobile element & DNA restriction |
| 868209 | 868751 | r | 7 | 0736 | d | d | d | d | d | n | — | transposase | 8 = deleted | Mobile element & DNA restriction |
| 868816 | 869103 | r | 7 | 0737 | d | d | d | d | d | n | — | hypothetical protein | 8 = deleted | Carbon source transport & catabolism |
| 869142 | 869264 | r | 7 | 0738 | d | d | d | d | d | n | — | hypothetical protein | 8 = deleted | Unclear |
| 869269 | 869403 | r | 7 | 0739 | d | d | d | d | d | n | — | hypothetical protein | 8 = deleted | Carbon source transport & catabolism |
| 869453 | 869608 | r | 7 | 0740 | k | d | d | d | d | n? | — | hypothetical protein | 8 = deleted | Unclear |
| 869727 | 870719 | r | 7 | 0741 | d | d | d | d | d | n | — | CCTTC-recognizing Type II restriction modification system (MmyCII) endonuclease subunit | 8 = deleted | Mobile element & DNA restriction |
| 870721 | 873225 | r | 7 | 0742 | d | d | d | d | d | n | — | CCTTC-recognizing Type II restriction modification system (MmyCII) adenine/cytosine DNA methyltransferase subunit | 8 = deleted | Mobile element & DNA restriction |
| 873360 | 875396 | r | 7 | 0743 | d | d | d | d | d | n | — | phosphoenolpyruvate-dependent sugar PTS family porter, EIIA 2 component | 8 = deleted | Carbon source transport & catabolism |
| 875399 | 876334 | r | 7 | 0744 | d | d | d | d | d | n | — | putative 1-phosphofructokinase | 8 = deleted | Carbon source transport & catabolism |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 876334 | 877032 | r | 7 | 0745 | d | d | d | d | d | n | — | transcriptional regulator, DeoR family | 8 = deleted | Regulation |
| 877185 | 878165 | f | 7 | 0746 | d | d | d | d | d | n | — | hypothetical protein | 8 = deleted | Unclear |
| 879069 | 879533 | r | 7 | 0748 | d | d | d | d | d | n | — | DNA-binding helix-turn-helix protein | 8 = deleted | Mobile element & DNA restriction |
| 879588 | 880493 | r | 7 | 0749 | d | d | d | d | d | n | — | putative lysophospholipase | 8 = deleted | Unclear |
| 880596 | 883649 | r | 7 | 0750 | d | d | d | d | d | n | — | hypothetical protein | 8 = deleted | Unclear |
| 883674 | 886715 | r | 7 | 0751 | d | d | d | d | d | n | — | hypothetical protein | 8 = deleted | Unclear |
| 887085 | 887657 | f | 7 | 0752 | d | d | d | d | d | n | — | Fic/DOC family protein | 8 = deleted | Cell division |
| 887865 | 888137 | f | 7 | 0753 | d | d | d | d | d | n | — | addiction module antitoxin, RelB/DinJ family | 8 = deleted | Unclear |
| 888176 | 889081 | r | 7 | 0754 | d | d | d | d | d | n | — | GCATC-recognizing Type II methyltransferase | 8 = deleted | Mobile element & DNA restriction |
| 889074 | 890162 | r | 7 | 0755 | d | d | d | d | d | n | — | GCATC-recognizing TypeIIrestrictionmodification | 8 = deleted | Mobile element & DNA restriction |
| 890279 | 892318 | f | 7 | 0756 | d | d | d | d | d | n | — | GCATC-recognizing TypeIIrestrictionmodification | 8 = deleted | Mobile element & DNA restriction |
| 892356 | 893441 | r | 7 | 0757 | d | d | d | d | d | n | — | PF05913 family protein | 8 = deleted | Unclear |
| 893443 | 894831 | r | 7 | 0758 | d | d | d | d | d | n | — | glycoside hydrolase, family 1 | 8 = deleted | Carbon source transport & catabolism |
| 894824 | 895702 | r | 7 | 0759 | k | d | d | d | d | n | — | ROK family protein | 8 = deleted | Regulation |
| 895704 | 896162 | r | 7 | 0760 | k | d | d | d | d | n | — | phosphoenolpyruvate-dependent sugar PTS family porter, EIIA 2 component | 8 = deleted | Transport |
| 896176 | 898842 | r | 7 | 0761 | d | d | d | d | d | n | — | glycoside hydrolase, family 38, N-terminal domain protein | 8 = deleted | Carbon source transport & catabolism |
| 898854 | 900695 | r | 7 | 0762 | d | d | d | d | d | n | — | PTS system EIIC component | 8 = deleted | Carbon source transport & catabolism |
| 900710 | 901486 | r | 7 | 0763 | d | d | d | d | d | n | — | lipoprotein, putative | 8 = deleted | Lipoprotein |
| 901652 | 902203 | r | 7 | 0764 | k | d | d | d | d | n | — | HGPRTase: hypoxanthine phosphoribosyltransferase | 8 = deleted | Nucleotide salvage |
| 902239 | 903537 | r | 7 | 0765 | d | d | d | d | d | n | — | purB: adenylosuccinate lyase | 8 = deleted | Nucleotide salvage |
| 903530 | 904828 | r | 7 | 0766 | k | d | d | d | d | n | — | purA: adenylosuccinate synthase | 8 = deleted | Nucleotide salvage |
| 905049 | 905201 | r | 7 | 0767 | k | d | d | d | d | n | — | hypothetical protein | 8 = deleted | Unclear |
| 905182 | 905697 | r | 7 | 0768 | d | d | d | d | d | n | — | GANTC-recognizing TypeIIrestrictionmodification | 8 = deleted | Mobile element & DNA restriction |
| 905859 | 906578 | r | 7 | 0769 | d | d | d | d | d | n | — | GANTC-recognizing TypeIIrestrictionmodification | 8 = deleted | Mobile element & DNA restriction |
| 906639 | 907484 | r | 7 | 0770 | d | d | d | d | d | n | — | PF03382 family protein | 8 = deleted | Unclear |
| 917651 | 918193 | f | 7 | 0780 | d | d | d | d | d | n | — | transposase | 8 = deleted | Mobile element & DNA restriction |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 918331 | 919062 | f | 7 | 0781 | d | d | d | d | d | n | — | integrase core domain protein | 8 = deleted | Mobile element & DNA restriction |
| 919157 | 920284 | f | 7 | 0782 | d | d | d | d | d | n | — | beta-lactamase | 8 = deleted | Unclear |
| 920380 | 921345 | f | 7 | 0783 | d | d | d | d | d | n | — | ROK family protein | 8 = deleted | Regulation |
| 921413 | 922345 | r | 7 | 0784 | d | d | d | d | d | n | — | putative carbamate kinase | 8 = deleted | Carbon source transport & catabolism |
| 922358 | 923821 | r | 7 | 0785 | k | d | d | d | d | n | — | C4-dicarboxylate anaerobic carrier | 8 = deleted | Carbon source transport & catabolism |
| 923900 | 924895 | r | 7 | 0786 | d | d | d | d | d | n | — | orni_carb_tr: ornithine carbamoyltransferase | 8 = deleted | Carbon source transport & catabolism |
| 928331 | 929518 | f | 7 | 0788 | d | d | d | d | d | n | — | hypothetical protein | 8 = deleted | Unclear |
| 939085 | 939381 | f | 8 | 0801 | d | d | d | d | d | n | — | rhodanese-like protein | 8 = deleted | Unclear |
| 939386 | 941581 | r | 8 | 0802 | d | d | d | d | d | n | — | putative peptidase | 8 = deleted | Lipoprotein |
| 953142 | 954020 | r | 8 | 0811 | d | d | d | d | d | n | — | galU | 8 = deleted | Unclear |
| 954550 | 955926 | r | 8 | 0812 | d | d | d | d | d | n | — | EpsG | 8 = deleted | Lipid salvage and biogenesis |
| 958936 | 959442 | r | 8 | 0928 | d | d | d | d | d | n | — | hypothetical protein | 8 = deleted | Unclear |
| 959417 | 959686 | f | 8 | 0929 | d | d | d | d | d | n | — | hypothetical protein | 8 = deleted | Unclear |
| 959695 | 960048 | f | 8 | 0816 | d | d | d | d | d | n | — | integrase core domain protein | 8 = deleted | Mobile element & DNA restriction |
| 987122 | 993043 | f | 8 | 0841 | k | d | d | d | d | n | — | hypothetical protein | 8 = deleted | Unclear |
| 993053 | 996010 | f | 8 | 0842 | k | d | d | d | d | n | — | ABC transporter, substrate-binding protein, family 5 | 8 = deleted | Lipoprotein |
| 996010 | 997083 | f | 8 | 0843 | k | d | d | d | d | n | — | ABC transporter, permease protein | 8 = deleted | Transport |
| 997085 | 998095 | f | 8 | 0844 | k | d | d | d | d | n | — | ABC transporter, permease protein | 8 = deleted | Transport |
| 998103 | 999548 | f | 8 | 0845 | k | d | d | d | d | n | — | oligopeptide/dipeptide transporter, C-terminal domain protein | 8 = deleted | Transport |
| 999541 | 1000863 | f | 8 | 0846 | k | d | d | d | d | n | — | ABC transporter, ATP-binding protein | 8 = deleted | Transport |
| 1000900 | 1001631 | r | 8 | 0267 | d | d | d | d | d | n | — | integrase core domain protein | 8 = deleted | Mobile element & DNA restriction |
| 1001769 | 1002311 | r | 8 | 0265 | d | d | d | d | d | n | — | transposase | 8 = deleted | Mobile element & DNA restriction |
| 1002392 | 1002898 | r | 8 | 0849 | d | d | d | d | d | n | — | lipoprotein, putative | 8 = deleted | Lipoprotein |
| 1003095 | 1003970 | r | 8 | 0850 | d | d | d | d | d | n | — | PF03382 family protein | 8 = deleted | Unclear |
| 1005324 | 1005833 | r | 8 | 0854 | d | d | d | d | d | i | — | dual specificity phosphatase, catalytic domain protein | 8 = deleted | Unclear |
| 1005833 | 1007533 | r | 8 | 0855 | d | d | d | d | d | n | — | PTS system EIIC component | 8 = deleted | Transport |
| 1007610 | 1009322 | r | 8 | 0856 | d | d | d | d | d | n | — | PTS system EIIC component | 8 = deleted | Transport |
| 1009630 | 1011018 | f | 8 | 0858 | d | d | d | d | d | n | — | divergent AAA domain protein | 8 = deleted | Regulation |
| 1011005 | 1011820 | r | 8 | 0857 | d | d | d | d | d | n | — | SIS domain protein | 8 = deleted | Unclear |
| 1014116 | 1014841 | r | 8 | 0860 | k | d | d | d | d | n | — | lipoprotein, putative | 8 = deleted | Lipoprotein |
| 1015242 | 1016126 | r | 8 | 0861 | d | d | d | d | d | n | — | aromatic cluster surface protein | 8 = deleted | Unclear |
| 1016113 | 1016943 | r | 8 | 0862 | k | d | d | d | d | n | — | aromatic cluster surface protein | 8 = deleted | Unclear |

TABLE 10-continued

The protein genes and 39 RNA genes in HMG, Syn2.0, Syn3.0, RGD1, and RGD2.Begin. The first nucleotide that is also part of the gene. As with genbank nomenclature, this may be the first nucleotide of the start codon or the complement of the last nucleotide of the stop codon. Numbering according to accession CP002027

| | | | | | | | | | | | | | |
|---|---|---|---|---|---|---|---|---|---|---|---|---|---|
| 1016930 | 1018279 | r | 8 | 0863 | d | d | d | d | n | — | aromatic cluster surface protein | 8 = deleted | Lipoprotein |
| 1018257 | 1018961 | r | 8 | 0864 | d | d | d | d | n | — | bacitracin ABC transporter, ATP-binding protein BcrA family protein | 8 = deleted | Transport |
| 1018963 | 1020834 | r | 8 | 0865 | d | d | d | d | n | — | ABC-2 family transporter protein | 8 = deleted | Transport |
| 1020973 | 1021860 | r | 8 | 0866 | d | d | d | d | n | — | aromatic cluster surface protein | 8 = deleted | Lipoprotein |
| 1021862 | 1022692 | r | 8 | 0867 | k | d | d | d | n | — | aromatic cluster surface protein | 8 = deleted | Unclear |
| 1022679 | 1023872 | r | 8 | 0868 | k | d | d | d | n | — | aromatic cluster surface protein | 8 = deleted | Lipoprotein |
| 1023891 | 1025786 | r | 8 | 0869 | k | d | d | d | n | — | membrane protein, putative | 8 = deleted | Transport |
| 1027731 | 1028438 | r | 8 | 0871 | k | d | d | d | n | — | PF01863 family protein | 8 = deleted | Proteolysis |
| 1037851 | 1038822 | r | 8 | 0880 | d | d | d | d | n | — | DNA-binding protein HU | 8 = deleted | Unclear |
| 1040770 | 1041414 | r | 8 | 0882 | d | d | d | d | in | — | hypothetical protein | 8 = deleted | Unclear |
| 1041471 | 1042451 | r | 8 | 0883 | d | d | d | d | n | — | putative aspartate-ammonia ligase | 8 = deleted | Metabolic process |
| 1042655 | 1043413 | f | 8 | 0884 | d | d | d | d | n | — | hypothetical protein | 8 = deleted | Unclear |
| 1048868 | 1049368 | f | 8 | 0888 | k | d | d | d | n | — | isochorismatase family protein | 8 = deleted | Unclear |
| 1049414 | 1050091 | r | 8 | 0889 | d | d | d | d | n | — | nucleotidyl transferase, PF08843 family | 8 = deleted | Unclear |
| 1050248 | 1050847 | r | 8 | 0890 | d | d | d | d | n | — | PF13338 domain protein | 8 = deleted | Unclear |
| 1051424 | 1052758 | f | 8 | 0891 | d | d | d | d | n | — | PF03382 family protein | 8 = deleted | Lipoprotein |
| 1053008 | 1054231 | f | 8 | 0892 | d | d | d | d | n | — | PAP2 family protein | 8 = deleted | Unclear |
| 1054362 | 1055567 | f | 8 | 0893 | d | d | d | d | n | — | PAP2 domain protein | 8 = deleted | Unclear |
| 1055650 | 1057914 | r | 8 | 0894 | d | d | d | d | n | — | hypothetical protein | 8 = deleted | Unclear |
| 1057924 | 1060185 | r | 8 | 0895 | d | d | d | d | n | — | hypothetical protein | 8 = deleted | Unclear |
| 1060502 | 1062757 | r | 8 | 0896 | d | d | d | d | n | — | hypothetical protein | 8 = deleted | Unclear |
| 1062767 | 1065028 | r | 8 | 0897 | d | d | d | d | n | — | hypothetical protein | 8 = deleted | Unclear |
| 1065223 | 1067475 | r | 8 | 0898 | d | d | d | d | n | — | hypothetical protein | 8 = deleted | Unclear |
| 1067499 | 1069739 | r | 8 | 0899 | d | d | d | d | n | — | hypothetical protein | 8 = deleted | Unclear |
| 1070055 | 1070690 | f | 8 | 0900 | d | d | d | d | n | — | lipoprotein, putative | 8 = deleted | Lipoprotein |
| 1070923 | 1071534 | f | 8 | 0901 | d | d | d | d | n | — | lipoprotein, putative | 8 = deleted | Lipoprotein |
| 1071824 | 1072303 | f | 8 | 0902 | d | d | d | d | n | — | lipoprotein, putative | 8 = deleted | Lipoprotein |
| 1072804 | 1073379 | f | 8 | 0903 | d | d | d | d | n | — | lipoprotein, putative | 8 = deleted | Lipoprotein |
| 1073640 | 1074323 | f | 8 | 0904 | d | d | d | d | n | — | hypothetical protein | 8 = deleted | Unclear |

In the course of making the HMG design, the following set of deletion rules were developed and used in the subsequent examples.

(1) Generally the entire coding region of each gene considered non-essential was deleted, including start and stop codons. (See exceptions below)
(2) When a cluster of more than one consecutive gene was deleted, the intergenic regions within the cluster were deleted also.
(3) Intergenic regions that flank a deleted gene, or a consecutive cluster of deleted genes, were retained.
(4) Parts of genes to be deleted were retained if they overlapped a retained gene.
(5) Parts of genes to be deleted were retained if they contained a ribosome binding site or promoter for a retained gene.
(6) When two genes were divergently transcribed, it was assumed the intergenic region separating them contained promoters for transcription in both directions.
(7) When a deletion resulted in converging transcripts a bidirectional terminator was inserted, if one was not already present.

Figure 2B:
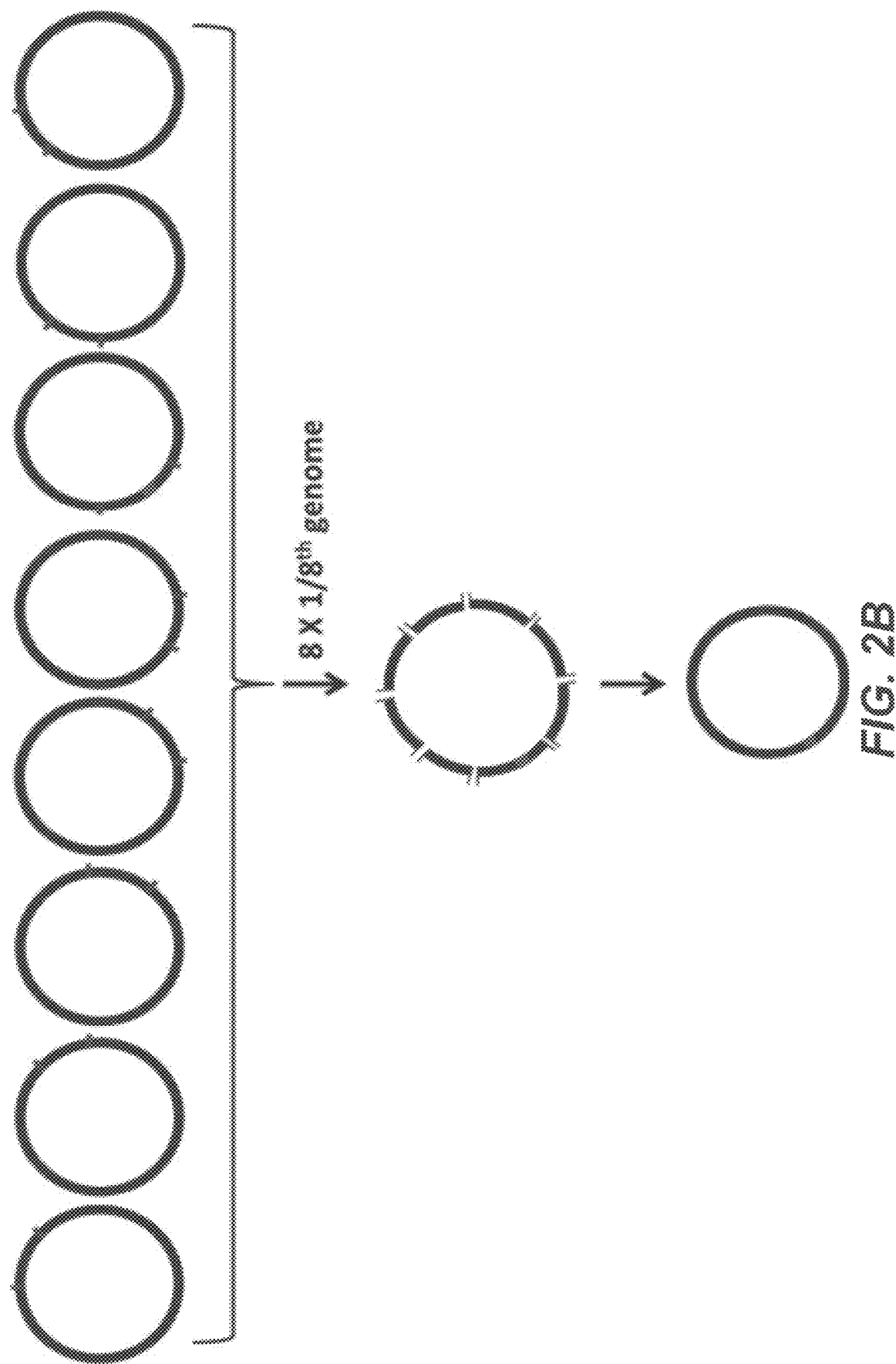
Figure 10:
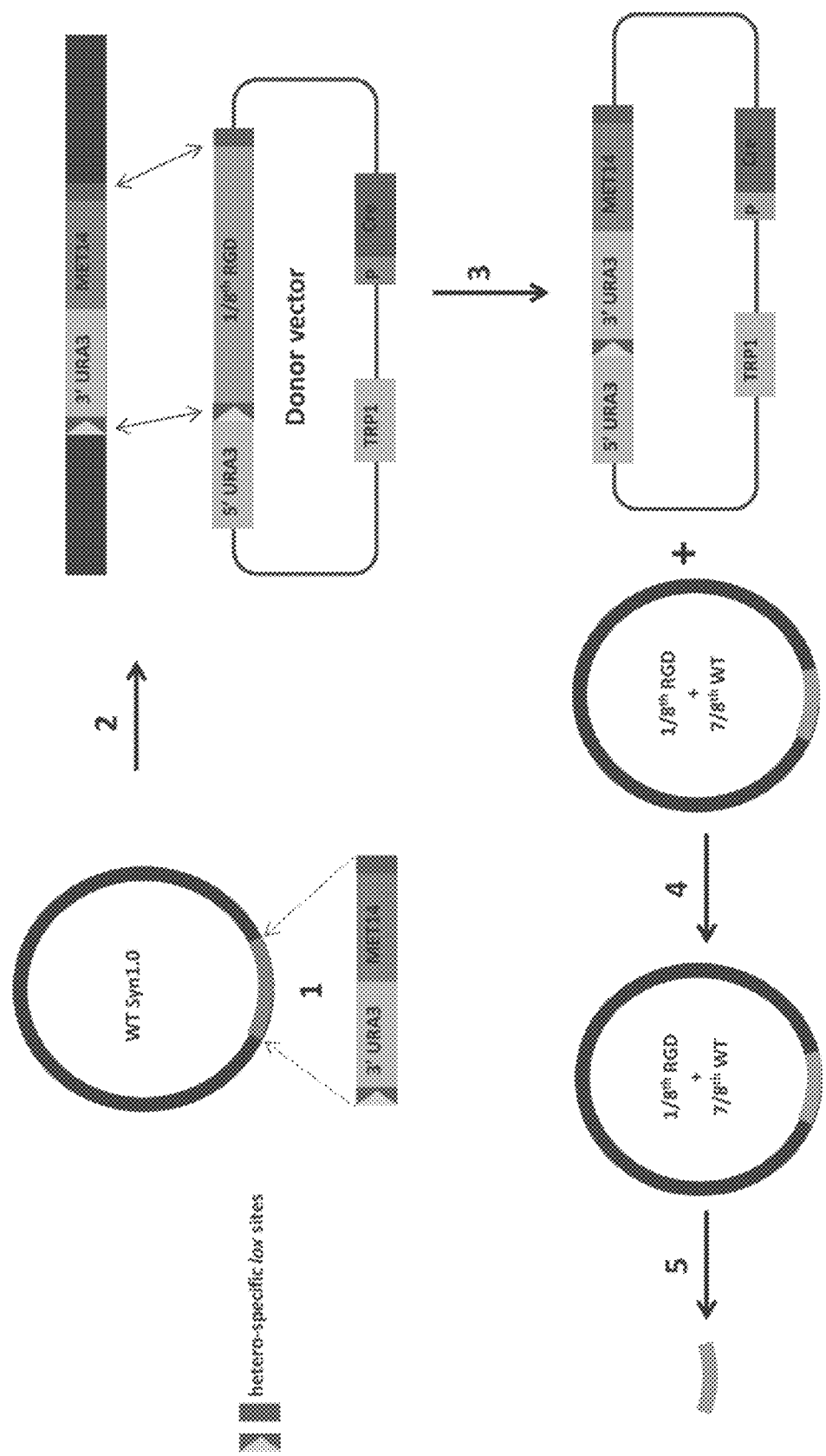

Each of the HMG and Syn1.0 genomes was divided into 8 overlapping segments was chemically synthesized and assembled. Each of the HMG genomic fragments had a corresponding Syn1.0 genomic segment, which allowed untested pieces to be mixed-and-matched with viable Syn1.0 pieces in one-pot combinatorial assemblies or purposefully assembled in any specified combination. Additionally, each of the eight target segments (i.e., the HMG fragments) was moved into a ⅞th Syn1.0 background by recombinase mediated cassette exchange (RMCE) (FIG. 10). Each of the eight target segments is referred to as a $⅛^{th}$ RGD, reduced genome design, in FIG. 10 and the Experimental Materials and Methods section. RMCE has been described in Noskov et al., Biol. Proced. Online. 17, 6 (2015), which is hereby incorporated by reference. Unique restriction sites (NotI) flanked each HMG or Syn1.0 segment in the resulting strains (FIGS. 2A2A-2C).

8 *mycoplasma* strains were produced as a result of moving each of the eight target segments into a ⅞th Syn1.0 background by recombinase mediated cassette exchange (RMCE), each carrying one HMG segment. 8 other *mycoplasma* strains, each carrying one Syn1.0 segment, in each case flanked by NotI sites, were also produced. This facilitated the production of HMG and Syn1.0 segments because they could be recovered from bacterial cultures, which produced much higher yields of better quality DNA than yeast. All 8 HMG segments were tested in a Syn1.0 background, but only one of the segment designs produced viable colonies (HMG segment 2), and the cells grew poorly. As described in subsequent examples, more rigorous evaluations of dispensable genes were performed. There was also a need to repeatedly assess which remaining genes were dispensable as smaller and smaller genomes were produced (See FIG. 25).

In the HMG work described here, a semi-automated DNA synthesis procedure capable of rapidly generating error-free large DNA constructs starting from overlapping oligonucleotides was used. The procedure included (i) single-reaction assembly of 1.4-kb DNA fragments from overlapping oligonucleotides, (ii) eliminating synthesis errors and permitting single-round assembly and cloning of error-free 7-kb cassettes, (iii) cassette sequence verification to simultaneously identify hundreds of error-free clones in a single run, and (iv) rolling circle amplification (RCA) of large plasmid DNA derived from yeast. This procedure significantly increased the rate at which the Design-Build-Test cycle (DBT) was carried out. A non-limiting schematic illustration of the strategy for the DNA synthesis is shown in FIG. 21.

Example 2

Identification of Essential, Quasi-Essential, and Non-Essential Genes Using Tn5 Transposon Mutagenesis This example shows the use of Tn5 transposon mutagenesis to identify essential, quasi-essential, and non-essential genes.

Figure 3:
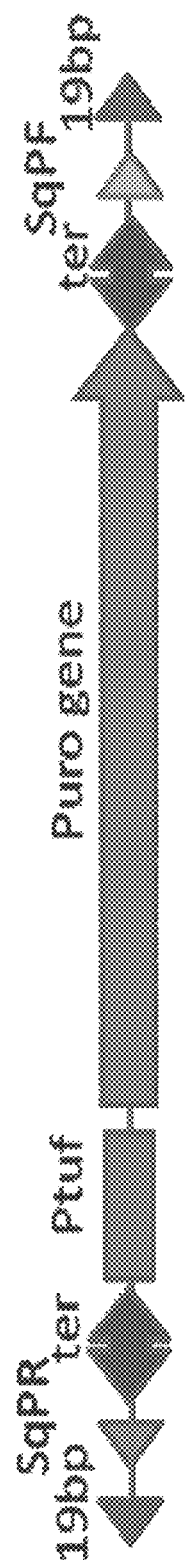

To obtain much better knowledge of which genes are essential versus non-essential, Tn5 transposon mutagenesis was performed (FIG. 3). An initial Tn5 disruption map was generated by transforming JCVI-Syn1.0 ARE AIS cells (Table 9) with an activated form of a 988-bp mini-Tn5 puromycin resistance transposon (FIG. 3). Transformed cells were selected on agar plates containing 10 µg/ml puromycin. Approximately 80,000 colonies, each arising from a single Tn5 insertion event, were pooled from the plates. A sample of DNA extracted from this P0 pool was mechanically sheared and analyzed for the sites of Tn5 insertion using inverse PCR and Miseq. The P0 data set contained ~30,000 unique insertions. To remove slow growing mutagenized cells, a sample of the pooled P0 cells was serially passaged for more than 40 generations, and DNA was prepared and sequenced to generate a P4 data set containing ~14,000 insertions (FIG. 4).

Genes were classified into 3 major groups according to the results of the Tn5 transposon mutagenesis: (1) genes that were not hit at all, or were sparsely hit in the terminal 20% of 3'-end or the first few bases of 5'-end were classified as essential "e" genes (also referred to as "e-genes"): (2) genes that were hit frequently by both P0 and P4 insertions were classified as non-essential "n" genes (also referred to as "n-genes"; and (3) genes hit primarily by P0 insertions but not P4 insertions were classified as quasi-essential, growth-impaired "i" genes (also referred to as "i-genes"). The use of transposon mutagenesis to identify nonessential genes has been described in Hutchison et al., Science 286:2165-9 (1999), which is hereby incorporated by reference. Cells with i-gene disruptions formed a continuum of growth impairment varying from minimal to severe. To highlight this growth continuum, i-genes with minimal growth disadvantage was designated as in-genes, and those with severe growth defect as "ie" genes. Of the 901 annotated protein and RNA coding genes in the Syn1.0 genome, 432 were initially classified as n-genes, 240 were e-genes, and 229 were i-genes (FIGS. 5, 22A-22B).

Figure 22A:
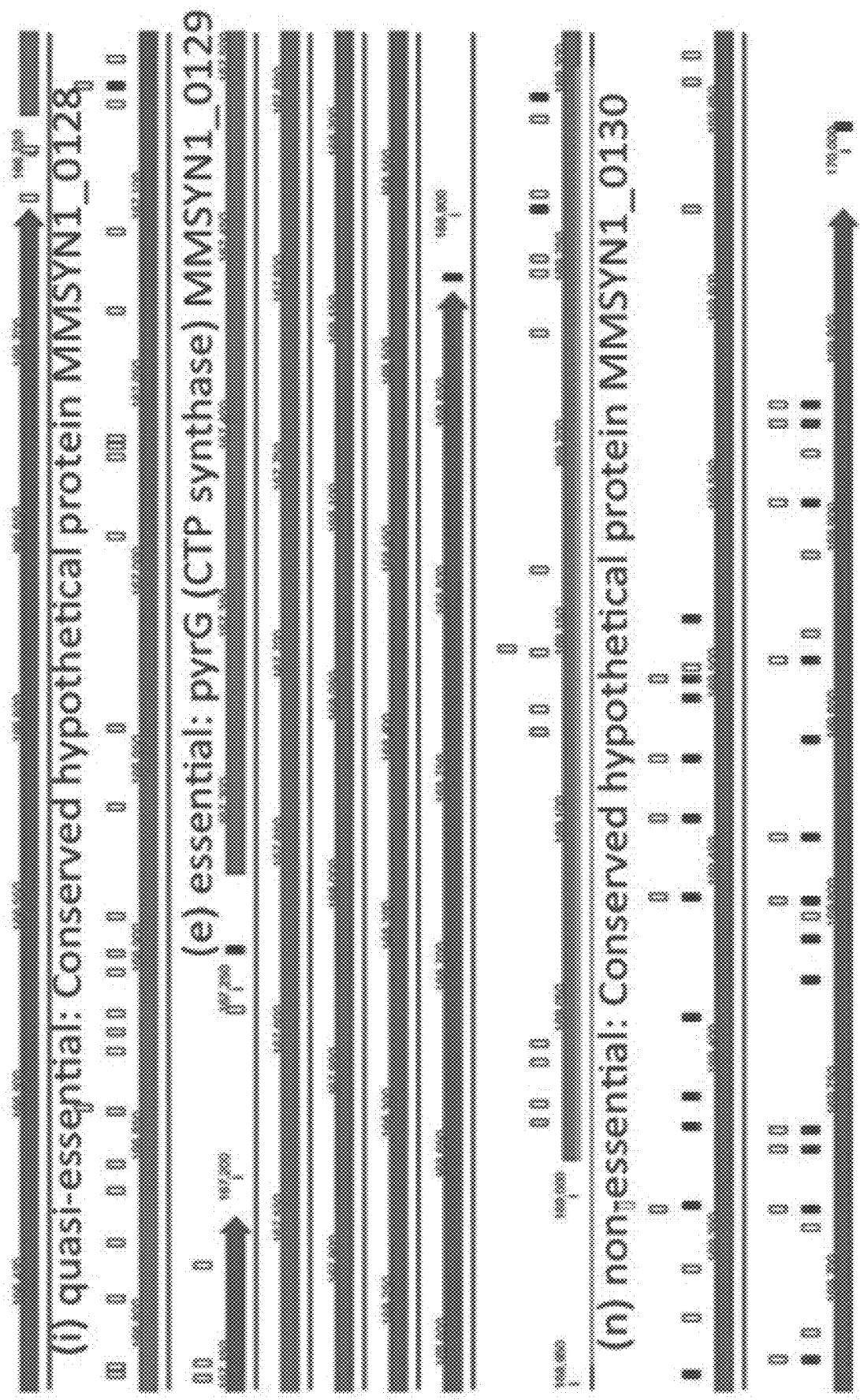
FIGS. 22A-22B show the three gene classifications based on Tn5 mutagenesis data.
Figure 22B:
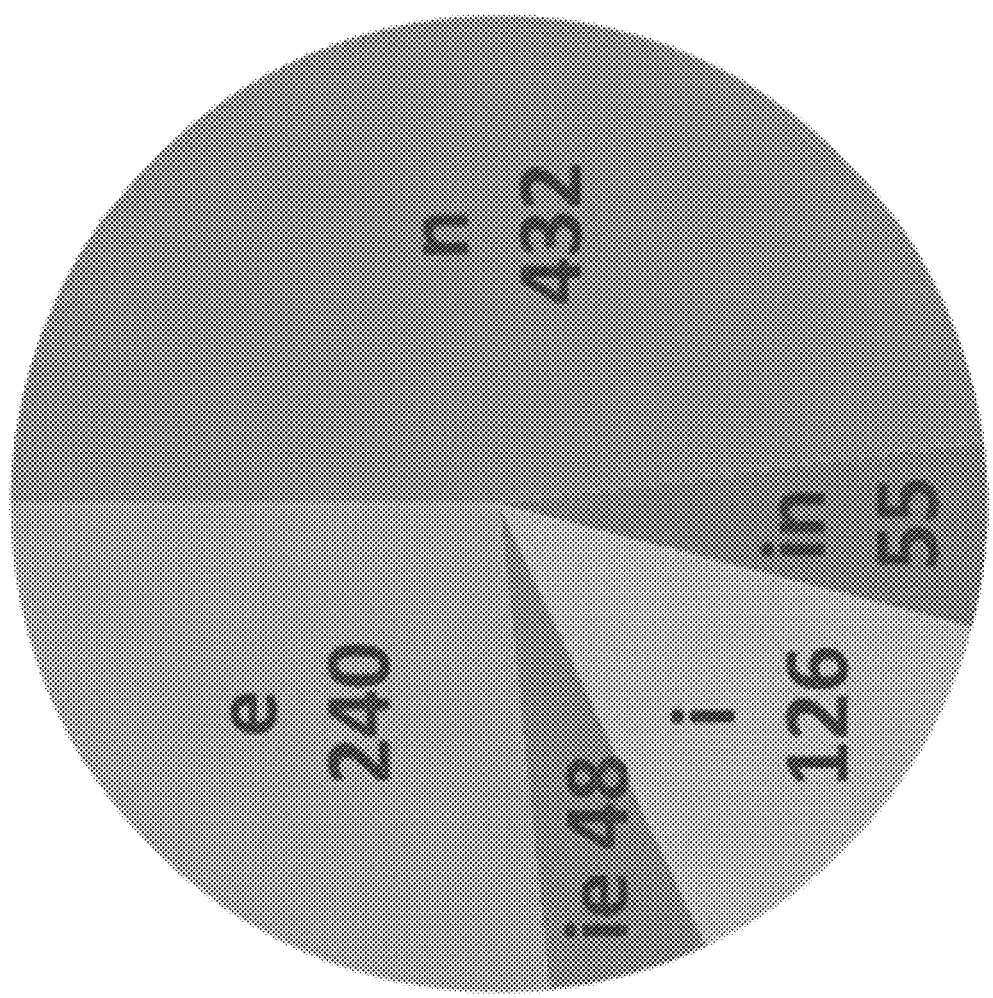

FIGS. 22A-22B show the three gene classifications based on Tn5 mutagenesis data. FIG. 22A shows a number of examples of the 3 gene classifications based on Tn5 mutagenesis data. The gene MMSYN1_0128 (the arrow starting at the right end of the top line) had P0 Tn5 inserts (open bars) and is a quasi-essential i-gene. The next gene (MMSYN1_0129) had no inserts and is an essential e-gene. The last gene (MMSYN1_0130) had both P0 (open bars) and P4 (black bars) inserts and is a non-essential n-gene. FIG. 22B shows the number of Syn1.0 genes in each Tn5 mutagenesis classification group. n-genes and in-genes were candidates for deletion in reduced genome designs.

Figure 15:
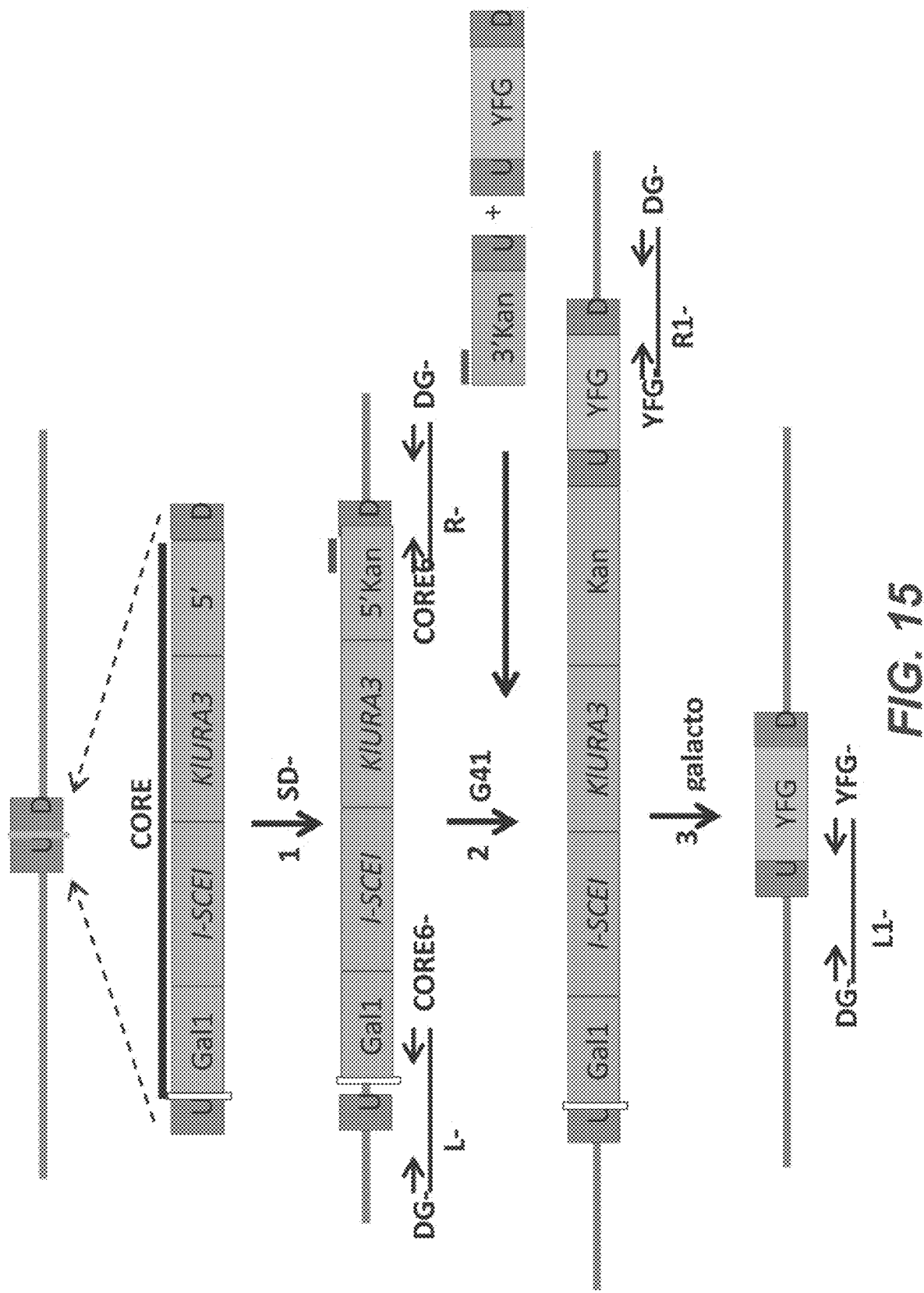

When displayed on the Syn1.0 gene map (FIG. 6), P4 insertions hit the n-genes at high frequency whereas the e-genes had no hits, and i-genes were sparsely hit or not at all. The map shows that non-essential genes tended to occur in clusters far more often than expected by chance. Deletion analysis was used to confirm that most of the n-gene clusters could be deleted without loss of viability or significantly affecting growth rate (when displayed on the Syn1.0 gene map, FIG. 15). Individual gene clusters (or in some cases single genes) were replaced by the URA3 marker as follows. 50 bp sequences flanking the gene(s) to be deleted were added to the ends of the URA3 marker by PCR and the DNA was introduced into yeast cells carrying Syn1.0 genome. Yeast clones were selected on plates not containing uracil, confirmed by PCR, and transplanted to determine viability. Deletions fell into 3 classes: (1) Those resulting in no transplants, indicating deletion of an essential gene, (2) Those resulting in transplants with normal or near normal growth rates, indicating deletion of non-essential genes, and (3) Those resulting in transplants with slow growth, indicating deletion of quasi-essential, i-genes.

A large number of deletions, including all of the HMG deletions, were individually tested for viability and yielded valuable information for subsequent reduced genome designs. The transposon insertion data used in the HMG design was all collected from passage P0. Consequently genes with insertions included the genes subsequently characterized as quasi-essential i-genes, so some HMG deletions gave very small colonies, or were non-viable.

In addition to deleting individual clusters, step-wise scarless deletion (FIG. 23) of medium to large clusters was undertaken to produce a series of strains with progressively greater numbers of genes removed. Strain D22 with 255 genes and 357 kb of DNA removed grew at a rate similar to Syn1.0 (Table 9). These deletion studies verified that the set of deletion rules routinely yielded viable knockouts.

Figure 23:
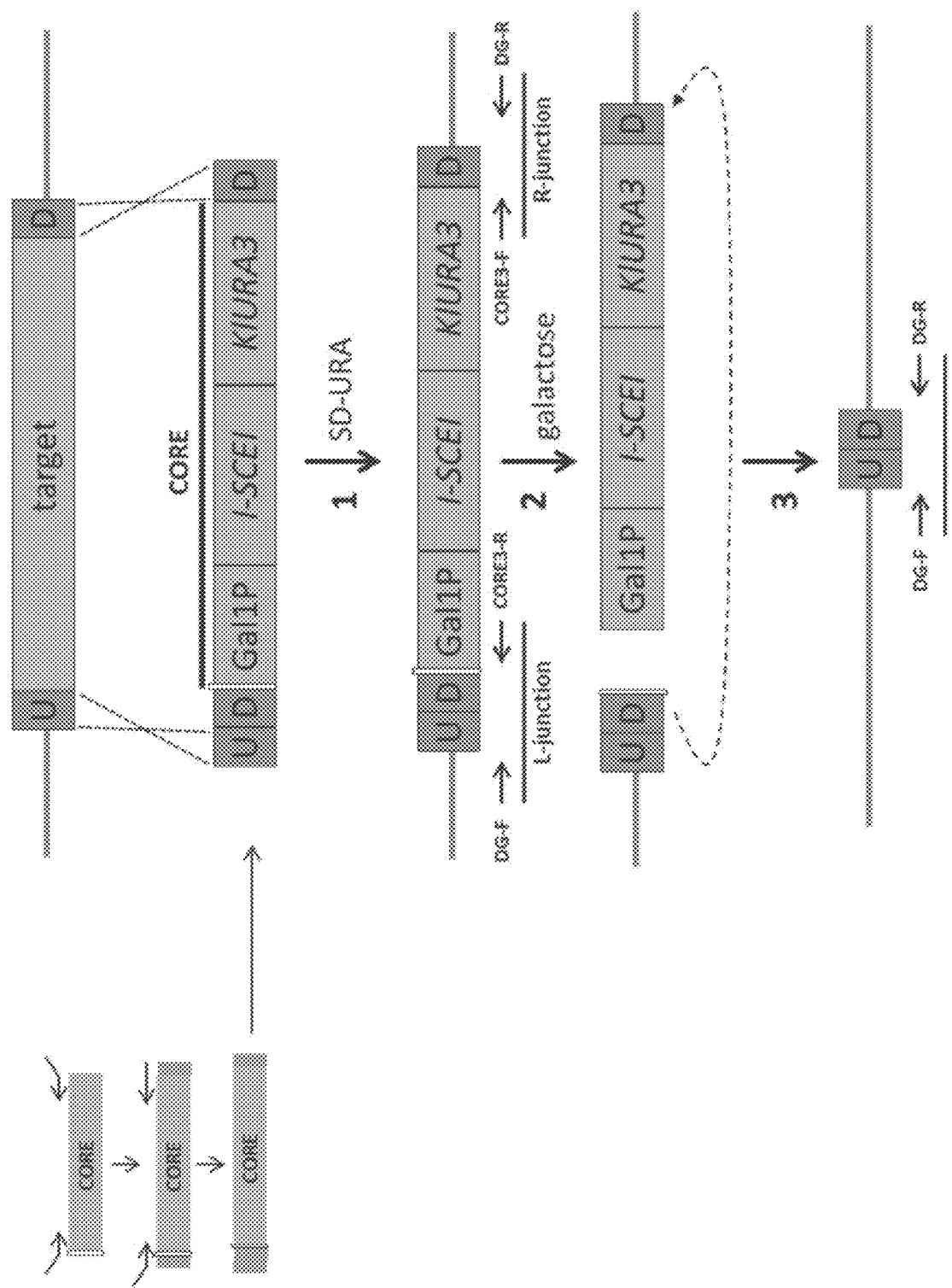
FIG. 23 is a non-limiting exemplary schematic illustration showing the TREC deletion method.

FIG. 23 is a schematic illustration showing the TREC deletion method. To generate a scarless deletion, the CORE cassette was PCR-amplified in two rounds to produce the knock-out cassette contained a 50 bp ("U" block) for homologous recombination, 50 bp ("D" block) repeated sequence, and a 50 bp ("D" block) for homologous recombination. Step 1, the cassette was transformed into a yeast strain harboring a mycoides genome and selected on SD minus plate. Correct target knock out was identified by PCR screening for insertion junctions (L and R). Step 2, galactose induction resulted in the expression of I-Sce I endonuclease, which cleaved the 18-bp I-Sce I site (open bar) to create a double-strand break that promoted homologous recombination between two tandem repeat sequences ("D" block). Step 3, recombination between two repeat sequences generated a scarless deletion. The deletion of a target region was confirmed by PCR using primers located up and down stream of the target region.

Step-Wise Genome Deletions (D Serial Genome Reduction)

Making D-deletions. The scarless TREC (tandem repeat coupled with endonuclease cleavage) deletion method was used to generate a series of reduced genomes in yeast. The scarless TREC deletion has been described in Lartigue et al., Science 325:1693-1696 (2009) and Noskov et al., Nucleic Acids Res. 38:2570-2576 (2010) which are hereby incorporated by reference. Six insertion element (IS) and two genes (MMSYN1_460 and _463) flanking one of IS element were sequentially deleted in the genome of JCVI-Syn1.0 Δ1-6 to produce the Syn1/ΔREΔIS genome. The Syn1/ΔREΔIS genome has been described in Karas et al., Nature methods 10:410-412 (2013), which is hereby incorporated by reference. Based on the Tn5 insertion data, twenty-two clusters were selected and subjected to deletion sequentially in the Syn1/ΔREΔIS genome to produce 22 strains (D1 to D22). In each round of the deletion, the genome was tested for viability by transplantation. The detailed information of deleted gene clusters is shown in the Table 9.

TABLE 9

Stepwise D-series deletions of JCVI Syn1.0.

| strains | deletion size (bp) | number of Δ genes | gene names | deletion coordinates | genome size (bp) | no. of genes deleted |
|---|---|---|---|---|---|---|
| JCVI Syn1.0 | | | | | 1,078,809 | |
| Syn1.0ΔRE | 16,626 | 17 | RE systems | | 1,062,183 | 17 |
| Syn1.0ΔREΔIS | 13,553 | 14 | IS elements | | 1,048,690 | 31 |
| D1 | 69,607 | 41 | 0550-0591 | 657179 . . . 728756 | 979,083 | 72 |
| D2 | 10,014 | 6 | 0698-0703 | 832678 . . . 842691 | 969,069 | 78 |
| D3 | 24,910 | 16 | 0889-0904 | 1049414-1074323 | 944,159 | 94 |
| D4 | 12,449 | 7 | 0180-0186 | 236820 . . . 249268 | 931,710 | 101 |
| D5 | 8,063 | 5 | 0084-0088 | 112555 . . . 120617 | 923,647 | 106 |
| D6 | 14,716 | 6 | 0241-0246 | 308601 . . . 323316 | 908,931 | 112 |
| D7 | 30,989 | 27 | 0734-0770 | 865972 . . . 907484 | 877,942 | 139 |
| D8 | 11,671 | 10 | 0860-0869 | 1014116 . . . 1025786 | 866,271 | 149 |
| D9 | 22,006 | 18 | 0170-0179 and 0187-0194 | 222395 . . . 256849 | 844,265 | 167 |
| D10 | 15,364 | 8 | 0841-0850 | 987122 . . . 1003970 | 828,901 | 175 |
| D11 | 12,094 | 13 | 0455-0474 | 563782 . . . 581943 | 816,807 | 188 |
| D12 | 11,301 | 7 | 0337-0343 | 424400 . . . 435700 | 805,506 | 195 |
| D13 | 10,840 | 5 | 0272-0276 | 345463 . . . 356302 | 794,666 | 200 |
| D14 | 9,904 | 7 | 0318-0324 | 402993 . . . 412896 | 784,762 | 207 |
| D15 | 9,631 | 9 | 0204-0212 | 266238 . . . 275868 | 775,131 | 216 |
| D16 | 11,136 | 8 | 0118-0125 | 145646 . . . 156781 | 763,995 | 224 |
| D17 | 6,994 | 6 | 0711-0716 | 849525 . . . 856518 | 757,001 | 230 |
| D18 | 7,481 | 5 | 0309-0313 | 392042 . . . 399522 | 749,520 | 235 |
| D19 | 6,496 | 5 | 0854-0857 and 0858 | 1005325 . . . 1011820 | 743,024 | 240 |
| D20 | 5,516 | 4 | 0673-0676 | 806351 . . . 811866 | 737,508 | 244 |
| D21 | 9,443 | 5 | 0594-0598 | 731220 . . . 740662 | 728,065 | 249 |
| D22 | 6,205 | 6 | 0019-0024 | 36687 . . . 42891 | 721,860 | 255 |

* the gene annotation and sequence coordinate are based on JCVI-Syn1.0
a: MMSYN1 0921-0922; 0449-0450; 0460-0463; 0735-0736; 0780-0781; 0265 + 0267
b: deletion of 6 regions: IS1 (35184 . . . 36668), IS3 (553595 . . . 555079), IS4+ (566641 . . . 572708), IS5 (867317 . . . 868801), IS6 (917601 . . . 919085), and IS8 (1000877 . . . 1002361)

The Scarless TREC Deletion Method for Producing the D-Series Deletions.

The TREC method was used to produce scarless deletions (FIG. 23). The design of a knock-out cassette is described in the Experimental Materials and Methods section, except the length of a repeated sequence was reduced to 50 bp, illustrated in FIG. 23. Unique knock-out cassettes were produced by 2 rounds of PCR using the Advantage HD Polymerase (Clontech) according to the manufacturer's instructions. The first round of PCR was performed for 18 cycles using the pCORE3 plasmid as a DNA template and a primer pair 1. The second round of PCR was performed for 22 cycles using the first round PCR product as DNA template and primer pair 2. Chimeric primers in the first round PCR would generate a CORE cassette flanked by a 50 bp repeated sequence on 5' end and 50 bp sequences for homologous recombination on 3' end. The generation of a CORE cassette using chimeric primers in the first round of PCR has been described in Noskov et al., Nucleic Acids Res. 38:2570-2576 (2010), which is hereby incorporated by reference. Chimeric primers in the second round PCR would generate a final knock-out cassette containing, from the 5' to 3' end, a 50 bp for homologous recombination, 50 bp repeated sequence, and a 50 bp for homologous recombination, illustrated in FIG. 23. The second round of PCR product was purified by the MinElute PCR Purification Kit (Qiagen). Approximately 0.5 to 1 µg purified PCR product was used for yeast transformation by the lithium acetate method.

The procedure of TREC deletion and cassette recycling was described previously in Fraser et al., Science 270:397-403 (1995) and Fleischmann et al., Science 269:496-512 (1995), which are hereby incorporated by reference. Briefly, after transformation, cells were plated out on SD (−) URA. Clones were screened by PCR analysis for the boundaries between the cassette and target site. Positive clones were grown on the YEPG media to induce the expression of the endonuclease I-SceI. A double strand cleavage by the endonuclease promoted a homologous recombination between two repeated sequences, leading to removal of the CORE cassette. After induction, cells were grown in SD (−) HIS (+) 5-FOA to select for the removal of the cassette. The precise recycling of the cassette was verified by junction PCR (FIG. 23). Primers were designed for screening knock-out and CORE3 cassette recycling. Primers were designed to amplify the CORE3 cassette for the deletion of gene clusters, and to detect junctions of the CORE3 cassette insertion and the cassette recycling (pop out).

All together, this example shows how genes in a genome can be classified as essential e-genes, non-essential n-genes, quasi-essential, and growth-impaired i-genes.

Example 3

Retention of Quasi-Essential Genes Yielded Eight Viable Segments

This example shows that the retention of quasi-essential genes yielded eight viable segments, but no complete viable genome.

To improve on the design of the HMG, a reduced genome was redesigned using the Tn5 and deletion data described in the Experimental Materials and Methods section and Example 2. This reduced genome design (RGD1.0) achieved a 50% reduction of Syn1.0 by removing approximately 90% of the n-genes (Table 1). In a few cases n-genes were retained if their biochemical function appeared essential or if they were singlet n-genes separating 2 large e- or i-gene clusters. This approach was employed to increase the possibility that the segments and the assembled genome would be viable. To preserve the expression of genes upstream and downstream of deleted regions the design rules used in the HMG design in Example 1 was followed.

Figure 13:
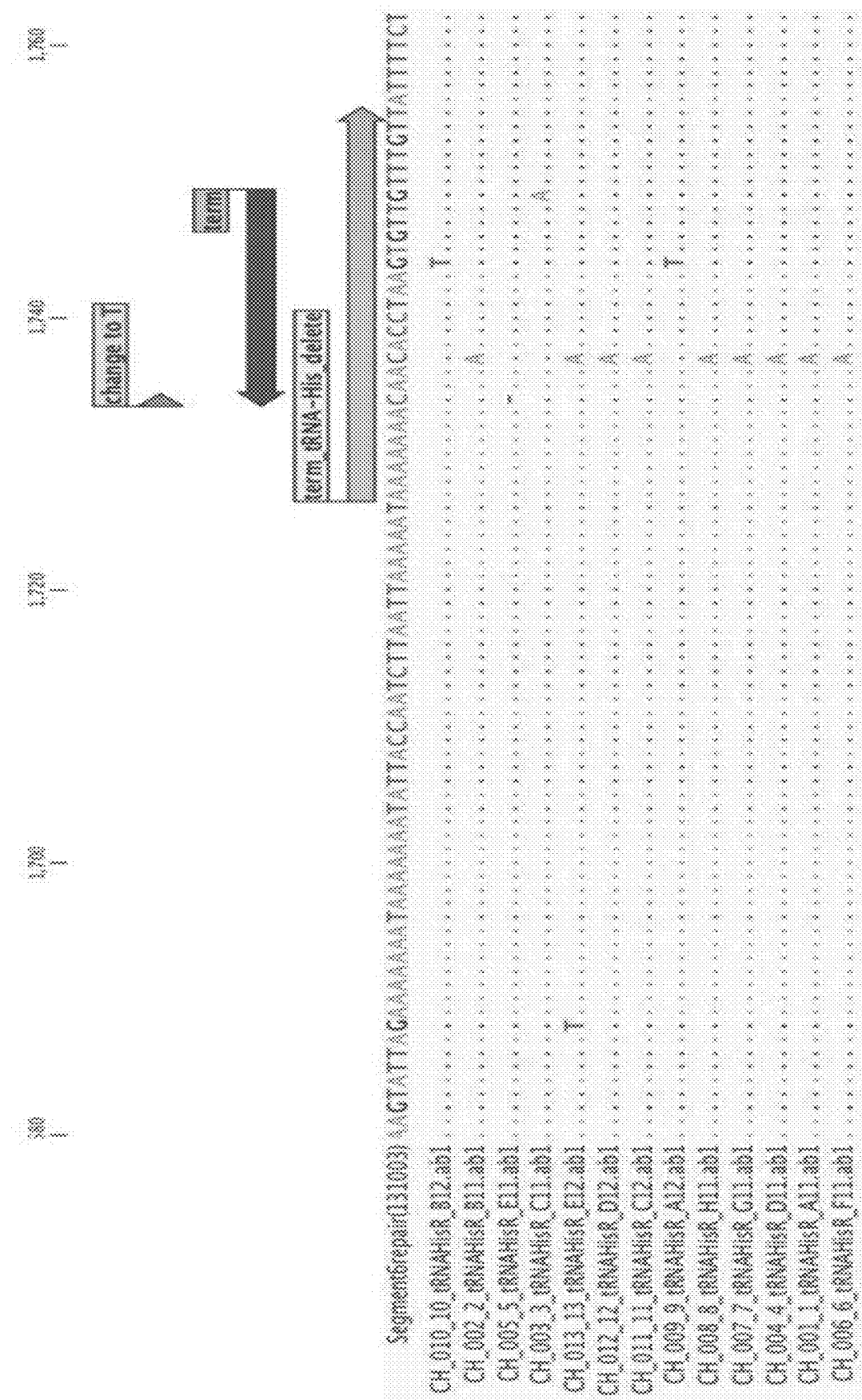

The 8 segments of RGD1.0 were chemically synthesized and each synthetic reduced segment was inserted into a ⅞th JCVI-Syn1.0 background in yeast using recombinase-mediated cassette exchange (RMCE) (Experimental Materials and Methods section, FIG. 10). RMCE has been described in Noskov et al., Biol. Proced. Online. 17, 6 (2015), which is hereby incorporated by reference. Each ⅛ RGD+⅞ Syn1.0 genome was then transplanted out of yeast to test for viability. Each of the 8 reduced segments produced a viable transplant; however, segment 6 gave a very small colony only after 6 days. On further growth over the next 6 days, sectors of faster growing cells developed (FIGS. 11A-11G). Several isolates of the faster growing cells were sequenced and found to have destabilizing mutations in a transcription terminator that had been joined to an essential gene when the non-essential gene preceding it had been deleted (FIGS. 12, 14). Another mutation produced a consensus TATAAT box in front of the essential gene (FIG. 13). This illustrates the potential for expression errors when genes are deleted, but shows that these can sometimes be corrected by subsequent spontaneous mutation. Ultimately, a promoter that had been overlooked and erringly deleted was identified. When this region was resupplied in accordance with the design rules, cells containing the redesigned segment 6 grew rapidly. This solution was incorporated in later designs.

When all eight reduced RGD1.0 segments, including self-corrected segment 6 were combined into a single genome, a viable transplant was not obtained (see the Experimental Materials and Methods section) The eight RGD1.0 segments were mixed with the eight Syn1.0 segments to perform combinatorial assembly of genomes in yeast (see the Experimental Materials and Methods section). A number of completely assembled genomes were obtained in yeast that contained various combinations of RGD1.0 segments and Syn1.0 segments. When transplanted, several of these combinations gave rise to viable cells (Table 4B). One of these (RGD2678), containing RGD1.0 segments 2, 6, 7, and 8 plus Syn1.0 segments 1, 3, 4, and 5 with an acceptable growth rate (105 min doubling time versus 60 min for Syn1.0) was analyzed in more detail.

All together, these data indicate that several combinations of the reduced RGD1.0 segments and Syn1.0 segments gave rise to viable cells even though all eight reduced RGD1.0 segments when combined into a single genome did not give rise to a viable transplant.

Example 4

Discovery of Essential Function Redundancies (EFRs) Contributed to Obtaining a Complete Viable Genome This example shows that the discovery of essential function redundancies (EFRs) contributed to obtaining a complete viable genome.

It was suspected that the failure of the RDG1.0 design to yield a complete viable genome was because of undiscovered essential function redundancies (EFRs) carried by more than one segment. In bacteria, it is common for certain essential (or quasi-essential) functions to be provided by more than one gene. The genes may or may not be paralogs, and in fact, often are not. Suppose gene A and gene B, each supply the essential function E1. The pair represents an EFR. Either gene can be deleted without loss of E1, so each gene by itself in a single knockout study is classified as non-essential. However, if both are deleted, the cell will be dead because E1 is no longer provided. EFRs are common in bacterial genomes, although less so in genomes that have undergone extensive evolutionary reduction such as the mycoplasmas. And thus, undiscovered EFRs in which gene A had been deleted from one segment and gene B from another segment can facilitate the generation of a viable genome with a reduced size. Each RDG1.0 segment was viable in the context of a ⅞ Syn1.0 background, but when combined the resulting cell was non-viable, or grew more slowly in the case of a shared quasi-essential function. The number of redundant essential functions present in different segments were not known, but at least for segments 2, 6, 7, and 8 none of the genes with shared essential functions was deleted and therefore when combined these four segments gave a viable cell.

To discover these EFRs, RGD2678 obtained in Example 3 was subject to Tn5 mutagenesis and it was found that some n-genes in the Syn1.0 segments 1, 3, 4, and 5 had converted to i- or e-genes in the genetic context of RGD2678 (Table 2). Without being limiting to a particular theory, it is believe that these genes encoded EFRs of which one member of the redundant pair had been deleted in RGD2678.

In addition, 39 gene clusters and single genes that had been deleted in the design of RGD1.0 segments 1, 3, 4 and 5 were examined (Table 5). These were deleted one at a time in an RGD2678 background (Tables 5, 6) and tested for viability by transplantation. No transplants, or slow growth, were obtained in several cases suggesting they contained one or more genes functionally redundant with genes that had been deleted in segments 2, 6, 7, or 8.

The combined Tn5 and deletion data identified 26 genes (Tables 2, 10) as candidates for adding back to RGD1.0 segments 1, 3, 4 and 5 to produce a new RGD2.0 design for these segments (Tables 1, 2, FIG. 7). Table 10 shows the 26 genes for the redesign of RGD segments 1, 3, 4, and 5. 4 RGD1.0 version of segments 1, 3, 4, and 5 were re-synthesized by adding back 26 genes to produce RGD2.0-1, -3, -4, and 5.

TABLE 10

26 genes for the redesign of RGD segments 1, 3, 4, and 5.

| Segment | systematic name | gene product |
|---|---|---|
| 1 | MMSYN1_0035 | conserved hypothetical protein |
|  | MMSYN1_0036 | D-lactate dehydrogenase |
|  | MMSYN1_0037 | malate permease |
|  | MMSYN1_0038 | conserved hypothetical protein |
|  | MMSYN1_0051 | conserved hypothetical protein |
|  | MMSYN1_0054 | AhpC/TSA family protein |
|  | MMSYN1_0060 | putative membrane protein |
|  | MMSYN1_0077 | putative hydrolase of the HAD family |
|  | MMSYN1_0078 | putative hydrolase from alpha/beta family |
|  | MMSYN1_0080 | conserved hypothetical protein |
| 2 | MMSYN1_0217 | glycerol uptake facilitator protein |
|  | MMSYN1_0218 | glycerol kinase |
|  | MMSYN1_0219 | glycerol oxydase |
|  | MMSYN1_0232 | pantetheine-phosphate adenylyltransferase |
|  | MMSYN1_0245 | putative membrane protein |
|  | MMSYN1_0246 | E1-E2 ATPase subfamily, putative |
|  | MMSYN1_0251 | conserved hypothetical protein |
|  | MMSYN1_0252 | oxidoreductase |
|  | MMSYN1_0256 | Amino acid permease superfamily protein |
|  | MMSYN1_0275 | putative lipoprotein |
| 3 | MMSYN1_0332 | conserved hypothetical protein |
|  | MMSYN1_0338 | putative lipoprotein |
| 4 | MMSYN1_0444 | endopeptidase O |
|  | MMSYN1_0477 | conserved hypothetical protein |
|  | MMSYN1_0494 | putative N-acetylmannosamine-6-phosphase 2-ipimeras |
|  | MMSYN1_0504 | conserved hypothetical protein |

Figure 24:
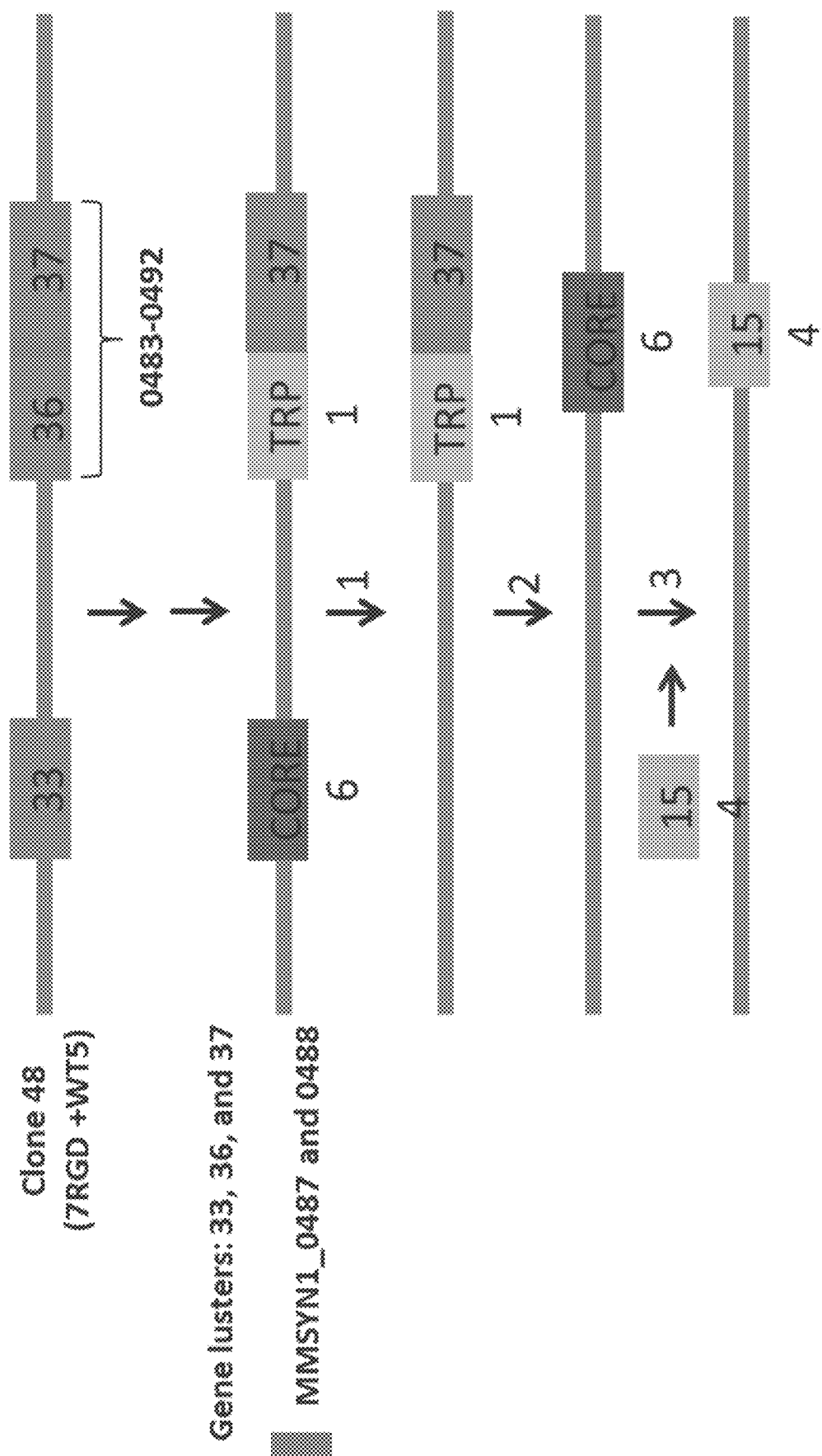
FIG. 24 is a non-limiting exemplary schematic illustration showing genome engineering to produce the Syn2.0 in yeast.

An assembly was carried out in yeast using the newly designed and synthesized RGD2.0 segments 1, 3, 4, and 5 together with RGD1.0 segments 2, 6, 7, and 8 (Tables 7, 4B). This assembly was still not viable, but substituting Syn1.0 segment 5 for RGD2.0 segment 5 resulted in a viable transplant. Working with this strain, a cluster of genes (0454-0474) was deleted from the Syn1.0 segment 5 and replaced another cluster of genes (0483-0492) with gene MMSYN1_0154 (FIGS. 8, 24, Table 11).

Gene MMSYN1_0154 was originally deleted from segment 2 in the RGD1.0 design but was re-classified as quasi-essential in the RGD2678 background. The described revision of Syn1.0 segment 5 in the RGD2.0 genetic context gave a viable cell, which was referred to as JCVI-Syn2.0 (abbreviated Syn2.0, see FIG. 25). With Syn2.0, it was achieved for the first time, a minimized cell with a genome smaller than that of the smallest known natural bacterium *M. genitalium*. Syn2.0 doubled in laboratory culture every 92 minutes, and its genome was 576 kb in size and contained 478 protein and 38 RNA coding genes.

Detailed Derivation of the JCVI-Syn2.0 Genome from 7RGDs+WT5 Genome

Among all *M. mycoides* strains with various intermediate RGD constructs, clone 48 was the smallest genome with an acceptable growth rate (≤120 min). Step-wise cluster deletions were used to explore a maximum reduction within the WT 5 segment in the clone 48. Of 39 genes and gene clusters (Table 5), 3 clusters (33, 36, and 37) located in WT 5 segment (Table 5) were selected for deletion by marker replacement. A number of deletion constructs were generated and transplanted. These constructs included all single cluster deletions, a double cluster deletion (Δ33Δ36), and a triple cluster deletion (Δ33Δ 36 Δ37). All constructs were able to produce viable transplants. In addition, the genome with a deletion region, called cluster 0483-0492, covering the cluster 36, 37, and two genes (MMSYN1_0487 and 0488) between these 2 clusters was also able to produce viable transplants. At this point, the size of the genome after the triple cluster deletion had been reduced to ~564 kb which was smaller than the 580 kb genome of *M. genitalium* which was the smallest organism that had been cultured in the laboratory. The growth rate of the triple cluster deletion was about 120 min which was about 2 times slower than that of Syn1.0.

*M. mycoides* contained two copies of the leucyl aminopeptidase gene (MMSYN1_0154 and 0190). These two genes were originally categorized as n-genes, thus were deleted in the RGD1.0 design. However, data from the Tn5 mutagenesis on the D10 genome indicated that lack of both genes impaired cell growth, thus adding back a leucyl aminopeptidase gene to clone 48 or its reduced derivatives should facilitate cell growth.

A complementation was carried out by replacing the cluster 0483-0492 with gene 0154 in a clone 48 lacking the cluster 33 (Table 10). A CORE6 cassette used to delete the cluster 33 was first recycled in the genome with double cluster deletion (Δ33Δ36), followed by insertion of the gene 0154 to the genome and cassette recycling (FIG. 24). After genome transplantation, multiple clones were isolated and characterized. Once the leucyl aminopeptidase gene was inserted into the genome, transplanted cells exhibited an improved growth rate. The final 576 kb JCVI-Syn2.0 genome was confirmed by sequencing.

FIG. 24 is a schematic illustration of genome engineering to produce the Syn2.0 in yeast. A double clusters deletion (33 and 36) in the 7RGD+WT5 genome was produced by 2 rounds of deletions by the CORE6 cassette containing the KIURA3 and the TRP1 marker, respectively. Step 1, the CORE6 cassette was seamlessly recycled via homologous recombination between 2 repeated sequences flanking the cassette. Step 2, the CORE6 cassette was then used again to replace the region covering both cluster 33 and 36, and two genes (MMSYN1_0483 and 0492). Step 3, MMSYN1_0154 was inserted into the genome via a knock-in module, followed by the cassette recycling.

Table 11 shows the genes that had been deleted in the design of RGD2.0-5. The final Syn2.0 genome was produced by deletion of the cluster 33 (0454-0474) and replacement of the cluster 0483-0492 with MMSYN1_0154 in clone 48. See Table 9 for segment composition of clone 48.

TABLE 11

Genes Deleted in the Design of RGD2.0-5.

| | |
|---|---|
| MMSYN1_0417 | cdse |
| MMSYN1_0436 | uracil-DNA glycosylase (UDG) |
| MMSYN1_0454 | hypothetical protein |
| MMSYN1_0455 | putative membrane protein |
| MMSYN1_0924 | conserved domain protein |
| MMSYN1_0460 | bacterial surface protein26-residuerepeatprotein |
| MMSYN1_0463 | NADH dependent flavin oxidoreductase |
| MMSYN1_0464 | lipoate-protein ligase |
| MMSYN1_0465 | conserved hypothetical protein |
| MMSYN1_0466 | glycine cleavage system H protein |
| MMSYN1_0467 | triacylglycerol lipase |
| MMSYN1_0468 | lipase-esterase |
| MMSYN1_0469 | lipase-esterase |
| MMSYN1_0470 | conserved hypothetical protein |
| MMSYN1_0471 | hypothetical protein |
| MMSYN1_0472 | putative liporotein |
| MMSYN1_0473 | ABC transporter, ATP binding protein |
| MMSYN1_0474 | ABC transporter, ATP binding protein |
| MMSYN1_0476 | N-acetylglucosamine-6-phosphate deacetylase |
| MMSYN1_0480 | conserved hypothetical protein |
| MMSYN1_0483 | holliday junction DNA helicase RuvA |
| MMSYN1_0484 | holliday junction ATP-dependent DNA helicaseRuvB |
| MMSYN1_0485 | dihydrolipoamide dehydrogenase |
| MMSYN1_0486 | conserved hypothetical protein |
| MMSYN1_0487 | conserved hypothetical protein |
| MMSYN1_0488 | ribosome biogenesis GTPase YqeH |
| MMSYN1_0489 | DNA polymerase IV |
| MMSYN1_0490 | papain family cysteine protease, putative |
| MMSYN1_0491 | uridine kinase |
| MMSYN1_0492 | conserved hypothetical protein |
| MMSYN1_0494 | putativeN-acetylmannosamine-6-phosphate2-epimeras |
| MMSYN1_0495 | ROK family protein |
| MMSYN1_0496 | conserved hypothetical protein |
| MMSYN1_0497 | sodium:solute symporter family |
| MMSYN1_0498 | N-acetylneuraminatelyase(N-acetylneuraminicacidal |
| MMSYN1_0503 | conserved hypothetical protein |
| MMSYN1_0504 | rRNA small subunit)S-adenosylmethionine-dependent methyltransferase |
| MMSYN1_0505 | putative liporotein |

Cluster Deletions and Gene MMSYN1-0154 Complementation.

A 2-cluster deletion (433436) in the clone 48 genome was used to create the final RGD genome (JCVISyn2.0). To remove the CORE6 cassette, the recycling construct consisting of 3' truncated KanMX4 gene and a 50 bp repeat sequence was produced by 2 rounds of PCR amplification. The 3' KanMX4 gene was PCR-amplified for 18 cycles using the pFA6a-kanMX4 as template. The second round of PCR was performed using the first round PCR product as DNA template. After transformation, cells were selected on Geneticin G418 plates as described in the Experimental Materials and Methods section. Correct insertions were screened by junction PCR. The procedure for the removal of the cassette was described in the Experimental Materials and Methods section. The resulting genome was subjected to gene knock-in by TREC-IN method (FIG. 7). The CORE6 cassette was generated by 2 rounds of PCR amplification using pCORE6 as DNA template. After transformation, cells were selected on SD minus URA. A correct integration was verified by junction PCR using 2 primer sets at the L junction, and the R junction. Positive clones were subjected to the second round of transformation to insert the gene 0154. The strategy of gene insertion was same as the insertion of gene cluster 0217-0219 as described in the Experimental Materials and Methods section. The 3' KanMX4 gene was PCR-amplified in 2 rounds and the gene 0154 was PCR-amplified using the Syn1.0 genome as DNA template. The 2 PCR products were purified and co-transformed into yeast and selected on G418 plates. A correct insertion was screened by junction PCR. Positive clones were subjected to the cassette recycling procedure as described in the Experimental Materials and Methods section. A precise removal of the cassette was verified by junction PCR. Multiple positive clones were isolated and subjected to transplantation.

All together, these data indicate that with Syn2.0, a minimized cell with a genome smaller than that of the smallest known natural bacterium *M. genitalium* was achieved for the first time.

Example 5

A Third Design Stage, RGD3.0, with Removal of 42 Additional Genes, Yielded an Approximately Minimal Cell, Syn3.0

This example demonstrates that a third design stage, RGD3.0, with removal of 42 additional genes from Syn2.0, yielded an approximately minimal cell, Syn3.0.

A new round of Tn5 mutagenesis was performed on Syn2.0. In this new genetic background, transition of some i-genes to apparent n-genes was a possibility. The composition of the P4 serial passage population was depleted of original n-genes and the faster growing i-gene knockouts predominated and were called n-genes by the classification rules. Ninety genes were classified as apparently non-essential. These were sub-divided into 3 groups. The first group contained 26 genes frequently classified as i- or e-genes in previous rounds of mutagenesis. The second group contained 27 genes that were classified as i- or borderline i-genes in some of the previous Tn5 studies. The third group contained 37 genes that had previously been classified as non-essential in several iterations of Tn5 mutagenesis involving various genome contexts. To create the new RGD3.0 design these 37 were selected for deletion from Syn2.0 along with two vector sequences, bla and lacZ, and the rRNA operon in segment 6 (Table 12, FIG. 25).

TABLE 12

Non-essential genes deleted from Syn2.0 to yield Syn3.0. Tn5 mutagenized cells were passaged 6 times to deplete quasi-essential genes (last column).

| MMSYN1 | SGI Annotation | syn2_P0 | syn2_P1 | syn2_P2 | syn2_P6 |
|---|---|---|---|---|---|
| _0013 | Mycoides cluster lipoprotein, LppA/P72 family | 168 | 88 | 145 | 93 |
| _0028 | Cold—shock DNA—binding protein family | 17 | 12 | 12 | 6 |
| _0031 | Heat shock protein 33, redox regulated chapero | 31 | 13 | 30 | 13 |
| _0035 | Variable surface protein | 115 | 45 | 91 | 48 |
| _0036 | D—isomer specific 2—hydroxyacid dehydrogenase | 98 | 52 | 73 | 62 |

TABLE 12-continued

Non-essential genes deleted from Syn2.0 to yield Syn3.0. Tn5 mutagenized cells were passaged 6 times to deplete quasi-essential genes (last column).

| MMSYN1 | SGI Annotation | syn2_P0 | syn2_P1 | syn2_P2 | syn2_P6 |
|---|---|---|---|---|---|
| _0037 | Transporter, auxin efflux carrier (AEC) family pr | 97 | 59 | 77 | 62 |
| _0038 | ATPase (AAA+ superfamily) | 106 | 58 | 69 | 60 |
| _0048 | Cytidine and deoxycytidylate deaminase zinc—bi | 32 | 16 | 23 | 13 |
| _0062 | Macrophage Migration Inhibitory Factor | 19 | 7 | 21 | 5 |
| _0078 | Alpha/beta hydrolase fold family protein | 56 | 28 | 46 | 22 |
| _0096 | Proline dipeptidase | 17 | 7 | 6 | 7 |
| _0217 | Glycerol uptake facilitator protein. | 113 | 57 | 88 | 58 |
| _0219 | FAD/NAD(P)—binding domain | 113 | 53 | 60 | 25 |
| _0258 | NAD(P)—binding Rossmann—fold domains | 54 | 21 | 40 | 25 |
| _0278 | PTS system fructose—specific enzyme iiabc comp | 218 | 108 | 183 | 133 |
| _0279 | Membrane protein | 33 | 20 | 25 | 20 |
| _0284 | Lysophospholipase Monoglyceride lipase | 30 | 18 | 19 | 15 |
| _0333 | Lipoprotein, putative (VlcA) | 24 | 6 | 28 | 18 |
| _0334 | Lipoprotein, putative (VlcB) | 34 | 13 | 34 | 25 |
| _0335 | Lipoprotein, putative (VlcC) | 37 | 13 | 30 | 17 |
| _0336 | Phosphotransferase system PTS, IIA component | 26 | 10 | 16 | 11 |
| _0351 | Holliday junction resolvase RecU | 13 | 2 | 11 | 6 |
| _0355 | Lipoprotein, PARCEL family | 42 | 16 | 36 | 31 |
| _0370 | Single—strand binding family protein | 23 | 14 | 18 | 12 |
| _0417 | Prophage protein (Ps3) | 23 | 13 | 24 | 38 |
| _0436 | Uracil—DNA Glycosylase| subunit E | 34 | 14 | 24 | 16 |
| _0446 | Membrane protein | 19 | 6 | 6 | 9 |
| _0476 | N—acetylglucosamine—6—phosphate deacetylase | 75 | 44 | 57 | 27 |
| _0477 | Membrane protein | 27 | 20 | 23 | 13 |
| _0480 | Conserved predicted protein | 90 | 71 | 100 | 135 |
| _0496 | | 8 | 3 | 9 | 4 |
| _0497 | Solute:sodium symporter (SSS) family transport | 117 | 57 | 98 | 74 |
| _0498 | N—acetylneuraminate lyase | 70 | 35 | 46 | 30 |
| _0514 | Membrane family protein | 46 | 25 | 24 | 24 |
| _0677 | Membrane protein | 38 | 27 | 30 | 26 |
| _0829 | Hydrolase, TatD deoxyribonuclease family prot | e47 | 18 | 31 | 18 |
| _0905 | | 6 | 2 | 10 | 4 |

The 8 newly designed RGD3.0 segments were synthesized and propagated as yeast plasmids. These plasmids were amplified in vitro by RCA (Experimental Materials and Methods section). All 8 segments were then reassembled in yeast to obtain several versions of the RGD3.0 genome as yeast plasmids (Experimental Materials and Methods section). These assembled RGD3.0 genomes were transplanted out of yeast. Several were viable. One of these, RGD3.0 clone g-19 (Table 13) was selected for detailed analysis and named JCVI-Syn3.0.

Figure 25:
FIG. 25 is a non-limiting exemplary Syn1.0 gene map showing the three DBT cycles involved in building Syn3.0.

FIG. 25 shows the three DBT cycles involved in building Syn3.0. This detailed map shows syn1.0 genes that were deleted or added back in the various cycles going from syn1.0 to syn2.0, and finally to syn3.0 (Compare with FIG. 9). The long white dotted arrows indicate the 8 Not assembly segments. Light grey arrows represent genes that were retained throughout the process. Genes that are deleted in both syn2.0 and syn3.0 are shown in black. White arrows (slightly offset) represent genes that were added back. The original RGD1.0 design was not viable, but a combination of syn1.0 segments 1,3,4,5 and designed segments 2,6,7,8 produced a viable cell referred to as RGD2678. Addition of the genes shown in white resulted in syn2.0, which has 8 designed segments. Additional deletions (shown in dark grey) produced syn3.0 (531,560 bp, 473 genes).

Table 13 shows that eighth molecule RGD3-1 was synthesized with and without rDNA operon I and eighth molecule RGD3-6 was synthesized with and without rDNA operon II in order to generate three RGD3 genomes: (E) absence of rDNA operon I, (F) presence of rDNA operons I and II, and (G) absence of rDNA operon II. Although full-length RGD3 genomes were assembled in yeast for all three, only (F) and (G) genome versions could generate transplants. One transplant from (G), assigned clone 19-1, was further characterized and later named Syn3.0.

TABLE 13

RGD3 Genome Constructions in Yeast and Transplantation Results

| Genome Construction | # Full-length RGD3 constructs (out of 48) | Transplantation Results |
|---|---|---|
| (E) RGD3 Δ rDNA operon I | 3 | 0 out of 3 |
| (F) RGD3 | 3 | 3 out of 3 |
| (G) RGD3 Δ rDNA operon II | 10 | 2 out of 10 |

A final round of Tn5 mutagenesis was performed on Syn3.0 to determine which genes continue to show Tn5 insertions after serial passaging (P4). Non-essential vector genes and intergenic sequences were the most frequent insertion sites. Cells with insertions in genes originally classified as quasi-essential made up almost the whole population of P4 cells that had insertions in *mycoplasma* genes. The genes in Syn3.0 were then predominantly essential e-genes, or quasi-essential i-genes by the original Syn1.0 classification. Of these, only the i-genes can tolerate Tn5 insertions without producing lethality. The most highly represented in-, i-, and ie-genes are shown in Tables 3A-3C. In addition, there were a dozen genes originally classified as non-essential that continued to retain that classification (Table 3D, Table 8).

All together, these data indicate that the removal of 42 additional genes from Syn2.0 yielded an approximately minimal cell, Syn3.0.

genes]) proceed left to right from nearly complete certainty about a gene's activity (equivalog) to no functional information (unknown). White space indicates no homologs to Syn3.0 in that organism.

The TIGRfam 'equivalog' family of HMMs was used to annotate such genes (Haft et al., Nucleic Acids Ress 31:371-373 (2003), ~49% of the genes). The less certain classes were produced in a stepwise manner. Biological functions could not be assigned to about 31% of the genes in the generic and unknown classes. Nevertheless, potential homologs for a number of these were found in diverse organisms. Many of these genes may represent universal proteins whose functions were yet to be characterized. Each of the five sectors had homologs in species ranging from *mycoplasma* to man. However, some of each annotation class is blank, indicating that no homologs for these genes

TABLE 14 summarizes the generation process leading to syn3.0. Starting with JCVI-syn1.0, four rounds of design (i.e., the HMG, the RGD1.0, RGD2.0, and RGD3.0) were made. The first three rounds of design (i.e., HMG, RGD1.0, and RGD2.0) did not yield complete viable cellular genomes. But in each case, one or more of the 8 segments yielded a viable genome when combined with syn1.0 segments for the remainder of the genome. The composition of several of these intermediate strains is listed in Table 14. RGD3.0, named as JCVI-syn3.0, did yield a viable cell.
14. Genome Designs

| Genome design (1) | Design size (2) | Cellular genome segment composition for key viable strains (3) | Cellular genome size (4) | Growth (5) |
|---|---|---|---|---|
| — | | JCVI-syn1.0 (syn1.0)-all 8 syn1.0 segments | 1079 kb | Td = 60 min |
| HMG | 483 kb | HMG segment 2 + 7/8 syn1.0 | 1003 kb | slow growing |
| RGD1.0 | 544 kb | RGD1.0 segments 2, 6, 7, 8 + syn1.0 segments 1, 3, 4, 5 | 758 kb | Td = 100 min |
| RGD1.0 | 544 kb | RGD1.0 segments 1, 2, 4, 6, 8 + syn1.0 segments 3, 5, 7 | 718 kb | slow growing |
| RGD2.0 | 575 kb | RGD2.0 segments 1, 2, 3, 4, 6, 7, 8 + syn1.0 segment 5 | 617 kb | ? |
| RGD2.0 | 575 kb | JCVI-syn2.0 (syn2.0) = RGD2.0 segments 1, 2, 3, 4, 6, 7, 8 + syn1.0 segment 5 with genes MMSYN1_0454-0474 and MMSYN1_0483-0492 deleted | 576 kb | Td = 92 min |
| RGD3.0 | 531 kb | JCVI-syn3.0 (syn3.0, all 8 segments of RGD3.0) | 531 kb | Td = 180 min |

Column (1) lists the four rounds of genome design, or "-" for the starting genome, syn1.0;
Column (2) shows the size of the designed genome
Column (3) shows the genome composition for viable cell strains. For non-viable designs, a viable strain with the highest number of segments from the design is shown, as well as a more robust alternative for RGD1.0, and a smaller derivative for RGD2.0, named syn2.0);
Column (4) shows the size of the corresponding genome in column 3
Column (5) shows a quantitative or qualitative estimate of the growth rate of cells with the genome described Example 6

Classification of Genes Retained in Syn3.0

This example demonstrates that Syn3.0 retained essential genes for known core cellular functions, but 150 genes cannot be assigned a specific biological function and 80 of these cannot be assigned to a functional category.

Figure 26:
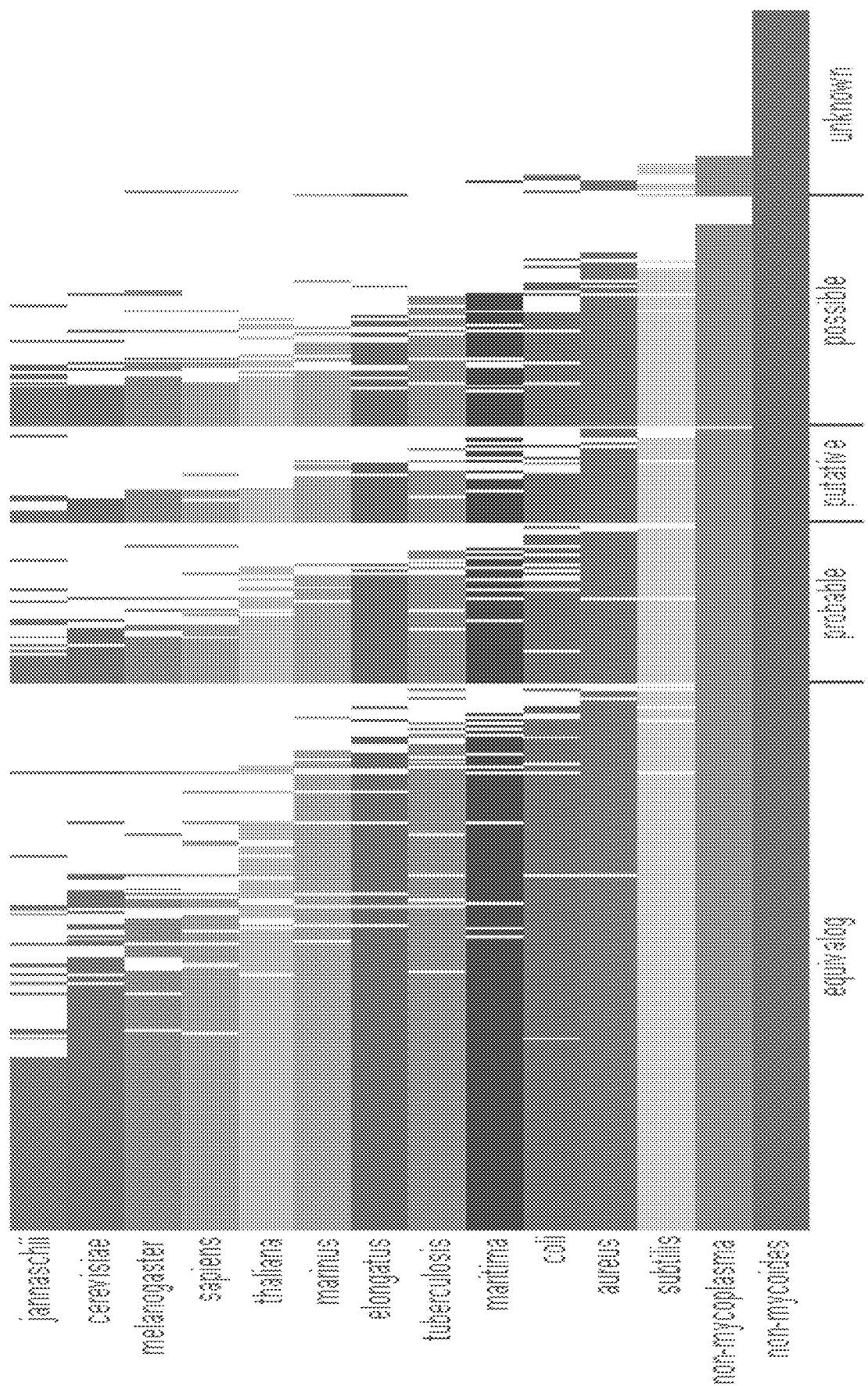
FIG. 26 is a non-limiting exemplary BLAST map showing proteins in Syn3.0 and homologs found in other organisms.

Syn3.0 had 442 protein and 35 RNA coding genes. The 477 genes were assigned to five classes: equivalog, probable, putative, generic, and unknown based on the confidence levels of their precise functions (FIG. 26 and Table 8). Many of the genes had been studied exhaustively and their primary biological functions were known.

FIG. 26 shows a BLAST map of proteins in Syn3.0 and homologs found in other organisms. A BLASTp score of $1e^{-5}$ was used as the similarity cutoff. Functional classifications (equivalog [233 genes]: probable [58 genes]: putative [36 genes]: generic [83 genes]; and unknown [67 were found among the 15 organisms chosen for display. Since mycoplasmas evolve rapidly, some of the whitespace in FIG. 26 corresponds to sequences that have diverged so far from the norm as to align poorly with representatives from other organisms.

Table 15 shows the assignment of Syn1.0 genes to 30 functional categories and indicates how many were kept or deleted in Syn3.0. Of the 424 deleted genes, the largest group was the unassigned genes: 133 out of 213 were deleted. All of the 73 mobile element and DNA modification and restriction genes were removed, as well as most genes encoding lipoproteins (71 out of 87). Just these 3 categories alone accounted for 65% of the deleted genes. In addition, because of the rich growth medium used in the examples supplied almost all needed small molecules, many genes involved in transport, catabolism, proteolysis, and other metabolic processes had become dispensable. For example, because glucose was plentiful in the medium, most genes for transport and catabolism of other carbon sources were deleted (32 out of 36), while all 15 genes involved in glucose transport and catabolism were retained.

TABLE 15

JCVI-Syn1.0 genes listed by functional category and whether kept or deleted in JCVI-Syn3.0. Categories in bold type were mostly kept in Syn3.0 while those in non-bold type were depleted in Syn3.0.

| Functional Category | Keep | Delete |
|---|---|---|
| Glucose transport & catabolism | 15 | 0 |
| Ribosome biogenesis | 14 | 1 |
| Protein export | 10 | 0 |
| Transcription | 9 | 0 |
| RNA metabolism | 7 | 0 |
| DNA topology | 5 | 0 |
| Chromosome segregation | 3 | 0 |
| DNA metabolism | 3 | 0 |
| Protein folding | 3 | 0 |
| Translation | 89 | 2 |
| RNA (rRNAs, tRNAs, small RNAs) | 35 | 4 |
| DNA replication | 16 | 2 |
| Lipid salvage and biogenesis | 21 | 4 |
| Cofactor transport and salvage | 21 | 4 |
| rRNA modification | 11 | 4 |
| tRNA modification | 14 | 5 |
| Efflux | 7 | 3 |
| Nucleotide salvage | 19 | 8 |
| DNA repair | 8 | 6 |
| Metabolic processes | 11 | 9 |
| Membrane transport | 32 | 31 |
| Redox homeostasis | 4 | 4 |
| Proteolysis | 10 | 11 |
| Regulation | 9 | 10 |
| Unassigned | 80 | 133 |
| Cell division | 1 | 3 |
| Lipoprotein | 16 | 71 |
| Carbon source transport and catabolism | 4 | 32 |
| Acylglycerol breakdown | 0 | 4 |
| Mobile elements and DNA restriction | 0 | 73 |
| Total | 477 | 424 |

In contrast, almost all of the genes involved in the machinery for reading and expressing the genetic information in the genome and in assuring the preservation of the genetic information from generation to generation were retained. The first of these two fundamental life processes, expressing the genetic information as proteins, required retention of 201 genes in the categories of transcription, regulation, RNA metabolism, translation, protein folding, protein export, RNA (rRNA, tRNA, small RNAs), ribosome biogenesis, rRNA modification, and tRNA modification. The second of these two fundamental processes, preservation of genome sequence information, required retention of 36 genes in the categories of DNA replication, DNA repair, DNA topology, DNA metabolism, chromosome segregation, and cell division. These 2 processes together required 237 (50%) of the 477 total genes in Syn3.0 (FIG. 27).

Figure 27:
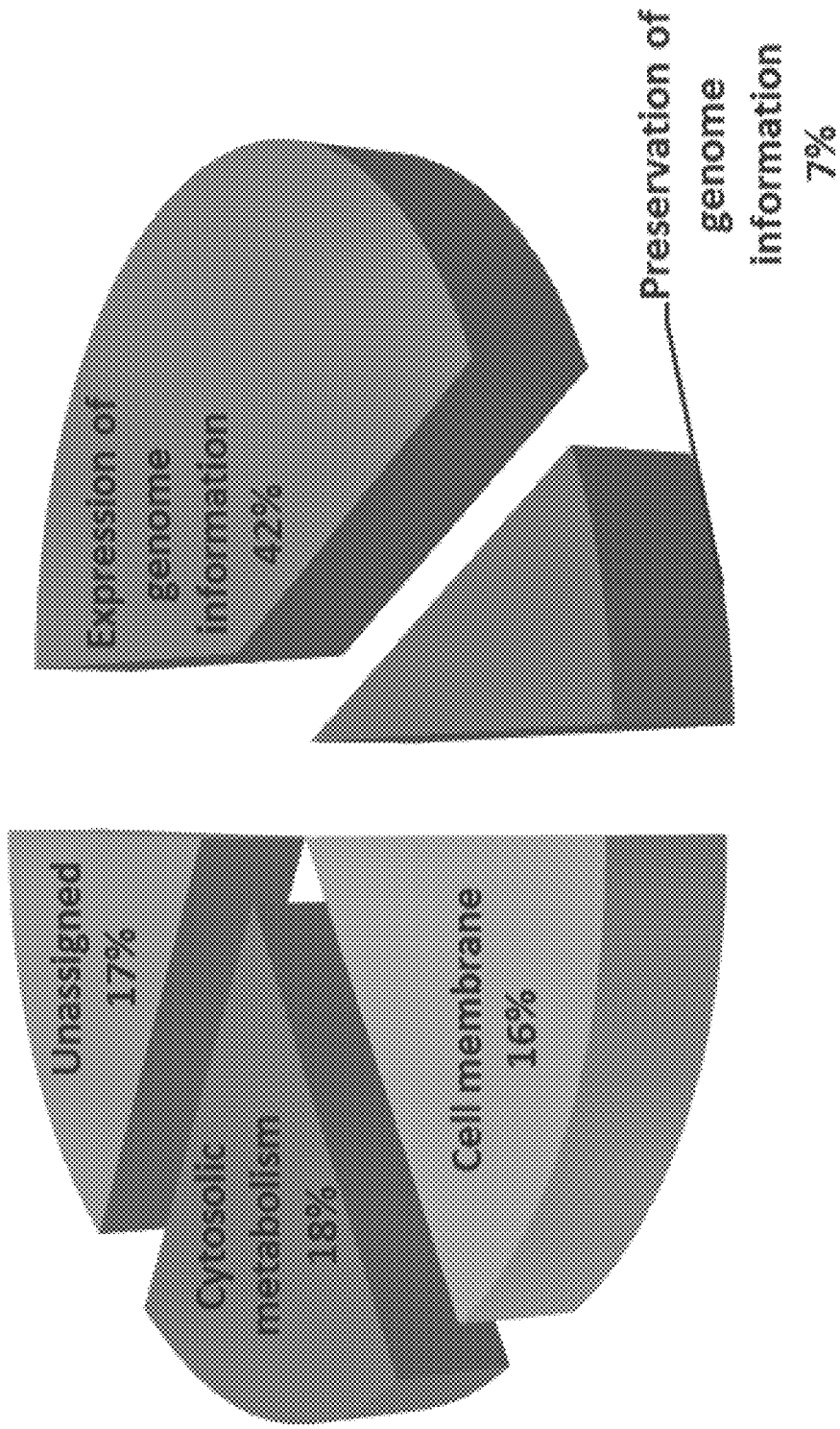
FIG. 27 is a non-limiting exemplary pie chart showing the partition of genes into four major functional groups.

FIG. 27 shows the partition of genes into four major functional groups. Syn3.0 had 477 genes. Of these, 80 had no assigned functional category (Table 15). The remainder can be assigned to 4 major functional groups: (1) expression of genome information (201 genes, 42%): (2) preservation of genome information (36 genes): (3) cell membrane structure and function (76 genes, 16%); and (4) cytosolic metabolism (84 genes, 18%). The percentage of genes in each group is indicated.

In addition to the two important biological processes described above—that is, the process of expressing genetic information and the process of preservation of genome sequence information), another major component of living cells is the cell membrane that separates the outer medium from the cytoplasm and governs molecular traffic into and out of the cell. It is an isolatable structure and many of the Syn3.0 genes coded for its protein constituents. Since the minimal cell was largely lacking in biosynthesis of amino acids, lipids, nucleotides, and vitamins, it depended on the rich medium to supply almost all these required small molecules. This necessitated numerous transport systems within the membrane. In addition, the membrane was rich in lipoproteins. Membrane related genes accounted for 76 (16%) of the 477 total Syn3.0 genes. Included categories from Table 15 are lipoproteins, cofactor transport, efflux systems, and other membrane transport systems. Finally, 84 (18%) genes primarily involved in cytosolic metabolism were retained in the categories of nucleotide salvage, lipid salvage and biogenesis, proteolysis, metabolic processes, redox homeostasis, carbon source transport and catabolism, and glucose transport and catabolism (FIG. 27).

Without being limited by a particular theory, it is believe that most of the 80 genes not assigned to a functional category belonged to one or another of these same 4 major groups. Among these 80 genes, 67 had completely unknown function and 13 had generic assignments, for example a hydrolase for which neither the substrate nor the biological role was discernable. The other 70 of the 83 genes in the generic class were assigned to a functional category on the basis of their generic assignment. For example, an ABC transporter was assigned to membrane transport even though the substrate was unknown. Some of these unassigned essential genes matched domains of unknown function ("duf" s) that had been found in a wide variety of organisms.

Example 7

Characterization of Syn3.0

In this example, the growth characteristics of Syn3.0 were studied.

Growth Rate of Syn3.0

Comparison of Syn3.0 to the starting cell Syn1.0 (FIG. 28A) showed that both had a similar colony morphology, characteristic of the natural, wall-less *M. mycoides* subsp. capri on which the synthetic Syn1.0 genome was originally based. Syn1.0 has been described in Gibson et al., Science 329:52-6 (2010), which is hereby incorporated by reference. The smaller colony size of Syn3.0 suggested a slower growth rate and possibly altered colony architecture on solid medium. A corresponding reduction in the growth rate of Syn3.0 in static liquid culture (FIG. 28B), from a doubling time of ~60 minutes (min) for Syn1.0 to ~180 min, confirmed the lower intrinsic rate of propagation for Syn3.0. This rate, however, greatly exceeded the 16 hour (h) doubling time of *M. genitalium*, described in Jensen et al., *J. Clin. Microbiol.* 34:286-91 (1996).

In contrast to the reduction in growth rate, striking changes in macro- and microscopic growth properties of Syn3.0 cells were found. Whereas Syn1.0 grew in static culture as non-adherent planktonic suspensions of predominantly single cells with a diameter of ~400 nm, Syn3.0 cells under the same conditions formed matted sediments. The growth of Syn1.0 in static culture has been described in Gibson et al., Science 329:52-6 (2010). Microscopic images of these undisturbed cells revealed extensive networks of long, segmented filamentous structures along with large vesicular bodies (FIG. 28C), particularly prevalent at late stages of growth. Both of these structures were easily disrupted by physical agitation, yet such suspensions contained small replicative forms that passed 0.2 µm filters to render colony forming units (CFU). This same procedure retained 99.9% of the CFU in planktonic Syn1.0 cultures.

Figure 28A:
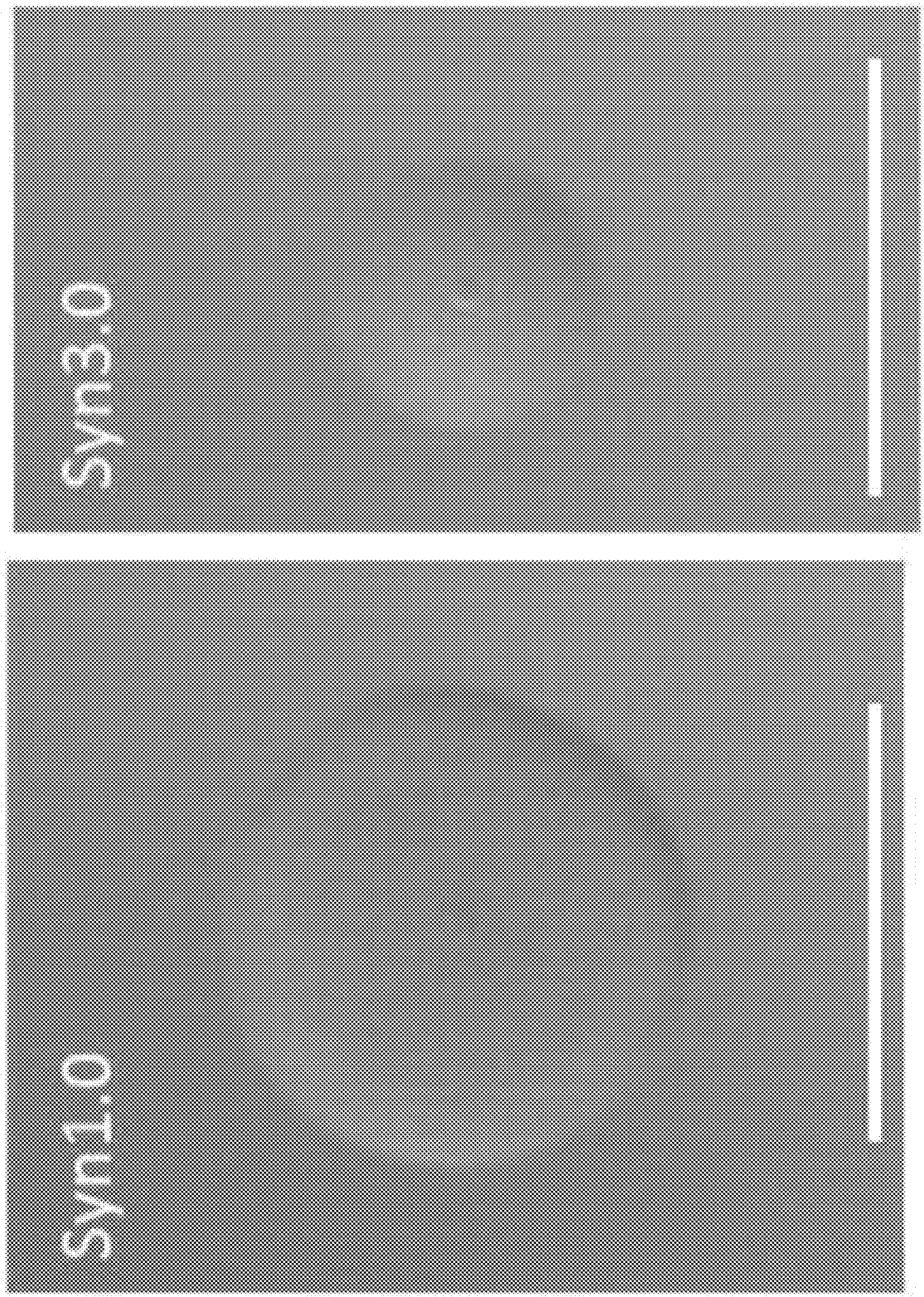
Figure 28B:
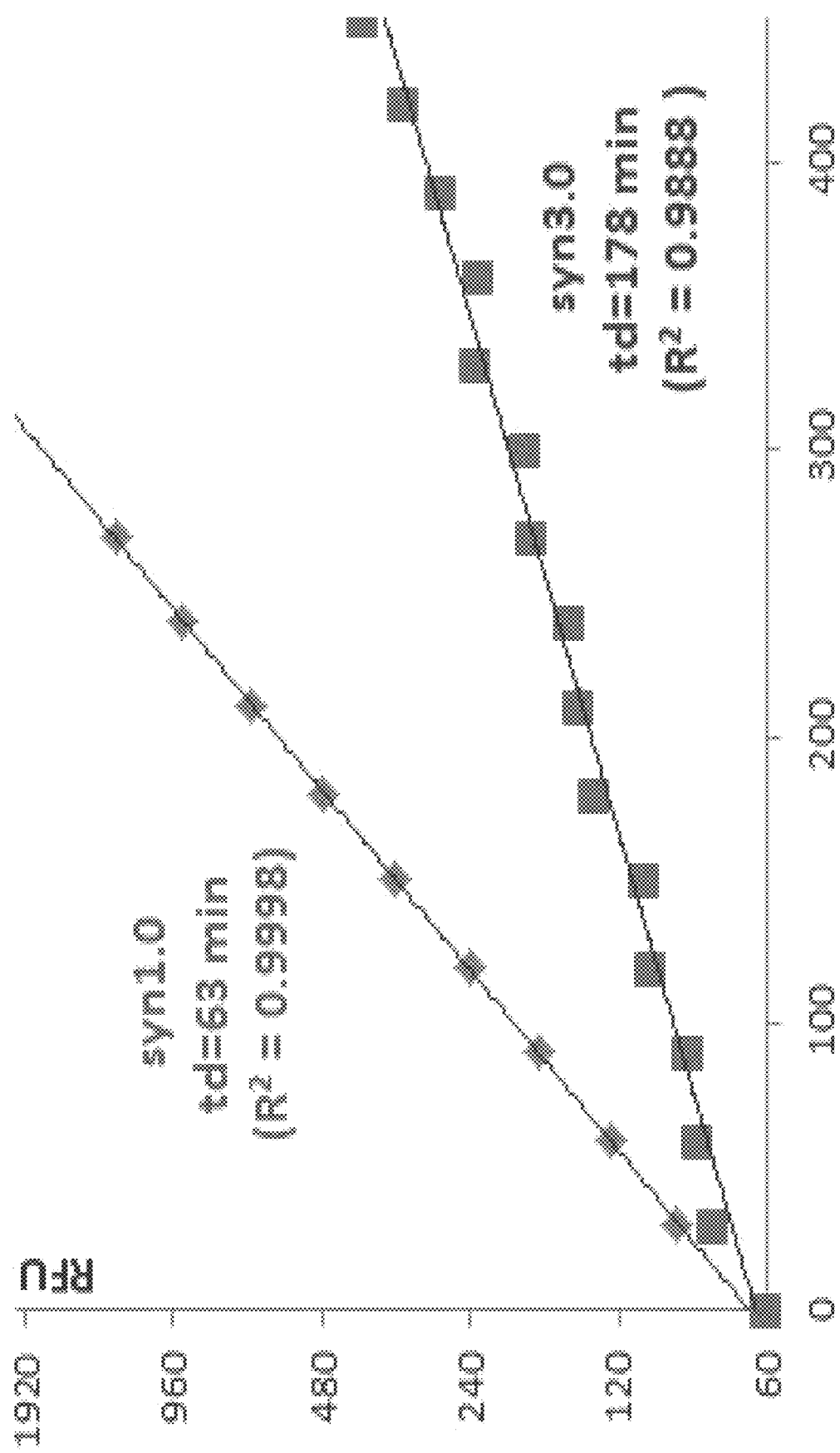
Figure 28D:
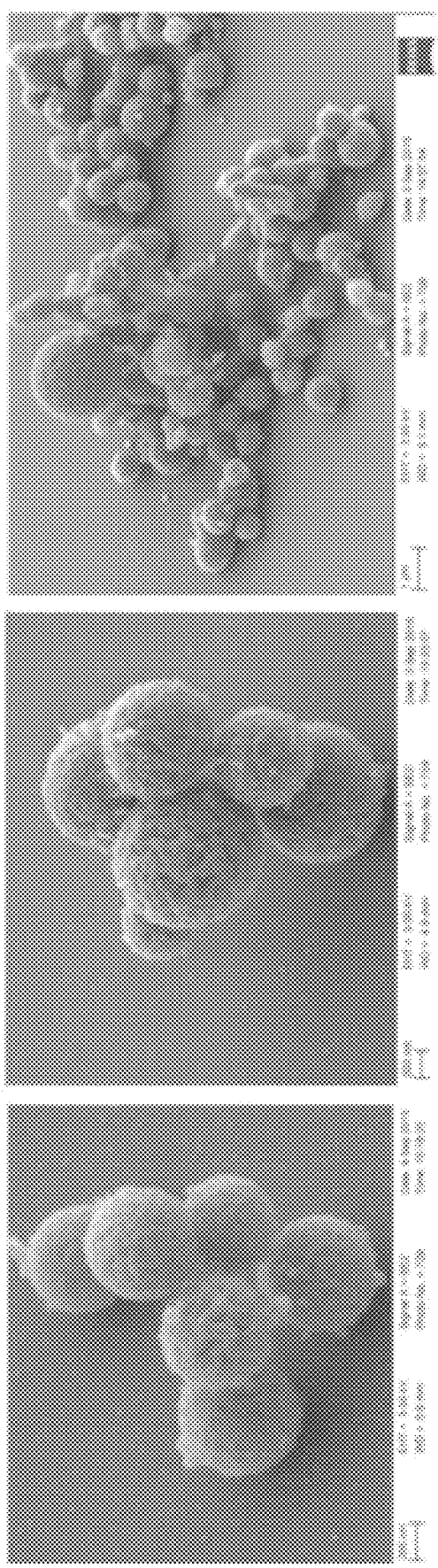

FIGS. 28A-28D show the comparison of Syn1.0 and Syn3.0 growth features. The two panels of FIG. 28A compare colony sizes and morphologies of Syn1.0 and Syn3.0 cells derived from 0.2 µm-filtered liquid cultures diluted and plated on agar medium for 96 h (scale bars=1.0 mm). FIG. 28B shows that the growth rates in liquid static culture determined using a fluorescent measure (RFU) of dsDNA accumulation over time to calculate doubling times (td). FIG. 28C shows native cell morphology in liquid culture imaged in wet mount preparations using differential interference contrast microscopy (scale bars=10 µm). Arrowheads indicate assorted forms of segmented filaments (white) or large vesicles (black). FIG. 28D are scanning electron micrographs of Syn1.0 (left, scale bars=200 nm) and Syn3.0 (middle, scale bars=200 nm and right, scale bars=1 µm). The panel on the right shows a variety of the structures observed in Syn3.0 cultures.

Growth Conditions and Colony Purification

To characterize growth properties of JCVI-Syn1.0 and derivative transplant strains with reduced genomes, cultures were grown at 37° C. in SP-4 liquid medium (containing 17% fetal bovine serum) or on solid medium of the same composition, supplemented with 1% agarose. Initial transplant colonies obtained under selection were picked and propagated in SP4 liquid medium without selection. Static liquid cultures were mixed by trituration and passed through 0.2-µm syringe filters (Acrodisc R), Pall Life Sciences) with gentle pressure. The filtrate was immediately diluted in SP4 medium and 10-fold dilutions were plated on solid SP4 agarose medium. Well-separated colonies from near-limit dilutions were imaged for comparison of size with a stereo-microscope (SZM-45T2, AmScope) and picked for subsequent growth and molecular genetic or phenotypic characterization. Notably, all populations analyzed were filter cloned by this procedure and ultimately were propagated from replicative units that passed through 0.2-µm filters.

Measurement of Growth Rates

To avoid factors that can confound both the measurement of *mycoplasma* cell growth and the comparison of cells with altered genome content (e.g. differences in the mode of replication, physical aggregation, rates of cell death, altered metabolic indicators, or interference by serum proteins in growth medium), a method was developed (PMID: 25654978. PMID: 25101070) to compare replication rates by a direct measure of cell-associated nucleic acid. Specifically the fluorescent stain Quant-iT™ PicoGreen R: (Molecular Probes R, Invitrogen™) which binds dsDNA (and to a far lesser extent dsRNA) was used to quantify the rate of increase during logarithmic-phase cultures in liquid medium.

Procedure To measure logarithmic growth rates, *mycoplasma* transplants were grown in static, planktonic culture at 37° C. in SP4 liquid medium (without tetracycline or Xgal). Overnight late-logarithmic phase cultures were diluted approximately 500-fold with pre-warmed medium and distributed in replicate 0.80-mL aliquots into graduated 1.7-mL microcentrifuge tubes. Individual tubes were removed at selected times and placed on wet ice to arrest growth. To obtain cells without material loss or contaminating medium components, the collected culture aliquots (or controls containing only medium) were underlain in situ with 0.40-mL sucrose cushions (0.5 M sucrose, 20 mM Tris HCl: pH 7.5) and cells were sedimented by centrifugation at 16,000×g for 10 min. The top layer of medium and cushion were removed by vacuum aspiration and the remaining clear cushion was further adjusted to 100-µL without disrupting pellets. Cells were lysed by adding 50 µL of 0.3% (w/v) SDS in TE, pH7.5 (final concentration 0.1%) followed by trituration and incubation at 37° C. for 5 min. Lysates were diluted to 0.01% SDS by adding 1.35 mL of TE, and mixed by rotary inversion for 1 hr at room temperature. To quantify nucleic acid, equal volumes (80 µL) of diluted lysate and Quant-iT™ PicoGreen R reagent (prepared as described by the manufacturer) were mixed in wells of opaque black 96-well plates (Costar, cat. 3915) and incubated in the dark at room temperature for 5 min. Fluorescence was measured using a FlexStation 3 fluorimeter (Molecular Devices) with excitation at 488 nm, emission collected at 525 nm, and a cutoff setting of 515 nm. The net relative fluorescence units (RFU) of samples (after subtraction of RFU from medium control lacking cells), were plotted as $\log_2$ (RFU) vs. time (min) and the doubling times were calculated from the slopes of exponential regression curves ($R^2$, FIG. 29) using the formula: doubling time=ln2/exponential rate.

Figure 29:
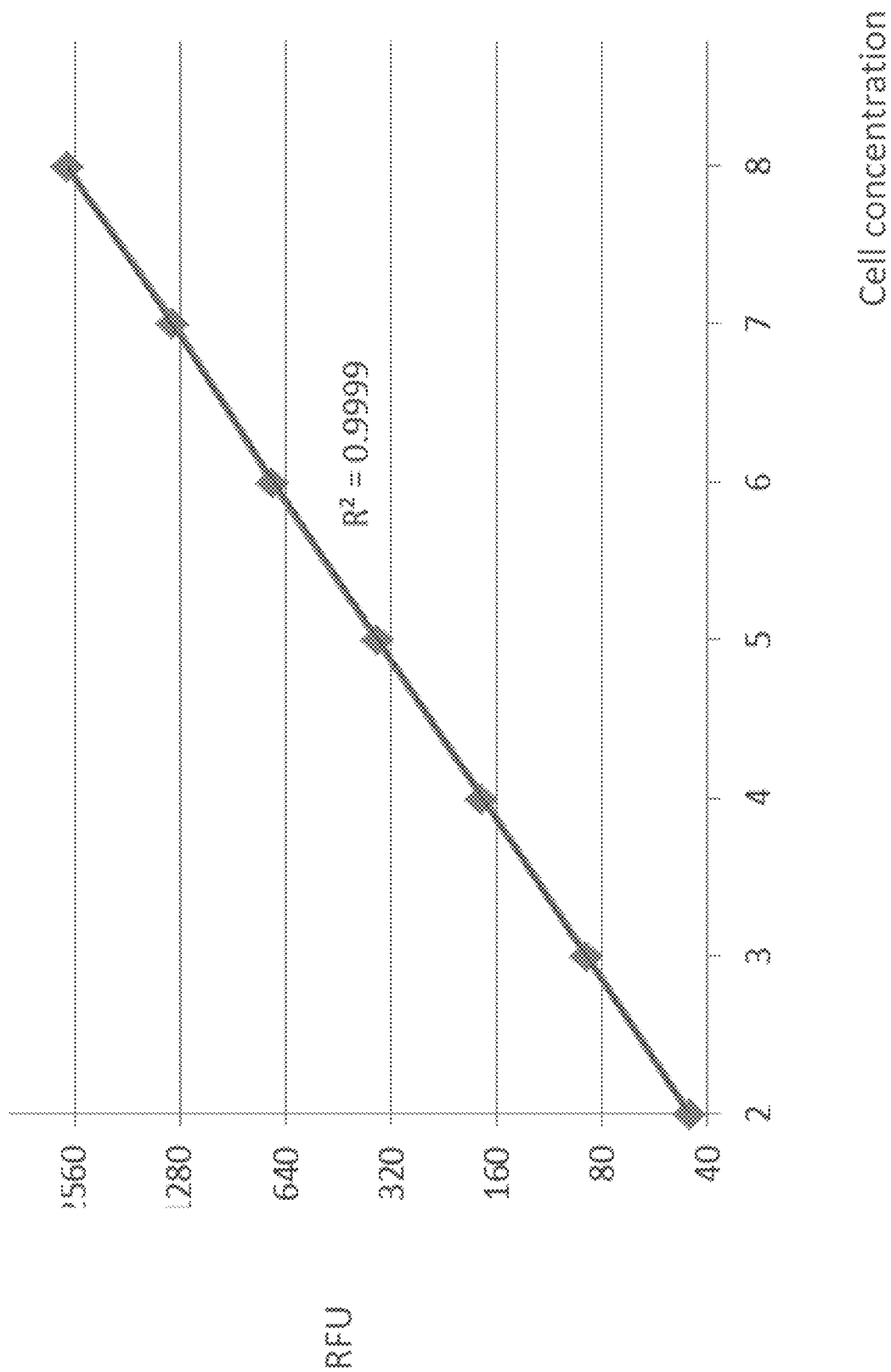
FIG. 29 is a non-limiting exemplary plot of RFU vs. cell concentration showing the correlation of PicoGreen fluorescence with cell concentration.
Figure 30:
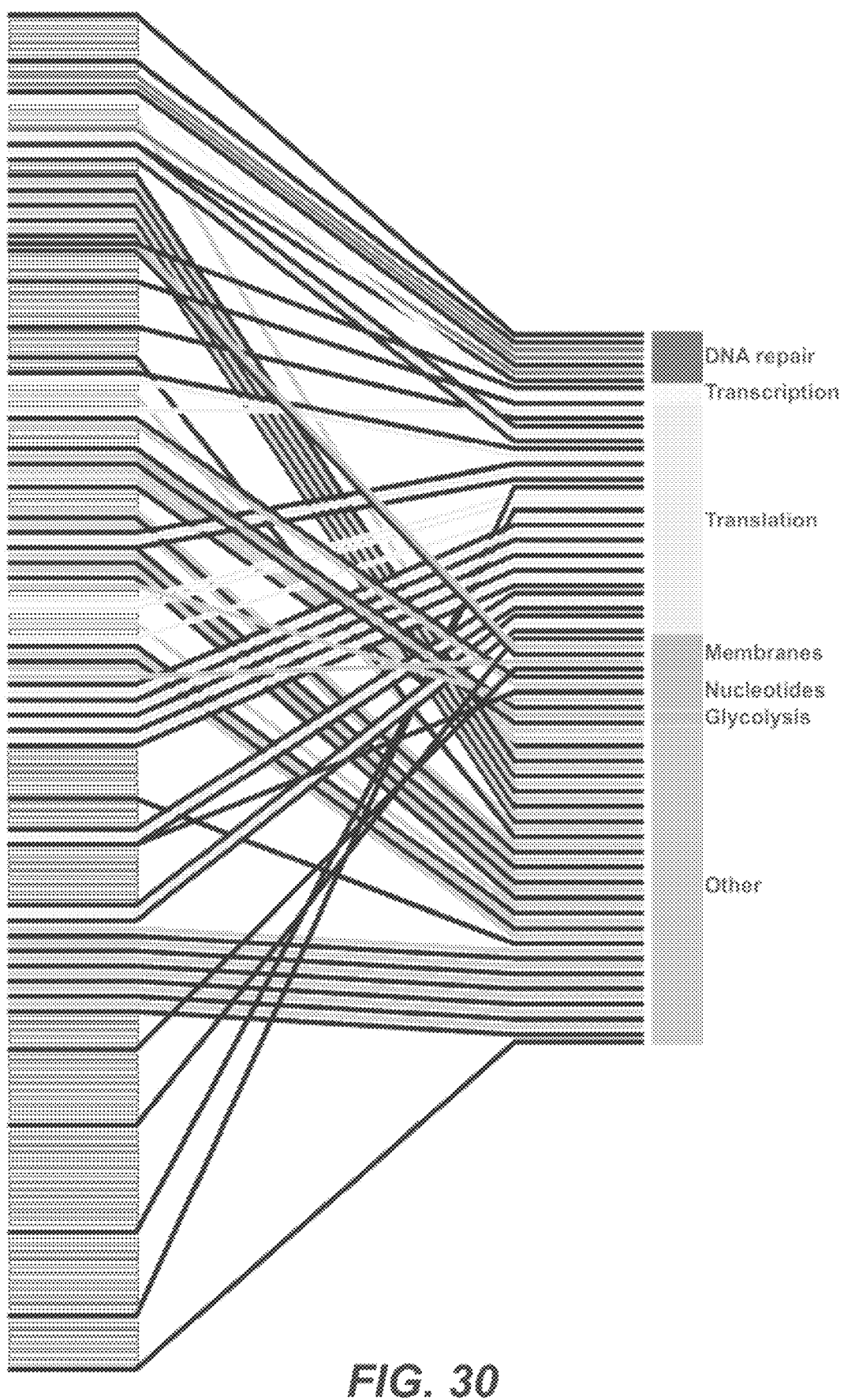
FIG. 30 is a non-limiting illustrative diagram showing the reorganization of gene order in segment 2.
Figure 31A:
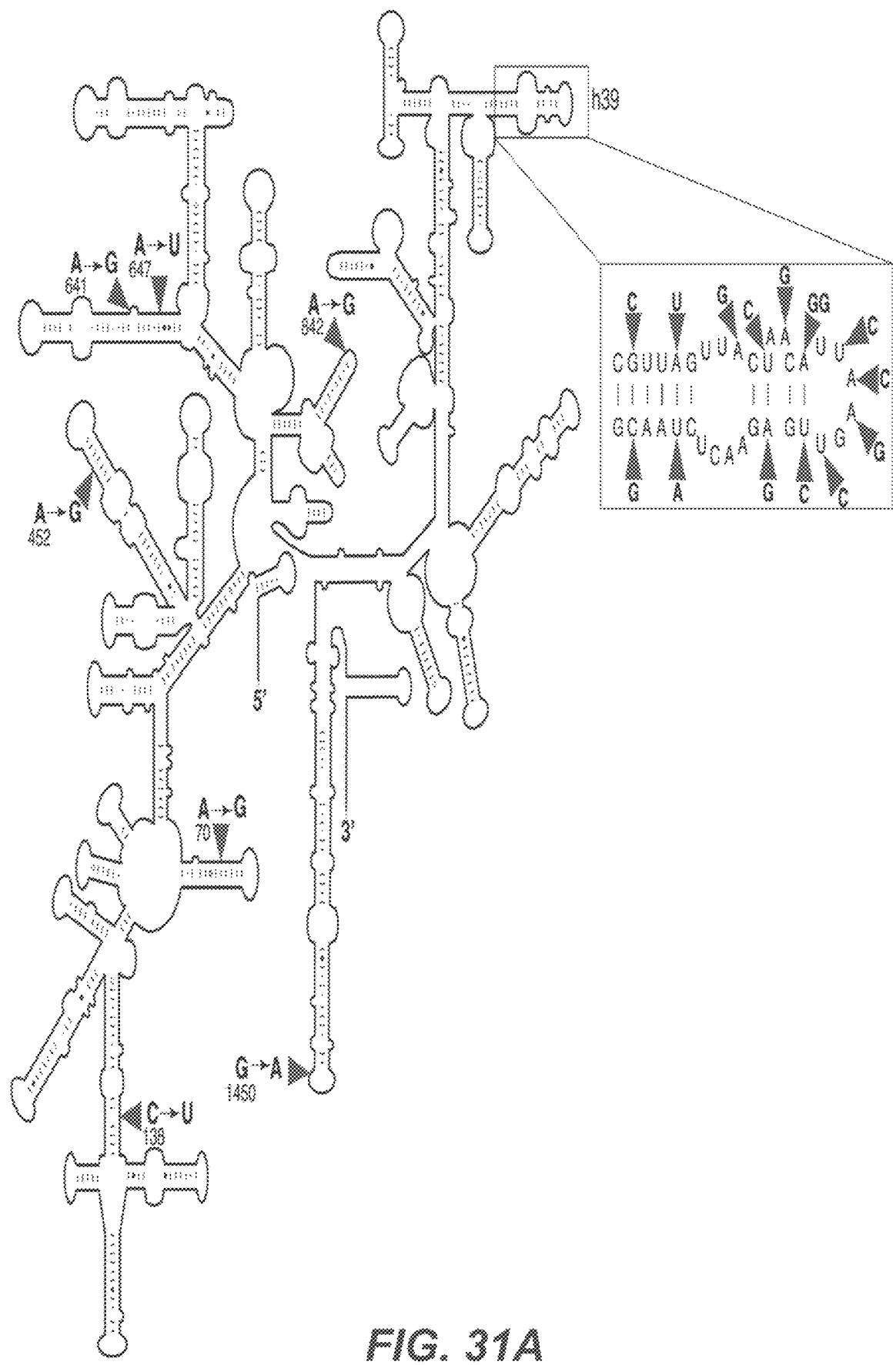
FIGS. 31A-31B show the testing of gene content and codon usage principles using the DBT cycle.
Figure 31B:
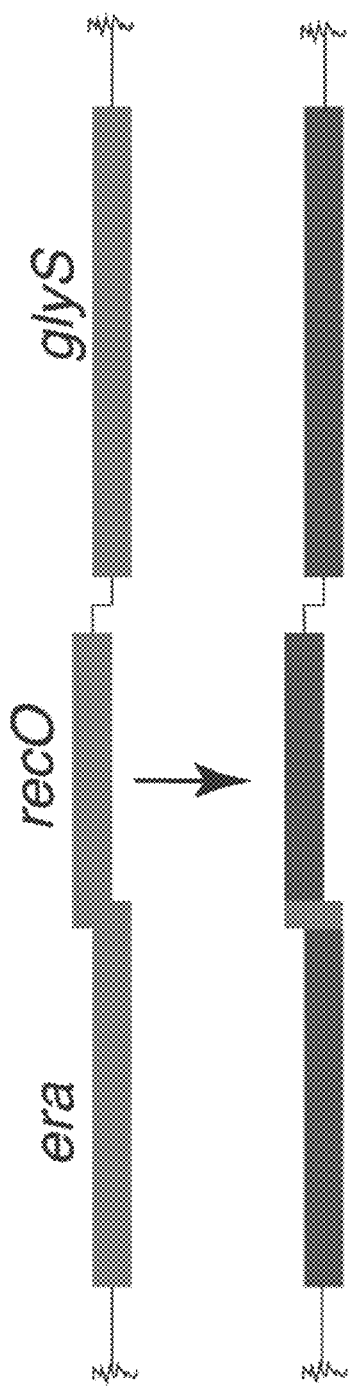

FIG. 29 shows the correlation of PicoGreen fluorescence with cell concentration. RFU measurements were obtained from a late logarithmic phase culture of JCVI-Syn1.0 cells diluted with SP4 medium in a 2-fold series (right to left) prior to processing. Medium controls generated a value, RFU=14, that was subtracted from each sample to give the net RFU values shown.

Assay Parameters

Exponential curves generated from cultures diluted 2-fold with complete medium prior to sample processing demonstrated a high correlation between $\log_2$ RFU and cell concentration, over a RFU range of approximately 64-fold (FIG. 29). Linear regions of semi-logarithmic plots within this range were used to calculate exponential replication rates from growing cultures. The accuracy and reproducibility of the technique (reflected in $R^2$ values) allowed the use of single samples. To avoid minor variables such as batch differences among medium preparations and temperature fluctuations, constructs were compared under identical conditions and within a single experiment.

Light Microscopy

To observe natural cell morphologies in static cultures without manipulation, wet mounts in medium were prepared by depositing 3 µL of settled cells, carefully removed by micro pipette tip from round-bottom culture tubes, onto an untreated glass slide and applying a 18×18 mm cover slip. Light microscopy was performed using a Zeiss Axio Imager 1 microscope with a Zeiss plan/apochromatic 63× oil 1.4 objective and differential interference contrast (DIC) optics.

Electron Microscopy

Cells grown in SP4 medium were centrifuged at room temperature for 4 min at 2,000×g to produce a loose pellet. Medium (950 µl) was removed and replaced with 1 ml of fixative. The fixative solution was 2.5% glutaraldehyde, 100 mM sodium cacodylate, 2 mM calcium chloride and 2% sucrose (fixative was added cold and samples were stored at 4° C.). Cells were immobilized on polyethylenimine or poly-D-lysine coated ITO glass coverslips for 2 min and washed in 0.1 M cacodylate buffer with 2 mM calcium chloride and 2% sucrose for 5×2 min on ice. Cells were post fixed in 2% osmium tetroxide with 2% sucrose in 0.1 M cacodylate for 30 min on ice. Cells were rinsed in double distilled water and dehydrated in an ethanol series (20, 50, 70, 100%) for 2 min each on ice. Samples were critical point dried (with $CO_2$) and sputter-coated with a thin layer of Au/Pd. Samples were imaged with a Zeiss Merlin Fe-SEM at 2.5 kev, 83 pA probe current and 2.9 mm working distance (zero tilt) using the in-lens SE detector.

All together, these data indicate that Syn3.0 and Syn1.0 had similar colony morphology and characteristic of the natural, wall-less *Mycoplasma mycoides* subsp. capri on which the synthetic Syn1.0 genome was originally based.

Example 8

Study of Reorganized Genomes

In this example, gene order was reorganized to study if gene order is a major contribution to cell viability.

To further refine the genome-design rules, prospects for logically organizing genomes as well as recoding them at the nucleotide level were investigated for clarifying whether gene order and gene sequence were major contributors to cell viability. Surprisingly, gene order was not critical. About an eighth of the genome was reconfigured into seven contiguous DNA cassettes that comprised six biological systems—the seventh cassette contained genes whose system-level assignment was somewhat equivocal. Numerous intergenic regions (i.e. promoters and terminators) were reassigned to new genes, transcription units were broken apart, etc. Overall, fine-scale gene arrangement was dramatically altered (FIG. 30).

FIG. 30 shows the reorganization of gene order in segment 2. Genes involved in the same process were grouped together in the design for "modularized segment 2". At the far left the gene order of Syn1.0 segment 2 is indicated. Genes deleted in Syn3.0 are indicated by white lines. Retained genes are indicated by grey lines matching the functional groups they belong to, which are shown on the right side of the figure. Each line connects the position of the corresponding gene in Syn1.0 with its position in the modularized segment 2. Black lines represent intergenic sequences containing promoters or transcriptional terminators.

The resulting organism grew as well in the laboratory as a natural counterpart. While it seems that the details of genetic organization impinge upon survival in hyper-competitive natural environments, it was concluded that gene order was not fundamental to the cell viability.

All together, these data indicate that gene order was not fundamental to life itself even though the details of genetic organization impinge upon survival in hyper-competitive natural environments.

Example 9

Recoding and rRNA Gene Replacement Provide Additional Examples of Genome Plasticity This example demonstrates genome plasticity by recoding and rRNA gene replacement.

The DBT cycle for bacterial genomes allowed the assessment of the plasticity of gene content in terms of sequence and functionality. This included testing modified versions of genes that are fundamentally essential for life. To demonstrate this, it was tested whether an altered 16S rRNA gene (rrs), which is essential, could support life (FIG. 31A). The single copy of the Syn3.0 rrs gene was designed and synthesized to include seven single-nucleotide changes corresponding to those contained in the *M. capricolum* rrs gene. In addition, helix h39 (35 nucleotides) was replaced with that from a phylogenetically-distant *E. coli* rrs counterpart. This unique 16S gene was successfully incorporated into Syn3.0 without noticeably affecting growth rate, providing a "watermark" to quickly identify this strain.

The underlying codon usage principles in the M. *mycoides* genome, which has extreme adenine and thymine (AT) content, was tested. M. *mycoides* uses "TGA" as a codon for the amino acid tryptophan instead of a stop codon, occasionally uses non-standard start codons, and the codon usage is heavily biased towards high-AT content. This uncommon codon usage was modified in a 5-kb region containing three essential genes (era, recO and glyS) to determine its significance. Specifically, this region was modified to include (i) M. *mycoides* codon adaptation index (CAI) but with unusual start codons recoded and tryptophan encoded by the TGG codon instead of TGA, (ii) *E. coli* CAI but tryptophan still encoded by TGA, or (iii) *E. coli* CAI and standard codon usage (TGG encoding tryptophan) (FIG. 31B). Surprisingly, all three versions were found to be functional and resulted in M. *mycoides* cells without noticeable growth differences. Without being limited to any particular theory, it is believed that large-scale changes in codon usage may need to accompany modifications in the tRNA dosage levels to ensure efficient translation.

FIGS. 31A-31B show the testing of gene content and codon usage principles using the DBT cycle. FIG. 31A is a diagram of the modified rrs gene showing its secondary structure that was successfully incorporated into the Syn3.0 genome carrying *M. capricolum* mutations and h39 (inset) swapped with that of *E. coli*. Positions with nucleotide changes are indicated by black arrows and *E. coli* numbering is used to indicate the position of *M. capricolum* mutations. FIG. 31B shows that three different codon optimization strategies were used for modifying the sequence of the essential genes era, recO and glyS by using M. *mycoides* codon adaption index (CAI) or that of *E. coli* with the codons TGG or TGA encoding tryptophan. GC-content of the wild type and the genes modified using the three strategies are noted. JCat codon adaptation tool was used for this exercise to optimize the three open reading frames (ORFs) with the exception of the overlapping gene fragment.

All together, these data indicate genome plasticity in terms of sequence and functionality.

Example 10

Defragmentation of a Eukaryotic Genome

Eukaryotic yeast *Kluyveromyces marxianus* (*K. marxianus*) has a genome about 11 MB in size and divided among 8 chromosomes. This example describes the defragmentation of the genome of *K. marxianus*.

Generation of Tri-Shuttle Vector

A yeast centromeric plasmid (YCp) that is capable of replicating and segregating in *K. marxianus* yeast cells was built and tested. The YCp contains a *K. marxianus* centromere and origin of replication and a selectable marker, as well as *S. cerevisiae* and *E. coli* vector elements. It was found that this "tri-shuttle vector", which is around 10 kb in size, can be reliably transferred between *K. marxianus, S. cerevisiae*, and *E. coli*. Two versions of YCp have been generated: one containing the uracil selectable marker and one containing the histidine selectable marker. The respective *K. marxianus* auxotroph strains (ura3Δ and his3Δ) have been generated to accommodate these vectors. In addition, counter-selection with the uracil system using 5-Fluoroorotic Acid (FOA) has been established. Uracil is useful in selecting for engineering chromosomes and FOA is useful for selecting against the native chromosome.

Furthermore, to aid homologous recombination, the robust NHEJ (non-homologous end-joining) activity of *K. marxianus* has been removed by deleting the Ku70 locus. It was found that 0-10 bp overlaps do not lead to recombination and only 30-60 bp of homology is required to promote robust sequence-specific homologous recombination, allowing efficient and accurate genetic assembly similar to *S. cerevisiae*.

Sequencing, Annotation, and Transcriptomic and Proteomic Analysis of *K. marxianus* Genome A *K. marxianus* strain is modified to be ku70Δ ura3Δ his3Δ and sequenced on both the PacBio and MiSeq platforms. The fully polished complete genome sequence will then be annotated using homology-based strategies, where the function of genes is predicted based on the function of genes with similar sequences in other species. RNA-Seq will be carried out at several growth stages in minimal (defined) growth medium containing glucose, and at 40° C. to maintain thermotolerance. These experiments will help to determine transcript boundaries, identify transcripts potentially missed at the genome annotation stage, quantify the transcription level of genes, and contribute to the interpretation of dispensability data and to create a catalog of promoter locations, strengths, and transcript boundaries. Samples from several genetically engineered strains with minimized genomes, harvested at different growth stages, including comparisons to wild-type versions of *K. marxianus* will be analyzed using a state-of-the-art-shotgun proteomic method. Mass spectrometry data will be searched with the *K. marxianus* protein sequence database and quantitatively analyzed to assess dynamic proteome changes resulting from specific growth states and genetic/genomic mutations. Together with other 'omics and phenotypic features, this data will allow an assessment of functional consequences of genomic minimization of strains. This data can aid in generating a metabolic network of the yeast. Based on limitations of the scope of work, we may use fixed growth conditions (e.g. 45° C. in minimal medium containing glucose) to compare different *K. marxianus* minimized-genome strains.

A GenBank file containing the complete genome sequence of *K. marxianus* with high accuracy is generated, with all genes (and known functions) annotated, and transcription unit boundaries including promoter locations and strengths indicated.

Identification of Dispensable Genes in the *K. marxianus* Genome

A comparative genomics analysis between numerous *K. marxianus* strains, *Pichia pastoris*, *S. cerevisiae*, *Schizosaccharomyces pombe*, and other yeast species is conducted. *S. cerevisiae* database contains information for each gene and whether it is dispensable, indispensable, or lethal when combined with another gene deletion. Similar information is also available for *S. pombe*. The data from transcriptomics and proteomics studies described above can be used to determine genes that are transcribed and translated. These "omics" analyses can generate a candidate list of dispensable genes that can then be tested (see below). The comparison can provide information as to how accurately we can predict the fitness consequences of deleting single genes in a given species given what we know about other genes.

To generate a candidate list of dispensable genes, perform a genome-wide transposon mutagenesis study is performed in *K. marxianus*. The Tn5-transposase system (Epicentre) is used followed by DNA sequencing on a MiSeq instrument to identify the genes that are disrupted. A transposon map is generated and a single chromosome is selected for minimization. Genes heavily hit with transposons on that chromosome is further validated for dispensability and potential consequences to growth rate by directly knocking out that gene in vivo. Growth rates for individual knockouts is noted and scored as E (essential), N (non-essential), or I (pseudo-essential, impaired growth). Only E and I genes are included in the chromosome design (below). N genes, superfluous DNA sequence, intergenic sequence, transposable elements, and introns are excluded. The Tn5 transposition protocol is modified such that N genes are enriched in the analysis through competitive growth. The results of these experiments are compared with the predictions above.

In parallel, algorithms are developed for selecting genes and gene boundaries to be retained. Upstream and downstream elements including localization signals, enhancers, promoters, ribosome-binding sites, and terminators, are retained. Important intergenic sequence (e.g., origins of replication and the centromere) are identified and retained. Prior to generating a DNA sequence for a single minimal yeast chromosome, a paralog analysis is preformed to ensure essential functions remain intact, especially within the minimal chromosome built. Known synthetic lethal data available for other yeasts, for example *S. cerevisiae*, are used.

A comparative analysis of predicted and empirically-determined non-essential genes; and a file containing a designed DNA sequence for one *K. marxianus* chromosome with minimized gene content are generated.

Generation of a Minimized *K. marxianus* Genome

Synthetic Genome Design. For the design, a computational framework is assembled with the goal of defining a hierarchy of functional gene modules and predicting which modules can safely be deleted. The main inputs for the computational framework are 1) networks module definitions based on the protein interaction and genetic interaction maps that have been previously generated for *S. cerevisiae* and *S. pombe:* 2) evolutionary reconstruction of the history of *K. marxianus* genes; and 3) transcriptomics and proteomics data for *K. marxianus*. The computational framework is trained using machine learning and the resulting predictions are experimentally tested in incremental levels of complexity.

First, the computational framework is evaluated for how well it can predict single gene essentiality in *K. marxianus*. The single- and double-deletion data from other yeast species, as well as the paralogy relationships between *K. marxianus* gene pairs and the transcriptomics and proteomics data are integrated into an algorithm predicting which genes would be expected to have E, I or N phenotype. The predictions are compared with the results of the transposon experiment and the direct knockout experiments in which the entire ORF is replaced with a selectable marker. The precision is quantified and recall at which the computational framework can predict single gene essentiality.

Second, the computational framework is evaluated for how well it can predict the fitness of the deletion of an entire module. The optimization problem to solve by the algorithm, will be to predict which N genes are the least likely to transition to E or I state in a minimized background. To test the validity of our algorithm, a *K. marxianus* strain with one entire module deleted that is predicted to be dispensable by our computational framework, using, for example, the Green Monster technology (Suzuki et al., Nature Methods, 2011) is empirically constructed. Upon success, the computational framework is used to assign the letters E, N and I to entire gene modules. Only E and I modules are included in the minimal genome design. Genes in N modules, as well as superfluous intergenic sequences, transposable elements and introns with then be excluded from the native chromosome sequence. Important intergenic sequences (e.g., origins of replication and the centromere) are retained.

The chromosome is constructed as four overlapping sections with conserved overlaps inside essential genes. Later, the sections are designed so that all genes belonging to a given module is contiguous. Only exceptions are overlapping genes, which naturally will remain paired, and pleiotropic genes belonging to multiple modules, which will only be represented once in the designed genome. Because it is anticipated that the computational framework will be partially imperfect, reduced and non-reduced quarter molecules are mix and match either combinatorially or in a directed fashion to determine incompatible reduced sections.

Synthetic Chromosome Assembly. Chromosomes are synthesized by de novo chemically synthesis of oligonucleotides, by amplifying from genomic DNA template, or a combination thereof. For example, each transcription unit in the minimal chromosome design is PCR amplified and includes a unique 40-bp barcoded sequence within overlapping adjacent transcription units (the barcodes overlap and thus direct homologous recombination whether in vitro or in vivo). These PCR products are then individually cloned and sequence-verified. This strategy provides greater flexibility in the subsequent modularization work (see below). The transcription units are assembled (e.g. 400 units->40 cassettes->4 quarters->1 chromosome), using the in vitro and in vivo DNA assembly methods previously established. Briefly, the transcription units are either assembled enzymatically using a one-step isothermal reaction consisting of an exonuclease, polymerase, and ligase, or by co-transformation and assembly in S. cerevisiae cells. In general, transcription units are selected to begin and end 300 bp upstream and downstream of the open reading frame (ORF).

Synthetic Chromosome Installation. The minimized K. marxianus chromosome is either cloned in S. cerevisiae as a yeast centromeric plasmid or in E. coli as a bacterial artificial chromosome. The chromosome contains a HIS3 marker for selection and maintenance in K. marxianus. K. marxianus donor chromosomes are transferred from either S. cerevisiae or E. coli to K. marxianus by either electroporation or by the spheroplast fusion method. To aid in complete chromosome transplantation, selection is placed on the donor chromosome and counter-selective pressure is placed on the respective recipient chromosome, which is accomplished by using a recipient K. marxianus strain that is a histidine auxotroph and contains the URA3 gene on the respective native chromosome, which can be selected against by growth in the presence of FOA. Bacteria to yeast fusion has been previously demonstrated (Karas et al., Nature Methods, 2013). In this case, bacterial cells are mixed with yeast spheroplasts in the presence of polyethylene glycol and calcium chloride. Similarly, chromosomes from two different species of yeast strains can be combined in the same cell to generate interspecies hybrids. This process also requires the formation of yeast spheroplasts and is promoted by polyethylene glycol (A. Svoboda, Microbiology, 1978).

Certain combinations of gene deletions can be unpredictably lethal, troubleshooting strategies are designed up front. As above, following two stages of assembly, overlapping quarter molecules of the chromosome are constructed. To aid in troubleshooting, non-reduced versions of the quarter molecules (e.g., by TAR cloning or PCR) are constructed, which permits mixing and matching of reduced and non-reduced quarter molecules either combinatorially or in a directed fashion to determine incompatible reduced sections, and ultimately the genes that cannot be simultaneously disrupted. If, for example, only three of the four reduced segments can be simultaneously combined, another round of transposon bombardment on this strain is performed to identify the remaining genes that can be removed in the non-reduced quarter molecule.

A random "add-back" approach is developed. In this approach, a K. marxianus strain that has both the reduced (but incapable of supporting desired level of K. marxianus growth) and non-reduced chromosomes are provided. Plasmid DNA containing a quarter molecule or random sections of the non-reduced chromosome is transformed into these cells. Counter-selection is then applied to remove the complete non-reduced chromosome. If the cells now survive (due to dependence on the plasmid DNA), the plasmid DNA is sequenced to determine the gene(s) that need to be added back to the design. The plasmid DNA can be generated randomly by ligating a sheared population of DNA derived from purified non-reduced chromosomes or in a direct fashion by assembling a single gene or contiguous genes (previously removed in the design) into a plasmid by in vitro DNA assembly. Genome engineering approaches such as CRISPR/Cas9 and TREC (Tandem Repeat Endonuclease Cleavage), which have proven to be useful in S. cerevisiae, is also adapted for K. marxianus to facilitate the add-back of genes.

How to leverage barcodes in the design to distinguish between the native chromosome and the synthetic version is considered. Assuming the non-reduced and reduced chromosome can co-exist in the same cell, it is possible to identify non-expressed E/I genes in the synthetic chromosome by RNA-Seq. Important intergenic elements not incorporated in our design and uncovering mutations are identified.

A living K. marxianus yeast strain containing one minimized chromosome with its non-reduced counterpart eliminated from the cell is produced.

Generation of a Defragmented Version of the Minimized K. marxianus Genome

In parallel to the minimization efforts, chromosome defragmentation is carried out using well-characterized gene sets that are highly likely to be essential. Essential genes and intergenic regions (which will be defined, cloned, and sequence verified above) are used in the defragmentation process. Essential genes are classified according to function (e.g., replication, transcription, translation, metabolism, etc.). All genes and associated regulatory sequences belonging to a given functional module are represented as contiguous DNA. Only exceptions are pleiotropic genes belonging to multiple modules, which are represented once in the designed chromosome.

Assembly of the defragmented chromosome is carried out in a hierarchical fashion, as above. Alternatively, the original barcoded overlapping sequences and link transcription units are retained together, in a specific manner, using ssDNA oligos. In some instances, this latter approach has the advantage of generating fewer errors and can be leveraged to generate combinatorial libraries of chromosomes and sub-assemblies with varying arrangements of transcriptional units. When possible, combinatorial libraries representing thousands of chromosomal variants are assembled and installed in parallel. Survival and ability to form colonies are screened for.

The corresponding non-modularized quarter-chromosome subsections are cloned and sequence-verified to aid in troubleshooting, as discussed above. Prior to complete chromosome defragmentation, quarter molecules are first individually modularized. Once determined to be individually functional, the quarter molecules are further combined until the chromosome is completely defragmented. If a modularized quarter molecule is determined to be non-functional, it is further broken down into smaller modularized parts (e.g., defragmented eighth molecules) to identify the problematic section(s). The add-back and RNA-Seq troubleshooting strategies addressed above are also used.

The following products are generated: (1) a design for a defragmented version of the minimized K. marxianus chromosome generated above: (2) A design-build-test-troubleshoot workflow for constructing minimized and defragmented eukaryotic chromosomes; and (3) data supporting the construction and testing of the minimized K. marxianus chromosome.

Example 11

Mapping Essential and Non-Essential Genes in K. marxianus

This example describes mapping essential and non-essential genes in K. marxianus by non-homologous end joining insertions of a ura3 gene cassette.

The genome of K. marxianus strain Y-6860 G13 Δura3 Ku70+80+ was subjected to insertional mutagenesis using a 1122-bp PCR product carrying the Saccharomyces cerevisiae URA3 gene. Insertion required the Ku70 protein and thus presumably occurred by the non-homologous end joining (NHEJ) pathway. Analysis of eleven independent insertion events showed either precise insertion without loss of genome sequence, or small flanking genomic duplications and deletions. The inserted SCURA3 terminal sequences were unaltered. Large scale mapping of ScURA3 insertions revealed a greater than 2-fold preference per kilobase for intergenic sequence. Some genes contained no insertions (essential), some were sparsely hit, and others were more heavily hit (non-essential). This example shows that insertional mutagenesis can be a potentially useful alternative to transposon mutagenesis in organisms with an active NHEJ pathway.

High frequency insertion of a PCR product of the S. cerevisiae ScURA3 gene into the genome of K. marxianus DMKU3-1042, a thermotolerant yeast strain, by the non-homologous end joining (NHEJ) pathway have been reported (Abdel-Banet et al. Yeast 27, 29 (2010), the content of which is incorporated by reference in its entirety). To show that a high density ScURA3 insertion map analogous to that obtained by global transposon mutagenesis, nine ScURA3 transformants were analyzed by Southern hybridization in Nonklang et al., Applied and environmental microbiology 74, 7514 (2008) (the content of which is incorporated by reference in its entirety). Insertions sites were all different in the nine transformants and one transformant had multiple insertions.

In this example, high frequency URA3 insertional mapping of another strain of K. marxianus (K. marxianus strain G13 ura3Δ Ku70+80+) was generated. Approximately $8 \times 10^5$ ScURA3 transformants were obtained following transformation of a 1122-base linear DNA fragment and selection on uracil-lacking plates. Analysis of the insertions in chromosome 7, the smallest of the 8 chromosomes of K. marxianus showed 98 genes with 2 or more inserts in the central 60% of the gene after six passages of growth. These genes were classified as non-essential.

Preparation of S. cerevisiae URA3 Cassette DNA

A S. cerevisiae URA3 cassette (1122 bp) was PCR-amplified from plasmid pRS316 (ATCC® 77145™) using primers 5'-tgagagtgcaccacgcttttcaattc and 5-cagggtaataact-gatataattaaattg. The 5' OH PCR product was purified using the QIAquick PCR purification kit.

Preparation of Electrocompetent K. marxianus Cells

K. marxianus (G13 ura3Δ Ku70+80+) cells were grown in YPD (Difco™, Becton, Dickinson and Company) at 30° C. to OD600~1.0. Twenty-four cell culture aliquots (350 µl) were distributed in 50 ml tubes and centrifuged at 3,000 rpm for 5 minutes. Each cell pellet was washed with 50 ml ice cold sterile water, resuspended in 1 ml ice cold water and transferred to a 1.5 ml Eppendorf tube followed by centrifugation at 4600×g for 2 minutes. Each cell pellet was resuspended in 800 µl of LiAC/TE (100 µl 1M Lithium acetate, 100 µl 10×TE, 800 µl water). Twenty microliters of fresh 1 M dithiothreitol was added to each cell suspension followed by incubation at 30° C. for 45 minutes with gentle shaking (~100 rpm). Cells were washed with 1 ml ice cold sterile water followed by 1 ml ice cold 1M sorbitol. Cells were pooled in 2.4 ml of ice cold 1 M sorbitol.

Electroporations and Serial Passaging of URA3-Transformed Cells

Figure 32:
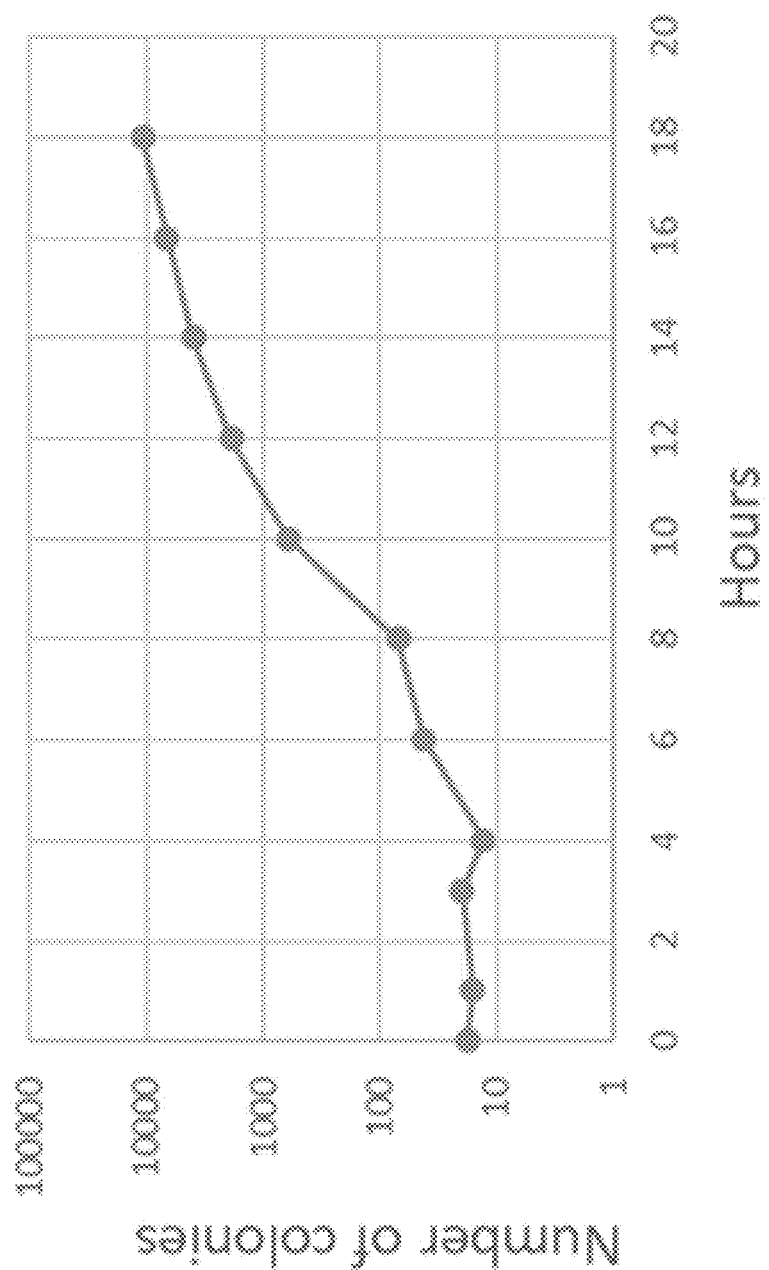

A large-scale preparation of ScURA3 transformant K. marxianus cells was carried out as follows. A total of 23 electroporations were performed. For each electroporation, 353 ng of ScURA3 PCR product DNA was mixed with 100 µl of electrocompetent cells (~$4.4 \times 10^8$ cells). The mixture was transferred into a chilled 2 mm electroporation cuvette and pulsed at 2500 V, 25 µF, and 200Ω. One milliliter of cold YPDS (YPD+1M sorbitol) was immediately added and cells were transferred to a 15 ml culture tube containing 1 ml cold YPDS. Electroporated cells were allowed to recover at 30° C. for 10 h (FIG. 32). The cells (2.1 ml) were then plated on 22.5 cm×22.5 cm CAA-URA plates (2% glucose, 0.6% casamino acid, 25 µg/ml adenine, 50 µg/ml tryptophan, 0.67% YNB (Difco, BD) without amino acids, and 2% agar). Total colonies were estimated by partially counting 2 of the 23 plates (5 of 4 cm×4 cm squares per plate: one in the center, four at the corners). Colonies were collected and pooled from the 23 plates in ~200 ml CAA-URA medium (passage P0). We estimated that there was a total of about $8.0 \times 10^5$ colonies representing a transformation efficiency of ~$1 \times 10^5$ colonies/µg of ScURA3 DNA.

Cells were allowed to recover in YPDS medium at 30° C. and plated at intervals on CAA-URA agar plates. As shown in FIG. 32, cell viability increased nearly 10-fold in the interval from 8 to 10 hours, and thereafter the cell number increased at about the doubling rate.

For serial passaging, 125 µl of P0 (~$1.3 \times 10^{10}$ cells/ml) was inoculated into 1 liter of CAA-URA medium and incubated at 30° C. for 24 hours (passage P1). P1 cells (0.5 ml) were inoculated into 250 ml CAA-URA medium and grown for 24 hours (passage P2) and so forth for 6 passages. Aliquots of each passage (P0 to P6) were centrifuged and stored at −20° C. as 200 µl pellets in Eppendorf tubes.

DNA Extraction

A frozen cell pellet from each passage (P0 to P6) was thawed on ice. A 100 µl packed volume of cell pellet was resuspended in 200 µl Qiagen P1buffer. 2 µl of Beta-mercaptoethanol (1.4 M) and 5 µl of Zymolase-100T (20 mg/ml) were added, followed by incubation at 37° C. for 1 h. Cells were lysed by addition of 200 µl Qiagen P2 buffer. The lysate was neutralized by addition of 200 µl Qiagen P3 buffer, followed by centrifugation at 16,000×g for 10 minutes. Supernatant was transferred to a clean microcentrifuge tube. DNA was precipitated by adding 600 µl isopropanol, followed by centrifugation at 16,000 g for 10 minutes. The DNA pellet was dissolved in 100 µl Qiagen EB buffer. RNA was digested with 1 µl of RiboShredder (Epicentre) at 37° C. overnight. After phenol-chloroform extraction, DNA was dissolved in 100 µl EB buffer (56-124 ng/µL).

ScURA3 Marker-Specific Sequencing

For identification of ScURA3-genomic junctions, an approach for mapping the location of transposon insertions was used (Yung et al., Journal of bacteriology 197, 3160 (2015), the content of which is hereby incorporated by reference in its entirety). The tagmentation reaction component of the Illumina Nextera XT library preparation method was used to insert Illumina adapter sequences at random locations throughout the genomic DNA (e.g., Adey et al., Genome biology 11, R119 (2010), the content of which is hereby incorporated by reference in its entirety). The resulting tagged DNA fragments were amplified using the standard barcoded Illumina P7 adapter and a custom primer containing the Illumina P5 adapter, a random nucleotide spacer, and a homology region to the upstream or downstream edge of the ScURA3cassette. The resulting libraries were size selected, pooled and sequenced on the NextSeq 500 at 2*150 read length. Read 1 contained the ScURA3-genomic DNA junctions.

URA3 Insertions into the K. marxianus Genome were Either Precise or Result in Small Deletions or Duplications of Genomic DNA.

In a study to investigate the nature of the ScURA3 insertions, the ScURA3 cassette DNA was transformed into K. marxianus strain G13 (ura3Δ Ku70-80+). Ten ScURA3 transformant colonies were patched and pooled. The DNA was extracted, and sequenced by Illumina Miseq. The results of sequence analysis of the ScURA3 transformants are shown in Table 16. Among the 10 transformants, there were 11 insertion events. In Table 16, the first column indicates the chromosome and nucleotide position of each insertion; column two indicates whether insertion is precise, or is accompanied by a flanking deletion or duplication event: the third column identifies disrupted genes; and the last column indicates corresponding non-essential genes in S. cerevisiae. The analysis showed 11 different SeURA3 insertion locations, thus one clone contained 2 inserts. Insertions were found in chromosomes 2, 4, 5, 6, and 8. Two insertions were precise with no loss of genome sequence. Two had flanking triplet duplications, and 7 had small flanking deletions, ranging from 1 to 31 bases at the site of insertion. Four of the inserts were in K. marxianus genes homologous to non-essential S. cerevisiae genes and 7 inserted in intergenic regions (Table 16). In all 11 cases, there was no loss of terminal sequences from the ScURA3 cassette.

TABLE 16

Sequence Analysis of 10 ScURA3 Transformants to Determine the Nature of the Insertion Event

| Chromosome: coordinate | Type of insertion | Gene disrupted | S. cerevisiae homolog |
|---|---|---|---|
| Chr2: 31221 | precise | JCVI1EUKG1592474, 31215 . . . 32045 | ATO2 |
| Chr2: 1075297-1075305 | 9 bp deletion | JCVI1EUKG1592976, 1073059 . . . 1075392 | SAP1 |
| Chr4: 731644-731646 | ATG duplication | JCVI1EUKT1594332, 729525 . . . 732428 | MNR2 |
| Chr4: 743043-743059 | 17 bp deletion | JCVI1EUKG1594339, 743048 . . . 744460 | RCH1/ YMR034C |
| Chr5: 531256-531259 | CAC duplication | intergenic region | |
| Chr5: 1339737 | precise | intergenic region | |
| Chr6: 601126-601127 | single G deletion | intergenic region | |
| Chr6: 894933-894963 | 31 bp deletion | intergenic region | |

TABLE 16-continued

Sequence Analysis of 10 ScURA3 Transformants to Determine the Nature of the Insertion Event

| Chromosome: coordinate | Type of insertion | Gene disrupted | S. cerevisiae homolog |
|---|---|---|---|
| Chr8: 34461-34463 | 3 bp deletion | intergenic region | |
| Chr8: 752421-752423 | 3 bp deletion | intergenic region | |
| Chr8: 829922-829952 | 31 bp deletion | intergenic region | |

Large-Scale ScURA3 Insertion Mapping of the K. marxianus Genome

Approximately $8.0 \times 10^5$ ScURA3 transformants were pooled from 23 large CAA-URA plates (P0). P0 cells were then serially passaged 6 times. DNA samples for each of passages, P0 through P6, were prepared and sequenced using the marker-specific method described in Methods. Two sets of data were obtained. One set was generated using the KB-URA3-Tn5-lib-5' primer and NexteraXT P7 primer to generate PCR fragments from 5'-end of ScURA3 into genomic sequence, and the other set used KB-URA3-Tn5-lib-3' primer and NexteraXT P7 primer to obtain junction sequences at 3'-ends of ScURA3 insertions. Insertion sites were precisely identified by Burrows-Wheeler Alignment searching for a gapless match of at least 20 nucleotides to the ends of the ScURA3 cassette followed by a 30 nucleotide flanking sequence which was then used to find a gapless match to the K. marxianus reference genome.

The 5' and 3' junction datasets were partially redundant. If sampling were complete, then each insertion site would be supported by both 5' and 3' junction sequences. However, because small duplications or deletions of genomic sequence at the junctions may occur, and because the junction sequence datasets were incomplete, it is not possible to definitively distinguish between insertion sites that occur within a few bases of each other. As a conservative approach to managing this redundancy, all insertion sites within 10 bp of one another across both data series were counted as a single insertion event. Without being bound by any particular theory, it is believed that this may result in undercounting of insertions in some cases.

Intergenic insertions slightly outnumbered those in genes. However, intergenic space only accounted for approximately 30% of the genome, thus the number of intergenic insertions per kilobase was more than twice as great (Table 17). This was to be expected since cells with insertions in essential genes will be lost from the population. For example, in an extreme case where all genes were essential, then only intergenic insertions will be represented. Individual cells in the P6 population were considered likely to had insertions primarily in non-essential genes.

Figure 33:
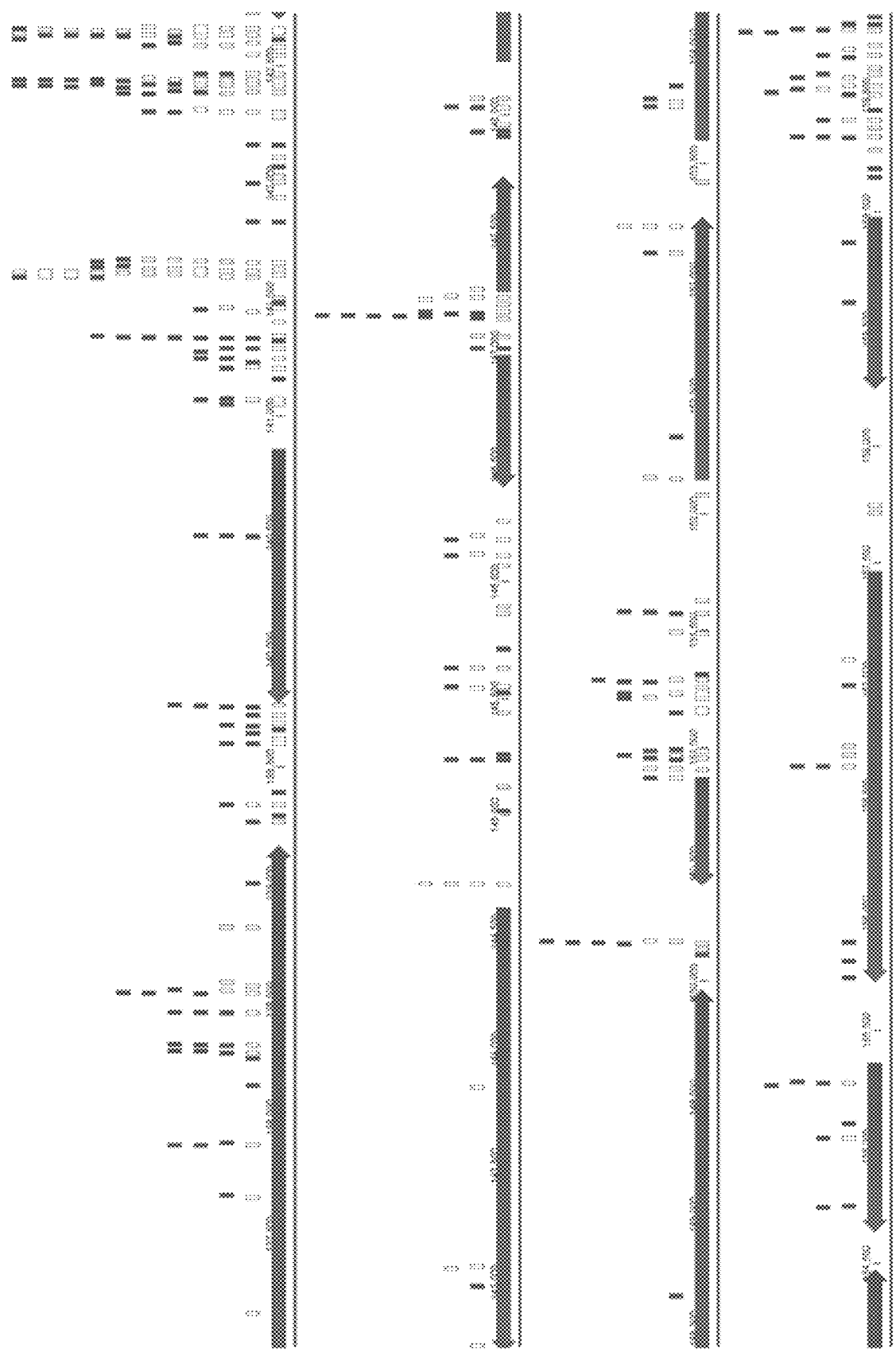

All unique insertions in chromosome 7 were tabulated and mapped to the smallest K. marxianus chromosome (Table 17). A total of 4129 insertions were found in P0 and 4018 in P6. FIG. 33 shows a map of P0 and P6 insertions in a small section of chromosome 7 with examples of putative essential and non-essential genes.

FIG. 33 is a non-limiting exemplary plot of a Section of the K. marxianus Chromosome 7 ScURA3 insertion map. P0 inserts are shown black boxes and P6 inserts are shown as white boxes. A gene was classified as non-essential (n) if there are at least two P6 inserts in the middle two-thirds of the gene, otherwise it was essential (e). Reading from top to bottom, gene assignments were: ne, e, ne, e, e, e, e, e, e, ne, and e.

Figure 34A:
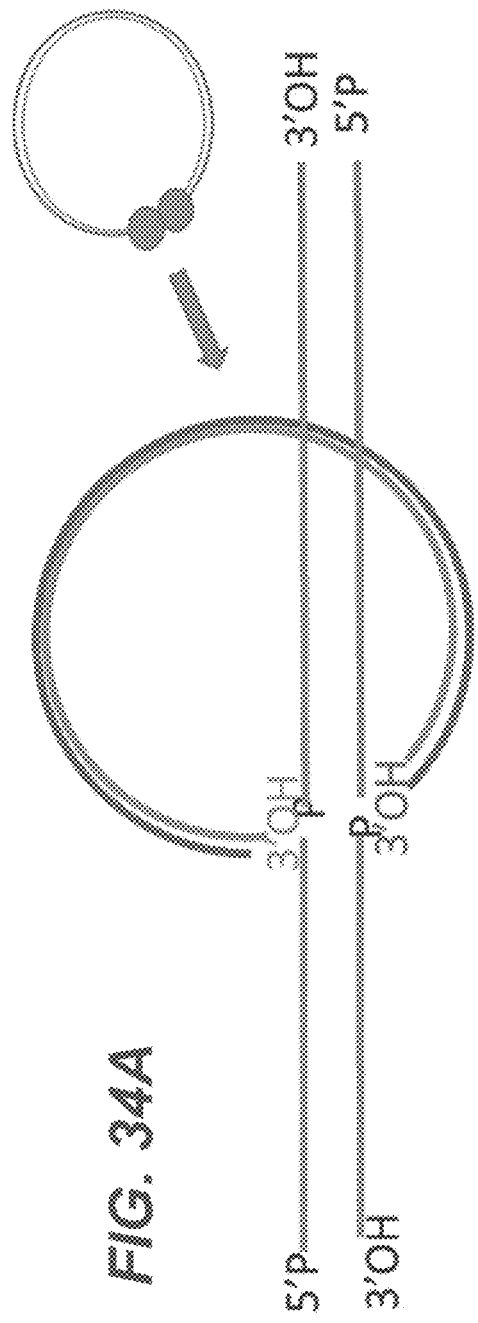

ScURA3 Cassettes are Inserted into the *K. marxianus* Genome by the NHEJ Pathway Since there is generally no homology of ScURA3 with the *K. marxianus* genome at the points of insertion, and since the Ku70) gene is required, the mechanism of insertion involves the NHEJ pathway can be inferred. The detailed NHEJ mechanism may not fully known, but it was clear that the Ku70)/Ku80 proteins bind to the ends of the DNA at double stranded breaks and hold them in proximity until local DNA repair and joining occurs. Several other proteins, XRCC4, XLF, and DNA ligase IV may participate in the repair and joining process (e.g., Brouwer et al., Nature 535, 566 (2016), and Sharma et al. Journal of nucleic acids (2010), the content of each is incorporated by reference in its entirety), but it was not known if these participate in the insertion mechanism which differs somewhat from DSB repair. The data in this example suggest that when the ScURA3 cassette DNA enters the cell and migrates to the nucleus, the two ends were complexed with the Ku70/Ku80 proteins and brought together to form a circle (FIG. 34A). The data further suggest that 3'OH groups at each end then carry out nucleophilic attacks on phosphate groups in close proximity but on opposite strands in the backbone of the genomic DNA in analogy to, for example, the Tn5 transposition mechanism. Depending on the positions of the two phosphates, the insertion was precise (no loss of genome sequence), or produced small duplications or deletions of genomic DNA (FIG. 34B).

Various outcomes may be possible when ScURA3 DNA is introduced into *K. marxianus*. The 5'OH ends of the ScURA3 PCR product could be immediately phosphorylated and ligated to produce circular DNA. Alternatively, the cassette ends could be joined by NHEJ. In addition, linear concatamers, and circular concatamers could be generated. These non-replicating forms would presumably be diluted out as the cells divide. Finally, linear ScURA3 DNA (including linear concatamers) could insert into genomic DNA as described in the above paragraph. The frequency of these various possible outcomes may account in part for strain differences in relative efficiency of the insertional mechanism.

Figure 34B:
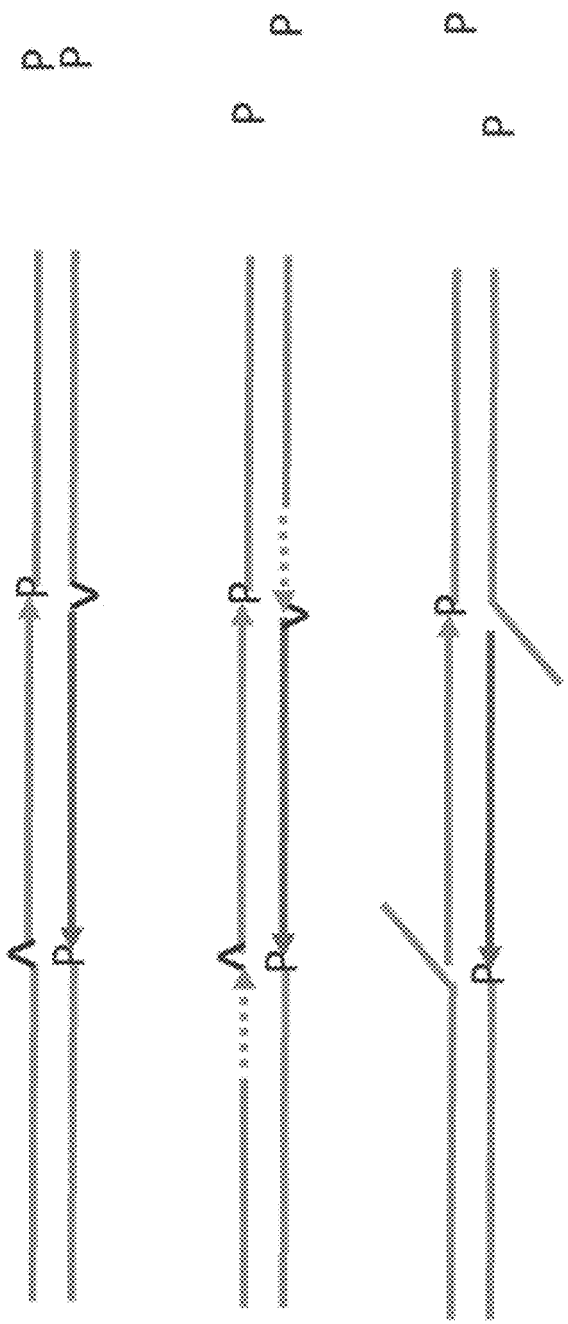

FIGS. 34A-34B show a non-limiting exemplary schematic illustration of a proposed NHEJ insertion mechanism to explain the observed types of ScURA3/genome junctions. FIG. 34A shows that Ku70/80 protein complexes bind to ends of SeURA3 DNA and hold the ends in close proximity. The 3'OH group at each end of SeURA3 DNA carries out nucleophilic attacks on P-atoms in the *K. marxianus* DNA backbone. FIG. 34 shows that depending on the relative positions of the attack on the P-atoms on the two strands of the helix, there may be either no loss of genome sequence or small insertions or deletions were produced. In the case of deletions, 3'-overhangs would be removed by an exonuclease followed by ligation to restore continuity. Ligation is indicated by A.

ScURA3 Insertion Map

Without being bound by any particular theory, it is believed that the NHEJ pathway produces random ScURA3 insertions. The observed insertions were not randomly distributed, which can be substantiated by multiple reasons. For example, about $8.0 \times 10^5$ initial ScURA3 transformants were not all independent since during recovery from electroporation some cells divided prior to plating. Secondly, the sequencing protocol involved PCR amplification of ScURA3 genome junction DNA, and it was expected that the degree of amplification will vary due to the different sizes and base compositions of the amplicons. Thirdly, transformants with inserts in essential genes did not produce colonies and were lost. In addition, insertions in some genes could result in slower growth and depletion from the population. These factors are believed to contribute to the >4-fold excess of intergenic versus intragenic insertions (See FIG. 33).

Table 17 tabulates for chromosome 7 the numbers of unique insertions observed for each passage from P0 to P6. Since cells in the P1 population were descendants of those in the P0 population, cells in P2 were descendants of P1, and so forth, the numbers in each subsequent passage should be equal to or less than in the preceding passage. However, inserts found by sequencing were slightly higher in the middle passages. Without being bound by any particular theory, it is believed that this was an artifact of the depth of sequencing achieved for each passage.

TABLE 17

Analysis of ura3 Insertions in *K. marxianus* Chromosome 7 by Passage Number

| Passage number | P0 | P1 | P2 | P3 | P4 | P5 | P6 |
| --- | --- | --- | --- | --- | --- | --- | --- |
| Total Unique Insertions in Chr 7 | 4129 | 4481 | 7101 | 6089 | 6274 | 6659 | 4018 |
| Total Unique insertions in Gene-Space | 1912 | 2082 | 3472 | 2893 | 3007 | 3253 | 1744 |
| Total Unique Insertions in Intergenic-Space | 2217 | 2399 | 3629 | 3196 | 3267 | 3406 | 2274 |
| Percent Insertions in Gene-Space | 46.31% | 46.46% | 48.89% | 47.51% | 47.93% | 48.85% | 43.40% |
| Percent Insertions in Intergenic-Space | 53.69% | 53.54% | 51.11% | 52.49% | 52.07% | 51.15% | 56.60% |

Table 17 shows that every P6 insertion should also be present in the P0 population. However, on inspection of a small portion of the *K. marxianus* ScURA3 insertion map shown in FIG. 33, some P6 insertions had no corresponding P0 insertion, although many did. Thus, it was evident that not all the insertion sites in the DNA samples were detected by our depth of sequence coverage.

Altogether, the data indicate that the ScURA3 insertion map can be used in identifying essential and non-essential genes in *K. marxianus* and potentially, other organisms with functional NHEJ mechanisms.

Example 12

Insertional Mutagenesis and Transposon Mutagenesis

This example describes comparing ScURA3 insertional mutagenesis with T5-transposon mutagenesis using PEG-LiAC-mediated transformation.

PEG-LiAc-Mediated transformation. PEG-LiAc-Mediated transformation has been described in Abdel-Banat et al. Yeast 27, 29 (2010), the content of which is incorporated herein in its entirety. *Kluyveromyces marxianus* cells were grown in 30 ml of YPD at 30° C. in a 250 ml flask with shaking (150 rpm) for 24 h. Cells were harvested by centrifugation at 3000 rpm for 5 minutes. Cell pellet was resuspended in 900 µl TFB (40% polyethylene glycol 3350, 100 mM DTT, 0.2 M lithium acetate) and transferred to a 1.5 ml Eppendorf tube. Cells were collected by centrifugation at 3000 rpm for 5 minutes, then resuspended in 600 µl TFB. Fifty microliters of cell suspension was mixed with ~70 ng purified ScURA3 fragment in a 1.5 ml Eppendorf tube, and incubated at 42° C. for 30 minutes. The mixture was resuspended in 100 µl CAA-URA medium, plated on CAA-URA plate, and incubated at 30° C. for 2-3 days.

TABLE 18

ScURA3 Insertional Mutagenesis vs. Tn5 Transposon Mutagenesis in *K. marxianus* via PEG-LiAC-Mediated Transformation

|  | ScURA3 (70 ng) | Transposome (1 µl) |
| --- | --- | --- |
| Wildtype (G13) | 914 transformants | 96 transformants |
| ku70Δ (G64) | None detected | None detected |

TABLE 19

ScURA3 Insertional Mutagenesis via Electroporation

|  | ScURA3 (70 ng) [10-hour recovery, 1/21 volume of electroporation was plated] |
| --- | --- |
| Wildtype (G13) | 612 transformants |
| ku70Δ (G64) | None detected |

TABLE 20

Tn5 Transposon Mutagenesis via Electroporation

|  | Transposome (1 µl) [14 hours recovery, 1/7 volume of electroporation was plated] |
| --- | --- |
| Wildtype (G13) | 1107 transformants |
| ku70Δ (G64) | 595 transformants |

ScURA3 insertional mutagenesis was compared with T5-transposon mutagenesis using PEG-LiAC-mediated transformation (Table 18). T5-transposon mutagenesis had a lower transformation efficiency in wildtype *K. marxianus*. No transformant was detected when ScURA3 insertional mutagenesis was performed using Aku70 cells. This suggested that ScURA3 insertional mutagenesis depends on NHEJ pathway. The fact that no T5-transposon mutagenesis transformants was found suggested that PEG-LiAc-mediated transformation may not be ideal for delivering T5-transposome into *K. marxianus*. Indeed, electroporation had a much higher transformation efficiency (Table 19) and can deliver T5-transposome into *K. marxianus*. Interestingly, the number of transformants generated from Aku70 was lower than wildtype cells (Table 20), suggesting that some free T5-transpson DNA fragment may be inserted in the genome of *K. marxianus*, similarly to ScURA3 insertional mutagenesis through the NHEJ pathway.

Altogether, the data presented in this Example indicate that ScURA3 insertional mutagenesis depends on NHEJ pathway, and that in some conditions, it can be advantageous to use ScURA3 insertional mutagenesis for studying gene-essentiality in *K. marxianus* than the T5-transposon mutagenesis method using PEG-LiAc-mediated transformation.

Example 13

Transfer DNA into *Kluyveromyces marxianus* by Conjugation

This example describes using conjugation to transfer DNA into *K. marxianus* with an oriT (origin of transfer)-containing plasmid.

Figure 35:
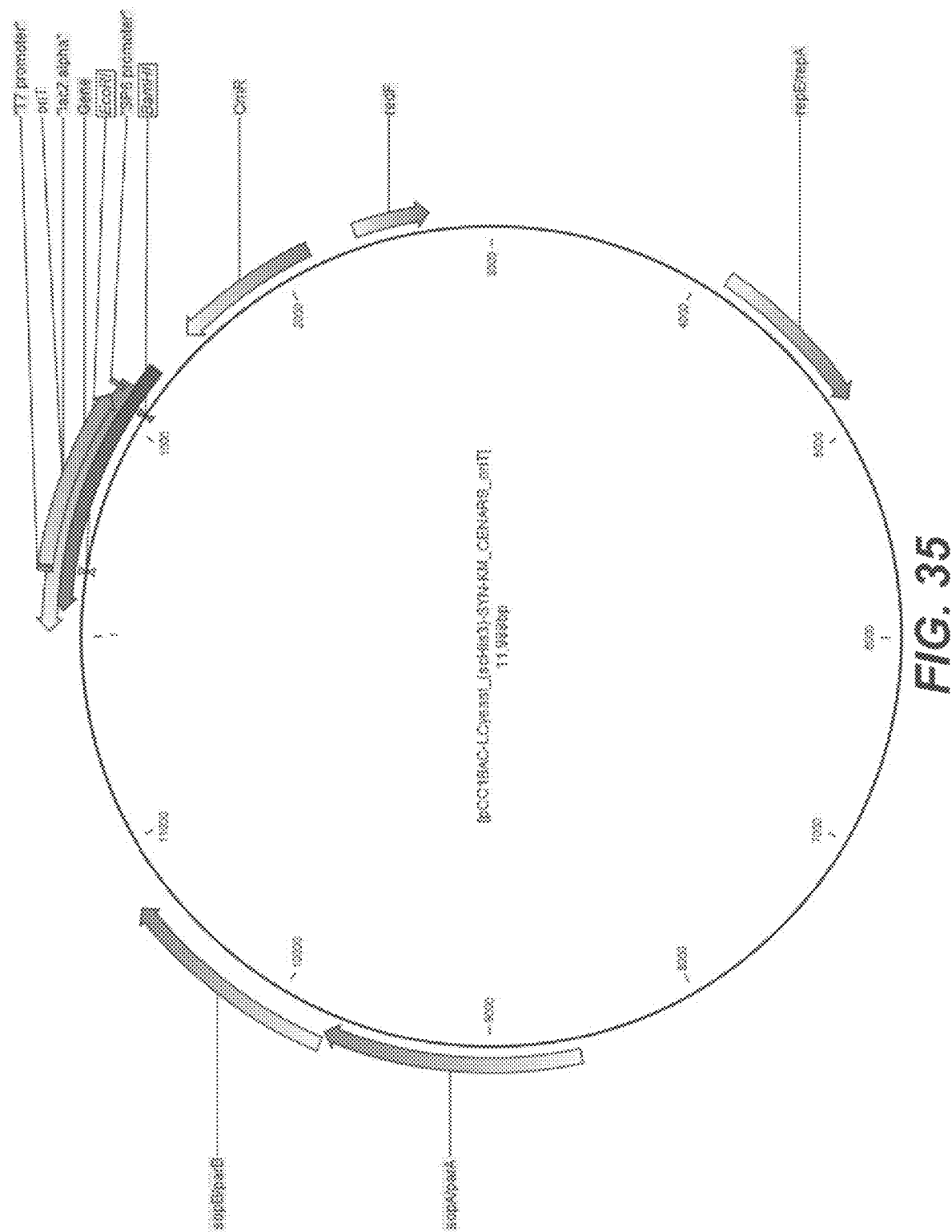

An oriT (origin of transfer)-containing plasmid can be transferred into diatom and *S. cerevisiae* from *E. coli* through conjugation (Karas et al., Nature Communications 6, 6925 (2015), and Moriguchi et al., PLOSOne 11, e0148989 (2016), the content of each is incorporated by reference in its entirety). This system was adopted for *K. marxianus*. First, the oriT sequence was inserted in pCC1BAC-LCyeast_(scHis3)-SYN-KM CENARS between EcoRI and BamHI restriction sites (FIG. 35). Using this plasmid, a protocol of *E. coli* to *K. marxianus* conjugation was established.

Figure 36:
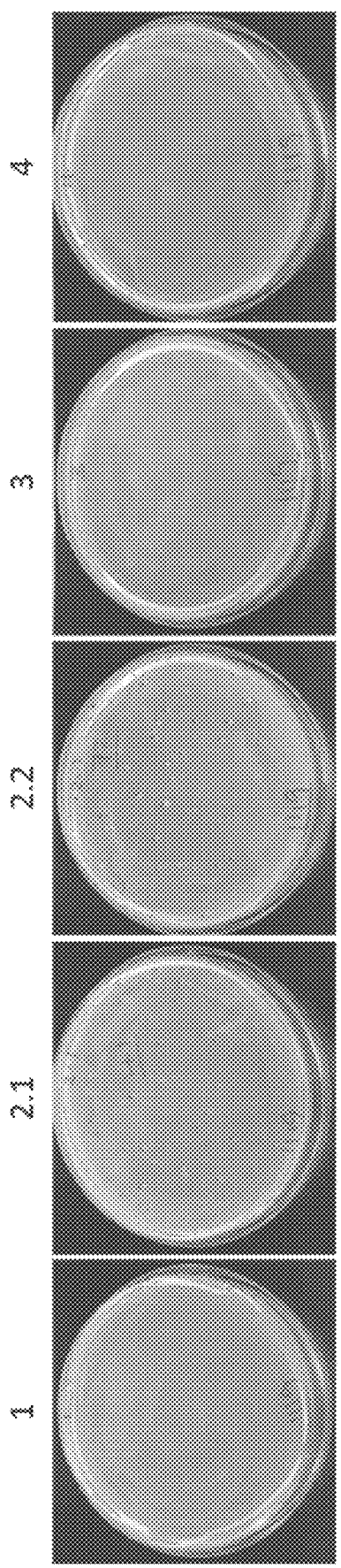
Figure 37:
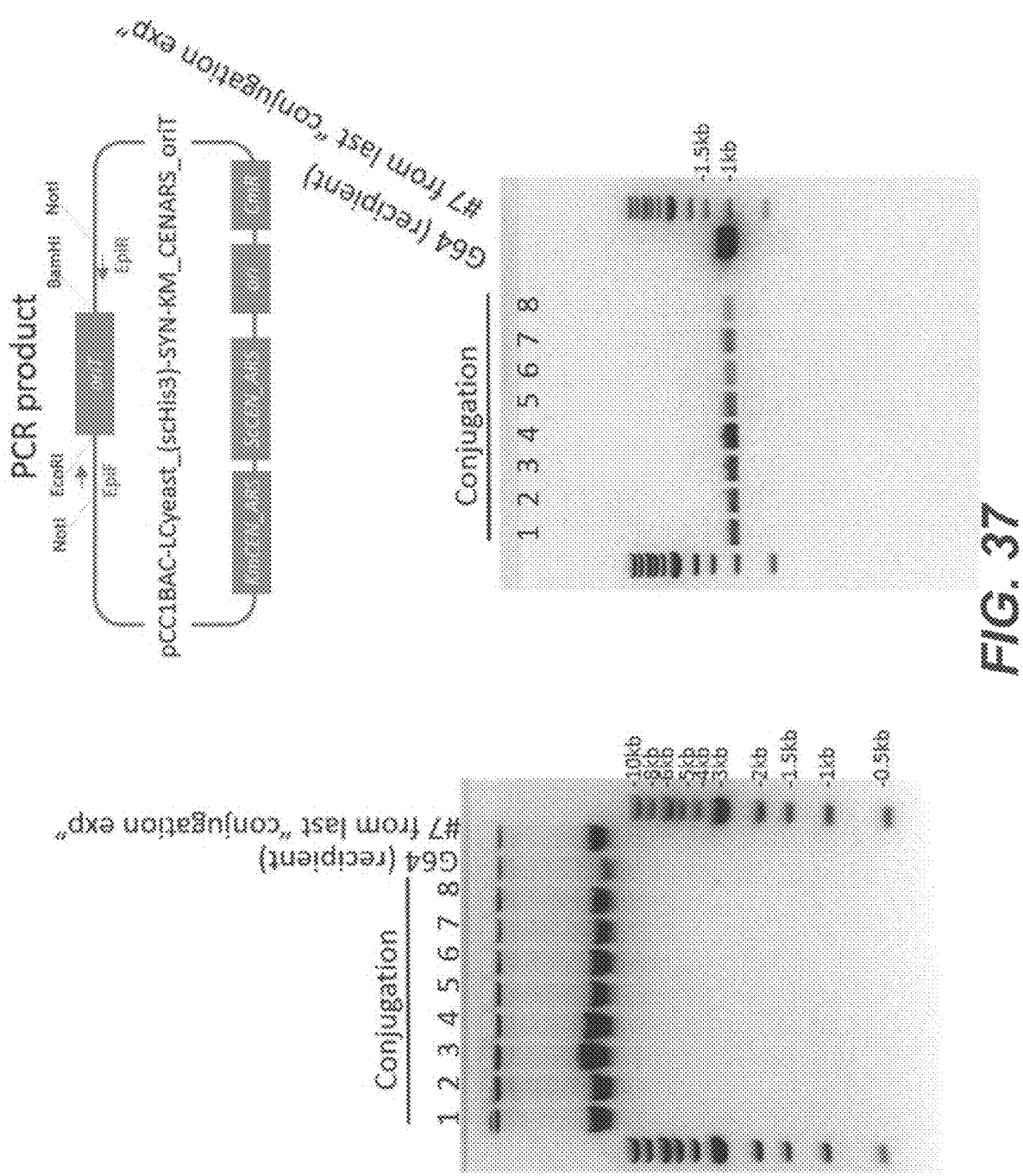
Figure 38:
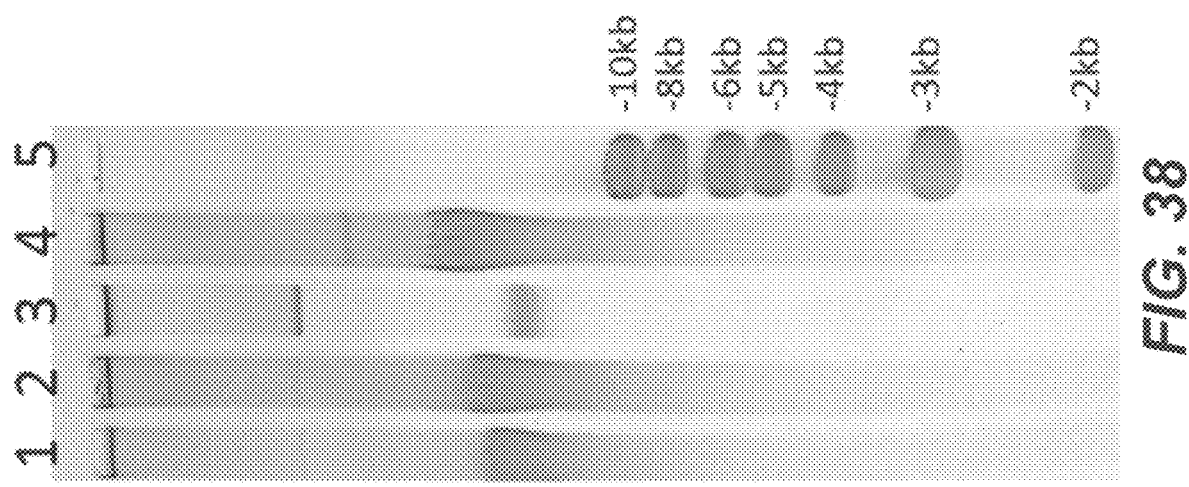

Conjugation. *E. coli* (plasmid to be transferred and helper plasmid) cells were grown in 5 ml LB+Chloramphenicol+Gentamycin medium at 37° C. overnight and *K. marxianus* were grown in 5 ml YPAD at 30° C. overnight. Cells were harvested by centrifugation at 3000 rpm for 5 minutes. *K. marxianus* was resuspended in 200 µl LB or SOC and *E. coli* was resuspended in 700 µl LB or SOC (Do not vertex *E. coli*). *K. marxianus* suspension was plated on a dry LB+Chloramphenicol+ Gentamycin plate and air dry. *E. coli* suspension was added on top of the *K. marxianus* (making sure that the *E. coli* suspension covers the entire plate). The plate was incubated at 37° C. overnight, then replica-plated onto a selective plate and incubated at 30° C. for 3 days.

pCC1BAC-LCyeast_(scHis3)-SYN-KM_CENARS_oriT was transferred into *K. marxianus* in the presence of the helper plasmid (pTA-MOB as described in Strand et al., PloS one 9, e90372 (2014), the content of which is whereby incorporated by reference in its entirety). FIG. 36 shows establishment of *E. coli* to *K. marxianus* conjugation. *E. coli* (EPI300) was transformed with plasmids in the bottom table. Eight *K. marxianus* conjugation colonies were screened for the presence of pCC1BAC-LCyeast_(scHis3)-SYN-KM_CENARS_oriT. Genomic DNA (FIG. 37, left panel): oriT PCR product (FIG. 37, right panel). Conjugation was also utilized to deliver DNA molecules of up to 100 kb from *E. coli* to *K. marxianus* via conjugation (Table 21 and FIG. 38). FIG. 38 is a non-limiting exemplary gel electrophoresis photograph showing that large DNA fragment can be transferred from *E. coli* to *K. marxianus* via conjugation. Lane 1. #4-55-clone 1: Lane 2. #4-55-clone 2: Lane 3. #4-55-*E. coli*; Lane 4. #3; Lane 5. NEB 1 kb ladder. (genomic DNA on TAE gel with SYBR Gold Staining)

TABLE 21

E. coli to K. marxianus Conjugation (*conjugations of different 1/10th molecules was performed at different times)

| 1/10th molecule of minimized K. marxianus Chromosome 7 | 1 | 2 | 3 | 4 | 5 | 9 |
|---|---|---|---|---|---|---|
| Size | 50883 bp | 71081 bp | 48341 bp | 100454 bp | 76643 bp | 53037 bp |
| #colonies* on selective plate | 258 | 3 | 65 | 203 | 17 | 40 |

Altogether, the data demonstrate that conjugation can be used to deliver chromosomal segment up to ~100 kb from E. coli to K. marxianus.

Example 14

Design-Build-Test Cycle in K. marxianus

This example describes a design-build-test cycle using a Cas9-expressing K. marxianus.

Figure 39:
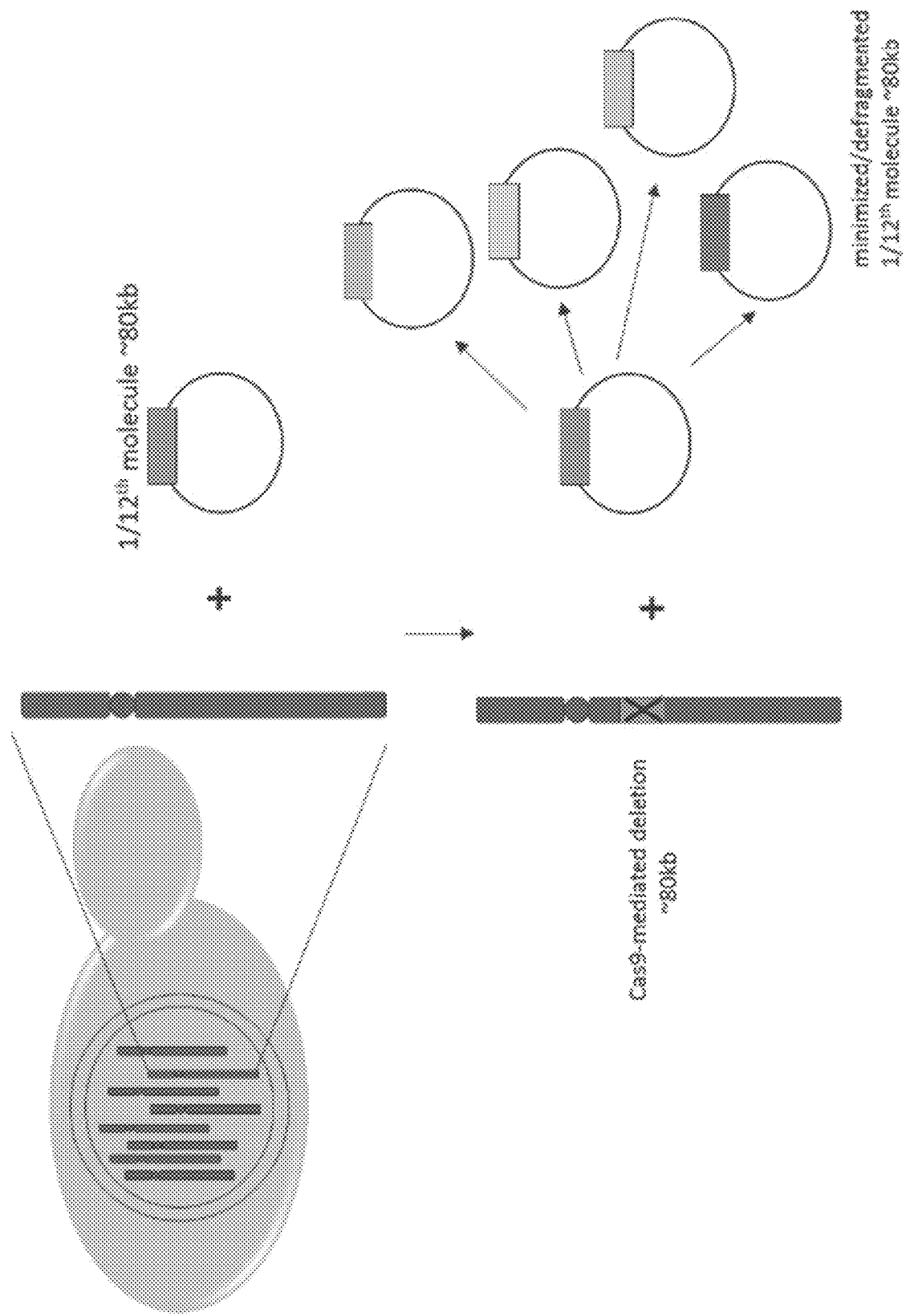

The unique method of hierarchical assembly of chromosome 7 of K. marxianus disclosed herein allowed choosing intermediate sub-assembly molecules for redesigning, and testing of the functionality of the redesigned molecules (strategy outlined in FIG. 39). Specifically, the Stage-II subassembly molecules (~80 kb) was chosen for redesigning and testing, one at a time. As a first step, the replication elements necessary for maintenance in K. marxianus were introduced into these subassembly molecules. Subsequently, these molecules were transformed into K. marxianus strain expressing Cas9 protein. After establishing stable maintenance of the 1/12th molecule, the corresponding segment would be deleted from chromosome 7 using CRISPR/Cas9. This resulted in a strain where a part of the genome was solely expressed from an episome, which enabled rapid replacement of this molecule with newly designed 1/12th molecules and verify functionality. Ultimately, the information obtained from each of these 1/12th molecules can be combined to create a redesigned chromosome.

Generating a Cas9-Expressing K. marxianus Strain

In order to streamline the process of testing our design using Cas9, a strain which expressed Cas9 on the chromosome was engineered. For this, the ade1 locus was chosen. Ade1 gene is involved in the biosynthesis of adenosine monophosphate. When this gene is interrupted, the biosynthesis of adenosine monophosphate is also arrested, which leads to the accumulation of P-ribosylaminoimidazole. This compound, upon oxidation under aerobic growth, turns red in color. Thus, interruption of the ade1 locus leads to the accumulation of yeast cells that are "red" in color.

Cas9 expressed from the plasmid was used to introduce Cas9 into the chromosome of K. marxianus, at the ade1 locus. The accumulation of the "red" pigment, led to the easy identification of the cells that were edited at the ade1 locus. The ade1 gene substitution with Cas9 was verified using genomic DNA isolation and subsequent PCR. The sequence of the Cas9 gene with its expression elements (promoter and terminator) was verified using MiSeq (Illumina, San Diego, CA).

Verifying the Utility of the Test Cycle Using a Positive Control

Figure 40:
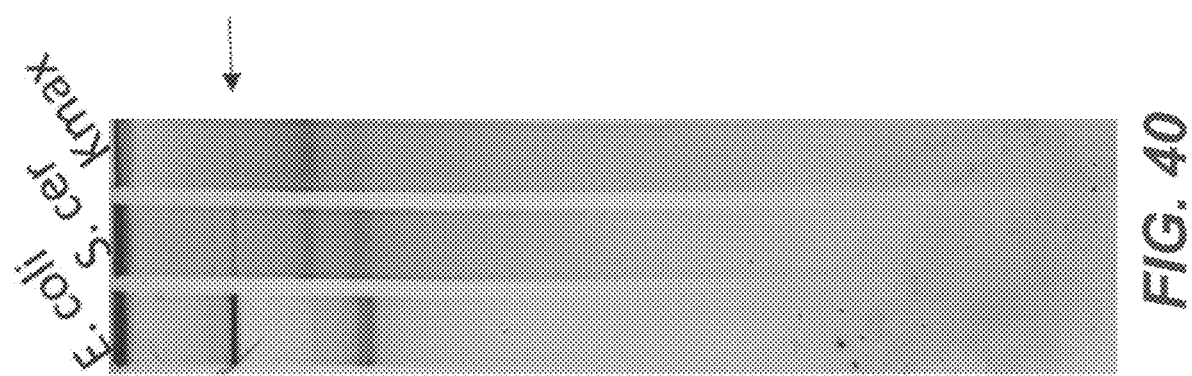

Initially, CRISPR/Cas9 based test cycle on "wild-type" subassembly molecule was tested. Specifically, one episomal Stage-II molecule of ~80 kb (wild-type) was introduced into K. marxianus and the corresponding segment from the chromosome was deleted using CRISPR/Cas9. Hence, in the final strain, ~80 kb of the genomic content was solely expressed from the episome. The Stage-II molecule, #6_12 was introduced into K. marxianus constitutively expressing Cas9. Shown in FIG. 40 is the verification of the presence of the Stage-II molecule, #6_12 after it was transformed into K. marxianus. As a comparison, the same molecule extracted from E. coli and S. cerevisiae were resolved in parallel on a 1% agarose gel for 3 hrs at 4.5V/cm and post-stained with SYBR-gold. Once the stable replication of the episomal molecule was established, this K. marxianus strain was transformed with gRNAs to direct Cas9-mediated cleavage of the chromosomal segment corresponding to the #6_12 molecule. Ultramer oligonucleotides were used to generate gRNA transcripts for deleting the chromosomal fragment encoded by Stage-II molecule #6-12 using Cas9. An ultramer oligonucleotide was used as a ssDNA donor during the Cas9-mediated deletion the chromosomal fragment encoded by Stage-II molecule #6-12. The ultramer oligonucleotide was used as a ssDNA donor to patch the two chromosomal arms after Cas9-mediated cleavage.

Once the transformation (with gRNAs and ssDNA) was performed cells were plated on selective media and screened using colony PCR. Primers were designed such that if the Cas9-mediated deletion occurred, ~465 bp single band should be observed: else a 300 bp band and a 400 bp band would be seen (wild-type). These primers were used to probe chromosomal deletion of the DNA encoded by Stage-II molecule #6-12.

Figure 41:
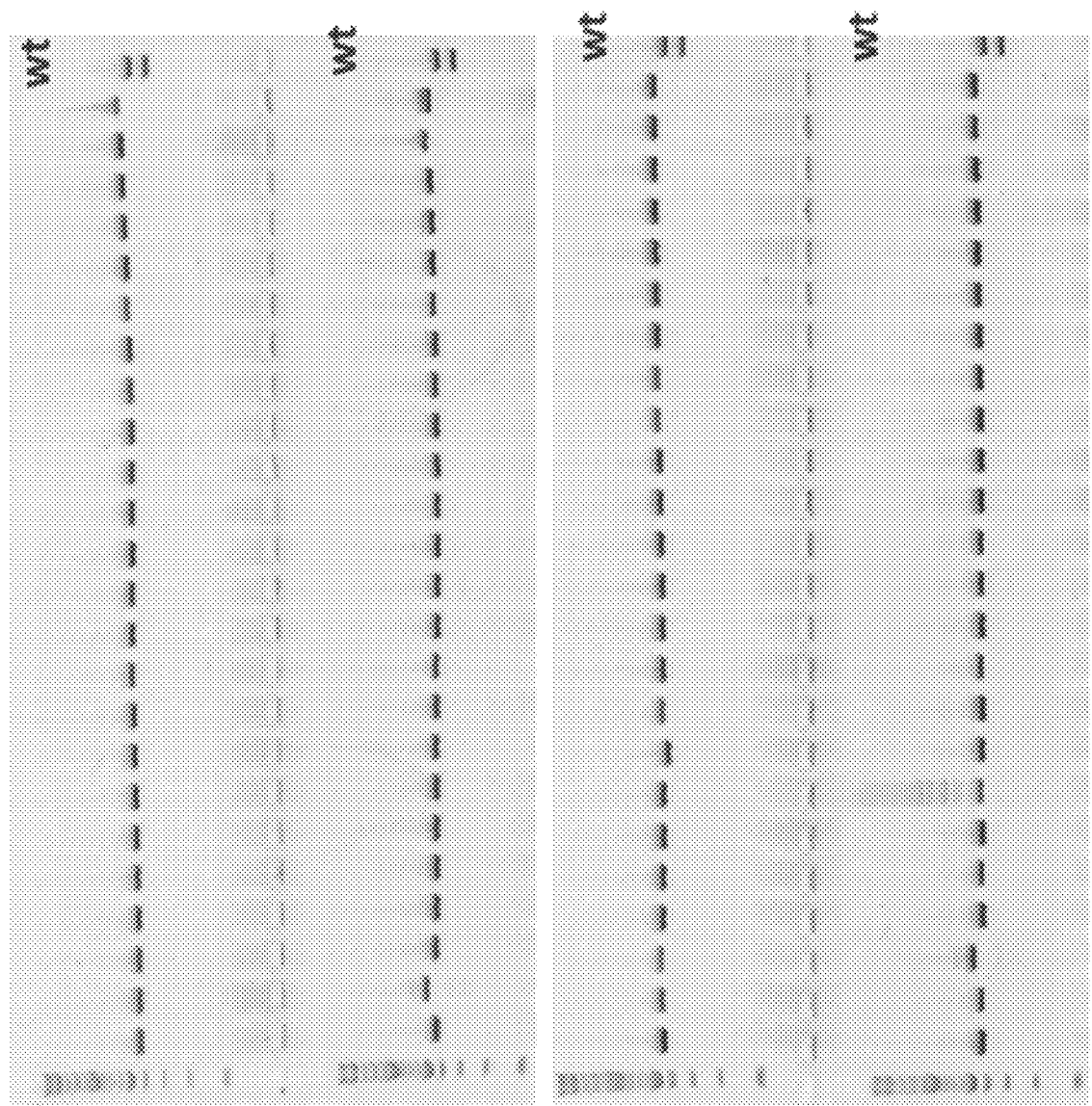
Figure 42:
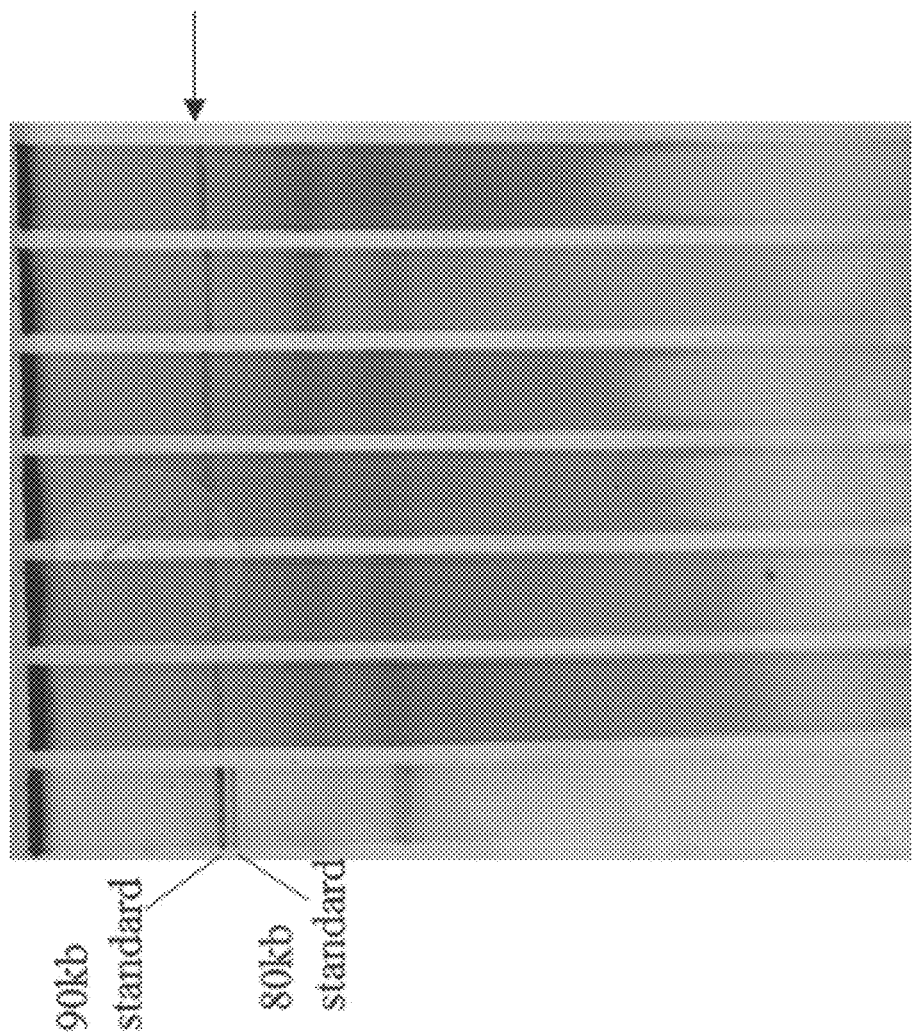

96 colonies were screened using the above listed primers to probe chromosomal deletion. Every single colony that was screened carried the deletion (FIG. 41). Six colonies from the transformants that tested positive for chromosomal deletion were subjected to DNA extraction to confirm the presence of the #6_12 episome in these strains (FIG. 42).

Figure 43:
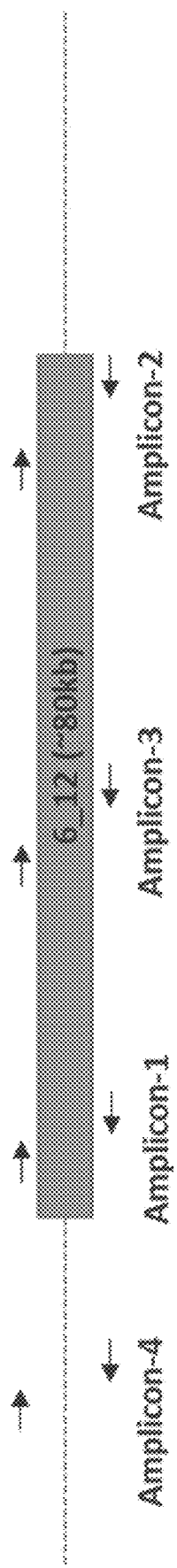
Figure 44:
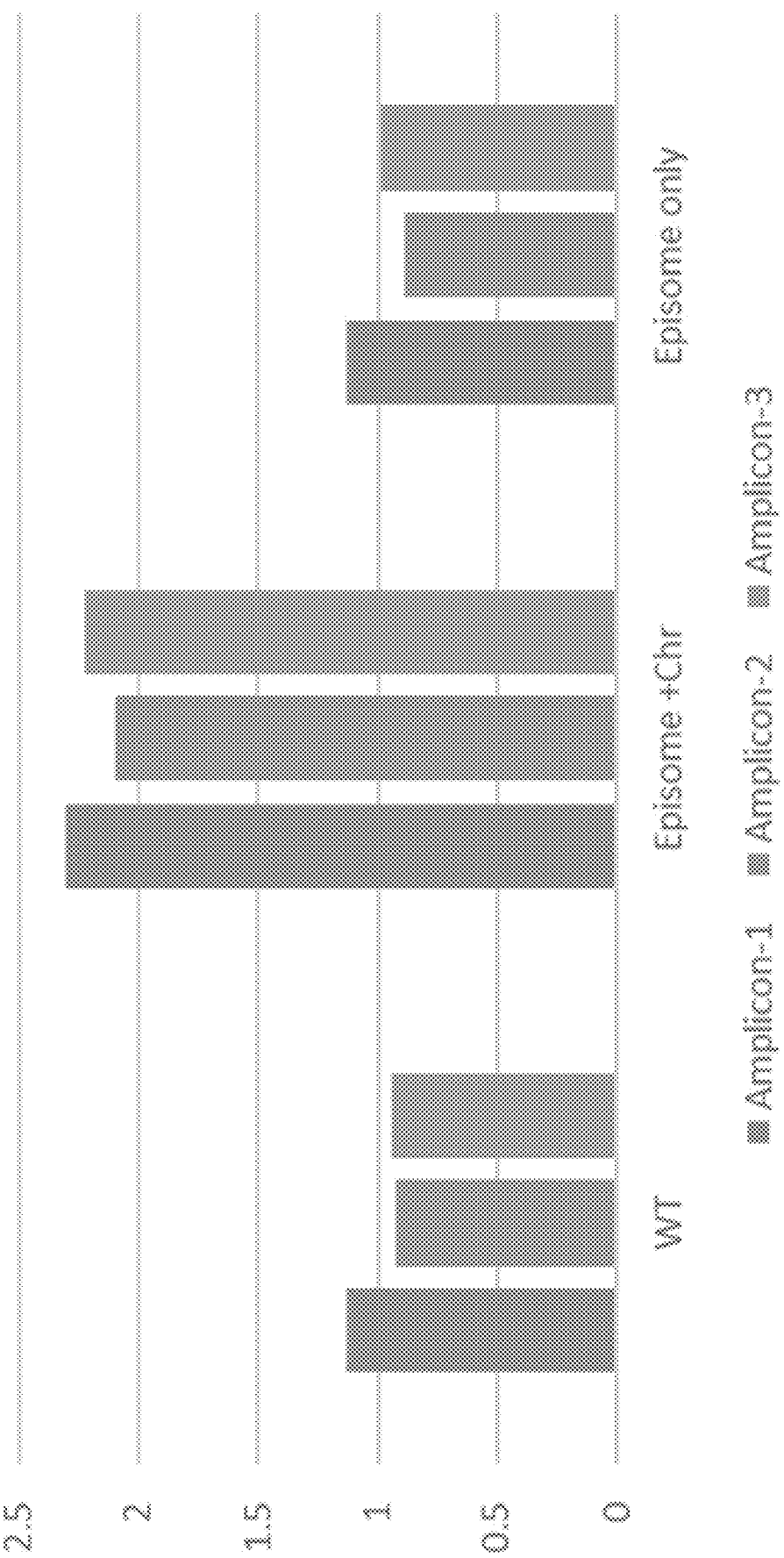
Figure 45:
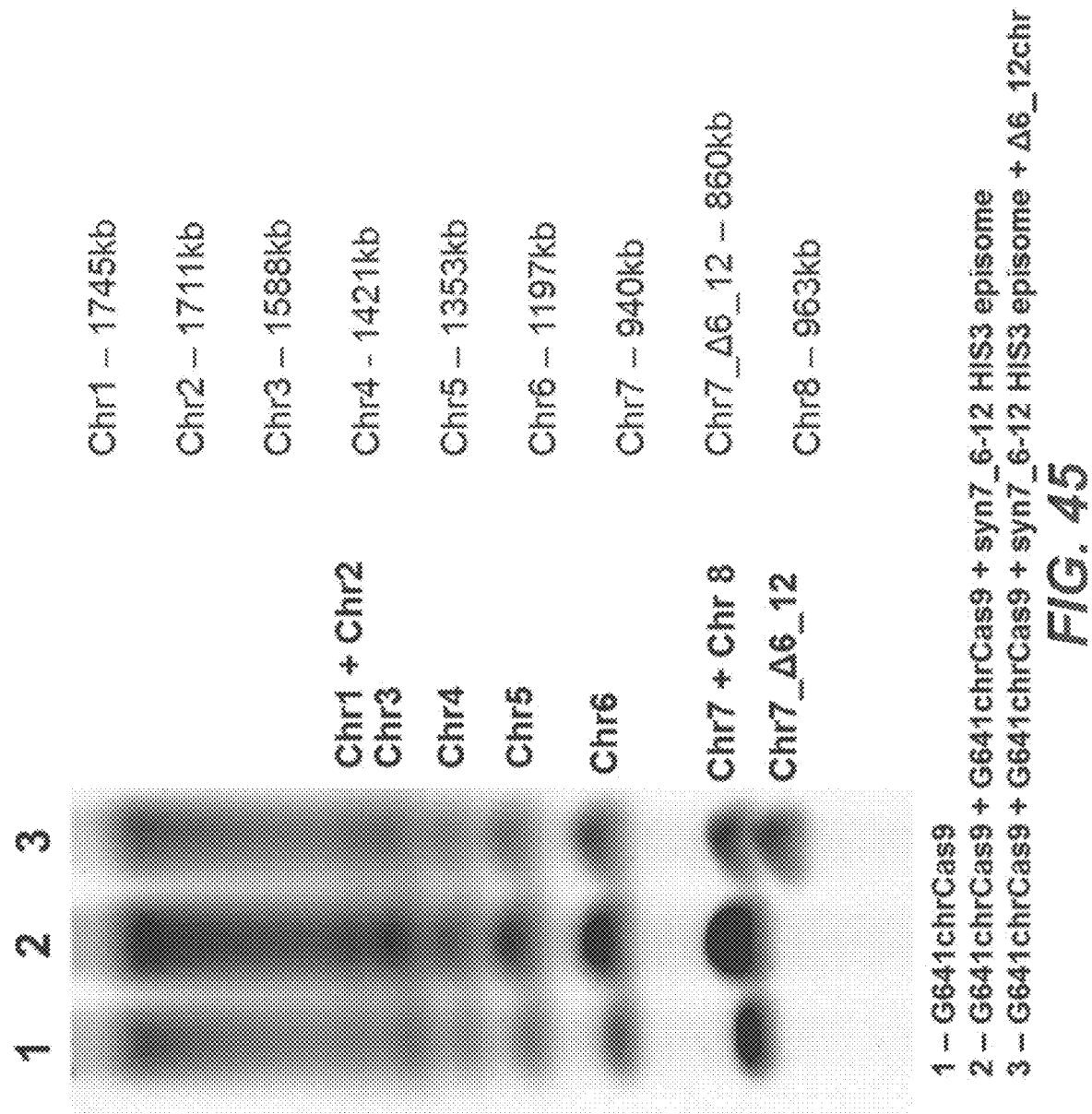

The chromosomal deletion of the DNA fragment encoded in the episome #6_12 was further verified using quantitative PCR (qPCR) (FIGS. 43-44, Table 22) and pulse-field gel-electrophoresis (PFGE) (FIG. 45). FIG. 43 shows a non-limiting exemplary qPCR design. Primers for four amplicons were designed such that three amplicons would be from different parts of the segment encompassed by #6_12 (amplicons 1-3) and one outside this segment (amplicon 4). qPCR would help determine the relative copy number of the DNA fragment encoded in #6_12 fragment. In the wild-type strain, amplicons 1-3 should be of the same relative amount in a qPCR as amplicon 4: when the episomal DNA #6_12 was introduced, the cell should carry two copies of the segment encoded in #6_12-one in the chromosome, another in the episome: this would result in twice amount of amplicons 1-3 relative to 4; however after the CRISPR/Cas9 mediated deletion, the copy number of segment #6_12 returns to one since there is only one copy of this DNA fragment—in the episome: this would result in the same relative amount of amplicons 1-3 compared to amplicon 4.

Genomic DNA was extracted from the wild-type strain (WT), strain carrying episomal DNA #6_12 (Episome+ chromosome ("chr")) and strain carrying episomal DNA #6_12 but with the corresponding chromosomal fragment deleted (Episome only). 50 ng of genomic DNA was used in each qPCR reaction using primers. Reactions were performed in triplicates and average Ct values were calculated. ΔCt values were calculated for each of the amplicons 1-3 relative to amplicon 4, for all three strains. The Ct and ΔCt values are listed in Table 22 and plotted in FIG. 44. The qPCR results confirmed that in the strain carrying the episomal DNA #6_12, the corresponding chromosomal fragment was indeed deleted using CRISPR/Cas9. In this strain, ~80 kb of genomic DNA was encoded solely from an episome.

Pulse-field gel-electrophoresis was used to confirm the CRISPR/Cas9 mediated deletion of the chromosomal ~80 kb fragment in the strain carrying episomal DNA #6_12. For this, genomic DNA was captured in agarose plugs in the following strains: wild-type strain (WT), strain carrying episomal DNA #6_12 (Episome+chr), and strain carrying episomal DNA #6_12 but with the corresponding chromosomal fragment deleted (Episome only).

Following genomic DNA preparation, chromosomes were resolved using Pulse-field gel-electrophoresis (FIG. 45). In the "episome only" strain, a faster-migrating chromosomal species was observed, hence confirming the ~80 kb deletion using CRISPR/Cas9 in chromosome 7.

Figure 46:
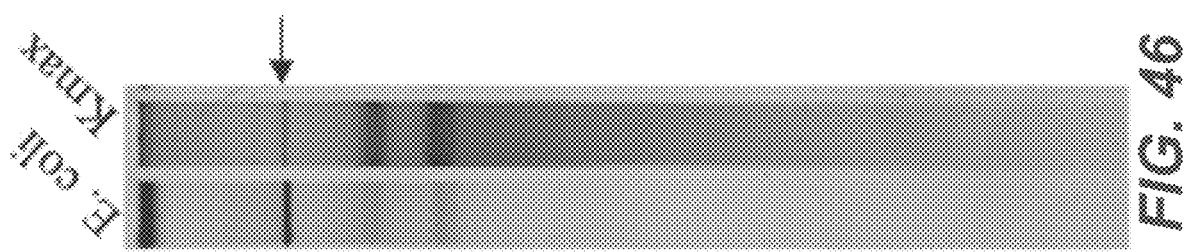

Cas9 method, the minimized molecule was not a replica of the corresponding chromosomal segment, instead lacked ~20 kb of genomic material due to minimization. This episome molecule, #2_37 was introduced into *K. marxianus* using conjugation (FIG. 46).

Once the stable replication of the episomal molecule was established, this *K. marxianus* strain was transformed with gRNAs to direct Cas9-mediated cleavage of the chromosomal segment corresponding to the #2_37 molecule. The gRNAs were prepared from ultramer oligonucleotides. Ultramer oligonucleotides used to generate gRNA transcripts for deleting the chromosomal fragment encoded by the minimized Stage-II molecule #2_37. Ultramer oligonucleotide was used as an ssDNA donor to patch the two chromosomal arms after Cas9-mediated cleavage. Ultramer oligonucleotide used as a ssDNA donor during the Cas9-mediated deletion the chromosomal fragment encoded by Stage-II molecule #2_37.

Figure 47:
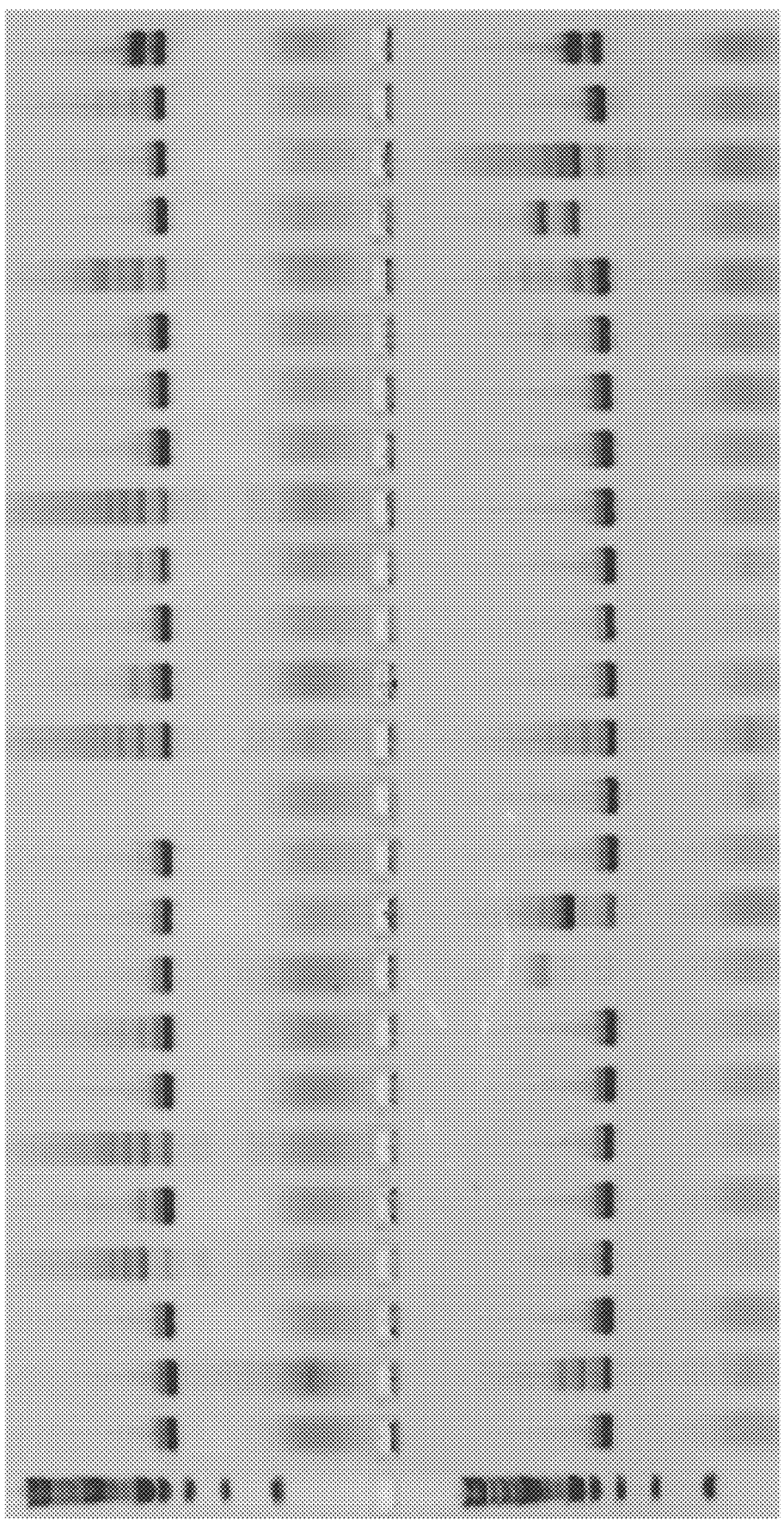
FIG. 47 show non-limiting exemplary gel electrophoresis photographs showing colony PCR analysis of CRISPR/Cas9 mediated chromosomal deletion. 48 transformants and a wild-type (wt) control were screened using primers. Wt PCR was loaded on the last lane of each row (24 samples each). Control colony produced 350 bp and 450 bp PCR amplicons, while none of the 48 transformants did so. Instead, several transformants produced a single ~360 bp PCR amplicon, indicative of a ~91 kb deletion of the chromosomal DNA corresponding to the #2_37 minimized episomal DNA.

Once the transformation (with gRNAs and ssDNA) was performed cells were plated on selective media and screened using colony PCR. Primers were designed such that if the Cas9-mediated deletion occurred, ~360 bp single band should be observed: else a 350 bp band and a 450 bp band would be seen (wild-type). Primer sequences used to probe chromosomal deletion of the DNA (~91 kb) encoded in minimized Stage-II molecule 2_37 (~71 kb). 48 colonies were screened using the above listed primers to probe chromosomal deletion (FIG. 47). The chromosomal deletion was further verified using qPCR and pulsed-field gel electrophoresis (PFGE) disclosed herein.

TABLE 22

Average and ΔCt Values Obtained from the qPCR Experiment Described in FIG. 43. 50 ng gDNA template

| | | Avg Ct | ΔCt | Fold-difference (normalized to amplicon-4) | |
|---|---|---|---|---|---|
| WT | Primer set_1 | 14.90333 | −0.18333 | 1.135504 | Amplicon-1 |
| | Primer set_2 | 15.19667 | 0.11 | 0.926588 | Amplicon-2 |
| | Primer set_3 | 15.17 | 0.083333 | 0.943874 | Amplicon-3 |
| | Primer set_4 | 15.08667 | 0 | | Amplicon-4 |
| Episome + chr | Primer set_1 | 13.45333 | −1.20667 | 2.308038 | Amplicon-1 |
| | Primer set_2 | 13.59333 | −1.06667 | 2.094588 | Amplicon-2 |
| | Primer set_3 | 13.50667 | −1.15333 | 2.224272 | Amplicon-3 |
| | Primer set_4 | 14.66 | 0 | | Amplicon-4 |
| Episome only | Primer set_1 | 14.59333 | −0.18 | 1.132884 | Amplicon-1 |
| | Primer set_2 | 14.94333 | 0.17 | 0.888843 | Amplicon-2 |
| | Primer set_3 | 14.79 | 0.016667 | 0.988514 | Amplicon-3 |
| | Primer set_4 | 14.77333 | 0 | | Amplicon-4 |

Altogether, the data demonstrate that a design-build-text cycle using a Cas9-expressing *K. marxianus* and the information obtained from each of these ¹⁄₁₂th molecules can be combined to create a redesigned chromosome.

Example 15

Utilizing the CRISPR/Cas9 Based Test Cycle to Verify Genomic Design of a Minimized Chromosomal Segment This example describes testing a CRISPR/Cas9-based method to evaluate the chromosomal minimization design.

A CRISPR/Cas9-based method was tested to evaluate the chromosomal minimization design. For this, we identified and built a minimized Stage-II molecule. Unlike the #6_12 Stage-II molecule that was used to evaluate the CRISPR/

Figure 49:
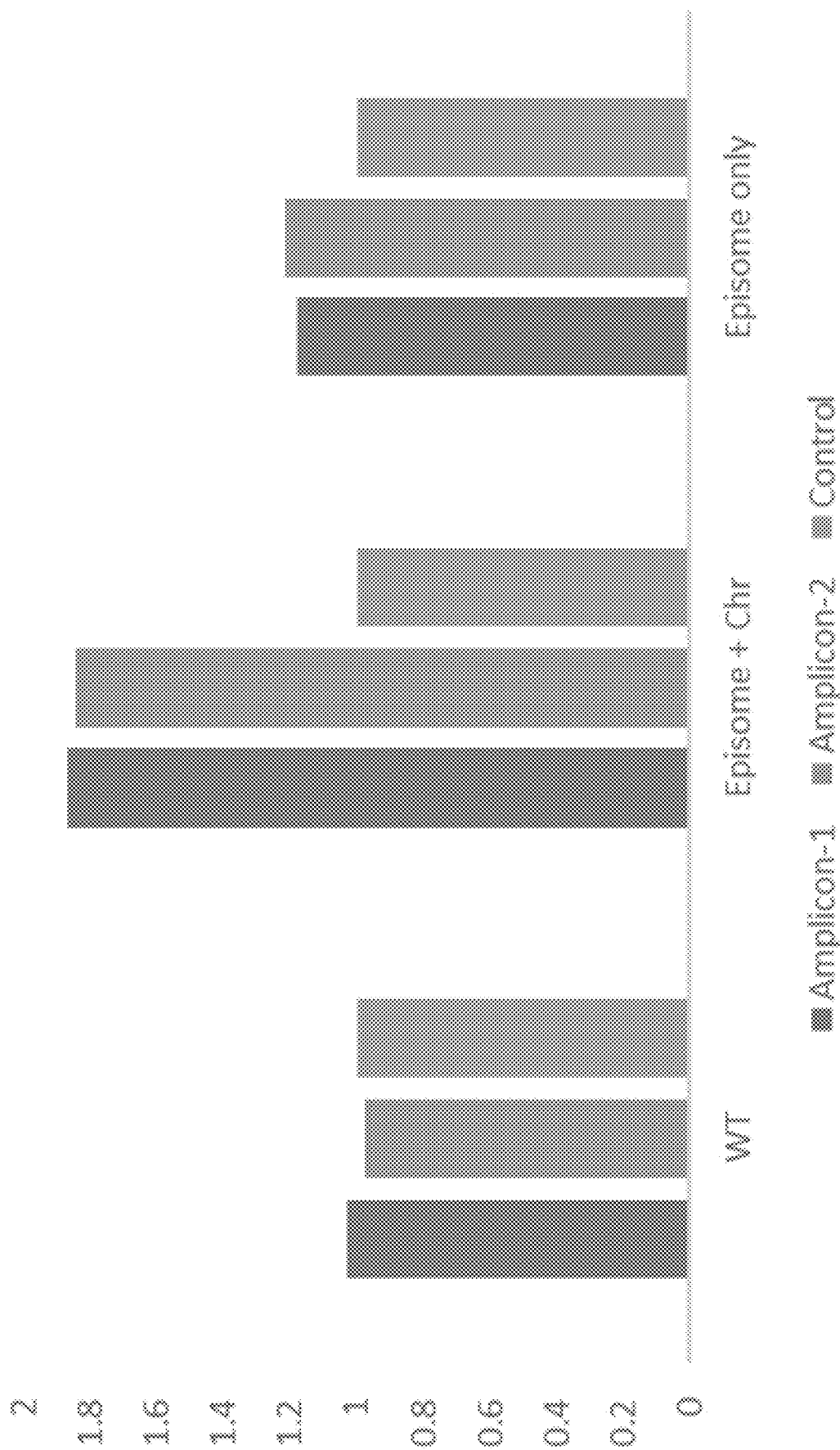
FIG. 49 is a non-limiting exemplary plot showing that qPCR was used to determine the copy number of #2_37 DNA fragment in the wild-type strain (WT), strain carrying the minimized episomal DNA #2_37 (Episome+chr) and strain carrying the minimized episomal DNA #2_37 but with the corresponding wildtype chromosomal fragment deleted (Episome only).

Genomic DNA was extracted from the wild-type strain (WT), strain carrying minimized episomal DNA #2_37 (Episome+chr) and strain carrying minimized episomal DNA #2_37 but with the corresponding chromosomal fragment deleted (Episome only). Reactions were performed in triplicates and average Ct values were calculated. ΔCt values were calculated for each of the amplicons 1-2 relative to amplicon 3, for all three strains. The Ct and ΔCt values are listed in Table 23 and plotted in FIG. 49. The qPCR results confirm that in the strain carrying the minimized episomal DNA #2_37, the corresponding wild-type chromosomal fragment was indeed deleted using CRISPR/Cas9. In this strain, ~91 kb of genomic DNA was deleted and instead a ~71 kb DNA from an episome is sufficient to support growth, thus verifying the genome minimization design in this subchromosomal fragment.

TABLE 23

Figure 48:
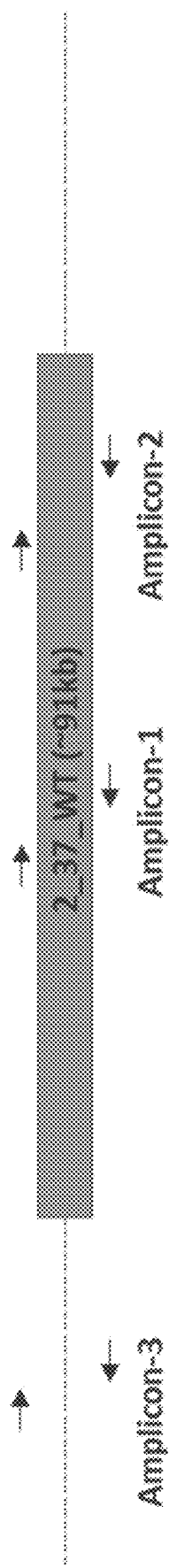
FIG. 48 is a non-limiting exemplary schematic illustration showing that primers for three amplicons were designed such that two amplicons would be from different parts of the segment encompassed by #2_37 (amplicons 1-2) and one outside this segment (amplicon 3). qPCR would help determine the relative copy number of the DNA fragment encoded in #2_37 fragment. In the wild-type strain, amplicons 1-2 should be of the same relative amount in a qPCR as amplicon 3: when the episomal DNA #2_37 was introduced, the cell should carry two copies of parts of the segment encoded in #2_37-one in the chromosome, another in the episome: this would result in twice amount of amplicons 1-2 relative to 3; however after the CRISPR/Cas9 mediated deletion, the copy number of segment #2_37 returned to one since there is only one copy of this DNA fragment—in the episome: this would result in the same relative amount of amplicons 1-2 compared to amplicon 3. Amplicons 1-2: probe: Amplicon 3: Control.

Average and ΔCt Values Obtained from the qPCR Experiment described in FIG. 48.

|  |  | Avg Ct | ΔCt | Fold-difference (normalized to amplicon-4) |  |
|---|---|---|---|---|---|
| WT | Primer set_1 | 16.72666667 | −0.043333333 | 1.03049202 | Amplicon-1 |
|  | Primer set_2 | 16.80667 | 0.036667 | 0.974905 | Amplicon-2 |
|  | Primer set_3 | 16.77 | 0 | 1 | Amplicon-3 |
| Episome + chr | Primer set_1 | 16.23 | −0.9 | 1.866066 | Amplicon-1 |
|  | Primer set_2 | 16.24667 | −0.88333 | 1.844632 | Amplicon-2 |
|  | Primer set_3 | 17.13 | 0 | 1 | Amplicon-3 |
| Episome only | Primer set_1 | 16.38667 | −0.23667 | 1.178267 | Amplicon-1 |
|  | Primer set_2 | 16.34333 | −0.28 | 1.214195 | Amplicon-2 |
|  | Primer set_3 | 16.62333 | 0 | 1 | Amplicon-3 |

Pulse-field gel-electrophoresis was used to confirm the CRISPR/Cas9 mediated deletion of the chromosomal ~91 kb wild-type fragment in the strain carrying minimized episomal DNA #2_37. For this, genomic DNA was captured in agarose plugs in the following strains: wild-type strain (WT), strain carrying minimized episomal DNA #2_37 (Episome+chr), strain carrying the minimized episomal DNA #2_37 but with the corresponding wild-type chromosomal fragment deleted (Episome only).

Figure 50:
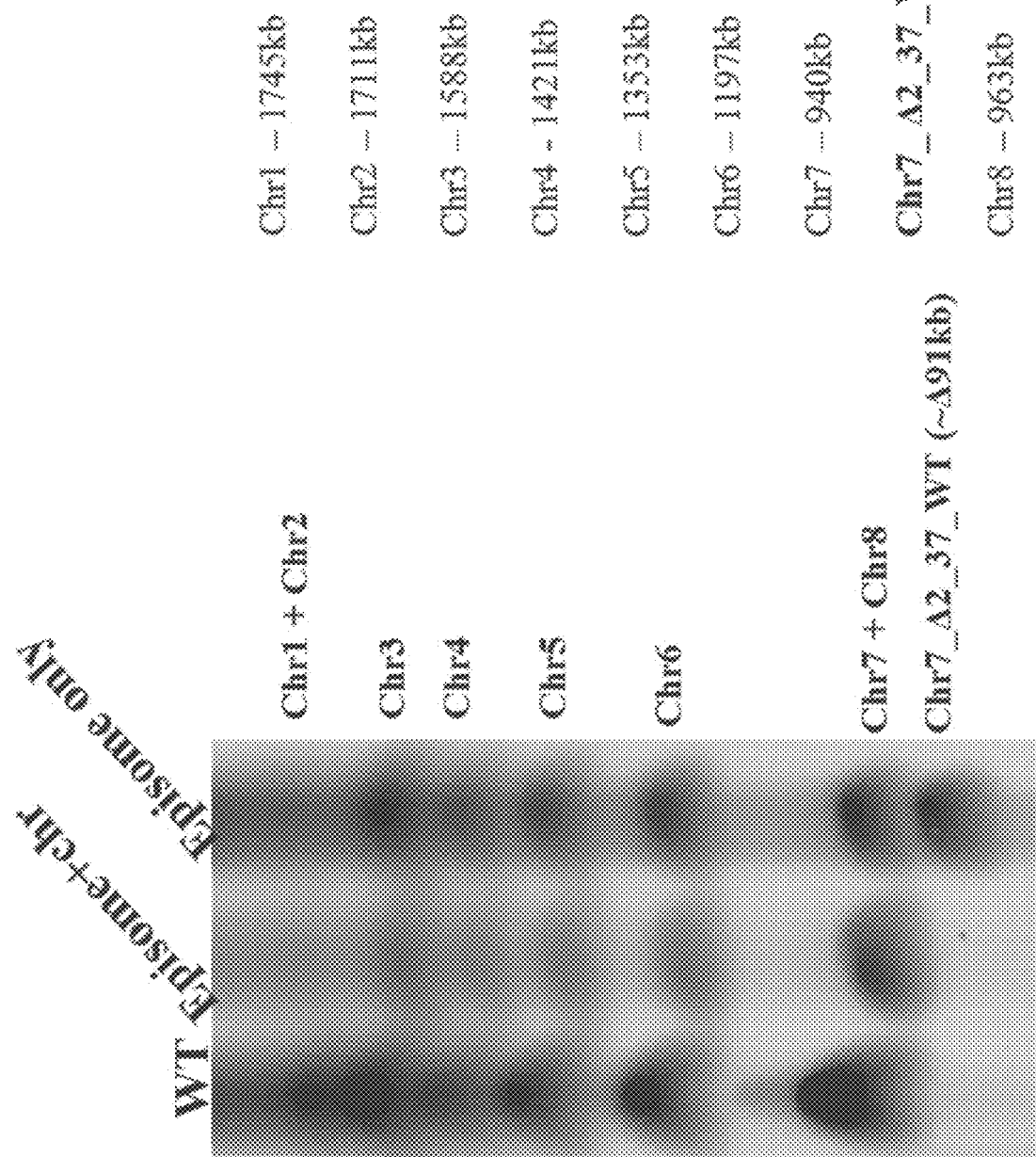
FIG. 50 is a non-limiting exemplary pulsed-field gel electrophoresis (PFGE) photograph confirming that ~91 kb deletion from the chromosome in the strain carrying the minimized episome #2_37. Lane 1-wild-type strain (WT), lane 2-strain carrying minimized episomal DNA #2_37 (Episome+chr), lane 3-strain carrying minimized episomal DNA #2_37 but with the corresponding wild-type chromosomal fragment deleted (Episome only). Chromosome 7 with the ~91 kb deletion migrates faster (lane 3) than the corresponding wild-type chromosome (lanes 1 and 2).

Following genomic DNA preparation, chromosomes were resolved using Pulse-field gel-electrophoresis (FIG. 50). In the "episome only" strain, a faster-migrating chromosomal species was observed, hence confirming the ~91 kb deletion using CRISPR/Cas9 in chromosome 7.

This example shows that a CRISPR/Cas9-based method can be used to evaluate the chromosomal minimization design by first identifying and building a minimized Stage-II molecule, introducing this Stage-II molecule into *K. marxianus* by conjugation, transforming this *K. marxianus* strain with gRNAs to direct Cas9-mediated cleavage of the chromosomal segment, and confirming the CRISPR/Cas9 mediated deletion using pulse-field gel-electrophoresis.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"): the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof.

Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for generating a synthetic genome of interest, comprising:
   (a) providing a first genome sufficient to sustain viability of a prokaryotic cell;
   (b) designing and providing a second genome comprising a reduced number of genes compared to the first genome;
   (c) dividing each of the first and second genomes into at least three corresponding fragments;
   (d) combining at least one fragment of the second genome with fragments of the first genome to generate a third genome having all the at least three corresponding fragments, further comprising grouping genes related to the same biological process in at least one fragment of the second genome prior to combining; or grouping genes related to the same biological process in the third genome after combining;
   (e) testing the third genome generated in step (d) for sufficiency to sustain viability of a cell; and
   (f) identifying the third genome as a synthetic genome of interest if it sustains viability of the prokaryotic cell; otherwise genetically modifying the at least one fragment of the second genome and repeating steps (d)-(f) in one or more iterations until a genome that sustains viability of the prokaryotic cell is obtained in the third genome.

2. The method of claim 1, wherein the first genome is a *Mycoplasma genome*.

3. The method of claim 1, wherein the first genome is a multi-chromosome genome.

4. The method of claim 1, wherein step (b) further comprises testing the second genome for a set of desired properties selected from the group consisting of: growth rate, ratio of growth rate to genome size, expression level of a gene of interest, ratio of viability to genome size, ratio of viability to expression level of a gene of interest, and ratio of growth rate to expression level of a gene of interest.

5. The method of claim 1, wherein designing the second genome further comprises modifying the first genome based on the information from literature resources, experimental data, or any combination thereof.

6. The method of claim 5, wherein the experimental data comprises data related to genes of essential function redundancies (EFR), or data obtained from a mutation study of the first genome, a genome related to the first genome, or any combination thereof.

7. The method of claim 1, wherein at least one of the at least three fragments is a chromosome of the first or second genome, or a portion of a chromosome of the first or second genome.

8. The method of claim 1, wherein testing the third genome for sufficiency to sustain viability of a cell comprises introducing the genome into a cell or a cell-like system.

9. The method of claim 1, wherein modifying at least one fragment of the second genome in step (f) further comprises conducting a mutation study of the at least one fragment and modifying the at least one fragment at least partly based on the mutation study.

10. The method of claim 1, wherein step (c) comprises dividing each of the first and second genomes into between 4 and 20 fragments.

11. The method of claim 1, wherein at least one fragment of the second genome is present in an extrachromosomal genetic element.

12. The method of claim 1, wherein the method generates a plurality of third genomes each having all of the at least three fragments.

13. The method of claim 1, wherein the combining step comprises chemically synthesizing and assembling the fragments of the first and second genomes to generate the third genome.

14. The method of claim 1 wherein the first genome known to sustain viability of a cell has a size of up to 5 Mb.

15. The method of claim 1 wherein the genes related to the same biological process are grouped onto one fragment of the second genome.

16. The method of claim 1 further comprising grouping the genes related to the same biological process as contiguous modules a) in the at least one fragment of the second genome, or b) on the third genome.

17. The method of claim 16 wherein the same biological process is selected from the group consisting of: transport and catabolism ribosome biogenesis, protein export, DNA repair, transcription, translation, nucleotide biosynthesis, metabolism and salvage, glycolysis, proteolysis, membrane transport, rRNA modification, and tRNA modification.

18. The method of claim 16 wherein step (c) comprises dividing each of the first and second genomes into at least 20 fragments.

19. The method of claim 16 wherein the same biological process is selected from the group consisting of: transcription, RNA metabolism, translation, protein folding, protein export, a gene encoding RNA, ribosome biogenesis, rRNA modification, and tRNA modification.

20. The method of claim 1 wherein the same biological process is selected from the group consisting of: expression of genome information, preservation of genome information, cell membrane structure and function, and cytosolic metabolism.

* * * * *